(12) United States Patent
Bell et al.

(10) Patent No.: US 8,097,621 B2
(45) Date of Patent: *Jan. 17, 2012

(54) PYRAZOLO[4,3-D]PYRIMIDINES AS PHOSPHODIESTERASE INHIBITORS

(75) Inventors: Andrew Simon Bell, Sandwich (GB); David Graham Brown, Sandwich (GB); Kevin Dack, Sandwich (GB); David Nathan Abraham Fox, Sandwich (GB); Ian Roger Marsh, Sandwich (GB); Andrew Ian Morrell, Sandwich (GB); Michael John Palmer, Sandwich (GB); Carol Ann Winslow, Sandwich (GB)

(73) Assignee: Pfizer Inc., New York, NY (US)

( * ) Notice: Subject to any disclaimer, the term of this patent is extended or adjusted under 35 U.S.C. 154(b) by 160 days.

This patent is subject to a terminal disclaimer.

(21) Appl. No.: 12/481,939

(22) Filed: Jun. 10, 2009

(65) Prior Publication Data

US 2009/0247539 A1    Oct. 1, 2009

Related U.S. Application Data

(63) Continuation of application No. 10/997,191, filed on Nov. 24, 2004, now Pat. No. 7,572,799.

(60) Provisional application No. 60/535,797, filed on Jan. 12, 2004.

(30) Foreign Application Priority Data

Nov. 24, 2003 (GB) .................................. 0327319.0

(51) Int. Cl.
*C07D 487/04* (2006.01)
*A61K 31/519* (2006.01)
*A61P 9/12* (2006.01)
*A61P 25/28* (2006.01)
*A61P 11/06* (2006.01)
*A61P 15/10* (2006.01)

(52) U.S. Cl. ................. 514/234.2; 514/262.1; 544/262; 544/118

(58) Field of Classification Search .................. 544/252, 544/118, 262; 514/262.1, 234.2
See application file for complete search history.

(56) References Cited

U.S. PATENT DOCUMENTS

| | | | |
|---|---|---|---|
| 3,951,980 A | 4/1976 | Henry et al. ................. 451/2 |
| 4,282,361 A | 8/1981 | Hecht et al. ................. 13/2 |
| 5,091,431 A | 2/1992 | Tulshian et al. ................. 514/262 |
| 5,391,771 A | 2/1995 | Weyer et al. ................. 549/326 |
| 5,442,044 A | 8/1995 | Hoover et al. ................. 5/6 |
| 6,001,830 A | 12/1999 | Lee et al. ................. 31/50 |
| 6,106,864 A | 8/2000 | Dolan et al. ................. 9/14 |
| 6,130,223 A | 10/2000 | Jonas et al. ................. 514/258 |
| 6,184,338 B1 | 2/2001 | Schwindeman et al. ................. 528/392 |
| 6,288,078 B1 | 9/2001 | Walsh et al. ................. 514/300 |
| 6,432,957 B1 | 8/2002 | Kodoma et al. ................. 31/496 |
| 6,465,486 B1 | 10/2002 | Baxter et al. ................. 31/47 |
| 6,566,360 B1 | 5/2003 | Niewohner et al. ................. 514/243 |
| 6,777,419 B1 | 8/2004 | Jonas et al. ................. 514/262.1 |
| 2001/0047013 A1 | 11/2001 | Lang et al. ................. 213/2 |
| 2002/0058668 A1 | 5/2002 | Yuan ................. 514/258 |
| 2002/0127593 A1 | 9/2002 | Reich et al. ................. 435/6 |
| 2003/0187261 A1 | 10/2003 | Havlicek et al. ................. 514/276 |
| 2004/0002990 A1 | 1/2004 | Sander et al. ................. 17/30 |
| 2004/0023990 A1 | 2/2004 | Eggenweiler et al. ..... 514/262.1 |
| 2004/0063730 A1 | 4/2004 | Eggenweiler et al. ..... 514/262.1 |
| 2004/0077664 A1 | 4/2004 | Eggenweiler et al. ..... 514/262.1 |

FOREIGN PATENT DOCUMENTS

| | | | |
|---|---|---|---|
| EP | 0296811 | 6/1987 | ................. 125/67 |
| EP | 0297858 | 7/1987 | ................. 471/8 |
| EP | 0349239 | 7/1988 | ................. 487/4 |
| EP | 319479 | 6/1989 | ................. 9/30 |
| EP | 400661 | 5/1990 | ................. 403/4 |
| EP | 0677519 | 11/1994 | ................. 311/22 |
| EP | 0778277 | 6/1997 | |
| EP | 0937459 | 8/1999 | ................. 31/40 |
| EP | 1072595 | 1/2001 | ................. 211/22 |
| EP | 0579496 | 11/2001 | ................. 401/4 |
| EP | 1176142 | 1/2002 | ................. 231/14 |
| EP | 1176147 | 1/2002 | ................. 487/4 |
| EP | 1241170 | 9/2002 | ................. 487/14 |
| EP | 1348707 | 10/2003 | |
| FR | 2248255 | 5/1975 | |
| FR | 2638745 | 11/1988 | ................. 281/2 |
| JP | 03142277 | 10/1989 | |
| JP | 2002255932 | 9/2002 | ................. 205/4 |
| WO | WO 9428902 | 12/1984 | |

(Continued)

OTHER PUBLICATIONS

Perry, M.J. et al, Current Opinion in Chemical Biology, 1998, 2,472-481.*
Corbin JD, Francis SH., Int J Clin Pract. Jul.-Aug. 2002;56(6):453-9.*
Cremers B, Bohm M., Herz. Jun. 2003;28(4):325-333.*
Schudt, C.; Eur. Respir. J.; 1995; 8; 1179-1183.*
Torphy et. al.; Environ. Health Perspect.; 1994; 79-84.*
Yogesh et al., Nucleosides and Nucleotides, 1991, 19(6), 1417-27.
Krishna et al., Nucleic Acids Research, 1986, 14(4), 1747-64.
Secrist et al., J. Med. Chem, 1985, 28(11), 1740-2.

(Continued)

*Primary Examiner* — Susanna Moore
(74) *Attorney, Agent, or Firm* — Robert T. Ronau; Gregg Benson

(57) ABSTRACT

This invention relates to compounds of formula (I)

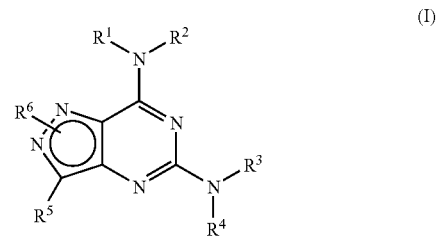

(I)

21 Claims, No Drawings

FOREIGN PATENT DOCUMENTS

| | | | |
|---|---|---|---|
| WO | WO 8605518 | 9/1986 | ............................ 1/68 |
| WO | WO 8605519 | 9/1986 | ............................ 1/68 |
| WO | WO 9301181 | 1/1993 | ...................... 401/12 |
| WO | WO 9306104 | 4/1993 | ........................ 487/4 |
| WO | WO 9307149 | 4/1993 | ........................ 487/4 |
| WO | WO 9312095 | 6/1993 | ...................... 239/91 |
| WO | WO 9400453 | 1/1994 | ...................... 473/30 |
| WO | WO 9405661 | 3/1994 | ........................ 471/4 |
| WO | WO 9413677 | 6/1994 | |
| WO | WO 9519978 | 7/1995 | ...................... 471/14 |
| WO | WO 9616657 | 6/1996 | ...................... 31/505 |
| WO | WO 9628429 | 9/1996 | |
| WO | WO 9808855 | 3/1998 | ...................... 19/167 |
| WO | WO 9817668 | 4/1998 | ........................ 495/4 |
| WO | WO 9849166 | 11/1998 | ........................ 487/4 |
| WO | WO 9928325 | 6/1999 | ........................ 495/4 |
| WO | WO 9945006 | 9/1999 | ...................... 413/14 |
| WO | WO 9954333 | 10/1999 | ........................ 487/4 |
| WO | WO 0024745 | 5/2000 | ........................ 487/4 |
| WO | WO 0117995 | 3/2001 | ...................... 413/12 |
| WO | WO 0118004 | 3/2001 | |
| WO | WO 0123389 | 4/2001 | ........................ 487/4 |
| WO | WO 0127112 | 4/2001 | ........................ 487/4 |
| WO | WO 0127113 | 4/2001 | ........................ 487/4 |
| WO | WO 0132646 | 5/2001 | |
| WO | WO 0147495 | 7/2001 | ............................ 9/14 |
| WO | WO 0147901 | 7/2001 | ........................ 271/6 |
| WO | WO 0200660 | 1/2002 | |
| WO | WO 0210171 | 2/2002 | ........................ 487/4 |
| WO | WO 0213798 | 2/2002 | |
| WO | WO 0242292 | 5/2002 | ........................ 401/6 |
| WO | WO 02062343 | 8/2002 | |
| WO | WO 02066481 | 8/2002 | ........................ 487/4 |
| WO | WO 02102314 | 12/2002 | |
| WO | WO 2004068867 | 1/2004 | |
| WO | WO 2004096810 | 11/2004 | ........................ 487/4 |

OTHER PUBLICATIONS

Vippagunta et al., Advanced Drug Delivery Reviews, 2001, 48, pp. 3-26.
Perry et al., Current Opinion in Chemical Biology, 1998, 2, pp. 472-481.
Corbin et al., Int J. Clin Pract., Jul.-Aug. 2002, 56(6), pp. 453-459.
Cremers et al., Herz. Jun. 28, 2003, (4), pp. 325-333.
Schudt., Eur. Respir. J., 1995, 8, pp. 1179-1183.
Torphy et al., Environ. Health Perspect., 1994, pp. 79-84.
Organic Reactions, vol. 41 and vol. 42, p. 42, 1992.
Chambers et al., Journal Organic Chem., 50, pp. 4736-4738, 1985.
Zeitschrift fur Chemie, 28, 2, pp. 59-60, 1988.
Webber et al., Journal Med. Chem, 41 (1), pp. 96-101, 1998.
Singh et al., J. Het. Chem, 14, p. 1413, 1977.
Hara et al., J. Het Chem. 19, p. 1285, 1982.
Orozco et al., J. Pharmaceutical Science, 79(2), pp. 133-137, 1990.
Orozco et al., Quantitative Struct-Act Relat., 8, pp. 109-114, 1989.
Orozco et al., Molecular Pharmacology, 35(2), pp. 257-264, 1988.
Upadhya et al., Nucleic Acids Research, 14(4), pp. 1747-1764, 1986.
Secrist III et al., Journal Med. Chem., 28(11), pp. 1740-1742, 1985.
Diederich, Wiley-VCH, 1998.
Norris et al., J. Chem. Soc Perkin Trans I., pp. 1615-1622, 2000.
Bochis et al., J. Med. Chem., 24(12), pp. 1518-1521, 1981.
Yakovlev et al., Chemistry of Heterocyclic Compound, 36(4), pp. 429-431, 2000.
Smith et al., Tetrahedron Letters, 43, pp. 899-902, 2002.
Barlocco et al., J. Med. Chem., 41, pp. 674-681, 1998.
Baraldi et al., IL Farmaco, 46(11), pp. 1337-1350, 1991.
Brown et al, J. Org. Chem., 50, pp. 1582-1589, 1985.
H C Van Der Plas, Rec. I Tray Chim Pays-Bas, 84, pp. 1101-1106, 1965.
Dumaitre et al., Journal of Medicinal Chemistry, American Chemical Society, 39(8), pp. 1635-1644, 1996.
Czarniecki et al., Annu Rep Med Chem., 31, pp. 61-70, 1996.
Troiani et al., Chem Eur J., 3(12), pp. 2063-2070, 1997.
Siegl, J. Het Chem, 18(8), pp. 1613-1618, 1981.
Buurman, J. Het chem., 24, pp. 1377-1380, 1987.
Giardina et al., J. Med. Chem., 37, pp. 3482-3491, 1994.

* cited by examiner

PYRAZOLO[4,3-D]PYRIMIDINES AS PHOSPHODIESTERASE INHIBITORS

This application is a continuation of U.S. application Ser. No. 10/997,191, filed Nov. 24, 2004, now U.S. Pat. No. 7,572,799, which claims the benefit of U.S. Provisional Patent Application No. 60/535,797, filed Jan. 12, 2004, and the benefit of UK Provisional Patent Application No. 0327319.0, filed Nov. 24, 2003.

The present invention relates to a series of novel 5,7-diaminopyrazolo[4,3-d]pyrimidines, which are cyclic guanylate monophosphate (cGMP)-specific phosphodiesterase type 5 inhibitors ("PDE-5 inhibitors") that are useful in the treatment of hypertension and other disorders, to processes for their preparation, intermediates used in their preparation, to compositions containing them and the uses of said compounds and compositions.

The prevalence of hypertension in developed countries is about 20% of the adult population, rising to about 60-70% of those aged 60 or more. Hypertension is associated with an increased risk of stroke, myocardial infarction, atrial fibrillation, heart failure, peripheral vascular disease and renal impairment. Despite the large number of drugs available in various pharmacological categories, the need for an effective treatment of hypertension is still not satisfied.

Vascular endothelial cells secrete nitric oxide (NO). This acts on vascular smooth muscle cells and leads to the activation of guanylate cyclase and the accumulation of cyclic guanosine monophosphate (cGMP). The accumulation of cGMP causes the muscles to relax and the blood vessels to dilate, leading to a reduction in blood pressure. The cGMP is inactivated by hydrolysis to guanosine 5'-monophosphate (GMP) by a cGMP-specific phosphodiesterase. One important cGMP-phosphodiesterase has been identified as Phosphodiesterase type 5 (PDE5). Inhibitors of PDE5 decrease the rate of hydrolysis of cGMP and so potentiate the actions of nitric oxide.

Inhibitors of PDE5 have been reported in several chemical classes, including: pyrazolo[4,3-d]pyrimidin-7-ones (e.g. Int'l Publications WO 93/06104, WO 98/49166, WO 99/54333, WO 00/24745, WO 01/27112, and WO 01/27113); pyrazolo[3,4-d]pyrimidin-4-ones (e.g. Int'l Publication WO 93/07149); pyrazolo[4,3-d]pyrimidines (e.g. International Publication WO 01/18004); quinazolin-4-ones (e.g. Int'l Publication WO 93/12095); pyrido[3,2-d]pyrimidin-4-ones (e.g. Int'l Publication WO 94/05661); purin-6-ones (e.g. Int'l Publication WO 94/00453); hexahydropyrazino[2',1':6,1]pyrido[3,4-b]indole-1,4-diones (e.g. Int'l Publication WO 95/19978) and imidazo[5,1-f][1,2,4]triazin-ones (e.g. Int'l Publication WO 99/24433). International Publications WO 02/00660 and WO 01/18004 discuss pyrazolo[4,3-d]pyrimidines with a PDE-5 inhibiting effect, which can be used for treating disorders of the cardiovascular system.

There remains a demand for new PDE5 inhibitors, particularly with improved pharmacokinetic and pharmacodynamic properties. The compounds provided herein are potent PDE5 inhibitors with improved selectivity in vitro and/or an extended half-life in vivo.

In some embodiments, the present invention provides compounds of formula (I)

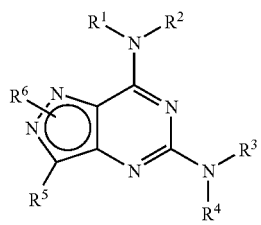

(I)

wherein
$R^1$ is a cyclic group selected from $R^A$, $R^B$, $R^C$ and $R^D$, each of which is optionally substituted with one or more $R^7$ groups;
$R^2$ is hydrogen or $C_1$-$C_2$ alkyl;
$R^3$ and $R^4$ are each independently $C_1$-$C_8$ alkyl, $C_2$-$C_8$ alkenyl, $C_2$-$C_8$ alkynyl or $C_3$-$C_{10}$ cycloalkyl, each of which is optionally substituted with one or more $R^8$ groups, or $R^E$, which is optionally substituted with one or more $R^9$ groups, or hydrogen;
or —$NR^3R^4$ forms $R^F$, which is optionally substituted with one or more $R^{10}$ groups;
$R^5$ is selected from —Y—$CO_2R^{15}$ and —Y—$R^{16}$;
$R^6$, which may be attached at $N^1$ or $N^2$, is $C_1$-$C_6$ alkyl, $C_1$-$C_6$ haloalkyl, $C_2$-$C_6$ alkenyl or $C_2$-$C_6$ alkynyl, each of which is optionally substituted by $C_1$-$C_6$ alkoxy, $C_1$-$C_6$ haloalkoxy or a cyclic group selected from $R^J$, $R^K$, $R^L$ and $R^M$, or $R^6$ is $R^N$, $C_3$-$C_7$ cycloalkyl or $C_3$-$C_7$ halocycloalkyl, each of which is optionally substituted by $C_1$-$C_6$ alkoxy or $C_1$-$C_6$ haloalkoxy, or $R^6$ is hydrogen;
$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;
$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, CN, $C_3$-$C_6$ cycloalkyl, $R^G$ or $R^H$, the last two of which are optionally substituted with one or more $R^9$ groups;
$R^9$ is $C_1$-$C_6$ alkyl, $C_1$-$C_6$ haloalkyl or $CO_2R^{12}$;
$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^2R^3$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;
$R^{11}$ is phenyl, $NR^{12}R^{13}$ or $NR^{12}CO_2R^{14}$;
$R^{12}$ and $R^{13}$ are each independently hydrogen, $C_1$-$C_6$ alkyl or $C_1$-$C_6$ haloalkyl;
$R^{14}$ is $C_1$-$C_6$ alkyl or $C_1$-$C_6$ haloalkyl;
$R^{15}$ is hydrogen or $C_1$-$C_6$ alkyl optionally substituted with one or more groups selected from phenyl, halo, OH, $C_1$-$C_6$ alkyloxy, $NH_2$, $NH(C_1$-$C_6$alkyl) and $N(C_1$-$C_6$ alkyl)$_2$;
$R^{16}$ is a carboxylic acid isostere selected from tetrazol-5-yl, 5-trifluoromethyl-1,2,4-triazol-3-yl, 5-(methylsulfonyl)-1,2,4-triazol-3-yl, 2,5-dihydro-5-oxo-1,2,4-oxadiazol-3-yl, —$SO_2NHR^{17}$ and —$CONHR^{18}$;
$R^{17}$ is selected from $C_1$-$C_6$ alkyl, phenyl, —CO—($C_1$-$C_6$ alkyl) and —CO-phenyl;
$R^{18}$ is selected from —$SO_2$—($C_1$-$C_6$ alkyl) and —$SO_2$-phenyl;
$R^A$ and $R^J$ are each independently a $C_3$-$C_{10}$ cycloalkyl or $C_3$-$C_{10}$, cycloalkenyl group, each of which may be either monocyclic or, when there are an appropriate number of ring atoms, polycyclic and which may be fused to either (a) a monocyclic aromatic ring selected from a benzene ring and a 5- or 6-membered heteroaromatic ring containing up to three heteroatoms selected from nitrogen, oxygen and sulphur, or (b) a 5-, 6- or 7-membered heteroalicyclic ring containing up to three heteroatoms selected from nitrogen, oxygen and sulphur;

$R^B$ and $R^K$ are each independently a phenyl or naphthyl group, each of which may be fused to (a) a $C_5$-$C_7$ cycloalkyl or $C_5$-$C_7$ cycloalkenyl ring, (b) a 5-, 6- or 7-membered heteroalicyclic ring containing up to three heteroatoms selected from nitrogen, oxygen and sulphur, or (c) a 5- or 6-membered heteroaromatic ring containing up to three heteroatoms selected from nitrogen, oxygen and sulphur;

$R^C$, $R^L$ and $R^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a $C_5$-$C_7$ cycloalkyl or $C_5$-$C_7$ cycloalkenyl group or a monocyclic aromatic ring selected from a benzene ring and a 5- or 6-membered heteroaromatic ring containing up to three heteroatoms selected from nitrogen, oxygen and sulphur;

$R^D$ and $R^M$ are each independently a 5- or 6-membered heteroaromatic ring containing up to three heteroatoms independently selected from nitrogen, oxygen and sulphur, which ring may further be fused to (a) a second 5- or 6-membered heteroaromatic ring containing up to three heteroatoms selected from nitrogen, oxygen and sulphur; (b) $C_5$-$C_7$ cycloalkyl or $C_5$-$C_7$ cycloalkenyl ring; (c) a 5-, 6- or 7-membered heteroalicyclic ring containing up to three heteroatoms selected from nitrogen, oxygen and sulphur; or (d) a benzene ring;

$R^E$, $R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur; and Y is a covalent bond, —$CH_2$—O—$CH_2$—, $C_1$-$C_6$ alkylenyl or $C_3$-$C_7$ cycloalkylenyl; a tautomer thereof or a pharmaceutically acceptable salt or solvate of said compound or tautomer.

As used herein, alkylenyl indicates an alkyl-m,n-diyl unit where m and n are the same or different, such as methylene (—$CH_2$—), ethylene (—$CH_2CH_2$—) and propane-1,2-diyl (—$CH(CH_3)CH_2$—)

As used herein, cycloalkylenyl indicates a cycloalkyl-m,n-diyl unit where m and n are the same or different, such as cyclopropane-1,1-diyl and cyclohexane-1,4-diyl.

Unless otherwise indicated, an alkyl or alkoxy group may be straight or branched and contain 1 to 8 carbon atoms, preferably 1 to 6 and particularly 1 to 4 carbon atoms. Examples of alkyl include methyl, ethyl, n-propyl, isopropyl, n-butyl, isobutyl, sec-butyl, pentyl and hexyl. Examples of alkoxy include methoxy, ethoxy, isopropoxy and n-butoxy.

Unless otherwise indicated, an alkenyl or alkynyl group may be straight or branched and contain 2 to 8 carbon atoms, preferably 2 to 6 and particularly 2 to 4 carbon atoms and may contain up to 3 double or triple bonds which may be conjugated. Examples of alkenyl and alkynyl include vinyl, allyl, butadienyl and propargyl.

Unless otherwise indicated, a cycloalkyl or cycloalkyloxy group may contain 3 to 10 ring-atoms, may be either monocyclic or, when there are an appropriate number of ring atoms, polycyclic. Examples of cycloalkyl groups are cyclopropyl, cyclopentyl, cyclohexyl and adamantyl.

Unless otherwise indicated, a cycloalkenyl group may contain 3 to 10 ring-atoms, may be either monocyclic or, when there are an appropriate number of ring atoms, polycyclic and may contain up to 3 double bonds. Examples of cycloalkenyl groups are cyclopentenyl and cyclohexenyl.

Aryl includes phenyl, naphthyl, anthracenyl and phenanthrenyl.

Unless otherwise indicated, a heteroalicyclyl group contains 3 to 10 ring-atoms up to 4 of which may be hetero-atoms such as nitrogen, oxygen and sulfur, and may be saturated or partially unsaturated. Examples of heteroalicyclyl groups are oxiranyl, azetidinyl, tetrahydrofuranyl, thiolanyl, pyrrolidinyl, pyrrolinyl, imidazolidinyl, imidazolinyl, sulfolanyl, dioxolanyl, dihydropyranyl, tetrahydropyranyl, piperidinyl, pyrazolinyl, pyrazolidinyl, dioxanyl, morpholinyl, dithianyl, thiomorpholinyl, piperazinyl, azepinyl, oxazepinyl, thiazepinyl, thiazolinyl and diazapanyl.

Unless otherwise indicated, a heteroaryl group contains 3 to 10 ring-atoms up to 4 of which may be hetero-atoms such as nitrogen, oxygen and sulfur. Examples of heteroaryl groups are furyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyrimidinyl, pyrazinyl, pyridazinyl, tetrazolyl, triazinyl. In addition, the term heteroaryl includes fused heteroaryl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, benzothiazolyl, phthalimido, benzofuranyl, benzodiazepinyl, indolyl and isoindolyl.

Halo means fluoro, chloro, bromo or iodo.

Haloalkyl includes monohaloalkyl, polyhaloalkyl and perhaloalkyl, such as 2-bromoethyl, 2,2,2-trifluoroethyl, chlorodifluoromethyl and trichloromethyl. Haloalkoxy includes monohaloalkoxy, polyhaloalkoxy and perhaloalkoxy, such as 2-bromoethoxy, 2,2,2-trifluoroethoxy, chlorodifluoromethoxy and trichloromethoxy. Halocycloalkyl includes monohalocycloalkyl, polyhalocycloalkyl and perhalocycloalkyl.

Unless otherwise indicated, the term substituted means substituted by one or more defined groups. In the case where groups may be selected from a number of alternative groups, the selected groups may be the same or different.

In one preferred embodiment, $R^1$ is $R^A$, which is optionally substituted with one or more $R^7$ groups; and $R^A$ is a $C_3$-$C_{10}$ cycloalkyl group, which may be either monocyclic or, when there are an appropriate number of ring atoms, polycyclic, which may be fused to either (a) a monocyclic aromatic ring selected from a benzene ring and a 5- or 6-membered heteroaromatic ring containing up to three heteroatoms selected from nitrogen, oxygen and sulphur, or (b) a 5-, 6- or 7-membered heteroalicyclic ring containing up to three heteroatoms selected from nitrogen, oxygen and sulphur.

Preferably, $R^A$ is a monocyclic $C_3$-$C_8$ cycloalkyl group.

More preferably, $R^A$ is a monocyclic $C_5$-$C_7$ cycloalkyl group.

Most preferably, $R^A$ is cyclopentyl or cyclohexyl.

In another preferred embodiment, $R^1$ is $R^B$, which is optionally substituted with one or more $R^7$ groups.

Preferably, $R^B$ is phenyl.

In another preferred embodiment, $R^1$ is $R^C$, which is optionally substituted with one or more $R^7$ groups.

Preferably, $R^C$ is a monocyclic saturated or partly unsaturated ring system containing between 3 and 8 ring atoms, of which at least one is a heteroatom selected from nitrogen, oxygen and sulphur.

More preferably, $R^C$ is a monocyclic saturated or partly unsaturated ring system containing between 5 and 7 ring atoms, of which at least one is a heteroatom selected from nitrogen, oxygen and sulphur.

Most preferably, $R^C$ is a monocyclic saturated ring system containing between 5 and 7 ring atoms, of which at least one is a heteroatom selected from nitrogen, oxygen and sulphur.

In another preferred embodiment, $R^1$ is $R^D$, which is optionally substituted with one or more $R^7$ groups.

Preferably, $R^D$ is a 5- or 6-membered heteroaromatic ring containing up to three heteroatoms independently selected from nitrogen, oxygen and sulphur.

More preferably, $R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms.

More preferably $R^D$ is furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl or pyrazinyl.

Most preferably, $R^D$ is pyrazolyl, imidazolyl, isoxazolyl, oxazolyl, oxadiazolyl, pyridyl, pyridazinyl, pyrimidyl or pyrazinyl.

Preferably, $R^7$ is halo, $C_1$-$C_6$ alkyl, $C_1$-$C_6$ haloalkyl, $OR^{12}$ or $CONR^{12}R^{13}$.

More preferably, $R^7$ is halo, $C_1$-$C_3$ alkyl, $C_1$-$C_3$ alkoxy, hydroxy or $CONH(C_1$-$C_3$ alkyl).

Most preferably, $R^7$ is fluoro, methyl, ethyl, hydroxy, methoxy, propoxy or CONHMe.

Preferably, $R^2$ is hydrogen or methyl.

More preferably, $R^2$ is hydrogen.

Preferably, $R^3$ is hydrogen, $C_1$-$C_6$ alkyl, which is optionally substituted with one or more $R^8$ groups, or $R^E$, which is optionally substituted with one or more $R^9$ groups; and wherein $R^E$ is a monocyclic or, when there are an appropriate number of ring atoms, polycyclic saturated ring system containing between 3 and 7 ring atoms, of which at least one is a heteroatom selected from nitrogen, oxygen and sulphur.

More preferably, $R^3$ is hydrogen, $C_1$-$C_4$ alkyl, which is optionally substituted with one or more $R^8$ groups, or $R^E$, which is optionally substituted with one or more $R^9$ groups; and wherein $R^E$ is a monocyclic saturated ring system containing between 3 and 7 ring atoms, of which at least one is a heteroatom selected from nitrogen, oxygen and sulphur.

In one preferred embodiment, $R^3$ is $R^E$, which is optionally substituted with one or more $R^9$ groups and wherein $R^E$ is a monocyclic saturated ring system containing between 3 and 7 ring atoms containing one nitrogen atom.

More preferably, $R^E$ is azetidinyl, pyrrolidinyl or piperidinyl.

In another preferred embodiment, $R^3$ is $C_1$-$C_4$ alkyl, which is optionally substituted with one or more $R^8$ groups and wherein $R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups.

More preferably, $R^8$ is hydroxy, methoxy, methoxyphenyl, $NH_2$, NHMe, $NMe_2$, $NHCO_2^tBu$, $NMeCO_2^tBu$, $CO_2H$, CONHMe, $R^G$ or $R^H$, the last two of which are optionally substituted with one or more $R^9$ groups.

In one preferred embodiment, $R^8$ is $R^G$, which is optionally substituted with one or more $R^9$ groups and wherein $R^G$ is a monocyclic saturated ring system containing between 3 and 7 ring atoms, of which at least one is a heteroatom selected from nitrogen, oxygen and sulphur.

More preferably, $R^G$ is a monocyclic saturated ring system containing between 3 and 7 ring atoms containing one nitrogen atom and optionally one oxygen atom.

Most preferably, $R^G$ is pyrrolidinyl, piperidinyl or morpholinyl.

In another preferred embodiment, $R^8$ is $R^H$, which is optionally substituted with one or more $R^9$ groups and wherein $R^H$ is a 5- or 6-membered heteroaromatic ring containing up to two nitrogen atoms.

More preferably, $R^H$ is pyrazolyl.

Preferably, $R^9$ is methyl or $CO_2^tBu$.

In another preferred embodiment, $R^3$ is hydrogen or $C_1$-$C_4$ alkyl, which is optionally substituted with one or more $R^8$ groups, or $R^3$ is azetidinyl, pyrrolidinyl or piperidinyl, each of which is optionally substituted with one or more $R^9$ groups, wherein $R^8$ is hydroxy, methoxy, methoxyphenyl, $NH_2$, NHMe, $NMe_2$, $NHCO_2^tBu$, $NMeCO_2^tBu$, $CO_2H$, CONHMe, pyrrolidinyl, piperidinyl, morpholinyl or pyrazolyl, the last four of which are optionally substituted with one or more $R^9$ groups and wherein $R^9$ is methyl or $CO_2^tBu$.

In one preferred embodiment, $R^4$ is hydrogen, $C_1$-$C_6$ alkyl, $C_1$-$C_6$ haloalkyl, $C_2$-$C_6$ alkenyl or $C_2$-$C_6$ alkynyl.

More preferably, $R^4$ is hydrogen, $C_1$-$C_6$ alkyl or $C_1$-$C_6$ haloalkyl.

Most preferably, $R^4$ is hydrogen, methyl or ethyl.

In another preferred embodiment, —$NR^3R^4$ forms $R^F$, which is optionally substituted with one or more $R^{10}$ groups and wherein $R^F$ is a monocyclic or, when there are an appropriate number of ring atoms, polycyclic saturated ring system containing between 3 and 10 ring atoms containing at least one nitrogen atom and optionally one other atom selected from oxygen and sulphur.

More preferably, $R^F$ is a monocyclic or, when there are an appropriate number of ring atoms, polycyclic saturated ring system containing between 3 and 10 ring atoms containing one or two nitrogen atoms and optionally one other atom selected from oxygen and sulphur.

Most preferably, $R^F$ is selected from azetidinyl, pyrrolidinyl, piperidinyl, piperazinyl, morpholinyl, 3-azabicyclo[3.1.0]hex-3-yl, homopiperazinyl, 2,5-diazabicyclo[4.3.0]non-2-yl, 3,8-diazabicyclo[3.2.1]oct-3-yl, 3,8-diazabicyclo[3.2.1]oct-8-yl, 2,5-diazabicyclo[2.2.1]hept-2-yl, 1,4-diazabicyclo[4.3.0]non-4-yl and 1,4-diazabicyclo[3.2.2]non-4-yl.

Preferably $R^{10}$ is halo, $OR^{12}$, $NR^{12}R^{13}$, $NR^{12}CO_2R^{14}$, $CO_2R^{13}$, oxo, $C_1$-$C_6$ alkyl or $C_1$-$C_6$ haloalkyl, the last two of which are optionally substituted by $R^{11}$.

More preferably, $R^{10}$ is halo, methyl, ethyl, isopropyl, hydroxy, methoxy, $NH_2$, NHMe, $NMe_2$, $NHCO_2^tBu$, $CO_2H$, $CO_2^tBu$, oxo, benzyl, —$CH_2NH_2$, —$CH_2NHMe$, $CH_2NMe_2$ or —$CH_2NMeCO_2^tBu$.

In one preferred embodiment, $R^5$ is —Y—$CO_2R^{15}$.

In one preferred embodiment, $R^{15}$ is hydrogen or $C_1$-$C_6$ alkyl optionally substituted with one or more groups selected from halo, OH, $C_1$-$C_6$ alkyloxy, $NH_2$, $NH(C_1$-$C_6$alkyl) and $N(C_1$-$C_6$ alkyl)$_2$. Preferably $R^{15}$ is hydrogen or $C_1$-$C_3$ alkyl. More preferably $R^{15}$ is hydrogen.

In another preferred embodiment, $R^{15}$ is $C_1$-$C_6$-alkyl or benzyl.

Preferably Y is a covalent bond or $C_1$-$C_6$ alkylenyl. More preferably, Y is a covalent bond or methylene. Most preferably Y is a covalent bond. In another preferred embodiment, $R^5$ is —Y—$R^{16}$. Preferably $R^{16}$ is a carboxylic acid isostere selected from —$CONHR^{18}$, tetrazol-5-yl and 2,5-dihydro-5-oxo-1,2,4-oxadiazol-3-yl. Preferably Y is a covalent bond or $C_1$-$C_6$ alkylenyl. More preferably, Y is a covalent bond or methylene.

Preferably, $R^6$ is positioned on $N^1$ to give the compound of formula ($I^A$):

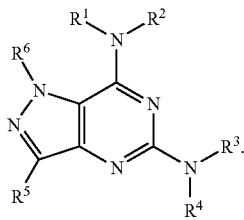

In an alternative embodiment of the present invention, $R^6$ may be positioned on $N^2$ to give the compound of formula ($I^B$):

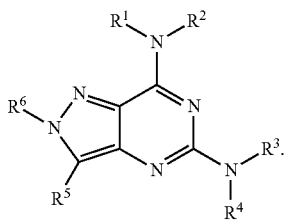

In the compounds of formulas (I), (IA), and (IB), preferably $R^6$ is $C_1$-$C_6$ alkyl or $C_1$-$C_6$ haloalkyl, each of which is optionally substituted by $C_1$-$C_6$ alkoxy, $C_1$-$C_6$ haloalkoxy or a cyclic group selected from $R^J$, $R^L$ and $R^M$, or $R^6$ is $R^N$ or hydrogen;

$R^J$ is a $C_3$-$C_7$ monocyclic cycloalkyl group;

$R^L$ and $R^N$ are each independently a monocyclic, saturated or partly unsaturated ring system containing between 4 and 7 ring atoms, of which at least one is a heteroatom selected from nitrogen, oxygen and sulphur; and $R^M$ is a 5- or 6-membered heteroaromatic ring containing up to three heteroatoms independently selected from nitrogen, oxygen and sulphur.

More preferably, $R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur; and $R^M$ is a 5- or 6-membered heteroaromatic ring containing a heteroatom selected from nitrogen, oxygen and sulphur.

In other preferred embodiments, $R^6$ is $C_1$-$C_4$ alkyl or $C_1$-$C_4$ haloalkyl, each of which is optionally substituted by $C_1$-$C_4$ alkoxy or a cyclic group selected from $R^J$, $R^L$ and $R^M$, or $R^6$ is $R^N$ or hydrogen;

$R^J$ is cyclopropyl or cyclobutyl;

$R^L$ and $R^N$ are each independently a monocyclic saturated ring system containing either 5 or 6 ring atoms containing one heteroatom selected from nitrogen, oxygen and sulphur; and $R^M$ is a 5- or 6-membered heteroaromatic ring containing one nitrogen atom.

More preferably, $R^6$ is $C_1$-$C_4$ alkyl or $C_1$-$C_4$ haloalkyl, each of which is optionally substituted by $C_1$-$C_4$ alkoxy, cyclopropyl, cyclobutyl, tetrahydrofuranyl, tetrahydropyranyl or pyridinyl, or $R^6$ is hydrogen or tetrahydropyranyl.

'Most preferably, $R^6$ is hydrogen, methyl, ethyl, isopropyl, isobutyl, methoxyethyl, methoxypropyl, ethoxyethyl, ethoxypropyl, propoxyethyl, 2,2,2-trifluoroethyl, tetrahydrofuranylmethyl, tetrahydropyranylmethyl, tetrahydropyranyl or pyridinylmethyl.

Preferred embodiments of compounds of formula (I) are those that incorporate two or more of the foregoing preferences.

In some embodiments of this invention, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$CO_2R^{15}$ or —Y—$R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or $CN$;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$, $CN$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, $CN$, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^A$ is a monocyclic $C_3$-$C_8$ cycloalkyl group;

$R^B$ is phenyl;

$R^C$ is a monocyclic saturated or partly unsaturated ring system containing between 3 and 8 ring atoms, of which at least one is a heteroatom selected from nitrogen, oxygen and sulphur;

$R^D$ is a 5- or 6-membered heteroaromatic ring containing up to three heteroatoms independently selected from nitrogen, oxygen and sulphur;

$R^E$ is a monocyclic saturated ring system containing between 3 and 7 ring atoms, of which at least one is a heteroatom selected from nitrogen, oxygen and sulphur;

$R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is a covalent bond or $C_1$-$C_6$ alkylenyl.

In other embodiments of this invention, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$CO_2R^{15}$ or —Y—$R^{16}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $C_2$-$C_6$ alkenyl, $C_2$-$C_6$ alkynyl, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{12}$, $CONR^{12}R^{13}$ or CN;

$R^8$ is halo, phenyl, $C_1$-$C_6$ alkoxyphenyl, $OR^{12}$, $OC(O)R^{12}$, $NO_2$, $NR^{12}R^{13}$, $NR^{12}C(O)R^{13}$, $NR^{12}C_2R^{14}$, $C(O)R^{12}$, $CO_2R^{12}$, $CONR^{12}R^{13}$, CN, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$alkyl or $C_1$-$C_6$ haloalkyl;

$R^{14}$ is $C_1$-$C_6$alkyl or $C_1$-$C_6$ haloalkyl;

$R^{15}$ is hydrogen or $C_1$-$C_3$ alkyl:

$R^{16}$ is tetrazol-5-yl, 5-trifluoromethyl-1,2,4-triazol-3-yl or 2,5-dihydro-5-oxo-1,2,4-oxadiazol-3-yl;

$R^A$ is a monocyclic $C_3$-$C_8$ cycloalkyl group;

$R^B$ is phenyl;

$R^C$ is a monocyclic saturated or partly unsaturated ring system containing between 3 and 8 ring atoms, of which at least one is a heteroatom selected from nitrogen, oxygen and sulphur;

$R^D$ is a 5- or 6-membered heteroaromatic ring containing up to three heteroatoms independently selected from nitrogen, oxygen and sulphur;

$R^E$ is a monocyclic saturated ring system containing between 3 and 7 ring atoms, of which at least one is a heteroatom selected from nitrogen, oxygen and sulphur;

$R^F$ and $R^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

$R^H$ is a 5- or 6-membered heteroaromatic ring containing up to three heteroatoms independently selected from nitrogen, oxygen and sulphur;

$R^J$ is cyclopropyl or cyclobutyl;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is a covalent bond or $C_1$-$C_6$ alkylenyl.

In some more preferred embodiments of this invention, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$CO_2R^{15}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}CO_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$alkyl or $C_1$-$C_6$ haloalkyl;

$R^{14}$ is $C_1$-$C_6$alkyl or $C_1$-$C_6$ haloalkyl;

$R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is a covalent bond or methylene.

In other more preferred embodiments of this invention, $R^1$ is a cyclic group selected from $R^A$, $R^B$, $R^C$ and $R^D$, each of which is optionally substituted with one or more $R^7$ groups;

$R^2$ is hydrogen or $C_1$-$C_2$ alkyl;

$R^3$ is hydrogen, $C_1$-$C_4$ alkyl, which is optionally substituted with one or more $R^8$ groups, or $R^E$, which is optionally substituted with one or more $R^9$ groups;

$R^4$ is hydrogen, $C_1$-$C_6$ alkyl or $C_1$-$C_6$ haloalkyl;

or —$NR^3R^4$ forms $R^F$, which is optionally substituted with one or more $R^{10}$ groups;

$R^5$ is —Y—$CO_2R^{15}$;

$R^6$ is $C_1$-$C_4$ alkyl or $C_1$-$C_4$ haloalkyl, each of which is optionally substituted by $C_1$-$C_4$ alkoxy, $C_1$-$C_4$ haloalkoxy or a cyclic group selected from $R^J$, $R^L$ and $R^M$, or $R^6$ is $R^N$ or hydrogen;

$R^7$ is halo, $C_1$-$C_6$ alkyl, $C_1$-$C_6$ haloalkyl, $OR^{12}$ or $CONR^{12}R^{13}$;

$R^8$ is halo, phenyl, $C_1$-$C_6$ alkoxyphenyl, $OR^{12}$, $NR^{12}R^{13}$, $NR^{12}C_2R^{14}$, $CO_2R^{12}$, $CONR^{12}R^{13}$, $R^G$ or $R^H$, the last two of which are optionally substituted with one or more $R^9$ groups;

$R^9$ is $C_1$-$C_6$ alkyl, $C_1$-$C_6$ haloalkyl or $CO_2R^{12}$;

$R^{10}$ is halo, $C_3$-$C_{10}$ cycloalkyl, $C_3$-$C_{10}$ halocycloalkyl, phenyl, $OR^{12}$, $OC(O)R^{12}$, $NO_2$, $NR^{12}R^{13}$, $NR^{12}C(O)R^{13}$, $NR^{12}CO_2R^{14}$, $C(O)R^{12}$, $CO_2R^{13}$, $CONR^{12}R^{13}$, CN, oxo, $C_1$-$C_6$ alkyl or $C_1$-$C_6$ haloalkyl, the last two of which are optionally substituted by $R^{11}$;

$R^{11}$ is phenyl, $NR^{12}R^{13}$ or $NR^{12}CO_2R^{14}$;

$R^{12}$ and $R^{13}$ are each independently hydrogen, $C_1$-$C_6$ alkyl or $C_1$-$C_6$ haloalkyl;

$R^{14}$ is $C_1$-$C_6$ alkyl or $C_1$-$C_6$ haloalkyl;

$R^{15}$ is hydrogen;

$R^A$ is a monocyclic $C_5$-$C_7$ cycloalkyl group;

$R^B$ is phenyl;

$R^C$ is a monocyclic saturated ring system containing between 5 and 7 ring atoms, of which at least one is a heteroatom selected from nitrogen, oxygen and sulphur;

$R^D$ is a 5-membered heteroaromatic ring containing a heteroatom selected from nitrogen, oxygen and sulphur and optionally up to two further nitrogen atoms in the ring, or a 6-membered heteroaromatic ring including 1, 2 or 3 nitrogen atoms;

$R^E$ is a monocyclic saturated ring system containing between 3 and 7 ring atoms containing one nitrogen atom;

$R^F$ is a monocyclic or, when there are an appropriate number of ring atoms, polycyclic saturated ring system containing between 3 and 10 ring atoms containing at least one nitrogen atom and optionally one other atom selected from oxygen and sulphur;

$R^G$ is a monocyclic saturated ring system containing between 3 and 7 ring atoms, of which at least one is a heteroatom selected from nitrogen, oxygen and sulphur;

$R^H$ is a 5- or 6-membered heteroaromatic ring containing up to two nitrogen atoms;

$R^L$ and $R^N$ are each independently a monocyclic saturated ring system containing either 5 or 6 ring atoms, of which at least one is a heteroatom selected from nitrogen, oxygen and sulphur;

$R^M$ is a 5- or 6-membered heteroaromatic ring containing a heteroatom selected from nitrogen, oxygen and sulphur; and Y is a covalent bond or methylene.

In an alternative embodiment, the present invention provides compounds of formula (I-AA)

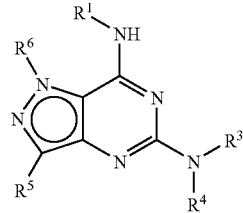

(I-AA)

wherein $R^1$ is a pyridyl optionally substituted with one or more $C_1$-$C_6$ alkyl groups;

$R^3$ and $R^4$ are each independently hydrogen or $C_1$-$C_6$ alkyl;

$R^5$ is —$CONHR^{18}$;

$R^6$ is $C_1$-$C_6$ alkyl, optionally substituted by a substituent selected from —OH, $C_3$-$C_6$ cycloalkyloxy, $C_1$-$C_6$ alkoxy and $C_1$-$C_6$ haloalkoxy;

$R^{18}$ is selected from the group consisting of —$SO_2$—($C_1$-$C_6$ alkyl) and —$SO_2$-phenyl; and tautomers thereof or a pharmaceutically acceptable salts, or solvates of said compounds or tautomers.

In one embodiment of the compounds of formula I-AA, $R^1$ is 2-pyridinyl substituted with one or more methyl. In another embodiment of the compounds of formula I-AA, $R^3$ and $R^4$ are independently selected from the group consisting of methyl, ethyl, propyl, and isopropyl. In another embodiment of the compounds of formula I-AA, $R^{18}$ is selected from the group consisting of —$SO_2CH_3$ and —$SO_2CH_2CH_3$. In another embodiment of the compounds of formula I-AA, $R^6$ is ethyl, optionally substituted by a substituent selected from the group consisting of hydroxyl, methoxy, ethoxy, propoxy, fluoromethoxy, fluoroethoxy, fluoropropoxy, difluoromethoxy, difluoroethoxy, difluoropropoxy, trifluoromethoxy, trifluoroethoxy, trifluoropropoxy, and cyclobutyloxy.

In another embodiment of the compounds of formula I-AA, $R^1$ pyridinyl is substituted with one or more methyl;

$R^3$ and $R^4$ are independently selected from the group consisting of hydrogen, methyl, ethyl, propyl and isopropyl;

$R^6$ is ethyl, optionally substituted by a substituent selected from the group consisting of —OH, $C_3$-$C_6$ cycloalkyloxy, $C_1$-$C_6$ alkoxy and $C_1$-$C_6$ haloalkoxy; and $R^{18}$ is selected from the group consisting of —$SO_2CH_3$ and —$SO_2CH_2CH_3$.

In another alternative embodiment of the present invention, the present invention provides compounds of formula (I-BB)

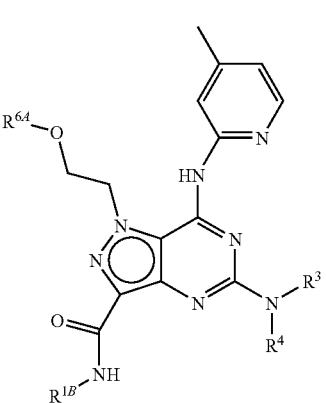

(I-BB)

wherein

R³ and R⁴ are each independently selected from the group consisting of methyl, ethyl, and isopropyl;

$R^{6A}$ is selected from the group consisting of methyl, ethyl, propyl, fluoromethyl, fluoroethyl, fluoropropyl, difluoroethyl, difluoropropyl, trifluoroethyl, and trifluoropropyl; and $R^{18}$ is selected from the group consisting of —SO₂CH₃, and —SO₂CH₂CH₃.

Most preferred compounds are:

methyl 5-((1S,4S)-2,5-diazabicyclo[2.2.1]hept-2-yl)-1-(2-ethoxyethyl)-7-(4-methyl-pyridin-2-ylamino)-1H-pyrazolo[4,3-d]pyrimidine-3-carboxylate, methyl 1-(2-ethoxyethyl)-5-(N-isopropyl-N-methylamino)-7-(6-methylpyridin-2-ylamino)-1H-pyrazolo[4,3-d]pyrimidine-3-carboxylate, ethyl 1-(2-ethoxyethyl)-5-(N-ethyl-N-methylamino)-7-(4-methylpyridin-2-ylamino)-1H-pyrazolo[4,3-d]pyrimidine-3-carboxylate, 2-(dimethylamino)ethyl 5-dimethylamino-1-(2-ethoxyethyl)-7-(4-methylpyridin-2-ylamino)-1H-pyrazolo[4,3-d]pyrimidine-3-carboxylate, 1-(2-ethoxyethyl)-5-(N-methyl-N-propylamino)-7-(4-methylpyridin-2-ylamino)-1H-pyrazolo[4,3-d]pyrimidine-3-carboxylic acid, 5-(N-isopropyl-N-methylamino)-7-(4-methylpyridin-2-ylamino)-1-(2-propoxy-ethyl)-1H-pyrazolo[4,3-d]pyrimidine-3-carboxylic acid, 7-(4,6-dimethylpyridin-2-ylamino)-1-(2-ethoxyethyl)-5-(N-isopropyl-N-methyl-amino)-1H-pyrazolo[4,3-d]pyrimidine-3-carboxylic acid, 5-(N-cyclobutyl-N-methylamino)-1-(2-ethoxyethyl)-7-(4-methylpyridin-2-ylamino)-1H-pyrazolo[4,3-d]pyrimidine-3-carboxylic acid, 1-(2-ethoxyethyl)-5-isopropylamino-7-(4-methylpyridin-2-ylamino)-1H-pyrazolo[4,3-d]pyrimidine-3-carboxylic acid, 1-(2-ethoxyethyl)-5-(N-ethyl-N-methylamino)-7-(2-methoxypyrimidin-4-ylamino)-1H-pyrazolo[4,3-d]pyrimidine-3-carboxylic acid, 3-[1-(2-ethoxyethyl)-5-(N-isopropyl-N-methylamino)-7-(4-methylpyridin-2-ylamino)-1H-pyrazolo[4,3-d]pyrimidin-3-yl]-2H-1,2,4-oxadiazol-5-one, 3-[1-(2-ethoxyethyl)-5-(N-ethyl-N-methylamino)-7-(4-methylpyridin-2-ylamino)-1H-pyrazolo[4,3-d]pyrimidin-3-yl]-2H-1,2,4-oxadiazol-5-one, 1-(2-ethoxyetyl)-7-(4-fluoro-3-methylphenylamino)-5-(N-isopropyl-N-methyl-amino)-1H-pyrazolo[4,3-d]pyrimidine-3-carboxylic acid, 1-(2-ethoxyethyl)-5-(N-ethyl-N-methylamino)-7-(4-fluoro-3-methylphenylamino)-1H-pyrazolo[4,3-d]pyrimidine-3-carboxylic acid, 7-(3,4-dimethylphenylamino)-1-(2-ethoxyethyl)-5-(N-ethyl-N-methylamino)-1H-pyrazolo[4,3-d]pyrimidine-3-carboxylic acid, 1-(2-(cyclopropylmethoxy)ethyl)-5-(N-isopropyl-N-methylamino)-7-(4-methyl-pyridin-2-ylamino)-1H-pyrazolo[4,3-d]pyrimidine-3-carboxylic acid, 1-(2-(cyclopropylmethoxy)ethyl)-5-(N-ethyl-N-methylamino)-7-(4-methyl-pyridin-2-ylamino)-1H-pyrazolo[4,3-d]pyrimidine-3-carboxylic acid, 1-(2-ethoxyethyl)-5-(N-isopropyl-N-methylamino)-7-(4-methylpyridin-2-ylamino)-1H-pyrazolo[4,3-d]pyrimidine-3-carboxylic acid, 1-(2-isopropoxyethyl)-5-(N-isopropyl-N-methylamino)-7-(4-methylpyridin-2-yl-amino)-1H-pyrazolo[4,3-d]pyrimidine-3-carboxylic acid, N-[1-(2-ethoxyethyl)-5-(N-isopropyl-N-methylamino)-7-(4-methylpyridin-2-yl-amino)-1H-pyrazolo[4,3-d]pyrimidine-3-carbonyl]methanesulfonamide, and N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide, and tautomers thereof and pharmaceutically acceptable salts or solvates of said compounds or tautomers.

Pharmaceutically acceptable salts of the compounds of this invention include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

For a review on suitable salts, see "Handbook of Pharmaceutical Salts: Properties, Selection, and Use" by Stahl and Wermuth (Wiley-VCH, Weinheim, Germany, 2002).

A pharmaceutically acceptable salt of the compounds this invention may be readily prepared by mixing together solutions of the compounds and the desired acid or base, as appropriate. The salt may precipitate from solution and be collected by filtration or may be recovered by evaporation of the solvent. The degree of ionisation in the salt may vary from completely ionised to almost non-ionised.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to the compounds of this invention include references to salts, solvates and complexes thereof and to solvates and complexes of salts thereof.

The compounds of the invention include compounds of formula (I) as hereinbefore defined, prodrugs, and isomers thereof (including optical, geometric and tautomeric isomers) as hereinafter defined and isotopically-labeled compounds of formula (I).

Also within the scope of the invention are so-called 'prodrugs' of the compounds of formula (I). Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in "Design of Prodrugs" by H Bundgaard (Elsevier, 1985).

Some examples of prodrugs in accordance with the invention include: (i) where the compound of formula (I) contains a carboxylic acid functionality (—COOH), an ester thereof, for example, replacement of the hydrogen with $(C_1-C_8)$alkyl; (ii) where the compound of formula (I) contains an alcohol functionality (—OH), an ether thereof, for example, replacement of the hydrogen with $(C_1-C_6)$alkanoyloxymethyl; and (iii) where the compound of formula (I) contains a primary or secondary amino functionality (—$NH_2$ or —NHR where R≠H), an amide thereof, for example, replacement of one or both hydrogens with $(C_1-C_{10})$alkanoyl.

Further examples of replacement groups in accordance with the foregoing examples and examples of other prodrug types may be found in the aforementioned references.

Finally, certain compounds of formula (I) may themselves act as prodrugs of other compounds of formula (I).

Compounds of formula (I) containing one or more asymmetric carbon atoms can exist as two or more stereoisomers. Where a compound of formula (I) contains an alkenyl or alkenylene group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E L Eliel (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2H$ and $^3H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) are inhibitors of PDE5. Accordingly, in a further aspect the present invention provides for the use of a compound of formula (I), or a tautomer, salt or solvate thereof, as a pharmaceutical agent, and particularly as a therapeutic agent for the treatment of a condition where inhibition of PDE5 is known, or can be shown, to produce a beneficial effect.

The term "treatment" includes palliative, curative and prophylactic treatment.

Conditions suitable for treatment with the compounds of the invention include hypertension (including essential hypertension, pulmonary hypertension, secondary hypertension, isolated systolic hypertension, hypertension associated with diabetes, hypertension associated with atherosclerosis, and renovascular hypertension), congestive heart failure, angina (including stable, unstable and variant (Prinzmetal) angina), stroke, coronary artery disease, congestive heart failure, conditions of reduced blood vessel patency (such as post-percutaneous coronary angioplasty), peripheral vascular disease, atherosclerosis, nitrate-induced tolerance, nitrate tolerance, diabetes, impaired glucose tolerance, metabolic syndrome, obesity, sexual dysfunction (including male erectile disorder, impotence, female sexual arousal disorder, clitoral dysfunction, female hypoactive sexual desire disorder, female sexual pain disorder, female sexual orgasmic dysfunction and sexual dysfunction due to spinal cord injury), premature labour, pre-eclampsia, dysmenorrhea, polycystic ovary syndrome, benign prostatic hyperplasia, bladder outlet obstruction, incontinence, chronic obstructive pulmonary disease, acute respiratory failure, bronchitis, chronic asthma, allergic asthma, allergic rhinitis, gut motility disorders (including irritable bowel syndrome), Kawasaki's syndrome, multiple sclerosis, Alzheimer's disease, psoriasis, skin necrosis, scarring, fibrosis, pain (particularly neuropathic pain), cancer, metastasis, baldness, nutcracker oesophagus, anal fissure and hemorrhoids.

In a further aspect, the present invention provides for the use of a compound of formula (I), or a tautomer, salt or solvate thereof, for the manufacture of a medicament for the treatment of such a condition.

The compounds of the present invention may be used alone or in combination with other therapeutic agents. When used in combination with another therapeutic agent the administration of the two agents may be simultaneous or sequential. Simultaneous administration includes the administration of a single dosage form that comprises both agents and the administration of the two agents in separate dosage forms at substantially the same time. Sequential administration includes the administration of the two agents according to different schedules provided that there is an overlap in the periods during which the treatment is provided. Suitable agents with which the compounds of formula (I) can be co-administered include aspirin, angiotensin II receptor antagonists (such as losartan, candesartan, telmisartan, valsartan, irbesartan and eprosartan), calcium channel blockers (such as amlodipine), beta-blockers (i.e. beta-adrenergic receptor antagonists such as sotalol, proporanolol, timolol, antenolol, carvedilol and metoprolol), CI1027, CCR5 receptor antagonists, imidazolines, sGCa's (soluble guanylate cyclase activators) antihypertensive agents, diuretics (such as hydrochlorothiazide, torsemide, chlorothiazide, chlorthalidone and amiloride), alpha adrenergic antagonists (such as doxazosin), ACE (angiotensin converting enzyme) inhibitors (such as quinapril, enalapril, ramipril and lisinopril), aldosterone receptor antagonists (such as eplerenone and spironolactone), neutral endopeptidase inhibitors, antidiabetic agents (such as insulin, sulfonylureas (such as glyburide, glipizide and glimepiride), glitazones (such as rosiglitazone and pioglitazone) and metformin), cholesterol lowering agents (such as atorvastatin, pravastatin, lovastatin, simvastatin, clofibrate and rosuvastatin), and alpha-2-delta ligands (such as gabapentin, pregabalin, [(1R,5R,6S)-6-(aminomethyl)bicyclo[3.2.0]hept-6-yl] acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (1α,3α,5α)-(3-aminomethyl-bicyclo[3.2.0]hept-3-yl)-acetic acid, (3S,5R)-3-aminomethyl-5-methyl-octanoic acid, (3S,5R)-3-amino-5-methyl-heptanoic acid, (3S,5R)-3-amino-5-methyl-nonanoic acid and (3S,5R)-3-amino-5-methyl-octanoic acid).

The compounds of formula (I) may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films (including muco-adhesive), ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patients, 11 (6), 981-986 by Liang and Chen (2001).

For tablet dosage forms, depending on dose, the drug may make up from 1 wt % to 80 wt % of the dosage form, more typically from 5 wt % to 60 wt % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 wt % to 25 wt %, preferably from 5 wt % to 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 wt % to 5 wt % of the tablet, and glidants may comprise from 0.2 wt % to 1 wt % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 wt % to 10 wt %, preferably from 0.5 wt % to 3 wt % of the tablet.

Other possible ingredients include anti-oxidants, colourants, flavouring agents, preservatives and taste-masking agents.

Exemplary tablets contain up to about 80% drug, from about 10 wt % to about 90 wt % binder, from about 0 wt % to about 85 wt % diluent, from about 2 wt % to about 10 wt % disintegrant, and from about 0.25 wt % to about 10 wt % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in "Pharmaceutical Dosage Forms: Tablets, Vol. 1", by H. Lieberman and L. Lachman, Marcel Dekker, N.Y., N.Y., 1980 (ISBN 0-8247-6918-X).

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Verma et al, Pharmaceutical Technology On-line, 25(2), 1-14 (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and PGLA microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or HPMC), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 10 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, poly(DL-lactic-coglycolic acid (PGLA). Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 1 μg to 20 mg of the compound of formula (I). The overall daily dose will typically be in the range 1 μg to 80 mg which may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in Int'l Publications WO 91/11172, WO 94/02518, and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of this invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.1 mg to 500 mg depending, of course, on the mode of administration. For example, oral administration may require a total daily dose of from 0.1 mg to 500 mg, while an intravenous dose may only require from 0.01 mg to 50 mg. The total daily dose may be administered in single or divided doses.

These dosages are based on an average human subject having a weight of about 65 kg to 70 kg. The physician will readily be able to determine doses for subjects whose weight falls outside this range, such as infants and the elderly.

Compounds of the invention may be prepared, in known manner in a variety of ways. In the following reaction schemes and hereafter, unless otherwise stated $R^1$ to $R^6$ are as defined in the first aspect. These processes form further aspects of the invention.

a) Compounds of formula ($I^C$), i.e. compounds of formula (I) wherein $R^5$ is —Y—CO$_2$R$^{15}$ and $R^{15}$ is H, may generally be prepared from the corresponding esters of formula (II) wherein $R^{15}$ is an alkyl group (particularly a methyl, ethyl, or tert-butyl group) or a benzyl group, as illustrated in Scheme 1.

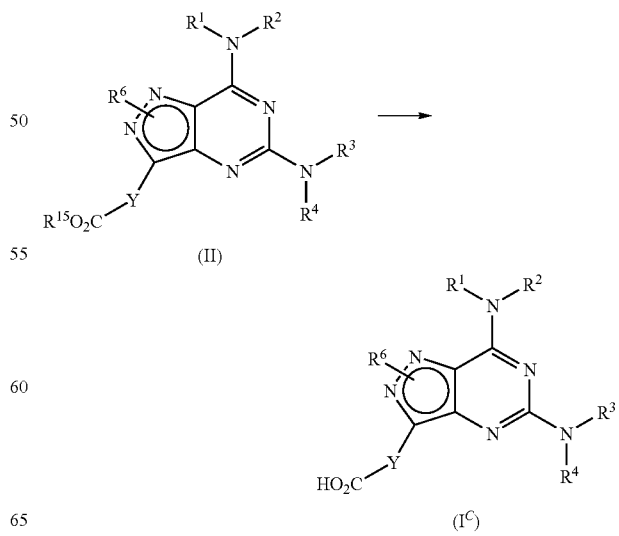

When $R^{15}$ is methyl or ethyl the conversion may conveniently be accomplished by treating the compound of formula (II) with an alkaline metal hydroxide such as lithium, sodium or potassium hydroxide in a suitable solvent at a temperature of between about 10° C. and the boiling point of the solvent. Suitable solvents include water, methanol, ethanol and mixtures of water with methanol, ethanol, tetrahydrofuran and dioxan. When $R^{15}$ is tert-butyl the conversion may be accomplished by treating the compound of formula (II) with an acid such as hydrogen chloride or trifluoroacetic acid in a suitable solvent at a temperature of between 0° C. and ambient temperature. Suitable solvents include dioxan and dichloromethane. When $R^{15}$ is benzyl the conversion may conveniently be accomplished by treating the compound of formula (II) with an alkaline metal hydroxide as discussed above, or by hydrogenolysis using molecular hydrogen or a suitable hydrogen donor such as ammonium formate in the presence of a transition metal or transition metal salt catalyst such as palladium-on-carbon, in a suitable solvent, such as methanol.

When there is a functional group in another part of the structure of ($I^C$) that is protected, such as an amino group in $R^1$ or $R^3$, it may be convenient to select $R^{15}$ and the protecting group such that they may both be removed in a single operation. For example, if there is an amine group protected by a BOC group, then selecting $R^{15}$ to be tert-butyl will allow both unmasking operations to be achieved with a single acid treatment. Similarly, if benzyloxycarbonyl is the preferred amine protecting group, the use of benzyl for $R^{15}$ permits simultaneous unmasking in a single hydrogenolysis step. Alternatively, the protecting group and $R^{15}$ may be chosen so as to be 'orthogonal', i.e. each is stable to the conditions used to cleave the other. Unmasking is then a two stage process, but the intermediate can be subject to a purification step.

b) Compounds of formula ($I^D$), i.e. compounds of formula (I) wherein $R^5$ is —Y—$CO_2R^{15}$ and $R^{15}$ is not hydrogen may be prepared by esterification of the corresponding acid of formula ($I^C$), as illustrated in Scheme 2, but this step is only necessary if the nature of $R^{15}$ is such that the ester group —$CO_2R^{15}$ is not compatible with one or more of the synthetic steps used.

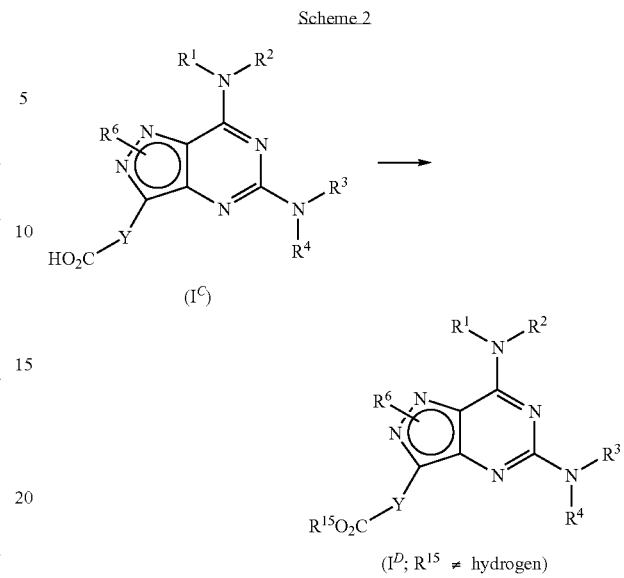

The conversion may conveniently be accomplished by treating a mixture of the acid of formula ($I^C$) and an alcohol $R^{15}$—OH in a suitable solvent with a condensing agent such as a carbodiimide, e.g. dicyclohexylcarbodiimide or N-(3-dimethylaminopropyl)-N'-ethylcarbodiimide, optionally in the presence of 4-dimethylaminopyridine, at a temperature of between 0° C. and the boiling point of the solvent. Suitable solvents include dichloromethane and dimethylformamide. Alternatively, the acid of formula ($I^C$) may be converted to the corresponding acid chloride using thionyl chloride or oxalyl chloride and then treated with the alcohol $R^{15}$—OH.

c) Compounds of formula ($II^A$) and ($II^B$), wherein $R^{6A}$ is as defined for $R^6$ except that it cannot be hydrogen, i.e. compounds of formula (II) wherein $R^6$ is other than H, can be prepared from compounds of formula ($II^C$), i.e. compounds of formula (II) wherein $R^6$ is H, as illustrated in Scheme 3.

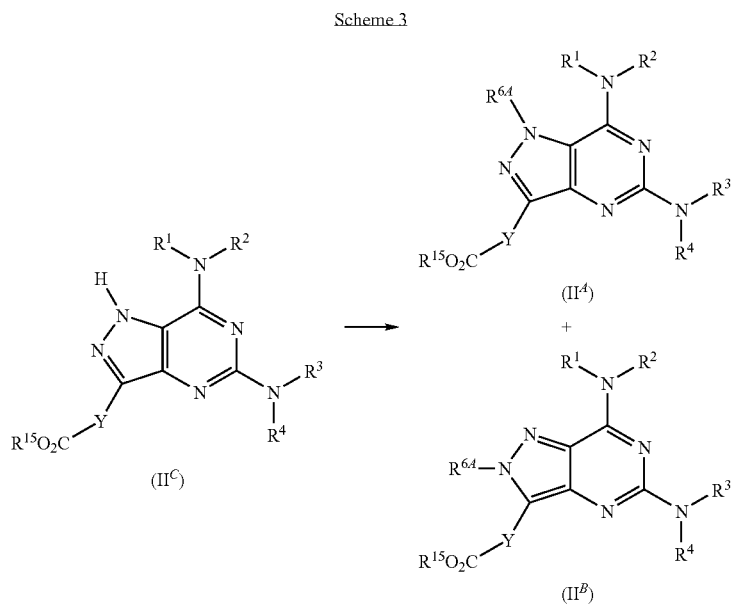

The compound of formula (II$^C$) is treated with a base such as an alkaline metal carbonate or bicarbonate, for example potassium carbonate or caesium carbonate, or a tertiary amine, for example triethylamine, diisopropylethylamine or pyridine, and the appropriate chloride (R$^{64}$—Cl), bromide (R$^{64}$—Br), iodide (R$^{64}$—I), mesylate (R$^{64}$—OSO$_2$CH$_3$) or tosylate (R$^{64}$—OSO$_2$Tol) in a suitable solvent at a temperature of between −70° C. and 100° C. Suitable solvents include ethers such as tetrahydrofuran and dioxan, dimethylformamide and acetonitrile. Stronger bases such as sodium hydride, potassium tert-butoxide and sodium or potassium hexamethyldisilazide may also be used. Alternatively, the transformation may be achieved using the Mitsunobu reaction, in which a solution of the compound of formula (II$^C$) and the appropriate alcohol R$^{64}$—OH in a suitable solvent is treated with triphenylphosphine and a dialkylazodicarboxylate such as diethyl azodicarboxylate or diisopropyl azodicarboxylate. A preferred solvent is tetrahydrofuran. The reaction is preferably performed at a temperature of between −10° C. and ambient temperature.

When the reaction gives a mixture of the two products (II$^A$) and (II$^B$), these can be separated using standard techniques.

The introduction of R$^6$ at this stage of the synthetic sequence is not always necessary. It is often more convenient to introduce R$^6$ at an early stage and carry it through to the final product.

d) Compounds of formula (II) can be prepared from the corresponding monochlorides of formula (III) by reaction with HNR$^3$R$^4$ as illustrated in Scheme 4.

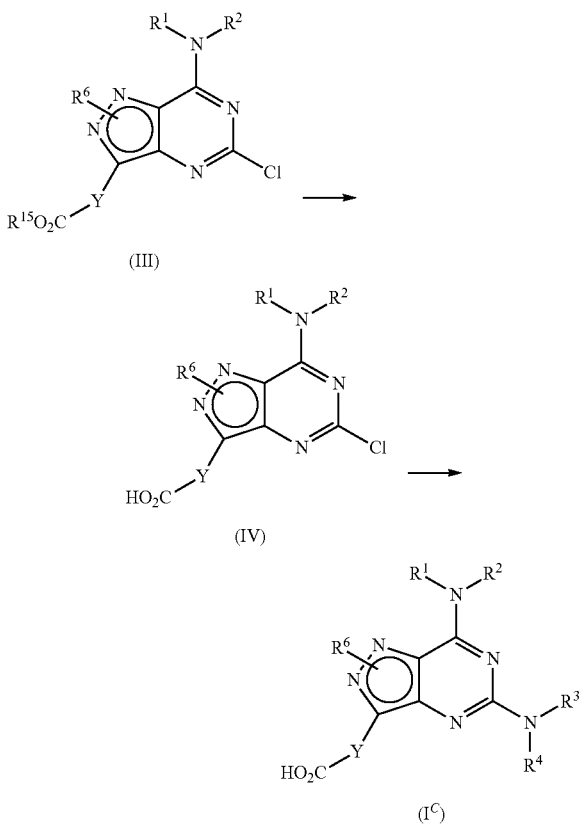

A solution of the monochloride (III) and the amine HNR$^3$R$^4$ in a suitable dipolar aprotic solvent are stirred at elevated temperature for between 1 and 24 hours. Suitable solvents include dimethylsulfoxide, dimethylformamide and N-methylpyrrolidinone. An excess of a tertiary amine such as N-ethyldiisopropylamine, N-methylmorpholine or triethylamine and/or a fluoride source such as caesium fluoride or tetraethylammonium fluoride may optionally be included. It is sometimes necessary to perform the reaction at elevated pressure in a closed vessel, particularly when the amine HNR$^3$R$^4$ or the solvent is volatile. It will be appreciated that any functional groups in HNR$^3$R$^4$, and particularly any primary or secondary amine groups, may need to be protected in order to allow this reaction to proceed successfully.

Preferably, the monochloride is treated with 3-5 equivalents of the amine HNR$^3$R$^4$ and optionally 2-5 equivalents of N-ethyldiisopropylamine in dimethylsulfoxide or N-methylpyrrolidinone, optionally in the presence of caesium fluoride or tetraethylammonium fluoride, at 80-125° C. for 12-18 hours, optionally in a closed vessel.

Alternatively, the compounds of formula (III) may be hydrolysed as described in part a) above to provide the corresponding carboxylic acid of formula (IV) which is then treated with amine HNR$^3$R$^4$ to provide compounds of formula (I$^C$), as illustrated in scheme 4a.

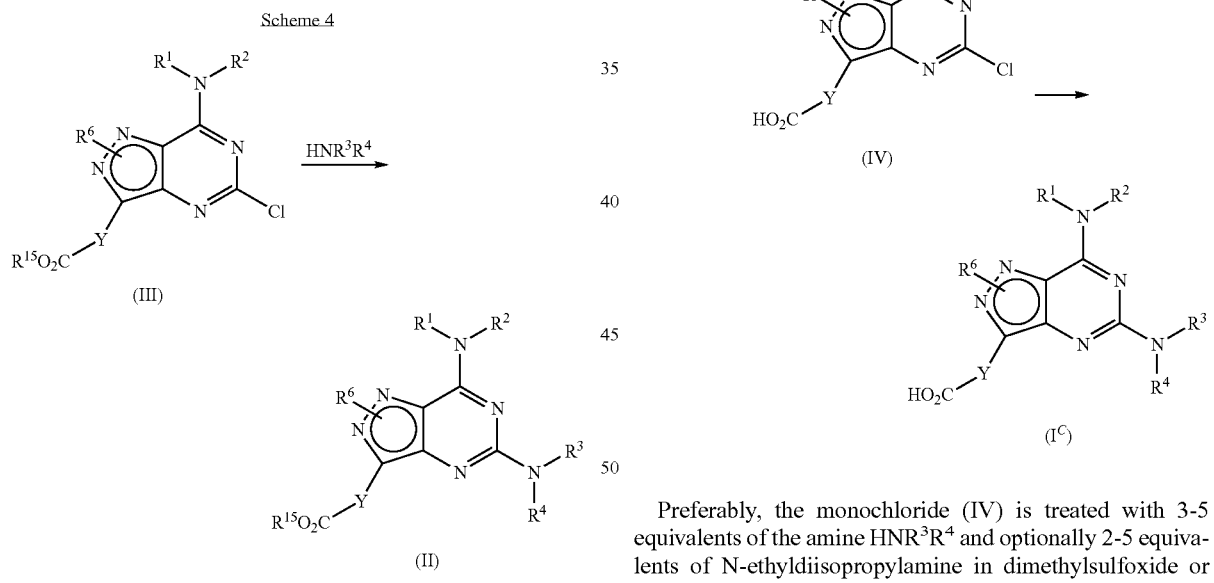

Preferably, the monochloride (IV) is treated with 3-5 equivalents of the amine HNR$^3$R$^4$ and optionally 2-5 equivalents of N-ethyldiisopropylamine in dimethylsulfoxide or N-methylpyrrolidinone, optionally in the presence of caesium fluoride or tetraethylammonium fluoride, at 80-125° C. for 12-18 hours, optionally in a closed vessel.

e) Compounds of formula (III) can be prepared from the corresponding dichlorides of formula (V) by reaction with HNR$^1$R$^2$ as illustrated in Scheme 5.

Preferably, the monochloride is treated with 3-5 equivalents of the amine HNR$^3$R$^4$ and optionally 2-5 equivalents of N-ethyldiisopropylamine in dimethylsulfoxide or N-methylpyrrolidinone, optionally in the presence of caesium fluoride or tetraethylammonium fluoride, at 80-125° C. for 12-18 hours, optionally in a closed vessel.

Scheme 5

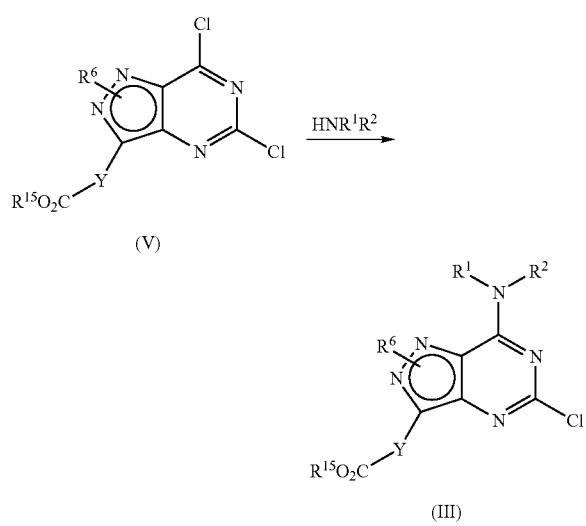

A solution of the dichloride (V), the amine HNR¹R² and optionally an excess of a tertiary amine such as N-ethyldiisopropylamine, N-methylmorpholine or triethylamine in a suitable solvent are stirred at ambient or elevated temperature for between 1 and 24 hours. Suitable solvents include dichloromethane, dimethylsulfoxide, dimethylformamide, acetonitrile, tetrahydrofuran and N-methylpyrrolidinone. It will be appreciated that any functional groups in HNR¹R², and particularly any primary or secondary amine groups, may need to be protected in order to allow this reaction to proceed successfully. Preferably, the monochloride is treated with 3-5 equivalents of the amine HNR¹R² and optionally 3-5 equivalents of N-ethyldiisopropylamine in dichloromethane, dimethylsulfoxide or a mixture of dimethylsulfoxide and N-methylpyrrolidinone at 25-90° C. for 1-18 hours.

Alternatively, a solution of the amine HNR¹R² in a suitable solvent is treated with butyllithium or sodium hexamethyldisilazide at low temperature, and the dichloride is added to the resulting solution. Suitable solvents include tetrahydrofuran, dioxan and N-methylpyrrolidinone.

In certain cases, particularly when Y is a covalent bond and the amine HNR¹R² is only weakly nucleophilic, the direct transformation of compounds of formula (V) into compounds of formula (III) gives unsatisfactory results and a more indirect alternative route may be employed. This route is described in part w) below.

f) Compounds of formula (V) can be prepared from the corresponding pyrazolopyrimidinediones of formula (VI) as illustrated in Scheme 6.

Scheme 6

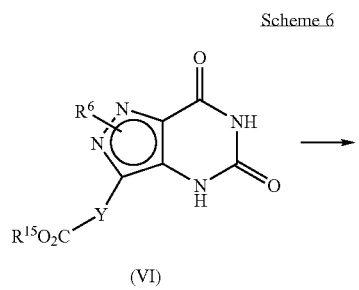

-continued

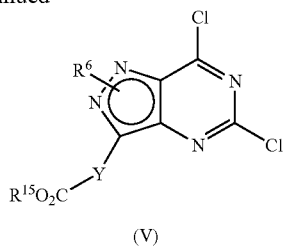

The dione is treated with a large excess of a suitable chlorinating reagent such as phosphorus oxychloride (POCl₃) or phenylphosphonyl dichloride (PhP(O)Cl₂) in the presence of a tertiary amine such as N-ethyldiisopropylamine, N-methylmorpholine, triethylamine or N,N-dimethylaniline at elevated temperature for 8-48 hours. Dimethylformamide can optionally be added as a catalyst. Alternatively, the dione is treated with POCl₃ or PhP(O)Cl₂ in a suitable solvent in the presence of a tetraalkylammonium chloride, such as tetraethylammonium chloride, and optionally in the presence of a tertiary amine such as N-ethyldiisopropylamine at elevated temperature. Suitable solvents include acetonitrile and propionitrile. Preferably, the dione is treated with 10-30 equivalents of POCl₃ and 3-5 equivalents of tetraethylammonium chloride in propionitrile or acetonitrile at reflux for 4-24 hours.

g) Compounds of formula (VI) can be prepared from the corresponding aminoamides of formula (VII) as illustrated in Scheme 7.

Scheme 7

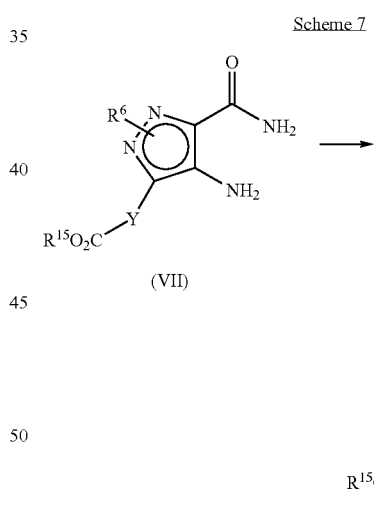

A solution of the pyrazolecarboxamide (VII) and phosgene or an equivalent thereof, such as 1,1'-carbonyldiimidazole, trichloromethyl chloroformate or bis(trichloromethyl)carbonate, in a suitable solvent is stirred at a temperature of between ambient temperature and the boiling point of the solvent, optionally at elevated pressure, for between 2 and 18 hours. Suitable solvents include acetonitrile, dichloromethane and dimethylformamide. Preferably, a solution of the amine of formula (VII) and 1-2.5 equivalent of 1,1'-carbonyldiimidazole in N,N-dimethylformamide, acetonitrile or dichloromethane is heated at between room temperature and the reflux temperature of the reaction for 1-18 hours.

h) Compounds of formula (VII) can be prepared from the corresponding nitroamides of formula (VIII) as illustrated in Scheme 8.

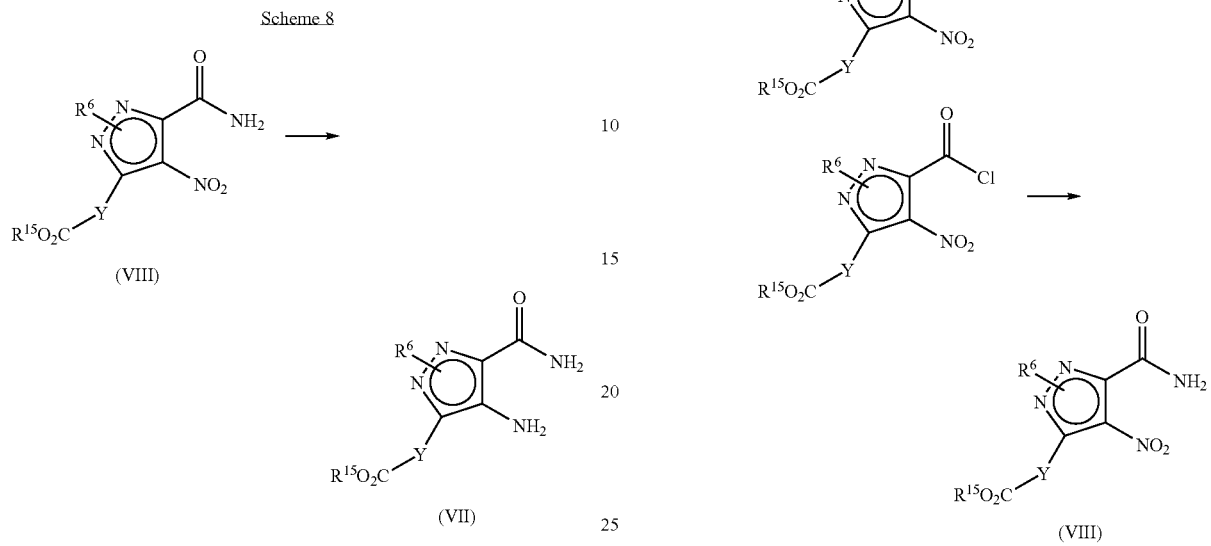

Reduction of the nitro group can be achieved by, for example, by transfer or catalytic hydrogenation, or by a dissolving metal reduction.

For transfer hydrogenation, the nitro compound is reacted with a suitable hydrogen donor, such as ammonium formate or cyclohexene, in a polar solvent, such as tetrahydrofuran, methanol or ethanol, in the presence of a transition metal or transition metal salt catalyst, such as palladium or palladium (II) hydroxide, optionally at elevated temperature and pressure.

For catalytic hydrogenation, a solution of the nitro compound in a polar solvent, such as tetrahydrofuran, methanol or ethanol, is stirred under a hydrogen atmosphere in the presence of a transition metal or transition metal salt catalyst, such as palladium or palladium(II) hydroxide, optionally at elevated pressure and temperature. The catalyst may be in solution (homogeneous catalysis) or in suspension (heterogeneous catalysis).

For dissolving metal reduction, the nitro compound is treated with a suitable reactive metal, such as zinc or tin, in the presence of an acid such as acetic acid or hydrochloric acid. Other reducing agents, such as tin(II) chloride, may also be used.

i) Compounds of formula (VIII) can be prepared from the corresponding nitroesters of formula (IX) as illustrated in Scheme 9.

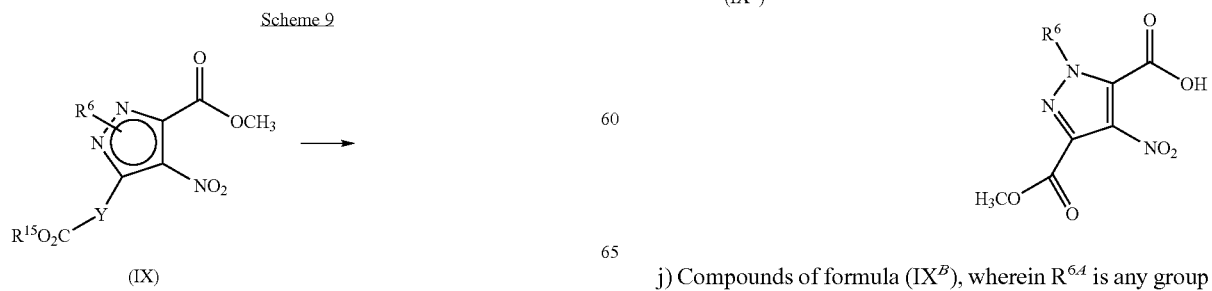

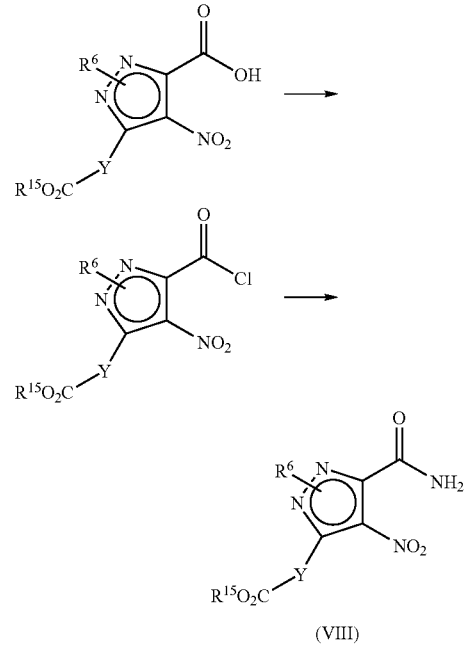

The methyl ester of the compounds of formula (IX) can be hydrolysed as described in part a) above. The acid is then converted to the corresponding acid chloride by treatment with oxalyl chloride and dimethylformamide in a suitable solvent such as dichloromethane, or with thionyl chloride. Finally, a solution of the acid chloride in a suitable solvent such as dichloromethane, tetrahydrofuran or dioxan is treated with gaseous ammonia or aqueous ammonia at between −78° C. and room temperature to provide the amide of formula (VIII).

In the embodiments ($IX^A$) in which Y is a covalent bond and $R^{15}$ is a methyl group, the use of one equivalent of metal hydroxide leads to the chemoselective hydrolysis of the ester group adjacent to the $R^6$ substituent (Chambers, D. et al., J. Org. Chem. 50, 4736-4738, 1985), as illustrated in scheme 9A.

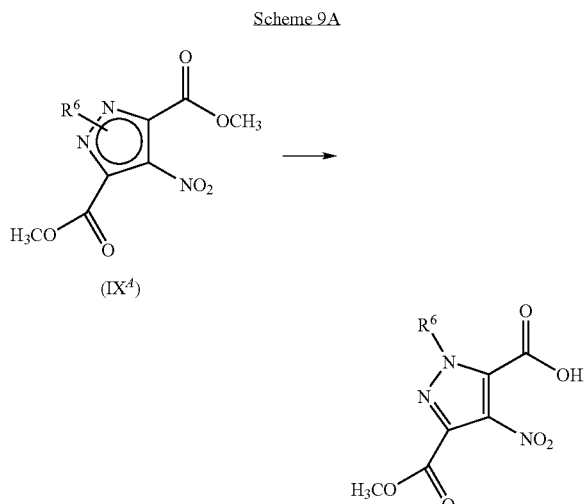

j) Compounds of formula ($IX^B$), wherein $R^{6A}$ is any group according to $R^6$ except hydrogen, i.e. compounds of formula (IX) except those wherein $R^6$ is hydrogen, can be prepared from the corresponding esters of formula (IX$^C$) as illustrated in Scheme 10.

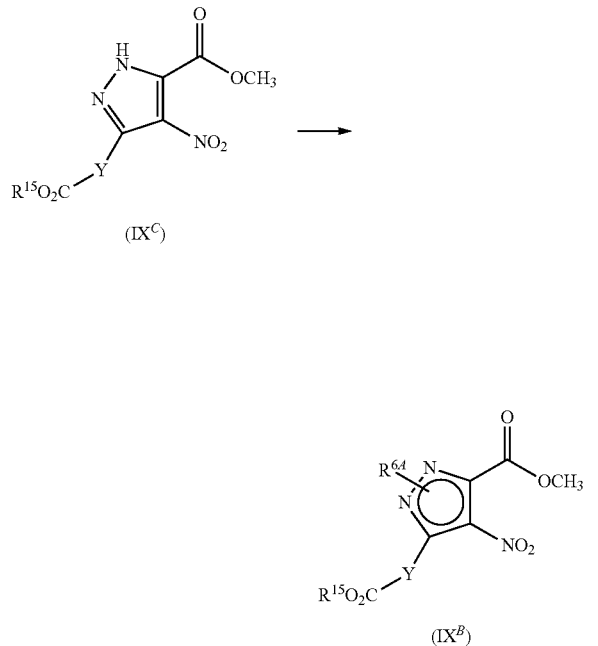

The compounds of formula (IX$^C$) are treated with a combination of an alkylating agent and a base, or with an alcohol, triphenylphosphine and a dialkyl azodicarboxylate, as described in part c) above.

k) The compound of formula (IX$^C$) wherein $R^{15}$ is methyl and Y is a covalent bond is described in published international patent application WO00/24745 (see preparation 2, page 48). Other compounds of formula (IX), and particularly compounds of formula (IX$^C$), can be prepared in two steps from the diacids of formula (X), as illustrated in scheme 11.

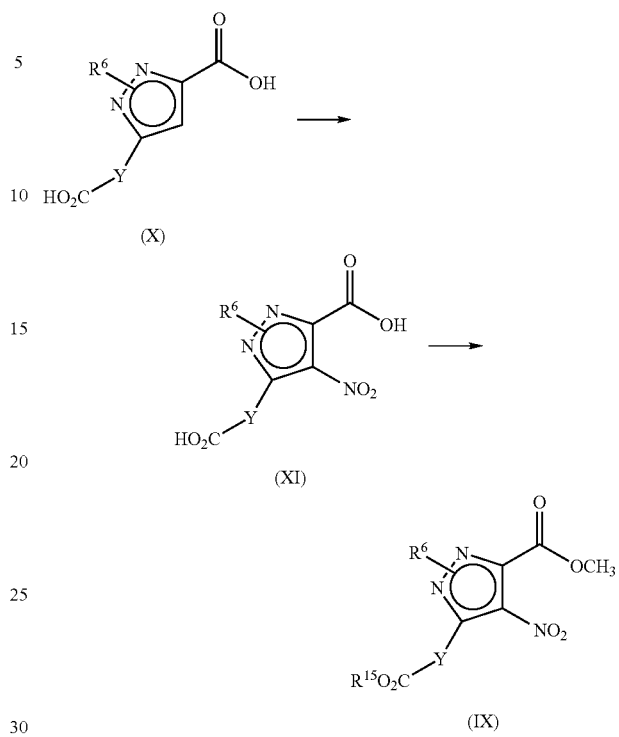

In the first step, the compounds of formula (X) are treated with a nitrating agent such as nitric acid or a mixture of nitric acid and sulphuric acid to provide the compounds of formula (XI). In the second step, the two carboxylic acid groups are esterified. When $R^{15}$ is methyl, this is conveniently achieved in a single operation. When $R^{15}$ is other than methyl, two sub-steps are necessary, and the order in which the two groups are esterified will depend on the nature of Y and $R^6$. Suitable conditions for forming esters are well known in the art. When $R^{15}$ is methyl, a preferred method is to treat the diacid with thionyl chloride so as to form the bis-chloride and then react this with methanol.

1) Certain compounds of formula (X) are commercially available or are described in the literature, in particular those wherein Y is a covalent bond. Compounds of formula (X) that are not items of commerce can be prepared as illustrated in Schemes 12, 13 and 14.

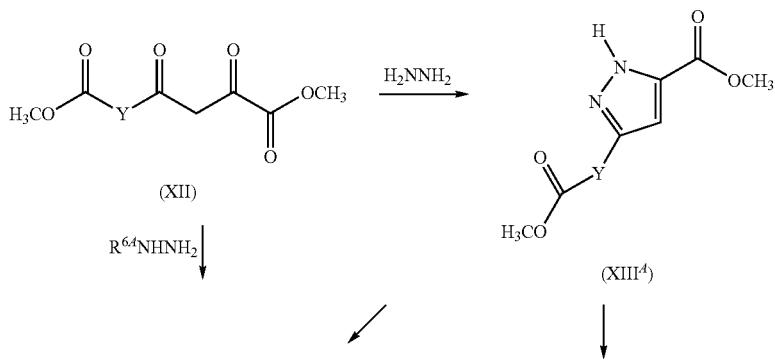

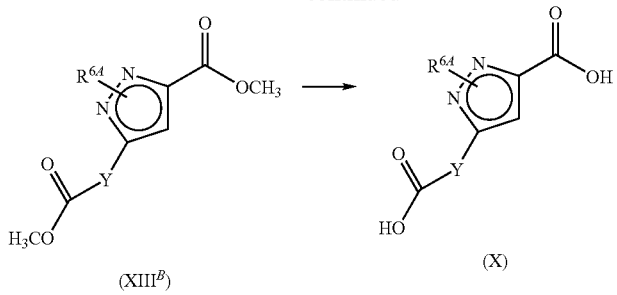

The method illustrated in Scheme 12 is the Knorr pyrazole synthesis. A 1,3-diketone of formula (XII) is reacted with hydrazine to give a pyrazole of formula (XIII$^A$), or with a substituted hydrazine R$^{6A}$—NHNH2, wherein R$^{6A}$ is as defined in part c) above, to give a pyrazole of formula (XIII$^B$).

Pyrazoles of formula (XIII$^B$) may also be obtained by N-alkylation of the corresponding pyrazoles of formula (XIII$^A$) following the method described in part c) above. Hydrolysis of the ester groups as described in part a) above then provides the compounds of formula (X).

Compounds of formula (XII) can be prepared from the corresponding methyl ketones of formula (XIV) using a crossed Claisen condensation as illustrated in Scheme 13.

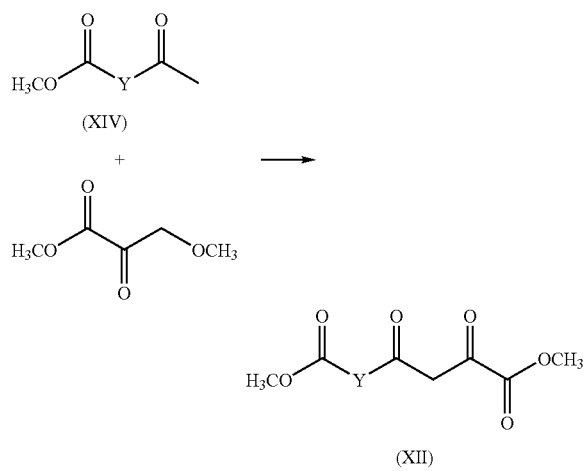

A methyl ketone of formula (XIV) is reacted with dimethyl oxalate in a suitable solvent in the presence of a suitable base. Suitable solvents include ethers, such as tetrahydrofuran. Suitable bases include sodium hydride, potassium tert-butoxide and lithium diisopropylamide. Alternatively, sodium methoxide may be used as the base and methanol as the solvent.

Scheme 14

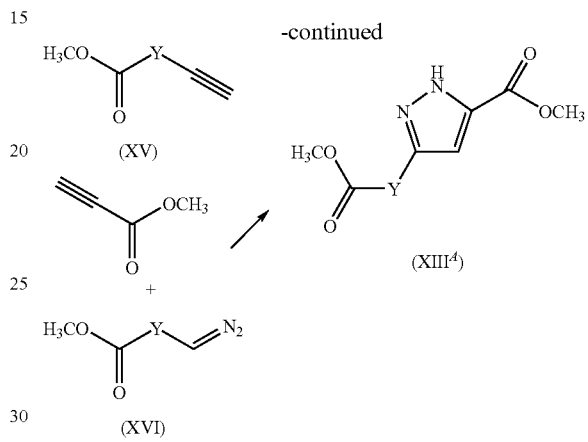

The method illustrated in scheme 14 is the Pechmann pyrazole synthesis. A diazo compound and an acetylene are combined to produce a pyrazole of formula (XIII$^A$). When Y is other than a covalent bond two variants of the method can be considered. An acetylene of formula (XV) can be combined with methyl diazoacetate, or a diazo compound of formula (XVI) can be combined with methyl propiolate. The product of formula (XIII$^A$) may be carried forward as described above.

In addition to the methods described above, certain compounds of general formulae (III) and (IV) may be prepared by modification of the substituent at the C-3 position of the pyrazolopyrimidine, as further illustrated below. It will be appreciated that the synthetic transformations discussed may also be used in the elaboration of precursor compounds such as the pyrazoles of formula (IX).

m) Compounds of formula (III$^A$), i.e. compounds of formula (III) wherein Y is CH$_2$, may be prepared from the corresponding compounds of formula (IV$^A$), i.e. compounds of formula (IV) wherein Y is a covalent bond, by a one-carbon homologation method such as the Arndt-Eistert reaction illustrated in Scheme 15.

Scheme 15

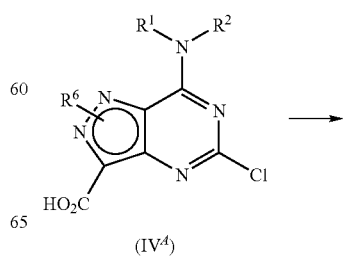

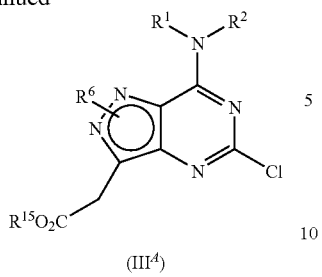

(III$^A$)

The carboxylic acid is converted to a reactive intermediate such as the acid chloride (by reaction with oxalyl chloride) or a mixed anhydride (by reaction with isobutyl chloroformate). The intermediate is reacted with diazomethane to provide an α-diazoketone. This is treated with silver oxide in the presence of R$^{15}$—OH to give the homologated ester of formula (III$^A$).

n) Compounds of formula (IV$^B$), i.e. compounds of formula (IV) wherein Y is CH$_2$, may be prepared from the corresponding nitrites of formula (XVII) by the method illustrated in Scheme 16.

Scheme 16

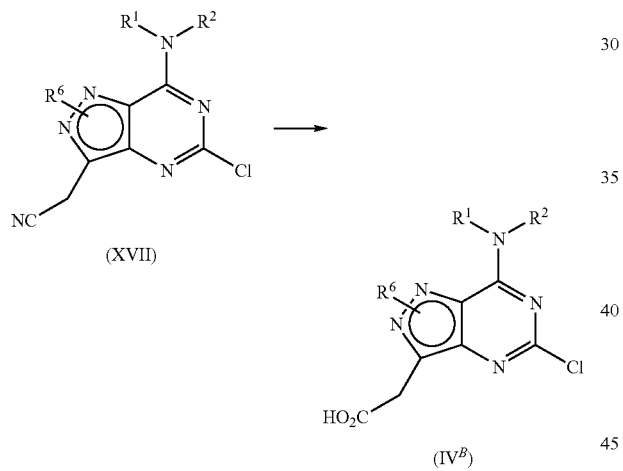

(XVII)

(IV$^B$)

The nitrile can be hydrolysed, e.g. by treatment with aqueous mineral acids, such as hydrochloric acid.

o) Compounds of formula (XVII) can be prepared from the corresponding chlorides of formula (XVIII) by the method illustrated in Scheme 17.

Scheme 17

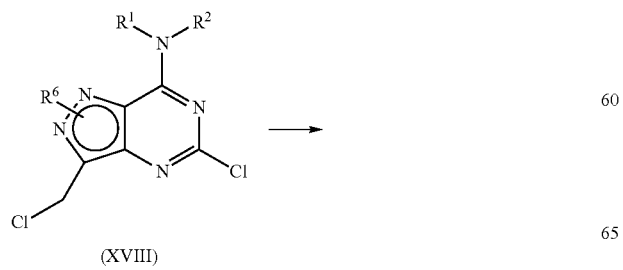

(XVIII)

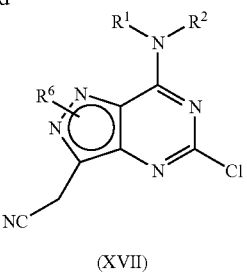

(XVII)

The chloride is treated with a metal cyanide, such as sodium cyanide or potassium cyanide in a suitable solvent, such as dimethylsulfoxide, dimethylformamide or ethanol.

p) Compounds of formula (XVIII) can be prepared from the corresponding alcohols of formula (XIX) by the method illustrated in Scheme 18.

Scheme 18

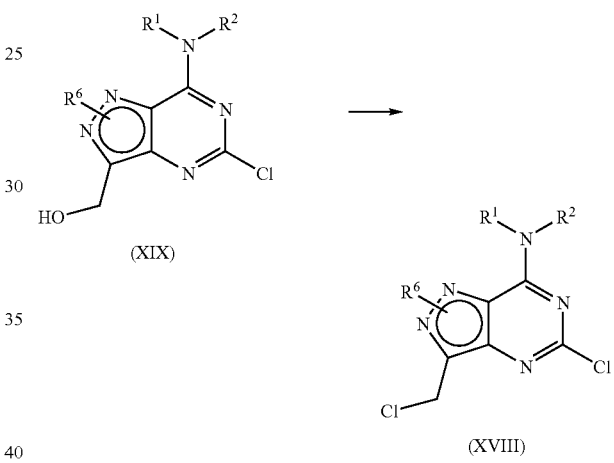

(XIX)

(XVIII)

The alcohol is treated with a mixture of triphenylphosphine and N-chlorosuccinimide or tetrachloromethane, or with thionyl chloride.

q) Compounds of formula (XIX) can be prepared from the corresponding esters of formula (III$^B$), i.e. compounds according to formula (III) wherein Y is a covalent bond, or from the corresponding acids of formula (IV$^A$) by the method illustrated in Scheme 19.

Scheme 19

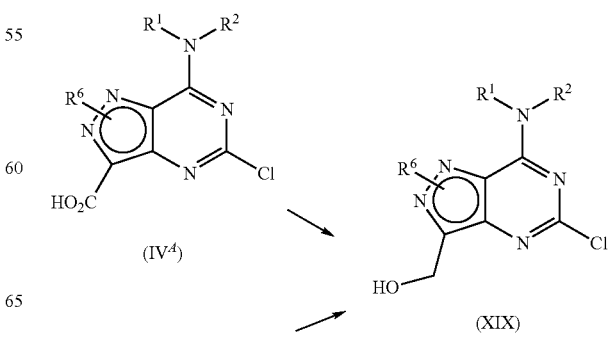

(IV$^A$)

(XIX)

-continued

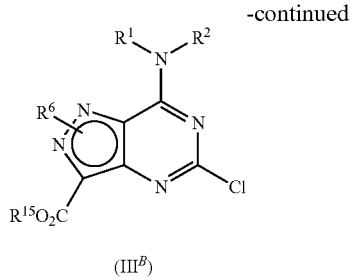

(III$^B$)

The acids of formula (IV$^A$) and the esters of formula (III$^B$) can be reduced to the alcohols of formula (XIX) by treatment with lithium aluminium hydride in a suitable solvent at a temperature of between 0° and the boiling point of the solvent. Suitable solvents include ethers such as tetrahydrofuran. The acids can also be reduced by treatment with isobutyl chloroformate and a tertiary amine base to provide a mixed anhydride, followed by reaction with sodium borohydride. The esters can also be reduced by treatment with disobutylaluminium hydride or lithium borohydride.

r) Compounds of formula (III$^C$), i.e. compounds of formula (III) wherein Y is CH$_2$CH$_2$ can be prepared from the corresponding acrylate ester of formula (XX) by the method illustrated in Scheme 20.

Scheme 20

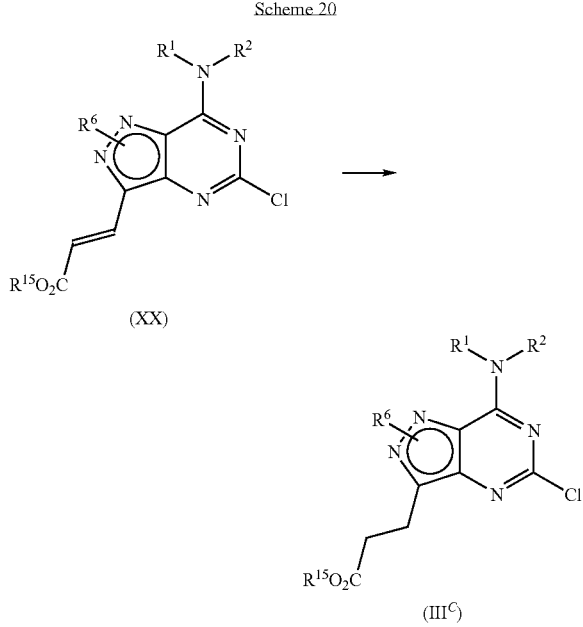

The reduction of the carbon-carbon double bond of (XX) to give the compounds of formula (III$^C$) can be accomplished by catalytic hydrogenation using molecular hydrogen in the presence of a transition metal catalyst such as palladium, platinum or nickel. When R$^{15}$ is benzyl the conditions can be chosen such that only the double bond is reduced or reduction is accompanied by hydrogenolytic cleavage of the ester to give the carboxylic acid.

The acrylates of formula (XX) can also be treated with alkylcopper reagents to give analogues of the compounds of formula (III$^C$) in which an alkyl substituent is introduced on the carbon atom adjacent to the pyrazolopyrimidine ring system, or with a sulphonium ylid or a carbene equivalent to give a 2-(pyrazolopyrimidinyl)-cyclopropane-1-carboxylate derivative.

s) Compounds of formula (XX) can be prepared from the corresponding aldehydes of formula (XXI) by the method illustrated in Scheme 21.

Scheme 21

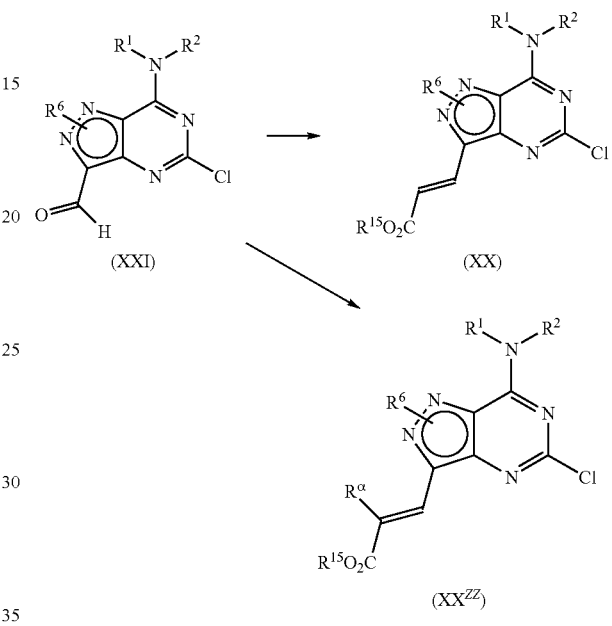

The aldehyde of formula (XXI) can be converted to the acrylate ester of formula (XX) by reaction with a phosphorus reagent following the protocols of the Wittig, Horner or Wadsworth-Horner-Emmons reactions. The reagent is prepared by treating a triphenylphosphonium salt Ph$_3$P$^+$CH$_2$CO$_2$R$^{15}$.X$^-$ (Wittig), a phosphine oxide Ph$_2$P(O)CH$_2$CO$_2$R$^{15}$ (Horner), or a phosphonate (EtO)$_2$P(O)CH$_2$CO$_2$R$^{15}$ (Wadsworth-Horner-Emmons), with a base such as butyllithium, a lithium dialkylamide or an alkaline metal alkoxide, in a suitable solvent such as tetrahydrofuran, wherein X$^-$ is a suitable anion such as a halide, for example chloride, bromide or iodide.

The method is not limited to the preparation of α-unsubstituted acrylate esters. The use of an alkyl-substituted phosphorus reagent such as Ph$_3$P$^+$CH(R$^α$)CO$_2$R$^{15}$.X$^-$ or the equivalent phosphine oxide or phosphonate, wherein R$^α$ is alkyl, and further wherein X$^-$ is a suitable anion such as a halide, for example chloride, bromide or iodide, gives access to the corresponding α-alkyl acrylate derivative (XX$^{ZZ}$).

The conversion of the aldehydes of formula (XXI) to acrylate esters of formula (XX) can also be achieved by reaction with a malonate derivative following the method of the Knoevenagel condensation.

t) Compounds of formula (XXI) can be prepared from the esters of formula (III$^B$) or more preferably from the corresponding alcohols of formula (XIX) by the methods illustrated in Scheme 22.

Scheme 22

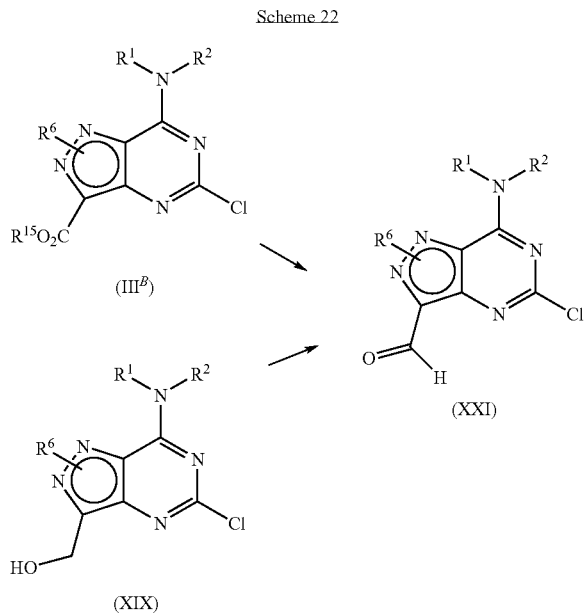

The reduction of the esters of formula (III$^B$) can be achieved using diisobutylaluminium hydride (DIBAL) in a suitable solvent at a temperature of less than 0° C., preferably less than −60° C. Suitable solvents include hydrocarbons such as pentane, hexane and toluene, ethers such as tetrahydrofuran, and mixtures thereof.

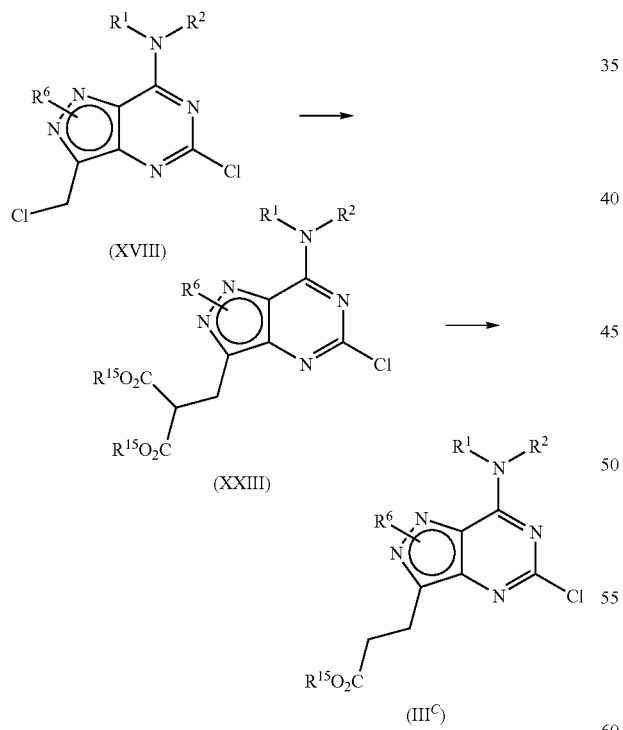

The chloride of formula (XVIII) is reacted with a dialkyl malonate $(R^{15}O_2C)_2CH_2$ and a base in a suitable solvent. Typically, the base is an alkaline metal alkoxide such as sodium ethoxide or potassium tert-butoxide, and the solvent is an alcohol such as ethanol or an ether such as tetrahydrofuran. Preferably the base and the solvent are chosen such as to minimise transesterification with the malonate reagent and the intermediate (XXIII). For example, when the reagent is diethyl malonate the base is preferably sodium ethoxide and the solvent is ethanol. The intermediate (XXIII) is then decarboxylated to give the product (III$^C$). This can be achieved by selective hydrolysis using one equivalent of an alkaline metal hydroxide, such as sodium hydroxide, followed by acidification, or by any other method known in the art.

The method is not limited to symmetrical malonates. For example, the use of tert-butyl methyl malonate would give an intermediate (XXIII) in which one $R^{15}$ is methyl and the other is tert-butyl. By choosing the appropriate conditions, decarboxylation could then be controlled to give a product (III$^C$) in which $R^{15}$ was either tert-butyl or methyl.

The method can be extended to substituted malonates $(R^{15}O_2C)_2CHR$, where R is an alkyl group. This gives access to compounds analogous to (IIF) in which the group R is a substituent on the carbon atom adjacent to the $R^{15}O_2C$ group. These compounds can also be prepared by alkylating the intermediate (XXIII) with R—Br or R—I in the presence of an alkaline metal alkoxide base.

w) As mentioned in part e) above, the reaction of compounds of formula (VA), i.e. compounds of formula (V) wherein Y is a covalent bond, with weakly nucleophilic amines HNR$^1$R$^2$ is sometimes not high yielding. An alternative route is illustrated in Schemes 25A and 25B.

Scheme 25A

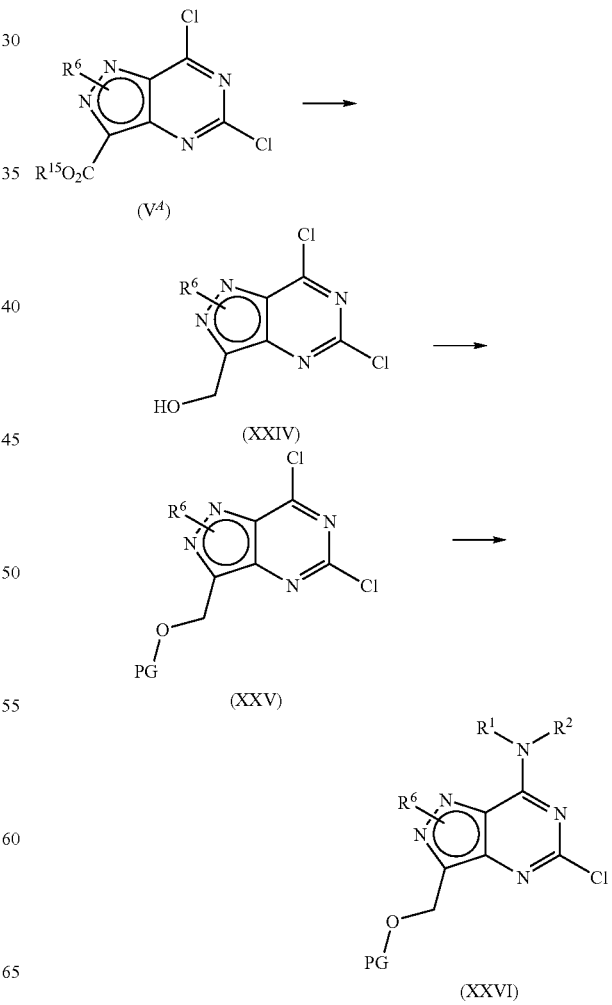

The esters of formula (V^4) can be reduced to the alcohols of formula (XXIV) according to the methods described in part q) above. A preferred method is reduction with diisobutylaluminium hydride at a temperature of between −20° C. and 0° C. The primary alcohol is then protected to give compounds of formula (XXV), wherein PG is an alcohol protecting group. A preferred protecting group is a trialkylsilyl group, particularly a tert-butyldimethylsilyl group. The compounds of formula (XXV) are then reacted with an amine $HNR^1R^2$ according to the methods described in part e) above to give compounds of formula (XXVI).

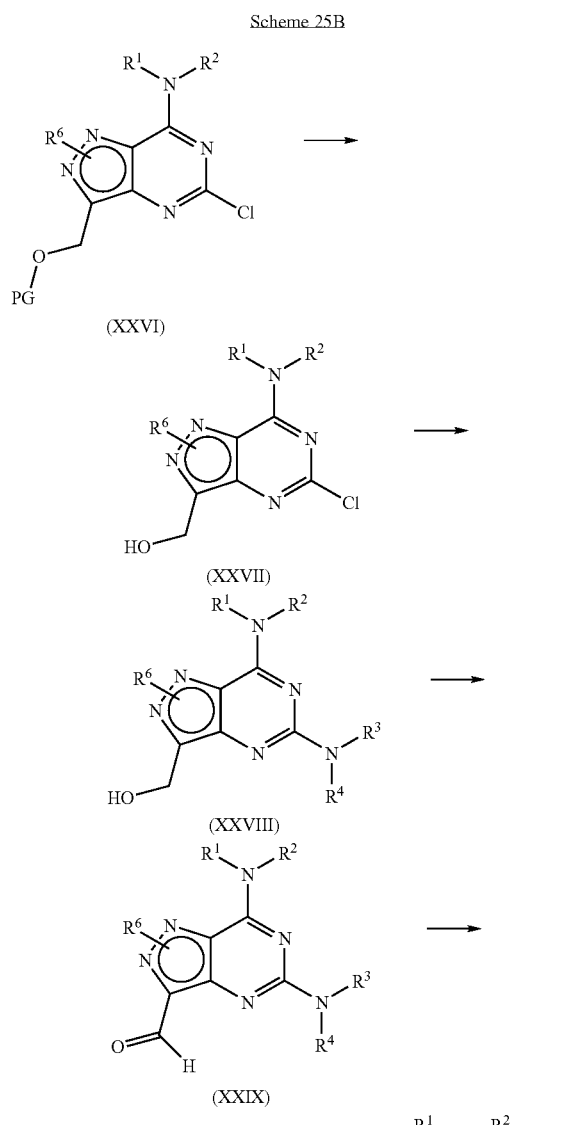

The compounds of formula (XXVI) are deprotected to provide the primary alcohols of formula (XXVII) using appropriate conditions. When PG is a trialkylsilyl group it may be removed by treatment with a fluoride salt, such as tetrabutylammonium fluoride, or with hydrochloric acid. The —$NR^3R^4$ group is then introduced according to the methods described in part d) above to provide compounds of formula (XXVIII). The primary alcohol is oxidised as described in part t) above to provide the aldehydes of formula (XXIX). A preferred oxidising agent is the Dess-Martin periodinane. Finally the aldehydes of formula (XXIX) are oxidised to provide the acids of formula ($I^D$), i.e. compounds of formula ($I^C$) wherein Y is a covalent bond. Suitable oxidising agents include potassium permanganate, Jones' reagent and sodium chlorite. A preferred method is to treat the aldehydes with sodium chlorite, sodium dihydrogenphosphate and 2-methyl-2-butene in tert-butanol at room temperature for about 1 hour.

Alternatively, it may be preferred to perform the oxidation of the alcohol of formula (XXVII) to the corresponding acid (via the corresponding aldehyde), using the methods previously described, prior to reaction with $HNR^3R^4$, to provide the compound of formula ($I^D$).

x) Compounds of formula ($I^E$), i.e. compounds of formula (I) wherein $R^5$ is —Y—$R^{16}$ can be prepared from the corresponding monochlorides of formula (XXX) as illustrated in Scheme 26.

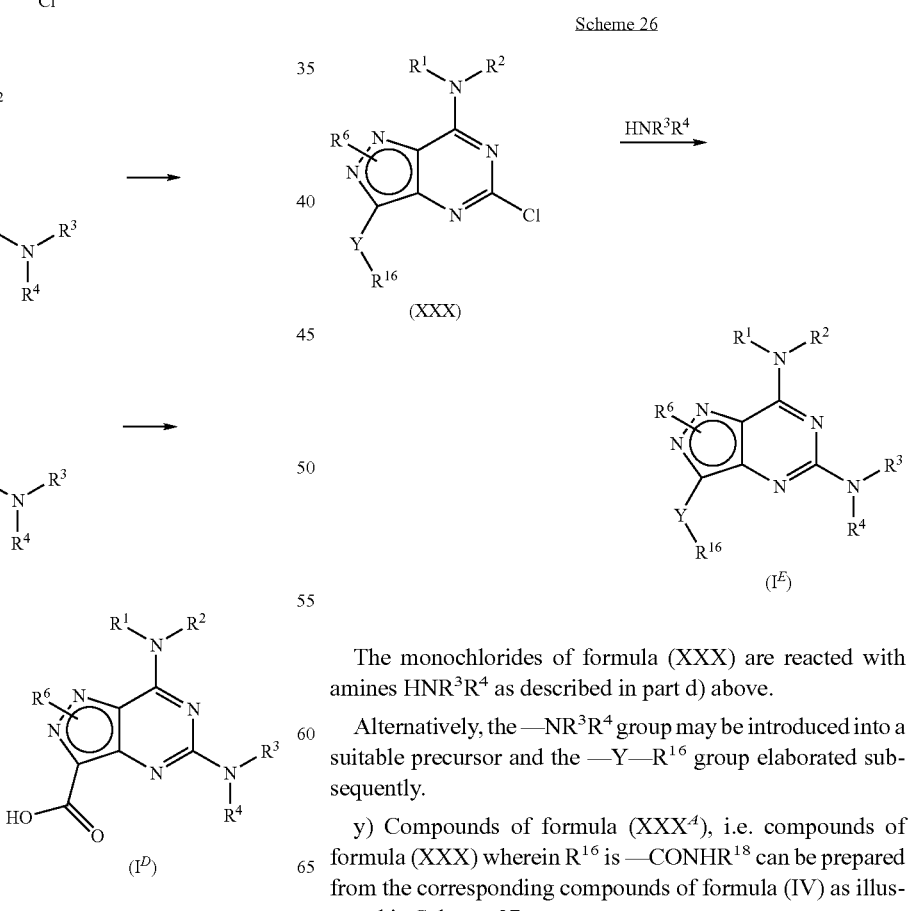

The monochlorides of formula (XXX) are reacted with amines $HNR^3R^4$ as described in part d) above.

Alternatively, the —$NR^3R^4$ group may be introduced into a suitable precursor and the —Y—$R^{16}$ group elaborated subsequently.

y) Compounds of formula ($XXX^4$), i.e. compounds of formula (XXX) wherein $R^{16}$ is —$CONHR^{18}$ can be prepared from the corresponding compounds of formula (IV) as illustrated in Scheme 27.

Scheme 27

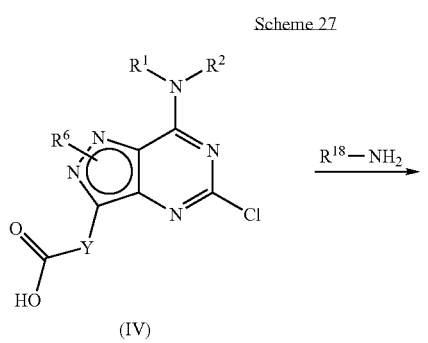
(IV)

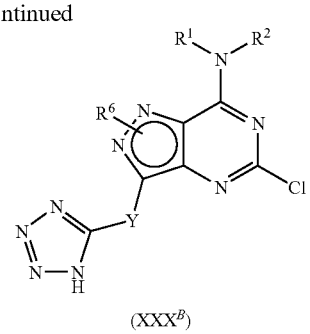
(XXX$^B$)

The nitrile of formula (XXXI) is treated with an azide, such as an alkaline metal azide (M=Na, K), a trialkylsilyl azide (M=alkyl$_3$Si) or a trialkyltin azide (M=alkyl$_3$Sn), in a suitable solvent at a temperature of between ambient temperature and the boiling point of the solvent. A preferred azide is tributyltin azide. A preferred solvent is dioxan.

Scheme 28B

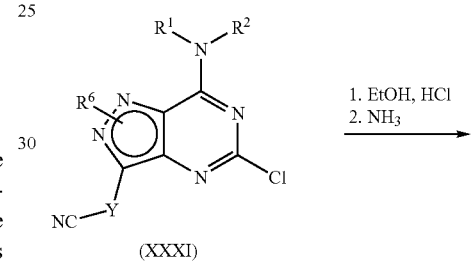

(XXX$^A$)

The acid of formula (IV) is treated with the appropriate sulfonamide $R^{18}$—NH$_2$ and a carbodiimide in a suitable solvent in the presence of 4-(dimethylamino)pyridine. A suitable solvent is dimethylformamide or dichloromethane. It is sometimes preferred to introduce the $R^{18}$—NH$_2$ group in the final step, i.e. after elaboration of the —NR$^3$R$^4$ group.

Preferably, the acid is treated with 1.3 equivalents of 1-(3-dimethylaminopropyl)-3-ethylcarbodiimide hydrochloride, 1.3 equivalents of 4-dimethylaminopyridine and 1.2-1.3 equivalents of the sulphonamide $R^{18}$NH$_2$, in dichloromethane at about room temperature for up to 18 hours.

z) Compounds of formula (XXX) wherein $R^{16}$ is a heterocyclic carboxylic isostere such as tetrazol-5-yl (compounds of formula (XXX$^B$)), 5-trifluoromethyl-1,2,4-triazol-3-yl (compounds of formula (XXX$^C$)) and 2,5-dihydro-5-oxo-1,2,4-oxadiazol-3-yl (compounds of formula (XXX$^D$)) can be prepared from compounds of formula (XXXI) using standard methods such as those illustrated in Scheme 28A, 28B and 28C.

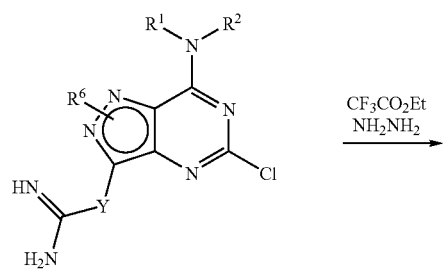

Scheme 28A

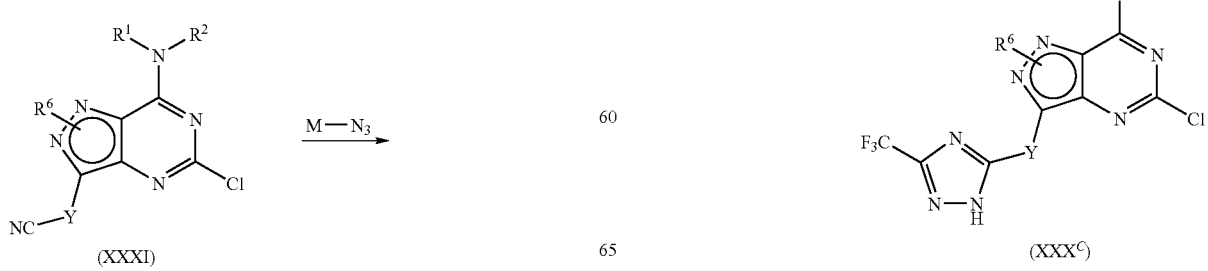

(XXXI)

(XXX$^C$)

The nitrile of formula (XXXI) is treated with ethanol and hydrogen chloride to form an imidate, which is then treated with ammonia to form an amidine. The amidine is treated with ethyl trifluoroacetate and hydrazine to provide the triazole of formula (XXX$^C$). The 5-(methylsulfonyl)-substituted triazole can be prepared in an analogous manner.

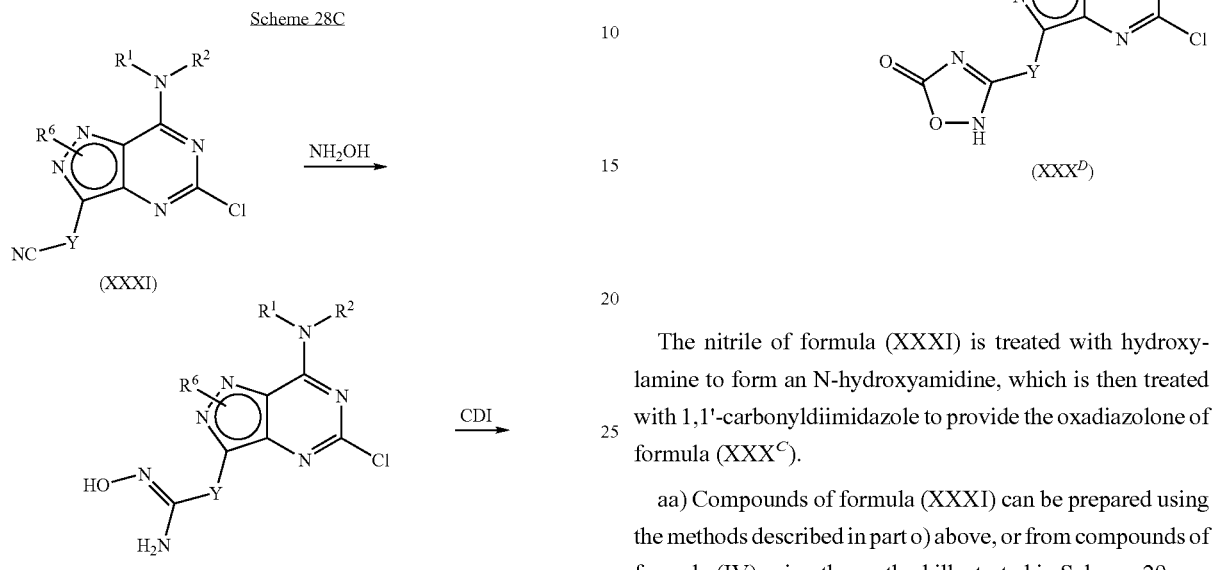

The nitrile of formula (XXXI) is treated with hydroxylamine to form an N-hydroxyamidine, which is then treated with 1,1'-carbonyldiimidazole to provide the oxadiazolone of formula (XXX$^C$).

aa) Compounds of formula (XXXI) can be prepared using the methods described in part o) above, or from compounds of formula (IV) using the method illustrated in Scheme 29.

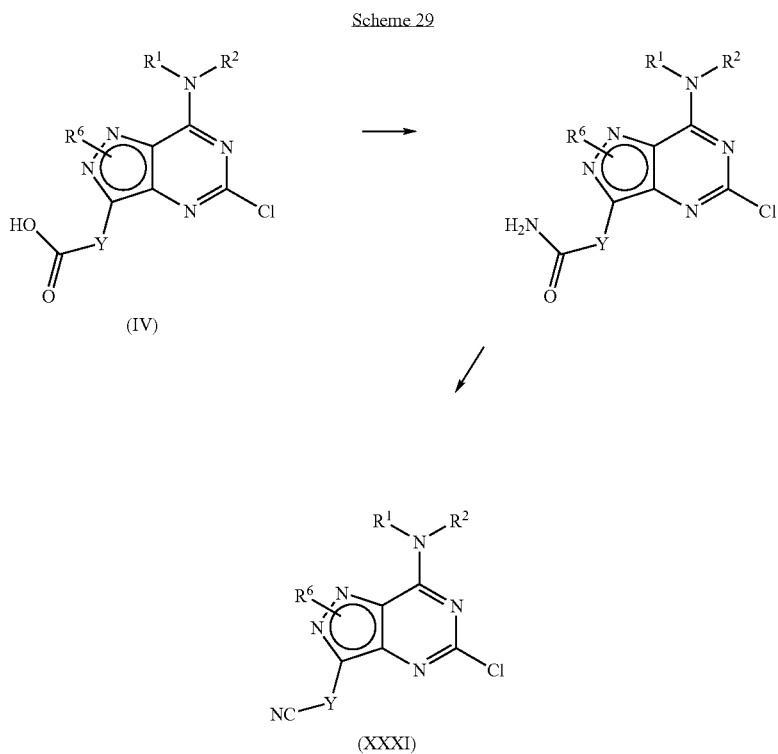

The acid of formula (IV) is converted into the corresponding primary amide following the method described in part i) above. The amide is then dehydrated using trifluoroacetic anhydride.

bb) Compounds of formula (III) or (XXXI) wherein Y is —$CH_2$—O—$CH_2$— may be prepared from the alcohols of formula (XIX) by alkylation with an alkyl α-haloacetate or an α-haloacetonitrile derivative, as illustrated in scheme 29.

Scheme 30

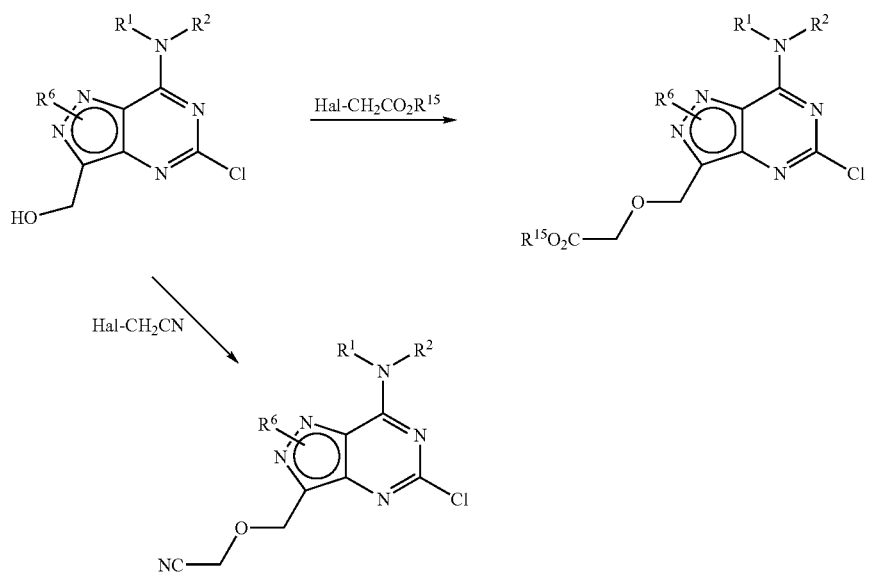

Hal is chlorine, bromine or iodine, preferably chlorine or bromine. The alcohol (XIX) and alkylating agent are combined in a suitable solvent in the presence of a base such as potassium carbonate or sodium hydride. Suitable solvents include tetrahydrofuran and dimethylformamide.

It will be appreciated by those skilled in the art that certain compounds of formula (I) may undergo standard chemical transformations to provide alternative compounds of formula (I), for example the preparation of example 184, by dealkylation of an alkyl ether. For some of the steps of the here above described process of preparation of the compounds of formula (I), it may be necessary to protect potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by P. J. Kocienski (*Protecting groups*, Georg Thieme Verlag, 1994), can be used.

The following compounds (and salts thereof) form further aspects of the present invention:

A compound of formula (III)

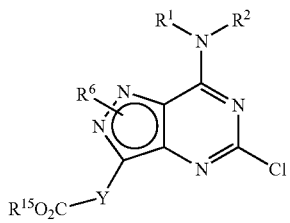

(III)

wherein $R^1$, $R^2$, $R^6$, $R^{15}$ and Y are as defined above. In some embodiments, $R^{15}$ is $C_1$-$C_6$-alkyl or benzyl.

Preferred is a compound of formula ($III^D$)

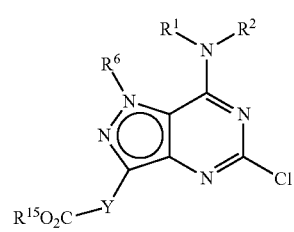

($III^D$)

wherein $R^1$, $R^2$, $R^6$, $R^4$ and Y are as defined above. In some embodiments, $R^{15}$ is $C_1$-$C_6$-alkyl or benzyl.

A compound of formula (V)

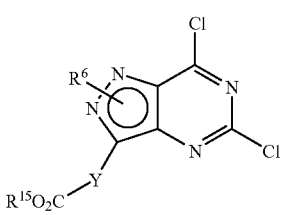

(V)

wherein $R^6$, $R^4$ and Y are as defined above. In some embodiments, $R^{15}$ is $C_1$-$C_6$-alkyl or benzyl.

Preferred is a compound of formula ($V^B$)

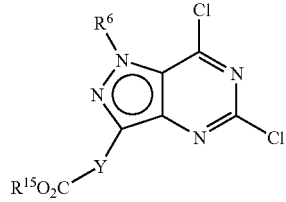

wherein $R^6$, $R^4$ and Y are as defined above.

The invention is further illustrated by the following, non-limiting examples. Melting points were determined on a Gallenkamp melting point apparatus using glass capillary tubes and are uncorrected. Unless otherwise indicated all reactions were carried out under a nitrogen atmosphere, using commercially available anhydrous solvents. '0.88 Ammonia' refers to commercially-available aqueous ammonia solution of about 0.88 specific gravity. Thin-layer chromatography was performed on glass-backed pre-coated Merck silica gel (60 F254) plates, and silica gel column chromatography was carried out using 40-63 □m silica gel (Merck silica gel 60). Ion exchange chromatography was performed using with the specified ion exchange resin which had been pre-washed with deionised water. Proton NMR spectra were measured on a Varian Inova 300, Varian Inova 400, or Varian Mercury 400 spectrometer in the solvents specified. In the NMR spectra, only non-exchangeable protons which appeared distinct from the solvent peaks are reported. Low resolution mass spectra were recorded on either a Fisons Trio 1000, using thermospray positive ionisation, or a Finnigan Navigator, using electrospray positive or negative ionisation. High resolution mass spectra were recorded on a Bruker Apex II FT-MS using electrospray positive ionisation. Combustion analyses were conducted by Exeter Analytical UK. Ltd., Uxbridge, Middlesex. Optical rotations were determined at 25° C. using a Perkin Elmer 341 polarimeter using the solvents and concentrations specified. Example compounds designated as (+) or (−) optical isomers are assigned based on the sign of optical rotation when determined in a suitable solvent.

ABBREVIATIONS, DEFINITIONS AND GLOSSARY

AcOH acetic acid
Amberlyst®15 Ion exchange resin, available from Aldrich Chemical Company
APCI Atmospheric Pressure Chemical Ionisation
Arbocel™ Filtration agent, from J. Rettenmaier & Sohne, Germany
atm Pressure in atmospheres (1 atm=760 Torr=101.3 kPa)
Biotage™ Chromatography performed using Flash 75 silica gel cartridge, from Biotage, UK
BOC tert-butoxycarbonyl
br Broad
c Concentration used for optical rotation measurements in g per 100 ml (1 mg/ml is c 0.10)
cat Catalytic
CBz benzyloxycarbonyl
CDI N,N'-carbonyldiimidazole
d Doublet
DCC N,N'-dicyclohexylcarbodiimide
DCM dichloromethane
dd Doublet of doublets
DEAD diethyl azodicarboxylate
Degussa® 101 10 wt % palladium on activated carbon, Degussa type E101 available from Aldrich Chemical Company
Dess-Martin periodinane 1,1,1-triacetoxy-1,1-dihydro-1,2-benziodoxol-3(1H)-one
Develosil Combi-RP $C_{30}$ hplc column Supplied by Phenomenex—manufactured by Nomura Chemical Co. RP $C_{30}$ hplc Composed of spherical silica particles (size 3 μm or 5 μm) which have a chemically bonded surface of C30 chains. These particles are packed into stainless steel columns of dimensions 2 cm internal diameter and 25 cm long.
DIAD diisopropyl azodicarboxylate
DIBAL diisobutylaluminium hydride
DMAP 4-dimethylaminopyridine
DMF N,N-dimethylformamide
DMSO dimethyl sulphoxide
Dowex® Ion exchange resin, from Aldrich Chemical Company
ee Enantiomeric excess
$Et_3N$ triethylamine
EtOAc ethyl acetate
EtOH ethanol
HOAT 1-hydroxy-7-azabenzotriazole
HOBT 1-hydroxybenzotriazole hydrate
HRMS High Resolution Mass Spectrocopy (electrospray ionisation positive scan)
Hünig's base N-ethyldiisopropylamine
Hyflo™ Hyflo Supercel®, from Aldrich Chemical Company
KHMDS potassium bis(trimethylsilyl)amide
liq Liquid
LRMS Low Resolution Mass Spectroscopy (electrospray or thermospray ionisation positive scan)
LRMS (ES⁻) Low Resolution Mass Spectroscopy (electrospray ionisation negative scan)
m Multiplet
m/z Mass spectrum peak
MCI™ gel High porous polymer, CHP20P 75-150 □m, from Mitsubishi Chemical Corporation
MeOH methanol
Mukaiyama's reagent 2-chloro-1-methylpyridinium iodide
NaHMDS sodium bis(trimethylsilyl)amide
NMM N-methylmorpholine
NMO 4-methylmorpholine N-oxide
NMP 1-methyl-2-pyrrolidinone
Phenomenex Luna C18 hplc column Supplied by Phenomenex. Composed of spherical silica particles (size 5 μm or 10 μm) which have a chemically bonded surface of C18 chains. These particles are packed into a stainless steel column of dimensions 2.1 cm internal diameter and 25 cm long.
psi Pounds per square inch (1 psi=6.9 kPa)
PyBOP® Benzotriazol-1-yloxytris(pyrrolidino)phosphonium hexafluorophosphate
PyBrOP® bromo-tris-pyrrolidino-phosphonium hexafluorophosphate
q Quartet
$R_f$ Retention factor on TLC
Singlet
Sep-Pak® Reverse phase $C_{18}$ silica gel cartridge, Waters Corporation
t Triplet
TBDMS—Cl tert-butyldimethylchlorosilane
TFA trifluoroacetic acid
THF tetrahydrofuran TLC Thin Layer Chromatography
TMS-CL chlorotrimethylsilane
WSCDI 1-(3-dimethylaminopropyl)-3-ethylcarbodiimide hydrochloride
δ Chemical shift The following Examples illustrate the preparation of the compounds of the formula (I):—

PREPARATION 1 tert-Butyl (3R)-3-methoxypyrrolidine-1-carboxylate

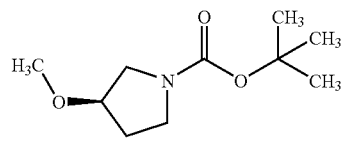

tert-Butyl (3R)-3-hydroxypyrrolidine-1-carboxylate (12.5 g, 66.70 mmol) was dissolved in tetrahydrofuran (334 mL) and the reaction mixture cooled to 0° C. in an ice bath. The reaction mixture was treated with 80% sodium hydride in mineral oil (2.20 g, 73.3 mmol) and stirred until back at room temperature. The reaction mixture was then treated with methyl iodide (14.5 g, 100.0 mmol) and stirred at room temperature for 18 hours. The reaction mixture was diluted with water (100 mL) and concentrated in vacuo until just the aqueous remained. The aqueous solution was treated with ethyl acetate (750 mL), the organic layer separated, dried over magnesium sulphate and concentrated in vacuo to yield the title product as a brown oil, 12.48 g. $^1$H NMR (CDCl$_3$, 400 MHz) δ: 1.41 (s, 9H), 1.95 (m, 2H), 3.30 (s, 3H), 3.40 (m, 4H), 3.86 (m, 1H)

PREPARATION 2 tert-Butyl (3S)-3-methoxypyrrolidine-1-carboxylate

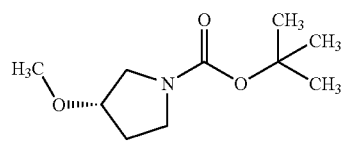

The title product was prepared by a method similar to that described for preparation 1 using tert-butyl (3S)-3-hydroxy-pyrrolidine-1-carboxylate. $^1$H NMR (CDCl$_3$, 400 MHz) δ: 1.41 (s, 9H), 1.95 (m, 2H), 3.30 (s, 3H), 3.40 (m, 4H), 3.86 (m, 1H)

PREPARATION 3

(3R)-3-Methoxy-pyrrolidine hydrochloride

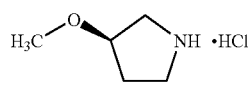

Hydrogen chloride gas was bubbled through an ice-cooled solution of the compound from preparation 1 (6.02 g, 30.0 mmol) in dichloromethane (30 mL), and the reaction then allowed to warm to room temperature and stirred for 48 hours. The solution was concentrated under reduced pressure and the residue triturated with ether. The resulting crystals were filtered off and dried in vacuo to afford the title compound. $^1$H NMR (CD$_3$OD, 400 MHz) δ: 2.06 (m, 1H), 2.20 (m, 1H), 3.26-3.42 (m, 7H), 4.17 (m, 1H).

PREPARATION 4

(3S)-3-Methoxy-pyrrolidine hydrochloride

The title compound was obtained from the compound from preparation 2, following a similar method to that described in preparation 3. $^1$H NMR (CD$_3$OD, 400 MHz) δ: 2.14 (m, 1H), 2.20 (m, 1H), 3.24-3.44 (m, 7H), 4.18 (m, 1H).

PREPARATION 5

2-Chloropyrimidin-4-ylamine

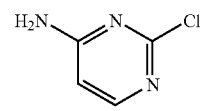

2,4-Dichloropyrimidine (625 mg, 4.23 mmol) was dissolved in n-butanol (3 mL) and the solution treated with ammonia (620 µL). The reaction mixture was heated to 100° C. for 20 minutes before being allowed to cool to room temperature. Methanol was added to help dissolved the precipitate formed on cooling and the solution was concentrated in vacuo. The residue was purified by column chromatography on silica gel eluting with dichloromethane:methanol 100:0 to 96:4. $^1$H NMR (CD$_3$OD, 400 MHz) δ: 6.41 (d, 1H), 7.90 (d, 1H)

PREPARATION 6

2-Methoxypyrimidin-4-ylamine

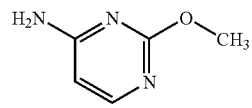

The chloro compound of preparation 5 (1.52 g, 11.8 mmol) was dissolved in methanol (17 mL) and the solution treated with a 4.62M solution of sodium methoxide in methanol (2.8 mL, 12.9 mmol). The reaction mixture was then refluxed under nitrogen for 6 hours. The reaction mixture was filtered whilst hot and concentrated in vacuo to a volume of 2 mL and the solid allowed to crystallise out. The crude product was recrystallised from methanol and dried in an oven to yield the title product, 390 mg. $^1$H NMR (DMSO-D$_6$, 400 MHz) δ: 3.75 (s, 3H), 6.05 (d, 1H), 6.80 (m, 2H), 7.80 (d, 1H)

PREPARATION 7

Dimethyl 4-nitro-1-(2-propoxyethyl)-1H-pyrazole-3,5-dicarboxylate

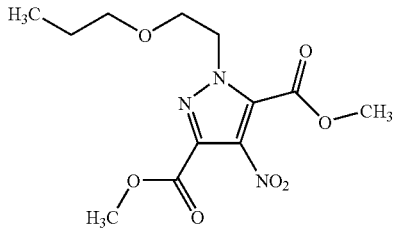

Dimethyl 4-nitro-1H-pyrazole-3,5-dicarboxylate (WO00/24745, page 48, preparation 2) (15 g, 60 mmol), 2-propoxyethanol (8.2 mL, 70 mmol) and triphenylphosphine (18.9 g, 70 mmol) were dissolved in tetrahydrofuran (150 mL) and the solution cooled to 0° C. The solution was treated with diisopropyl azodicarboxylate (14.2 mL, 70 mmol) and the reaction mixture stirred at 0° C. for 3 hours before being allowed to warm to room temperature. The reaction mixture was concentrated in vacuo and the residue purified by column chromatography on silica gel eluting with ethyl acetate:pentane 15:85 and then again eluting with dichloromethane to yield the title product. $^1$H NMR (CD$_3$OD, 400 MHz) δ: 0.82 (t, 3H), 1.47 (q, 2H), 3.34 (t, 2H), 3.78 (t, 2H), 3.91 (s, 6H), 4.76 (t, 2H). MS APCI+ m/Z 316 [MH]$^+$

PREPARATION 8

Dimethyl (2'R)-1-(2'-methoxypropyl)-4-nitro-1H-pyrazole-3,5-dicarboxylate

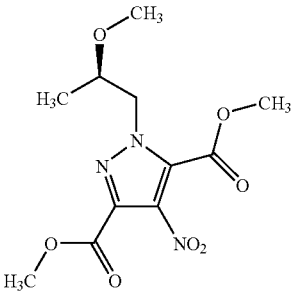

The title compound was prepared by a method similar to that described for preparation 7 using (2R)-2-methoxypropanol (Chem. Eur. J., 1997, 3 (12), 2063-2070). The title product was purified by column chromatography on silica gel eluting with pentane:dichloromethane 20:80. $^1$H NMR (CDCl$_3$, 400 MHz) δ: 1.18 (d, 3H), 3.20 (s, 3H), 3.70 (m, 1H), 3.92 (s, 3H), 3.94 (s, 3H), 4.42 (m, 1H), 4.74 (m, 1H). MS APCI+ m/z 302 [MH]$^+$

PREPARATION 9

Dimethyl 1-(2-isopropoxyethyl)-4-nitro-1H-pyrazole-3,5-dicarboxylate

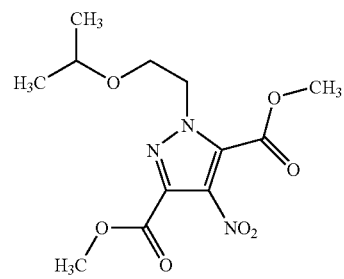

Dimethyl 4-nitro-1H-pyrazole-3,5-dicarboxylate (11.4 g, 50 mmol) was dissolved in tetrahydrofuran (200 mL) and the solution treated with triphenylphosphine (14.4 g, 55 mmol) and 2-isopropoxyethanol (6.36 mL, 55 mmol). The mixture was cooled on an ice bath to 0° C. and diisopropyl azodicarboxylate (10.8 mL, 55 mmol) added dropwise over 10 minutes, keeping the temperature between 20° C. and 30° C. The reaction mixture was then stirred at room temperature for 30 minutes. The reaction mixture was concentrated in vacuo and the crude product azeotroped with dichloromethane to yield the title product. $^1$H NMR (CDCl$_3$, 400 MHz) δ: 1.02 (d, 6H), 3.45 (m, 1H), 3.72 (t, 2H), 3.90 (s, 3H), 3.94 (s, 3H), 4.74 (t, 2H). MS ES+ m/z 216 [MH]$^+$ The following compounds, of the general formula shown below, were prepared by a method similar to that described for preparation 9, using the appropriate R$^6$OH alcohol.

| No | R$^6$ | Data |
|---|---|---|
| 10 | —(CH$_2$)$_2$CH(CH$_3$)OCH$_3$ | $^1$H NMR (CDCl$_3$, 400 MHz) δ: 1.10 (d, 3H), 2.00 (m, 2H), 3.20 (s, 3H), 3.30 (m, 1H), 3.86 (m, 6H), 4.62 (m, 2H) |
| 11 | cyclopropyl-CH$_2$-O-CH$_2$- | $^1$H NMR (CDCl$_3$, 400 MHz) δ: 0.11 (m, 2H), 0.48 (m, 2H), 0.92 (m, 1H), 3.22 (d, 2H), 3.90 (m, 2H), 3.97 (m, 6H), 4.81 (m, 2H), MS ES+ m/z 350 [MNa]$^+$ |
| 12 | tetrahydropyran-4-yl-CH$_2$- | $^1$H NMR (CDCl$_3$, 400 MHz) δ: 1.47 (m, 2H), 1.86 (m, 2H), 2.24 (m, 1H), 3.36 (m, 2H), 3.74 (m, 2H), 3.93 (s, 3H), 3.97 (s, 3H), 4.52 (d, 2H). MS ES+ m/z 328 [MH]$^+$ |

-continued

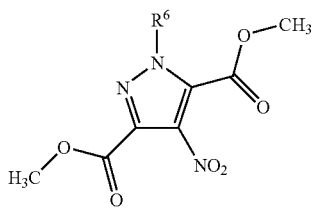

| No | R⁶ | Data |
|---|---|---|
| 13 | (tetrahydropyran-2-ylmethyl group) | ¹H NMR (CDCl₃, 400 MHz) δ: 1.50 (m, 4H), 1.84 (m, 2H), 3.27 (m, 1H), 3.60-3.90 (m, 2H), 3.92 (s, 3H), 3.94 (s, 3H), 4.45 (m, 1H), 4.73 (m, 1H). MS APCI+ m/z 328 [MH]⁺ |

Preparation 11 was prepared using 2-(cyclopropylmethoxy)ethanol (FR 2248255, Pg. 2, example 1) as the R⁶OH alcohol.
Preparation 12 was prepared using tetrahydro-2H-pyran-4-methanol (DE 4233431, Pg. 4, example 1) as the R⁶OH alcohol.

PREPARATION 14

Dimethyl 1-(2-ethoxyethyl)-4-nitro-1H-pyrazole-3,5-dicarboxylate

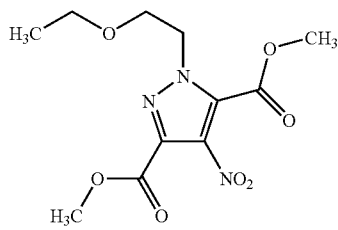

Dimethyl 4-nitro-1H-pyrazole-3,5-dicarboxylate (2.0 g, 8.83 mmol) was added to a solution of 2-ethoxyethyl bromide (1.18 mL, 10.45 mmol) and potassium carbonate (1.32 g, 9.56 mmol) in N,N-dimethylformamide (35 mL) and the reaction mixture stirred for 48 hours at room temperature. The reaction mixture was concentrated in vacuo and the residue partitioned between ethyl acetate (200 mL) and water (100 mL). The organic layer was separated, dried over magnesium sulphate and concentrated in vacuo. The crude product was purified by column chromatography on silica gel eluting with pentane:ethyl acetate 100:0 to 70:30 to yield the title product, 1.63 g. ¹H NMR (CDCl₃, 400 MHz) δ: 1.07 (s, 3H), 3.41 (q, 2H), 3.73 (t, 2H), 3.89 (s, 3H), 3.94 (s, 3H), 4.76 (t, 2H). MS APCI+ m/z 302, [MH]⁺

PREPARATION 15

Dimethyl 1-[2-(2-methoxyethoxy)ethyl]-4-nitro-1H-pyrazole-3,5-dicarboxylate

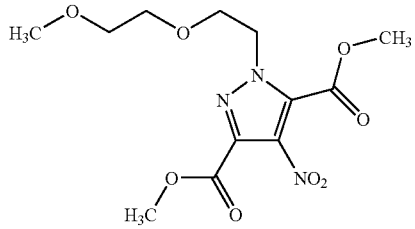

Dimethyl 4-nitro-1H-pyrazole-3,5-dicarboxylate (9.53 g, 41.6 mmol) and potassium carbonate (3.44 g, 25 mmol) were dissolved in N,N-dimethylformamide (140 mL) under nitrogen. The mixture was then treated with a solution of 1-bromo-2-(2-methoxyethoxy)ethane (9.90 g, 54 mmol) in N,N-dimethylformamide (10 mL). The reaction mixture was stirred at 30° C. for 18 hours and then allowed to cool to room temperature. Additional 1-bromo-2-(2-methoxyethoxy)ethane (9.90 g, 54 mmol) and potassium carbonate (3.44 g, 25 mmol) were added and the reaction mixture allowed to stir at 30° C. for 4 hours. The reaction mixture was concentrated in vacuo and the residue taken up in ethyl acetate (200 mL) and water (200 mL). The aqueous was separated and washed with ethyl acetate (200 mL), the organics were combined and washed with water. The organic layer was dried over magnesium sulphate and concentrated in vacuo to yield the title product. ¹H NMR (CDCl₃, 400 MHz) δ: 3.25 (s, 3H), 3.38 (m, 2H), 3.50 (m, 2H), 3.80 (t, 2H), 3.92 (s, 3H), 3.93 (s, 3H), 4.77 (t, 2H). MS APCI+ m/z 333 [MH]⁺

PREPARATION 16

Dimethyl 1-(2-methoxyethyl)-4-nitro-1H-pyrazole-3,5-dicarboxylate

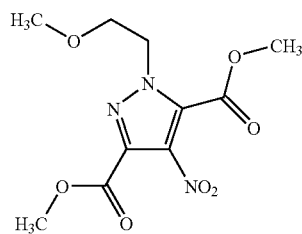

The title compound was prepared by a method similar to that described for preparation 15 using 1-bromo-2-methoxyethane. ¹H NMR (CDCl₃, 400 MHz) δ: 3.22 (s, 3H), 3.67 (m, 2H), 3.89 (m, 6H), 4.77 (m, 2H). MS ES+ m/z 288 [MH]⁺

PREPARATION 17

4-Nitro-1-(2-propoxyethyl)-1H-pyrazole-3,5-dicarboxylic acid 3-methyl ester

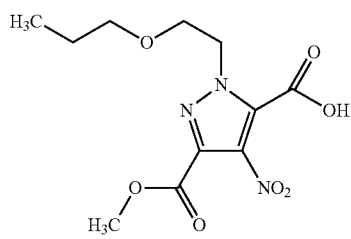

The ester of preparation 7 (150 mg, 0.5 mmol) and potassium hydroxide (29 mg, 0.55 mmol) were dissolved in methanol (2 mL) and the reaction mixture stirred at room temperature for 48 hours. The reaction mixture was concentrated in vacuo and the residue taken up in water. The aqueous was washed with ether (×2) and extracted with dichloromethane. The organic phase was then washed with 2M hydrochloric acid (×2) and water (×2), dried over magnesium sulphate and concentrated in vacuo to yield the title product. ¹H NMR (CD₃OD, 400 MHz) δ: 0.83 (t, 3H), 1.49 (q, 2H), 3.36 (t, 2H), 3.80 (t, 2H), 3.90 (s, 3H), 4.78 (t, 2H). MS APCI+ m/z 302 [MH]⁺

PREPARATION 18

4-Nitro-1-(2-ethoxyethyl)-1H-pyrazole-3,5-dicarboxylic acid 3-methyl ester

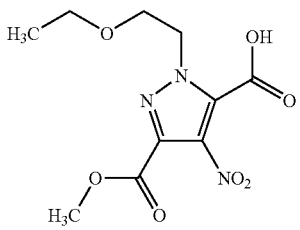

The ester of preparation 14 (1.63 g, 5.4 mmol) was added to a solution of potassium hydroxide (330 mg, 5.9 mmol) in methanol (20 mL) and the reaction mixture stirred at room temperature for 18 hours. The reaction mixture was concentrated in vacuo and the crude product dissolved in water and washed with ether. The aqueous phase was acidified with 2M hydrochloric acid and extracted into dichloromethane (3×100 mL). The organics were combined, dried over magnesium sulphate and concentrated in vacuo to yield the title product. ¹H NMR (CD₃OD, 400 MHz) δ: 1.07 (s, 3H), 3.47 (q, 2H), 3.80 (t, 2H), 3.88 (s, 3H), 4.77 (t, 2H). MS APCI+ m/z 288 [MH]⁺

PREPARATION 19

1-(2-Isopropoxyethyl)-4-nitro-1H-pyrazole-3,5-dicarboxylic acid 3-methyl ester

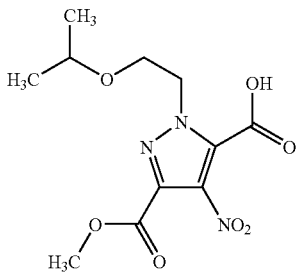

The ester of preparation 9 (15.8 g, 50 mmol) was dissolved in methanol (200 mL) and the solution cooled in an ice bath before being treated with potassium hydroxide (2.8 g, 50 mmol). The reaction mixture was then stirred at room temperature for 18 hours. The reaction mixture was concentrated in vacuo and the residue partitioned between dichloromethane (500 mL) and water (250 mL). The aqueous phase was separated, acidified with hydrochloric acid and then extracted with dichloromethane (2×500 mL). The combined dichloromethane extracts were dried over magnesium sulphate and concentrated in vacuo to yield the title product as a white solid, 11.4 g. ¹H NMR (DMSO-D₆, 400 MHz) δ: 0.92 (d, 6H), 3.45 (m, 1H), 3.67 (t, 2H), 3.82 (s, 3H), 4.66 (t, 2H). MS ES+ m/z 302 [MH]⁺

The following compounds, of the general formula shown below, were prepared by a method similar to that described for preparation 19 using the appropriate ester of preparations 8, 10, 11, 13, 15 and 16

| No | R⁶ | Data |
|---|---|---|
| 20 | —(CH₂)₂CH(CH₃)OCH₃ | ¹H NMR (DMSO-D₆, 400 MHz) δ: 1.02 (d, 3H), 1.90 (m, 2H), 3.18 (s, 3H), 3.28 (m, 3H), 3.37 (m, 1H), 4.58 (m, 2H). |
| 21 | —(CH₂)₂O(CH₂)₂OCH₃ | ¹H NMR (CDCl₃, 400 MHz) δ: 3.30 (s, 3H), 3.50 (m, 2H), 3.58 (m, 2H), 3.90 (m, 5H), 4.80 (t, 2H). MS APCI+ m/z 318 [MH]⁺ |
| 22 | H₃C—O—CH(CH₃)—CH₂— | ¹H NMR (DMSO-D₆, 400 MHz) δ: 1.05 (d, 3H), 3.14 (s, 3H), 3.72 (m, 1H), 3.84 (s, 3H), 4.48 (m, 1H), 4.60 (m, 1H). MS APCI+ m/z 288 [MH]⁺ |
| 23 | cyclopropyl-CH₂-O-CH₂— | ¹H NMR (CDCl₃, 400 MHz) δ: 0.12 (m, 2H), 0.48 (m, 2H), 0.95 (m, 1H), 3.32 (d, 2H), 3.91 (m, 5H), 4.83 (t, 2H). MS ES− m/z 312 [M − H]⁻ |
| 24 | —(CH₂)₂OCH₃ | ¹H NMR (DMSO-D₆, 400 MHz) δ: 3.22 (s, 3H), 3.71 (m, 2H), 3.83 (s, 3H), 4.77 (m, 2H), 9.95 (m, 1H). MS ES+ m/z 274 [MH]⁺ |
| 25 | tetrahydropyran-2-yl-CH₂— | ¹H NMR (DMSO-D⁶, 400 MHz) δ: 1.19 (m, 1H), 1.36 (m, 3H), 1.58 (m, 1H), 1.73 (m, 1H), 3.22 (m, 1H), 3.66 (m, 1H), 3.75 (m, 1H), 3.80 (s, 3H), 4.47 (m, 1H), 4.60 (m, 1H). MS APCI+ m/z 314 [MH]⁺ |

PREPARATION 26

4-Nitro-1-(tetrahydropyran-4-ylmethyl)-1H-pyrazole-3,5-dicarboxylic acid 3-methyl ester

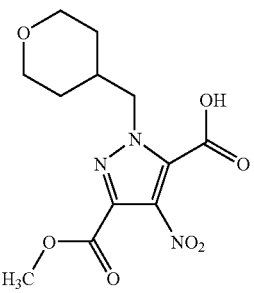

The ester of preparation 12 (13.7 g, 42 mmol) was added to a solution of potassium hydroxide (2.59 g, 46.2 mmol) in methanol (200 mL) and the reaction mixture stirred at room temperature for 18 hours. The reaction mixture was concentrated in vacuo and the residue partitioned between dichloromethane (300 mL) and water (200 mL). The dichloromethane layer was concentrated in vacuo and the residue partitioned between ether (200 mL) and water (200 mL). The aqueous was added to the first aqueous extract, washed with ether (2×200 mL) and acidified with hydrochloric acid. The solution was extracted with dichloromethane (3×400 mL), dried over magnesium sulphate and concentrated in vacuo to yield the title product. $^1$H NMR (DMSO-D$_6$, 400 MHz) δ: 1.24 (m, 2H), 1.36 (m, 2H), 2.10 (m, 1H), 3.20 (m, 2H), 3.78 (m, 2H), 3.84 (s, 3H), 4.43 (d, 2H). MS APCI+ m/z 314 [MH]$^+$

PREPARATION 27

Methyl 5-carbamoyl-4-nitro-1-(2-propoxyethyl)-1H-pyrazole-3-carboxylate

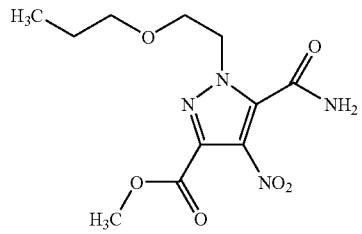

The carboxylic acid of preparation 17 (13.2 g, 44 mmol) was dissolved in dichloromethane (140 mL) and the solution treated with N,N-dimethylformamide (150 μL). The mixture was cooled in an ice bath with acetone to −5° C. and oxalyl chloride (11.48 mL, 132 mmol) added dropwise over 30 minutes. The reaction mixture was stirred at −5° C. for 1 hour and then allowed to warm to room temperature and stirred for a further 90 minutes. The reaction mixture was concentrated in vacuo and the residue azeotroped with dichloromethane (×2). The crude product was dissolved in tetrahydrofuran and cooled in an ice bath. 0.88 Ammonia (60 mL) was added to the reaction mixture over 10 minutes, the ice bath removed and the reaction mixture stirred for 1 hour until at room temperature. The reaction mixture was concentrated in vacuo and the residue taken up in water. The precipitate formed was filtered off and dried for 18 hours in an oven at 70° C. to yield the title product, 10.22 g. $^1$H NMR (DMSO-D$_6$, 400 MHz) δ: 0.81 (t, 3H), 1.45 (q, 2H), 3.32 (t, 2H), 3.74 (t, 2H), 3.90 (s, 3H), 4.40 (t, 2H), 8.33 (s, 1H), 8.48 (s, 1H)

PREPARATION 28

Methyl 5-carbamoyl-1-(2-methoxyethyl)-4-nitro-1H-pyrazole-3-carboxylate

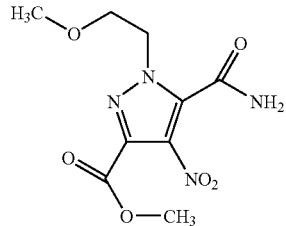

The title compound was prepared by a method similar to that described for preparation 27 using the carboxylic acid of preparation 24. $^1$H NMR (DMSO-D$_6$, 400 MHz) δ: 3.18 (s, 3H), 3.65 (m, 2H), 4.82 (s, 3H), 4.38 (m, 2H), 8.33 (m, 1H), 8.47 (m, 1H). MS ES+ m/z 273 [MH]$^+$

PREPARATION 29

Methyl 5-carbamoyl-1-(2-ethoxyethyl)-4-nitro-1H-pyrazole-3-carboxylate

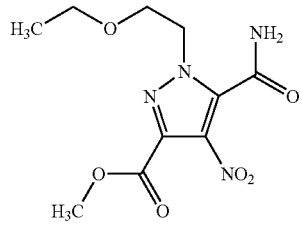

Oxalyl chloride (1.2 mL, 13.76 mmol) and N,N-dimethylformamide (39 μL) were added to a solution of the carboxylic acid of preparation 18 (1.33 g, 4.63 mmol) in dichloromethane (20 mL) and the reaction mixture stirred at room temperature for 2 hours. The reaction mixture was concentrated in vacuo and azeotroped from dichloromethane (3×50 mL). The product was dissolved in tetrahydrofuran (50 mL), cooled in an ice bath, treated with 0.88 ammonia solution (10 mL) and stirred for 18 hours at room temperature. The mixture was concentrated in vacuo and the residue partitioned between dichloromethane (200 mL) and water (50 mL). The organics phase was dried over magnesium sulphate and concentrated in vacuo to yield the title product. $^1$H NMR (DMSO-D$_6$, 400 MHz) δ: 1.06 (t, 3H), 2.48 (m, 2H), 3.77 (m, 2H), 3.84 (s, 3H), 4.38 (m, 2H), 8.35 (m, 1H), 8.46 (m, 1H). MS APCI+ m/z 287 [MH]$^+$

PREPARATION 30

Methyl 5-carbamoyl-1-[2-(2-methoxy-ethoxy)-ethyl]-4-nitro-1H-pyrazole-3-carboxylate

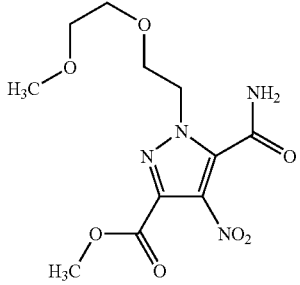

The title product was prepared by a method similar to that described for preparation 29 using the carboxylic acid of preparation 21. $^1$H NMR (CDCl$_3$, 400 MHz) δ: 3.30 (s, 3H), 3.50 (m, 2H), 3.58 (m, 2H), 3.90 (m, 2H), 3.99 (s, 3H), 4.50 (t, 2H), 6.25 (m, 1H), 7.80 (m, 1H). MS APCI+ m/z 317 [MH]$^+$

PREPARATION 31

Methyl 5-carbamoyl-1-(2-cyclopropylmethoxy-ethyl)-4-nitro-1H-pyrazole-3-carboxylate

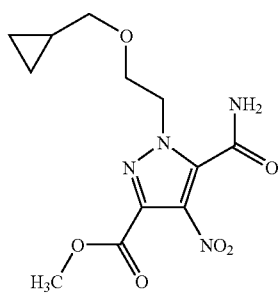

The title compound was prepared by a method similar to that described for preparation 29 using the carboxylic acid of preparation 23. $^1$H NMR (CDCl$_3$, 400 MHz) δ: 0.12 (m, 2H), 0.52 (m, 2H), 0.95 (m, 1H), 3.27 (m, 2H), 3.87 (t, 2H), 3.96 (s, 3H), 4.61 (t, 2H), 6.09 (m, 1H), 7.72 (m, 1H). MS ES+ m/z 335 [MNa]$^+$

PREPARATION 32

Methyl 5-carbamoyl-1-(2-isopropoxyethyl)-4-nitro-1H-pyrazole-3-carboxylate

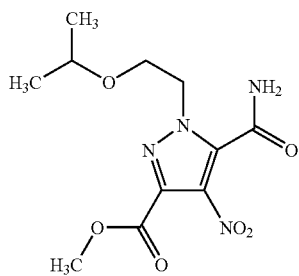

The carboxylic acid of preparation 19 (11.9, 37.8 mmol) was dissolved in dichloromethane (140 mL) and the solution treated with oxalyl chloride (4.0 mL, 45.4 mmol) and N,N-dimethylformamide (310 μL, 4 mmol). The reaction mixture was stirred at room temperature for 18 hours, then concentrated in vacuo and the residue azeotroped with dichloromethane (2×100 mL). The product was dissolved in tetrahydrofuran (200 mL) and the solution cooled in an ice bath and then treated with 0.88 ammonia (50 mL). The reaction mixture was stirred for 15 minutes before being concentrated in vacuo and partitioned between dichloromethane (1000 mL) and water (500 mL). The aqueous was separated and extracted with dichloromethane (3×300 mL), the organics were combined, dried over magnesium sulphate and concentrated in vacuo to yield the title product, 10.4 g. $^1$H NMR (DMSO-D$_6$, 400 MHz) δ: 0.95 (d, 6H), 3.44 (m, 1H), 3.68 (t, 2H), 3.83 (s, 3H), 4.66 (t, 2H). MS APCI+ m/z 301 [MH]$^+$ The following compounds, of the general formula shown below, were prepared by a method similar to that described for preparation 32, using the appropriate carboxylic acid of preparations 20 and 22.

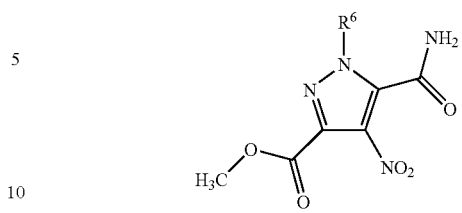

| No | R$^6$ | Data |
|---|---|---|
| 33 | —(CH$_2$)$_2$CH(CH$_3$)OCH$_3$ | $^1$H NMR (CDCl$_3$, 400 MHz) δ: 1.16 (d, 3H), 2.08 (m, 2H), 3.25 (s, 3H), 3.38 (m, 1H), 3.97 (s, 3H), 4.59 (t, 2H). MS ES– m/z 299 [M – H]$^-$ |
| 34 | H$_3$C–O–CH(CH$_3$)–CH$_2$– | $^1$H NMR (DMSO-D$_6$, 400 MHz) δ: 1.08 (d, 3H), 3.04 (s, 3H), 3.73 (m, 1H), 3.84 (s, 3H), 4.25 (m, 2H), 8.30 (s, 1H), 8.48 (s, 1H). MS ES+ m/z 309 [MNa]$^+$ |

PREPARATION 35

Methyl 5-carbamoyl-4-nitro-1-(tetrahydropyran-4-ylmethyl)-1H-pyrazole-3-carboxylate

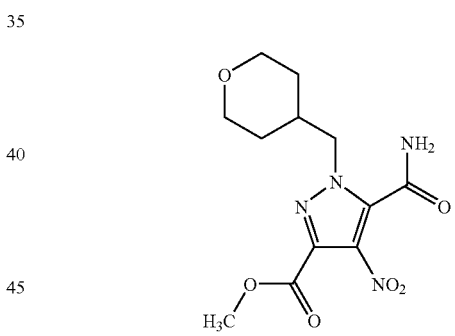

The carboxylic acid of preparation 26 (11.3 g, 36 mmol) was dissolved in dichloromethane (150 mL) and the solution treated with oxalyl chloride (38 mL, 43.2 mmol) and N,N-dimethylformamide (280 μL, 3.6 mmol). The reaction mixture was stirred at room temperature for 18 hours and then concentrated in vacuo. The residue was azeotroped from dichloromethane (2×200 mL) and the resulting solid dissolved in tetrahydrofuran and cooled to –30° C. The solution was treated with 0.88 ammonia (3.85 mL, 79.2 mmol) and stirred at –30° C. for 1 hour. The reaction mixture was concentrated in vacuo, diluted with water (100 mL) and extracted with ethyl acetate (2×400 mL). The combined organics were dried over magnesium sulphate and concentrated in vacuo. The residue was triturated with methanol and ether and dried in vacuo to yield the title product. $^1$H NMR (DMSO-D$_6$, 400 MHz) δ: 1.20 (m, 2H), 1.40 (m, 2H), 2.10 (m, 1H), 3.22 (m, 2H), 3.81 (m, 2H), 3.86 (s, 3H), 4.19 (d, 2H), 8.37 (m, 1H), 8.53 (m, 1H). MS APCI+ m/z 313 [MH]$^+$

PREPARATION 36

Methyl 5-carbamoyl-4-nitro-1-(tetrahydropyran-2-ylmethyl)-1H-pyrazole-3-carboxylate

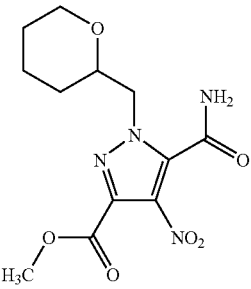

The title compound was prepared by a method similar to that described for preparation 35 using the carboxylic acid of preparation 25. $^1$H NMR (DMSO-D$_6$, 400 MHz) δ: 1.18 (m, 1H), 1.40 (m, 3H), 1.58 (m, 1H), 1.78 (m, 1H), 3.22 (m, 1H), 3.65 (m, 1H), 3.78 (m, 1H), 3.85 (s, 3H), 4.22 (m, 2H), 8.27 (m, 1H), 8.46 (m, 1H). MS APCI+ m/z 313 [MH]$^+$

PREPARATION 37

Methyl 4-amino-5-carbamoyl-1-(2-propoxyethyl)-1H-pyrazole-3-carboxylate

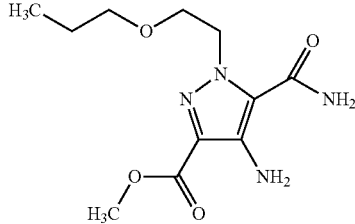

The nitro compound of preparation 27 (10 g, 33 mmol) was dissolved in ethanol (180 mL) and the solution treated with palladium(II) hydroxide (933 mg, 6.7 mmol) and heated to 75° C. Ammonium formate (21 g, 330 mmol) was added and the reaction mixture was stirred at 75° C. for 3 hours. The reaction mixture was filtered through Arbocel® under nitrogen washing through with ethanol. The filtrate was concentrated in vacuo to yield the title product as a pale pink solid, 9.1 g. $^1$H NMR (CD$_3$OD, 400 MHz) δ: 0.84 (t, 3H), 1.51 (q, 2H), 3.40 (t, 2H), 3.83 (t, 2H), 3.89 (s, 3H), 4.56 (t, 2H). MS APCI+ m/z 271 [MH]$^+$

PREPARATION 38

Methyl 4-amino-5-carbamoyl-1-(2-ethoxyethyl)-1H-pyrazole-3-carboxylate

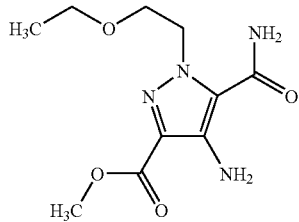

Palladium (II) hydroxide (100 mg) was added to a solution of the nitro compound of preparation 29 (970 mg, 3.39 mmol) in methanol (20 mL) and the mixture warmed to reflux. Ammonium formate (1.07 g, 16.97 mmol) was added and the reaction mixture stirred at reflux for 2 hours. The catalyst was removed by filtration through Arbocel® and the reaction mixture concentrated in vacuo to yield the title product. $^1$H NMR (DMSO-D$_6$, 400 MHz) δ: 1.02 (t, 3H), 3.33 (m, 2H), 3.66 (m, 2H), 4.80 (s, 3H), 4.57 (m, 2H), 5.11 (m, 2H), 7.49 (m, 2H). MS APCI+ m/z 257 [MH]$^+$ The following compounds, of the general formula shown below, were prepared by a method similar to that described for preparation 38 using the appropriate nitro-pyrazoles of preparations 30, 31, 32, 33, 34, 35 and 36.

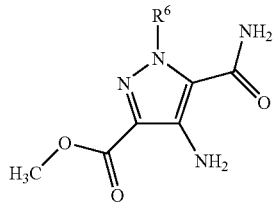

| No | R$^6$ | Data |
|---|---|---|
| 39 | —(CH$_2$)$_2$OCH(CH$_3$)$_2$ | $^1$H NMR (DMSO-D$_6$, 400 MHz) δ: 0.98 (d, 6H), 3.48 (m, 1H), 3.64 (m, 2H), 3.76 (s, 3H), 4.45 (t, 2H), 5.14 (m, 2H), 7.50 (m, 2H). MS ES+ m/z 293 [MNa]$^+$ |
| 40 | —(CH$_2$)$_2$CH(CH$_3$)OCH$_3$ | $^1$H NMR (CDCl$_3$, 400 MHz) δ: 1.10 (d, 3H), 1.90 (m, 2H), 3.25 (s, 3H), 3.30 (m, 1H), 3.90 (s, 3H), 4.50 (m, 2H), 4.92 (m, 2H), 6.50 (m, 2H). MS APCI+ m/z 271 [MH]$^+$ |
| 41 | —(CH$_2$)$_2$O(CH$_2$)$_2$OCH$_3$ | $^1$H NMR (CDCl$_3$, 400 MHz) δ: 3.30 (s, 3H), 3.50 (m, 2H), 3.58 (m, 2H), 3.90 (s, 3H), 3.99 (t, 2H), 4.50 (t, 2H). MS APCI+ m/z 309 [MNa]$^+$ |
| 42 | 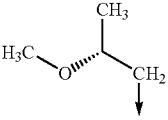 | $^1$H NMR (DMSO-D$_6$, 400 MHz) δ: 1.04 (d, 3H), 3.12 (s, 3H), 3.65 (m, 1H), 3.78 (s, 3H), 4.30 (m, 1H), 4.44 (m, 1H), 5.10 (m, 2H), 7.48 (m, 2H). MS APCI+ m/z 257 [MH]$^+$ |
| 43 | 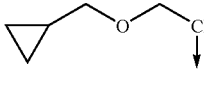 | $^1$H NMR (CDCl$_3$, 400 MHz) δ: 0.12 (m, 2H), 0.50 (m, 2H), 0.97 (m, 1H), 3.30 (d, 2H), 3.92 (m, 5H), 4.53 (t, 2H). MS ES+ m/z 305 [MNa]$^+$ |
| 44 | 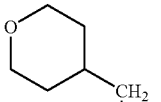 | $^1$H NMR (DMSO-D$_6$, 400 MHz) δ: 1.19 (m, 2H), 1.30 (m, 2H), 1.96 (m, 1H), 3.20 (m, 2H), 3.76 (m, 5H), 4.28 (d, 2H), 5.10 (m, 2H), 7.44 (m, 2H). MS APCI+ m/z 283 [MH]$^+$ |
| 45 | 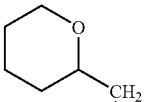 | $^1$H NMR (CD$_3$OD, 400 MHz) δ: 1.27 (m, 1H), 1.52 (m, 3H), 1.67 (m, 1H), 1.87 (m, 1H), 3.38 (m, 1H), 3.78 (m, 1H), 3.88 (s, 3H), 3.94 (m, 1H), 4.30 (m, 1H), 4.45 (m, 1H). MS APCI+ m/z 283 [MH]$^+$ |

PREPARATION 46

Methyl 4-amino-5-carbamoyl-1-(2-methoxyethyl)-1H-pyrazole-3-carboxylate

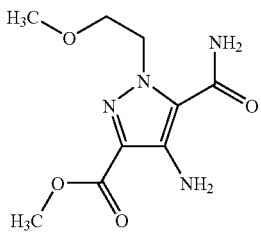

The nitro compound of preparation 28 (1.00 g, 3.7 mmol) was dissolved in ethyl acetate (15 mL) and treated with 10% Pd/C (100 mg). The reaction mixture was stirred at room temperature under 15 psi of hydrogen for 18 hours. The reaction mixture was filtered through Arbocel®, washing with ethyl acetate and the filtrate concentrated in vacuo. The residue was purified by column chromatography on silica gel eluting with pentane:ethyl acetate 50:50 to 34:66 to 0:100 to yield the title product. $^1$H NMR (DMSO-D$_6$, 400 MHz) δ: 3.16 (s, 3H), 3.60 (m, 2H), 3.76 (s, 3H), 4.45 (m, 2H), 5.07 (m, 2H), 7.42 (m, 2H). MS ES+ m/z 244 [MH]$^+$

PREPARATION 47

Methyl 5,7-dioxo-1-(2-propoxyethyl)-4,5,6,7-tetrahydro-1H-pyrazolo[4,3-d]pyrimidine-3-carboxylate

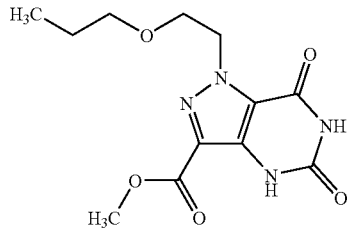

The amide of preparation 37 (9 g, 33 mmol) and N,N'-carbonyldiimidazole (5.4 g, 33 mmol) were dissolved in N,N-dimethylformamide (400 mL) and the reaction mixture stirred at room temperature for 30 minutes and then at 75° C. for 18 hours. Additional N,N'-carbonyldiimidazole (400 mg, 2.69 mmol) was added and the reaction mixture stirred for a further 90 minutes. The reaction mixture was concentrated in vacuo and the residue taken up in water and stirred for 30 minutes. The precipitate formed was filtered off to yield the title product as a pale pink solid, 6.05 g. $^1$H NMR (DMSO-D$_6$, 400 MHz) δ: 0.72 (t, 3H), 1.37 (q, 2H), 3.28 (t, 2H), 3.76 (t, 2H), 3.82 (s, 3H), 4.64 (t, 2H), 10.77 (s, 1H), 11.37 (s, 1H). MS APCI− m/z 295, [M-H]$^-$

PREPARATION 48

Methyl 1-(2-ethoxyethyl)-5,7-dioxo-4,5,6,7-tetrahydro-1H-pyrazolo[4,3-d]pyrimidine-3-carboxylate

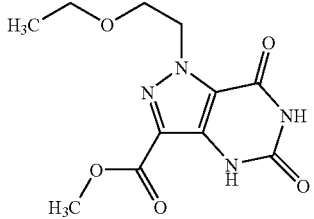

A solution of the amide of preparation 38 (570 mg, 3.38 mmol) in N,N-dimethylformamide (30 mL) was treated with N,N'-carbonyldiimidazole (658 mg, 4.06 mmol) and the reaction mixture stirred at room temperature for 1 hour and then at 90° C. for 18 hours. The reaction mixture was concentrated in vacuo and the crude product suspended in acetone and sonicated for 30 minutes. The solid product was filtered off and dried in vacuo to yield the title product. $^1$H NMR (DMSO-D$_6$, 400 MHz) δ: 1.02 (t, 3H), 3.37 (m, 2H), 3.77 (m, 2H), 4.83 (s, 3H), 4.63 (m, 2H), 10.75 (s, 1H), 11.40 (s, 1H). MS ES− m/z 281 [M-H]$^-$ The following compounds, of the general formula shown below, were prepared by a method similar to that described for preparation 48, using the appropriate amide of preparations 39, 40, 41, 42, 43 and 46.

| No. | R$^6$ | Data |
|---|---|---|
| 49 | —(CH$_2$)$_2$OCH(CH$_3$)$_2$ | $^1$H NMR (DMSO-D$_6$, 400 MHz) δ: 0.95 (d, 6H), 3.47 (m, 1H), 3.73 (t, 2H), 3.80 (s, 3H), 4.58 (t, 2H), 10.78 (m, 1H), 11.47 (m, 1H). MS ES+ m/z 319 [MNa]$^+$ |
| 50 | —(CH$_2$)$_2$CH(CH$_3$)OCH$_3$ | $^1$H NMR (DMSO-D$_6$, 400 MHz) δ: 1.02 (d, 3H), 1.90 (m, 2H), 3.17 (s, 3H), 3.30 (m, 1H), 3.80 (s, 3H), 4.50 (t, 2H), 7.00 (m, 1H), 7.60 (m, 1H). MS APCI− m/z 295 [M − H]$^-$ |
| 51 | —(CH$_2$)O(CH$_2$)$_2$OCH$_3$ | $^1$H NMR (DMSO-D$_6$, 400 MHz) δ: 3.15 (s, 3H), 3.30 (t, 2H), 3.45 (t, 2H), 3.80 (t, 5H), 4.60 (t, 2H). MS APCI+ m/z 311 [M − H]$^-$ |
| 52 | ![structure: H3C-O(stereo)-CH(CH3)-CH2-] | $^1$H NMR (DMSO-D$_6$, 400 MHz) δ: 1.07 (d, 3H), 3.14 (s, 3H), 3.74 (m, 1H), 3.82 (s, 3H), 4.40 (m, 1H), 4.60 (m, 1H), 10.76 (m, 1H), 11.37 (m, 1H). MS APCI+ m/z 283 [MH]$^+$ |

-continued

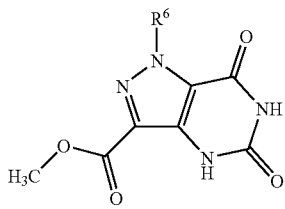

| No. | R⁶ | Data |
|---|---|---|
| 53 | CH₂−O−CH₂−cyclopropyl (arrow) | ¹H NMR (DMSO-D₆, 400 MHz) δ: 0.06 (m, 2H), 0.35 (m, 2H), 0.83 (m, 1H), 3.16 (d, 2H), 3.78 (t, 2H), 3.81 (s, 3H), 4.61 (t, 2H), 10.77 (m, 1H), 11.37 (m, 1H). MS ES+ m/z 331 [MNa]⁺ |
| 54 | —(CH₂)₂OCH₃ | ¹H NMR (DMSO-D₆, 400 MHz) δ: 3.17 (s, 3H), 3.69 (m, 2H), 3.80 (s, 3H), 4.61 (m, 2H), 10.74 (m, 1H), 11.37 (m, 1H). MS ES+ m/z 269 [MH]⁺ |

PREPARATION 55

Methyl 5,7-dioxo-1-(tetrahydropyran-4-ylmethyl)-4,5,6,7-tetrahydro-1H-pyrazolo[4,3-d]pyrimidine-3-carboxylate

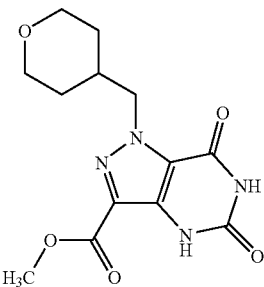

The amide of preparation 44 (9.8 g, 34.9 mmol) was dissolved in acetonitrile (100 mL) and the solution treated with N,N'-carbonyldiimidazole (6.8 g, 42 mmol). The reaction mixture was heated to reflux for 18 hours before being allowed to return to room temperature. The white precipitate formed was removed by filtration, washed with acetonitrile and dried in vacuo to yield the title product. ¹H NMR (DMSO-D₆, 400 MHz) δ: 1.24 (m, 2H), 1.36 (m, 2H), 2.08 (m, 1H), 3.21 (m, 2H), 3.80 (m, 2H), 3.83 (s, 3H), 4.40 (d, 2H), 10.78 (m, 1H), 11.37 (m, 1H). MS APCI− m/z 307 [M-H]⁻

PREPARATION 56

Methyl 5,7-dioxo-1-(tetrahydropyran-2-ylmethyl)-4,5,6,7-tetrahydro-1H-pyrazolo[4,3-d]pyrimidine-3-carboxylate

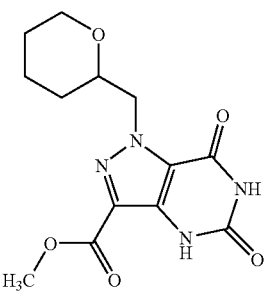

The title compound was prepared by a method similar to that described for preparation 55 using the amide of preparation 45. ¹H NMR (DMSO-D₆, 400 MHz) δ: 1.20 (m, 1H), 1.40 (m, 3H), 1.52 (d, 1H), 1.75 (m, 1H), 3.22 (m, 1H), 3.74 (m, 2H), 3.80 (s, 3H), 4.40 (m, 1H), 4.58 (m, 1H), 10.75 (m, 1H), 11.35 (m, 1H). MS APCI+ m/z 309 [MH]⁺

PREPARATION 57

Methyl 5,7-dichloro-1-(2-propoxyethyl)-1H-pyrazolo[4,3-d]pyrimidine-3-carboxylate

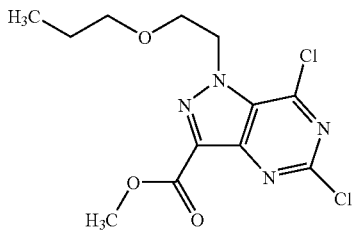

The dione of preparation 47 (3 g, 10 mmol), phosphorous oxychloride (14.2 mL, 152 mmol) and tetraethylammonium chloride (3.95 g, 30 mmol) were dissolved in propionitrile (80 mL) and the reaction mixture heated at 115° C. for 18 hours. The reaction mixture was concentrated in vacuo and the residue dissolved in additional propionitrile (80 mL) and treated with additional phosphorous oxychloride (15 mL, 145 mmol). The reaction mixture was then heated to 115° C. for a further 18 hours. The reaction mixture was concentrated in vacuo and the residue azeotroped with toluene. The crude product was taken up in ethyl acetate and cautiously treated with water. The two layers were separated and the aqueous layer re-extracted with ethyl acetate (×3). The combined organics were washed with brine, dried over magnesium sulphate and concentrated in vacuo. The crude product was purified by column chromatography on silica gel eluting with pentane:ethyl acetate 75:25 to yield the title product, 3.1 g. ¹H NMR (DMSO-D₆, 400 MHz) δ: 0.65 (t, 3H), 1.33 (q, 2H), 3.26 (t, 2H), 3.82 (t, 2H), 3.93 (s, 3H), 4.94 (t, 2H). MS APCI+ m/z 333, [MH]⁺

PREPARATION 58

Methyl 5,7-dichloro-1-(2-ethoxyethyl)-1H-pyrazolo[4,3-d]pyrimidine-3-carboxylate

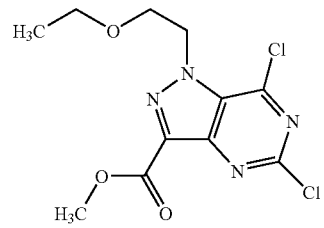

Phosphorous oxychloride (934 μL, 10.0 mmol) and tetraethylammonium chloride (195 mg, 1.50 mmol) were added to a solution of the dione of preparation 48 (140 mg, 0.50 mmol) in propionitrile (5 mL) and the reaction mixture refluxed for 18 hours. The reaction mixture was concentrated in vacuo and the crude product partitioned between ethyl acetate (50 mL) and water (50 mL). The organic layer was dried over magnesium sulphate and concentrated in vacuo. The crude product was purified by column chromatography on silica gel eluting with pentane:ethyl acetate 100:0 to 75:25 to yield the title product. $^1$H NMR (CDCl$_3$, 400 MHz) δ: 1.05 (t, 3H), 3.41 (m, 2H), 3.84 (m, 2H), 4.06 (s, 3H), 5.00 (m, 2H). MS APCI+ m/z 319 [MH]$^+$

PREPARATION 59

Methyl 5,7-dichloro-1-(2-isopropoxyethyl)-1H-pyrazolo[4,3-d]pyrimidine-3-carboxylate

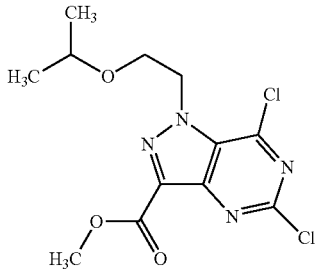

The dione of preparation 49 (2.37 g, 8.00 mmol) was suspended in acetonitrile (30 mL) and the solution treated with phosphorous oxychloride (15 mL, 160 mmol) and tetraethyl ammonium chloride (3.97 g, 24 mmol). The reaction mixture was stirred at reflux for 18 hours. The reaction mixture was allowed to cool and then concentrated in vacuo before being partitioned between dichloromethane (300 mL) and water (200 mL). The dichloromethane layer was separated, dried over magnesium sulphate and concentrated in vacuo. The crude product was purified by column chromatography on silica gel eluting with pentane:ethyl acetate 100:0 to 75:25 to yield the title product as a white solid, 1.54 g. $^1$H NMR (CDCl$_3$, 400 MHz) δ 0.96 (d, 6H), 3.43 (m, 1H), 3.86 (t, 2H), 4.08 (s, 3H), 4.96 (t, 2H). MS ES+ m/z 355 [MNa]$^+$ The following compounds, of the general formula shown below, were prepared by a method similar to that described for preparation 59 using the appropriate dione of preparations 50, 51, 52, 54, 55 and 56.

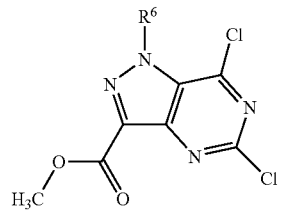

| No. | R$^6$ | Data |
|---|---|---|
| 60 | —(CH$_2$)$_2$CH(CH$_3$)OCH$_3$ | $^1$H NMR (CDCl$_3$, 400 MHz) δ: 1.18 (d, 3H), 2.00-2.15 (m, 2H), 3.20 (s, 3H), 3.30 (m, 1H), 4.01 (s, 3H), 4.90 (t, 2H). MS APCI+ m/z 333 [MH]$^+$ |
| 61 | —(CH$_2$)$_2$O(CH$_2$)$_2$OCH$_3$ | $^1$H NMR (CDCl$_3$, 400 MHz) δ: 3.20 (s, 3H), 3.30 (t, 2H), 3.45 (t, 2H), 3.99 (t, 2H), 4.10 (s, 3H), 5.00 (t, 2H) |
| 62 | H$_3$C—O—CH(CH$_3$)—CH$_2$— | $^1$H NMR (CDCl$_3$, 400 MHz) δ: 1.24 (d, 3H), 3.12 (s, 3H), 3.84 (m, 1H), 4.08 (s, 3H), 4.65 (m, 1H), 4.94 (m, 1H). MS APCI+ m/z 319 [MH]$^+$ |
| 63 | —(CH$_2$)$_2$OCH$_3$ | $^1$H NMR (CDCl$_3$, 400 MHz) δ: 3.25 (s, 3H), 3.84 (m, 2H), 4.09 (s, 3H), 4.98 (m, 2H). MS APCI+ m/z 305 [MH]$^+$ |
| 64 | tetrahydropyran-4-yl-CH$_2$— | $^1$H NMR (CDCl$_3$, 400 MHz) δ: 1.45 (m, 2H), 1.54 (m, 2H), 2.30 (m, 1H), 3.32 (m, 2H), 3.98 (m, 2H), 4.07 (s, 3H), 4.73 (s, 2H). MS APCI+ m/z 345 [MH]$^+$ |
| 65 | tetrahydropyran-2-yl-CH$_2$— | $^1$H NMR (CDCl$_3$, 400 MHz) δ: 1.34-1.60 (m, 4H), 1.66 (m, 1H), 1.89 (m, 1H), 3.23 (m, 1H), 3.81 (m, 2H), 4.07 (s, 3H), 4.67 (m, 1H), 4.96 (m, 1H). MS APCI+ m/z 345 [MH]$^+$ |

PREPARATION 66

Methyl 5,7-dichloro-1-(2-(cyclopropylmethoxy)ethyl)-1H-pyrazolo[4,3-d]pyrimidine-3-carboxylate

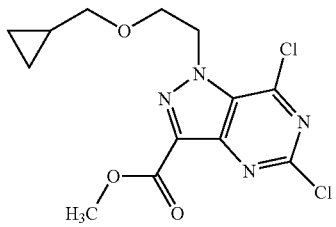

The dione of preparation 53 (2.52 g, 8.17 mmol) was suspended in acetonitrile (40 mL) and the suspension treated with phosphorous oxychloride (15 mL, 163.4 mmol) and tetraethylammonium chloride (4.08 g, 24.51 mmol). The reaction mixture was heated at reflux for 24 hours. The reaction mixture was concentrated in vacuo and the residue triturated with ether. The filtrate was concentrated in vacuo and purified by column chromatography on silica gel eluting with dichloromethane:ethyl acetate 50:50 to yield the title product as a colourless oil, 907 mg. $^1$H NMR (CDCl$_3$, 400 MHz) δ: 0.03 (m, 2H), 0.40 (m, 2H), 0.82 (m, 1H), 3.18 (d, 2H), 3.92 (t, 2H), 4.07 (s, 3H), 4.99 (t, 2H). MS ES+ m/z 345 [MH]$^+$

PREPARATION 67

Methyl 5-chloro-7-(4-methylpyridin-2-ylamino)-1-(2-propoxyethyl)-1H-pyrazolo[4,3-d]pyrimidine-3-carboxylate

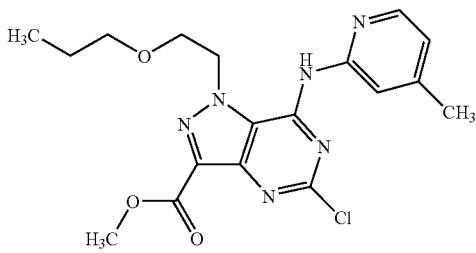

The dichloro compound of preparation 57 (400 mg, 1.2 mmol) and 2-amino-4-methylpyridine (649 mg, 6.0 mmol) were dissolved in dimethyl sulphoxide (5 mL) and the reaction mixture stirred at 30° C. for 1 hour. The reaction mixture was partitioned between dichloromethane and water and the aqueous layer extracted with dichloromethane (×2). The combined organics were washed with water (×2), aqueous citric acid and brine before being dried over magnesium sulphate and concentrated in vacuo to yield the title product as a yellow solid, 800 mg. MS APCI+ m/z 405 [MH]$^+$ Preparations 68 to 71

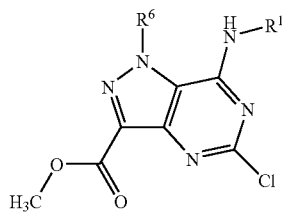

The following compounds of the general formula above were prepared by a method similar to that described for preparation 67 using the appropriate dichloro starting material of preparations 58 and 63, and the appropriate HNR$^1$R$^2$ amine.

| No. | | |
|---|---|---|
| 68 | 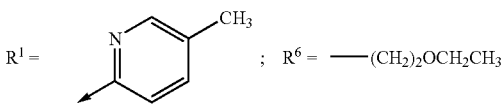 | |
| | $^1$H NMR (DMSO-D$_6$, 400 MHz) δ: 1.01 (t, 3H), 2.26 (s, 3H), 3.52 (m, 2H), 3.88 (m, 5H), 4.96 (m, 2H), 7.76 (m, 1H), 8.03 (m, 1H), 8.20 (m, 1H). MS APCI+ m/z 391 [MH]$^+$ | |
| 69 | 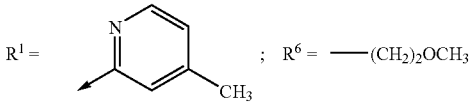 | |
| | $^1$H NMR (CDCl$_3$, 400 MHz) δ: 2.46 (s, 3H), 3.47 (m, 3H), 3.95 (m, 2H), 4.04 (s, 3H), 5.01 (m, 2H), 6.92 (m, 2H), 8.16 (m, 1H). MS APCI+ m/z 377 [MH]$^+$ | |

| No. | | | |
|---|---|---|---|
| 70 | $R^1 =$  | ; $R^6 =$ | —(CH$_2$)$_2$OCH$_2$CH$_3$ |

$^1$H NMR (CD$_3$OD, 400 MHz) δ: 1.16 (t, 3H), 1.85 (m, 2H), 2.16 (m, 2H), 2.48 (m, 2H), 3.58 (q, 2H), 3.90 (t, 2H), 3.98 (s, 3H), 4.64 (m, 1H), 4.79 (t, 2H).
MS APCI+ m/z 354 [MH]$^+$

| 71 | $R^1 =$  | ; $R^6 =$ | —(CH$_2$)$_2$OCH$_2$CH$_3$ |

$^1$H NMR (CD$_3$OD, 400 MHz) δ: 0.73 (m, 2H), 0.92 (m, 2H), 1.19 (t, 3H), 2.99 (m, 1H), 3.53 (q, 2H), 3.88 (t, 2H), 4.00 (s, 3H), 4.74 (t, 2H).
MS APCI+ m/z 340 [MH]$^+$

PREPARATION 72

Methyl 5-chloro-1-(2-ethoxyethyl)-7-(4-methylpyridin-2-ylamino)-1H-pyrazolo[4,3-d]pyrimidine-3-carboxylate

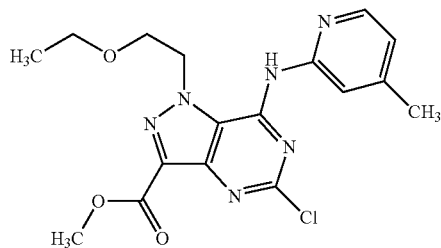

The dichloro compound of preparation 58 (1.98 g, 6.20 mmol) was dissolved in dimethyl sulphoxide (10 mL) and the solution treated with 2-amino-4-methylpyridine (1.34 g, 12.4 mmol). The reaction mixture was stirred at room temperature for 18 hours. The reaction mixture was partitioned between dichloromethane (300 mL) and water (500 mL) and the dichloromethane layer separated. The organic phase was washed with water (3×100 mL), dried over magnesium sulphate and concentrated in vacuo. The residue was purified by column chromatography on silica gel eluting with dichloromethane:methanol 100:0 to 98:2. The crude product was triturated with ether (50 mL), filtered and concentrated in vacuo to yield the title product, 1.2 g. $^1$H-NMR (CDCl$_3$, 400 MHz) δ: 1.06 (t, 3H), 2.49 (s, 3H), 3.62 (m, 2H), 4.00 (t, 2H), 4.06 (s, 3H), 5.05 (m, 2H), 6.98 (m, 1H), 8.16 (m, 1H), 8.50 (m, 1H). MS APCI+ m/z 391 [MH]$^+$ Preparations 73 to 85

The following compounds, of the general formula shown below, were prepared by a method similar to that described for preparation 72 using the appropriate HNR1R2 amine and the appropriate dichloro compound of preparations 58 and 61.

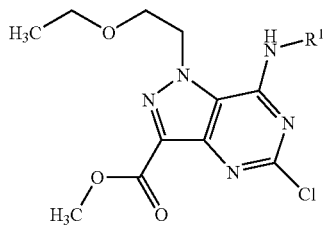

| No. | $R^1$ | Data |
|---|---|---|
| 73 | 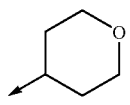 | $^1$H NMR (CD$_3$OD, 400 MHz) δ: 1.14 (t, 3H), 1.72 (m, 2H), 2.08 (m, 2H), 3.57 (m, 4H), 3.91 (t, 2H), 3.97 (t, 2H), 4.02 (m, 2H), 4.40 (s, 3H), 4.79 (t, 2H) |
| 74 | 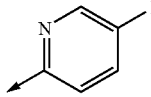 | $^1$H NMR (CD$_3$OD, 400 MHz) δ: 1.21 (t, 3H), 3.68 (q, 2H), 4.03 (t, 2H), 4.08 (s, 3H), 4.89 (t, 2H), 7.55 (m, 1H), 8.20 (d, 1H), 8.50 (m, 1H). MS APCI+ m/z 395 [MH]$^+$ |

-continued

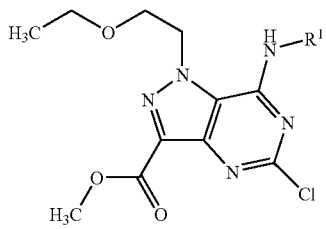

| No. | R¹ | Data |
|---|---|---|
| 75 | 6-methoxypyridin-3-yl | ¹H NMR (CDCl₃, 400 MHz) δ: 1.24 (t, 3H), 3.71 (q, 2H), 3.92 (s, 3H), 4.02 (t, 2H), 4.07 (s, 3H), 4.90 (t, 2H), 6.54 (d, 1H), 7.67 (t, 1H), 7.95 (d, 1H). MS APCI+ m/z 407 [MH]⁺ |
| 76 | phenyl | ¹H NMR (CDCl₃, 400 MHz) δ: 1.21 (t, 3H), 3.67 (q, 2H), 4.06 (t, 2H), 4.07 (s, 3H), 4.86 (t, 2H), 7.17 (t, 1H), 7.41 (m, 2H), 7.71 (d, 2H). MS APCI+ m/z 376 [MH]⁺ |
| 77 | 3-fluorophenyl | ¹H NMR (CDCl₃, 400 MHz) δ: 1.21 (t, 3H), 3.68 (q, 2H), 4.06 (t, 2H), 4.08 (s, 3H), 4.87 (t, 2H), 6.86 (m, 1H), 7.08 (m, 1H), 7.38 (m, 1H), 7.66 (m, 1H). MS APCI+ m/z 394 [MH]⁺ |
| 78 | 2-fluorophenyl | ¹H NMR (CDCl₃, 400 MHz) δ: 1.11 (t, 3H), 3.62 (q, 2H), 4.00 (t, 2H), 4.08 (s, 3H), 4.88 (t, 2H), 7.14 (m, 2H), 7.23 (m, 1H), 8.42 (t, 1H), 9.49 (m, 1H). MS APCI+ m/z 394 [MH]⁺ |
| 79 | 4-fluoro-3-methylphenyl | ¹H NMR (CDCl₃, 400 MHz) δ: 1.09 (t, 3H), 2.39 (s, 3H), 3.60 (q, 2H), 3.98 (t, 2H), 4.07 (s, 3H), 4.86 (t, 2H), 6.94 (m, 1H), 7.04 (t, 1H), 8.21 (d, 1H), 9.42 (m, 1H). MS APCI+ m/z 408 [MH]⁺ |
| 80 | 3,4-dimethylphenyl | ¹H NMR (CDCl₃, 400 MHz) δ: 1.20 (t, 3H), 2.27 (s, 3H), 2.31 (s, 3H), 3.66 (q, 2H), 4.04 (t, 2H), 4.07 (s, 3H), 4.84 (t, 2H), 7.16 (d, 1H), 7.41 (s, 1H), 7.47 (d, 1H), 9.31 (s, 1H). MS APCI+ m/z 404 [MH]⁺ |
| 81 | 3-methylphenyl | ¹H NMR (CDCl₃, 400 MHz) δ: 1.13 (t, 3H), 2.39 (s, 3H), 3.62 (q, 2H), 4.00 (s, 3H), 4.02 (t, 2H), 4.93 (t, 2H), 7.02 (d, 1H), 7.28 (t, 1H), 7.54 (s, 1H), 7.61 (d, 1H). MS APCI+ m/z 390 [MH]⁺ |
| 82 | cyclopentyl | ¹H NMR (CDCl₃, 400 MHz) δ: 1.20 (t, 3H), 1.50 (m, 2H), 1.71 (m, 4H), 2.21 (m, 2H), 3.56 (q, 2H), 3.93 (m, 2H), 4.02 (s, 3H), 4.47 (m, 1H), 4.67 (t, 2H), 7.35 (d, 1H). MS ES+ m/z 368 [MH]⁺ |
| 83 | (S)-tetrahydrofuran-3-yl | ¹H NMR (CDCl₃, 400 MHz) δ: 1.13 (t, 3H), 2.04 (m, 1H), 2.45 (m, 1H), 3.56 (q, 2H), 3.83 (m, 2H), 3.91 (t, 2H), 3.97 (s, 3H), 4.02 (m, 2H), 4.76 (m, 1H), 4.79 (m, 2H). MS ES+ m/z 356 [MH]⁺ |

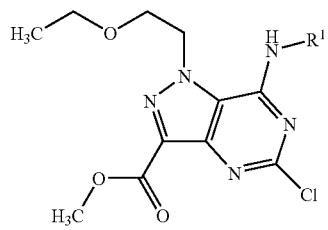

| No. | R[1] | Data |
|---|---|---|
| 84 | CH₃ pyridine with 2,6-dimethyl | $^1$H NMR (DMSO-D$_6$, 400 MHz) δ: 1.03 (m, 3H), 2.35 (s, 3H), 2.43 (m, 3H), 3.54 (m, 2H), 3.87 (m, 5H), 4.96 (m, 2H), 6.92 (m, 1H), 7.65 (m, 1H). MS APCI+ m/z 405 [MH]⁺ |
| 85 | | $^1$H NMR (CDCl$_3$, 400 MHz) δ: 2.50 (m, 3H), 3.40 (m, 3H), 3.70 (m, 2H), 4.10 (m, 7H), 5.10 (m, 2H), 7.02 (m, 2H), 8.18 (m, 1H). MS APCI– m/z 419 [M – H]⁻ |

Preparation 73 used tetrahydropyran-4-ylamine (WO 98/08855, Pg. 17, e.g. 3) as the HNR$^1$R$^2$ amine Preparation 75 used 6-methoxy-pyridin-2-ylamine (US 01/0047013, pg. 3, example 2) as the HNR$^1$R$^2$ amine Preparation 83 used (3R)-tetrahydrofuran-3-ylamine tosylate as the HNR$^1$R$^2$ amine with 1 eq of N-ethyldiisopropylamine.

PREPARATION 86

Methyl 5-chloro-1-(3-methoxybutyl)-7-(4-methylpyridin-2-ylamino)-1H-pyrazolo[4,3-d]pyrimidine-3-carboxylate

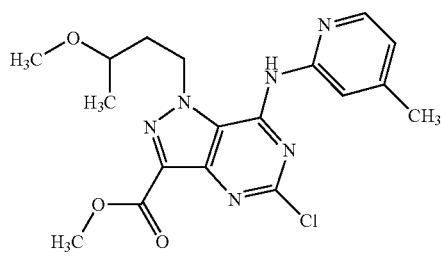

The dichloro compound of preparation 60 (700 mg, 2.11 mmol) and 4-methylpyridin-2-ylamine (1.14 g, 10.54 mmol) were dissolved in dimethyl sulphoxide (10 mL) and the reaction mixture heated to 30° C. under nitrogen for 3 hours. The reaction mixture was concentrated in vacuo and the residue taken up in dichloromethane (100 mL) and water (150 mL). The layers were separated and the aqueous layer washed with dichloromethane (50 mL). The organics were combined, washed with water (100 mL) and citric acid (50 mL) solution, dried over magnesium sulphate and concentrated in vacuo. The crude product was purified by column chromatography on silica gel eluting with dichloromethane:methanol 100:0 to 99:1 to yield the title product as a yellow solid, 330 mg. $^1$H NMR (CD$_3$OD, 400 MHz) δ: 1.20 (m, 3H), 2.10 (m, 2H), 2.45 (s, 3H), 3.30 (s, 3H), 3.40 (m, 1H), 3.98 (s, 3H), 5.00 (m, 2H), 6.90 (m, 1H), 7.30 (m, 1H), 8.00 (m, 1H). MS ES+ m/z 405 [MH]⁺

The following compounds, of the general formula shown below, were prepared by a method similar to that described for preparation 86 using the appropriate HNR$^1$R$^2$ amine and dichloro compound of preparations 58, 59, 62, 64 and 65.

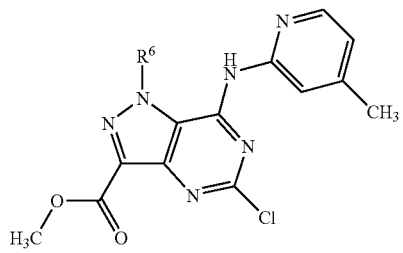

| No. | R⁶ | Data |
|---|---|---|
| 87 | —(CH₂)₂OCH(CH₃)₂ | $^1$H NMR (CDCl₃, 400 MHz) δ: 0.94 (d, 6H), 2.62 (s, 3H), 3.70 (m, 1H), 3.95 (t, 2H), 4.07 (s, 3H), 5.24 (m, 2H), 7.16 (d, 1H), 8.17 (d, 1H), 8.84 (m, 1H). MS ES+ m/z 427 [MNa]⁺ |
| 88 | H₃C—O—CH(CH₃)—CH₂— | $^1$H NMR (DMSO-D₆, 400 MHz) δ: 1.12 (d, 3H), 2.39 (s, 3H), 3.20 (s, 3H), 3.85 (s, 3H), 3.85 (m, 1H), 4.82 (d, 2H), 7.05 (d, 1H), 7.78 (s, 1H), 8.25 (d, 1H). MS ES+ m/z 391 [MH]⁺ |
| 89 | (tetrahydropyran-4-yl)CH₂— | $^1$H NMR (DMSO-D₆, 400 MHz) δ: 1.36 (m, 4H), 2.14 (m, 1H), 2.42 (s, 3H), 3.18 (m, 2H), 3.77 (m, 2H), 3.84 (s, 3H), 4.79 (d, 2H), 7.03 (d, 1H), 7.67 (s, 1H), 8.20 (d, 1H). MS APCI+ m/z 417 [MH]⁺ |
| 90 | (tetrahydropyran-2-yl)CH₂— | $^1$H NMR (DMSO-D₆, 400 MHz) δ: 1.24 (m, 1H), 1.45 (m, 3H), 1.72 (m, 1H), 1.79 (m, 1H), 2.40 (m, 3H), 3.39 (m, 1H), 3.85 (m, 1H), 3.90 (s, 3H), 3.96 (m, 1H), 4.83 (m, 2H), 7.08 (m, 1H), 7.82 (s, 1H), 8.25 (m, 1H). MS APCI+ m/z 417 [MH]⁺ |

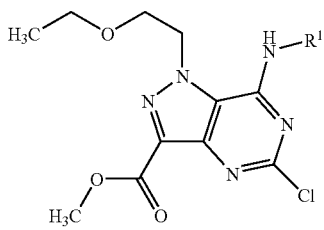

| No. | R¹ | Data |
|---|---|---|
| 91 | (4-ethyl-2-pyridyl)methyl— | $^1$H NMR (DMSO-D₆, 400 MHz) δ: 1.10 (t, 3H), 1.30 (t, 3H), 2.81 (q, 2H), 3.50 (q, 2H), 3.90 (m, 5H), 4.98 (t, 2H), 7.05 (d, 1H), 7.90 (m, 2H), 13.50 (m, 1H). MS APCI– m/z 403 [M – H]⁻ |
| 92 | (2-fluoro-5-methylphenyl)— | $^1$H NMR (DMSO-D₆, 400 MHz) δ: 0.94 (t, 3H), 2.06 (s, 3H), 3.42 (q, 2H), 3.80 (t, 2H), 3.88 (s, 3H), 4.97 (t, 2H), 6.73 (m, 1H), 7.20 (t, 1H), 7.46 (m, 1H). MS APCI– m/z 408 [M – H]⁻ |

-continued

| | | |
|---|---|---|
| 93 | 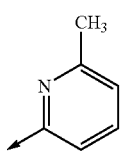 | $^1$H NMR (CDCl$_3$, 400 MHz) δ: 1.26 (t, 3H), 2.48 (s, 3H), 3.67 (q, 2H), 4.05 (t, 2H), 4.07 (s, 3H), 4.89 (t, 2H), 6.93 (d, 1H), 7.67 (t, 1H), 8.20 (d, 1H), 10.19 (s, 1H). MS APCI+ m/z 391 [MH]$^+$ |
| 94 | 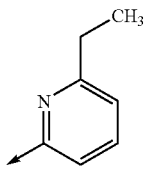 | $^1$H NMR (DMSO-D$_6$, 400 MHz) δ: 1.10 (t, 3H), 1.30 (t, 3H), 2.81 (q, 2H), 3.50 (q, 2H), 3.90 (m, 5H), 4.98 (t, 2H), 7.05 (d, 1H), 7.90 (m, 2H), 13.50 (m, 1H). MS APCI1 m/z 403 [M − H]$^-$ |
| 95 | 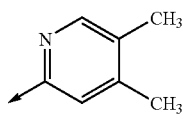 | $^1$H NMR (CDCl$_3$, 400 MHz) δ: 1.16 (t, 3H), 2.24 (s, 3H), 2.36 (s, 3H), 3.62 (q, 2H), 4.00 (t, 2H), 4.06 (s, 3H), 4.91 (t, 2H), 8.04 (m, 1H), 8.27 (m, 1H), 10.05 (m, 1H). MS APCI+ m/z 405 [MH]$^+$ |
| 96 | 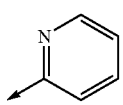 | $^1$H NMR (CDCl$_3$, 400 MHz) δ: 1.22 (t, 3H), 3.70 (q, 2H), 4.03 (t, 2H), 4.08 (s, 3H), 4.90 (t, 2H), 7.08 (t, 1H), 7.79 (t, 1H), 8.35 (d, 1H), 8.48 (d, 1H), 10.22 (m, 1H). MS APCI+ m/z 377 [MH]$^+$ |
| 97 | 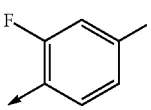 | $^1$H NMR (CDCl$_3$, 400 MHz) δ: 1.10 (t, 3H), 3.61 (q, 2H), 4.00 (t, 2H), 4.05 (s, 3H), 4.89 (m, 2H), 6.98 (m, 2H), 8.38 (s, 1H), 9.40 (m, 1H) |
| 98 | 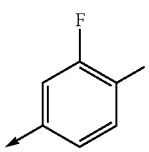 | $^1$H NMR (CDCl$_3$, 400 MHz) δ: 1.20 (t, 3H), 3.67 (q, 2H), 4.05 (m, 5H), 4.83 (m, 2H), 7.30 (m, 2H), 7.80 (m, 1H), 9.50 (s, 1H) |
| 99 | 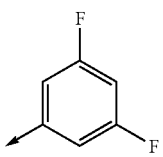 | $^1$H NMR (CDCl$_3$, 400 MHz) δ: 1.11 (t, 3H), 3.70 (q, 2H), 4.10 (m, 5H), 4.85 (m, 2H), 6.61 (m, 1H), 7.37 (m, 2H), 9.65 (s, 1H) |
| 100 | 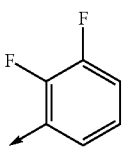 | $^1$H NMR (CDCl$_3$, 400 MHz) δ: 1.10 (t, 3H), 3.62 (q, 2H), 4.01 (m, 2H), 4.10 (s, 3H), 4.90 (m, 2H), 6.99 (m, 1H), 7.18 (m, 1H), 8.18 (m, 1H), 9.58 (s, 1H). MS APCI+ m/z 412 [MH]$^+$ |
| 101 | 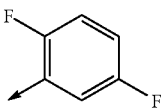 | $^1$H NMR (CDCl$_3$, 400 MHz) δ: 1.10 (t, 3H), 3.61 (q, 2H), 4.00 (t, 2H), 4.10 (s, 3H), 4.88 (m, 2H), 6.80 (m, 1H), 7.12 (m, 1H), 8.38 (m, 1H), 9.60 (s, 1H) |

Preparation 95 was prepared using 2-amino-4,5-dimethylpyridine (J. Het. Chem., 1981, 18 (8), 1613-1618, page 1616 as the HNR$^1$R$^2$ amine.

PREPARATION 102

Methyl 5-chloro-1-(2-(cyclopropylmethoxy)ethyl)-7-(4-methylpyridin-2-ylamino)-1H-pyrazolo[4,3-d]pyrimidine-3-carboxylate

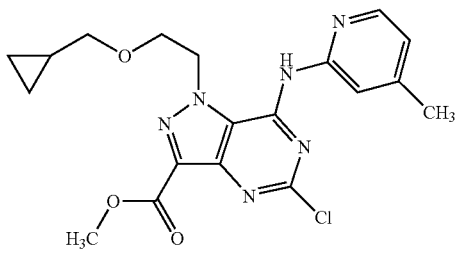

The dichloro compound of preparation 66 (900 mg, 2.61 mmol) was dissolved in dimethyl sulphoxide (10 mL) and the solution treated with 4-methylpyridin-2-ylamine (1.13 g, 10.46 mmol). The reaction mixture was then stirred at 35° C. in an oil bath for 1 hour. The reaction mixture was allowed to cool and treated with water to induce precipitation of a solid. The crude product was filtered off and dried in vacuo at 50° C. for 18 hours. The mother liquors were extracted with dichloromethane (2×50 mL) and then concentrated in vacuo. The combined solids were purified by column chromatography on silica gel eluting with dichloromethane:methanol 100:0 to 98:2. The crude product was then re-purified by column chromatography on silica gel eluting with dichloromethane:ethyl acetate 70:30 to yield the title product, 160 mg. $^1$H NMR (CDCl$_3$, 400 MHz) δ: 0.05 (d, 2H), 0.27 (m, 2H), 0.92 (m, 1H), 2.48 (s, 3H), 3.38 (d, 2H), 4.02 (m, 2H), 4.03 (s, 3H), 5.08 (m, 2H), 6.80 (m, 1H), 7.00 (m, 1H), 7.80 (m, 1H), 8.18 (m, 1H). MS ES+ m/z 439 [MNa]$^+$

PREPARATION 103

Methyl 5-chloro-7-(cyclohexyl)amino-1-(2-ethoxyethyl)-1H-pyrazolo[4,3-d]pyrimidine-3-carboxylate

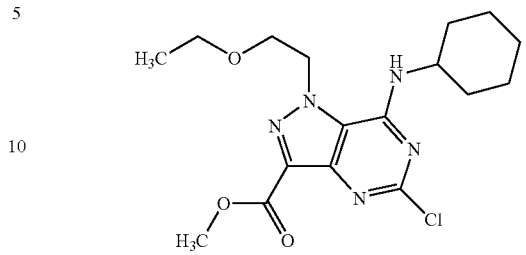

The dichloro compound of preparation 58 (2.50 g, 7.84 mmol) was dissolved in tetrahydrofuran (10 mL) and the solution treated dropwise with a solution of cyclohexylamine (4.48 mL, 39.20 mmol) whilst being cooled on an ice bath. The reaction mixture was stirred for 15 minutes at room temperature. The reaction mixture was diluted with water (50 mL) and ethyl acetate (50 mL) and the reaction mixture stirred for 1 hour. The solid present was collected by filtration, washed with water and dried in vacuo. The ethyl acetate layer was separated and washed with water, dried over magnesium sulphate and concentrated in vacuo. The residue was triturated with ether to yield further solid. A total of 2.25 g of the desired product was collected. $^1$H NMR (CDCl$_3$, 400 MHz) δ: 1.18 (t, 3H), 1.27 (m, 2H), 1.47 (m, 2H), 1.53-1.75 (m, 2H), 1.78 (m, 2H), 2.12 (m, 2H), 3.76 (q, 2H), 3.92 (t, 2H), 4.00 (s, 3H), 4.12 (m, 1H), 4.70 (t, 2H), 7.20 (d, 1H). MS ES+ m/z 382 [MH]$^+$

Preparations 104 to 117

The appropriate monochloro compound (1 eq), the appropriate HNR$^3$R$^4$ amine (3-5 eq), N-ethyldiisopropylamine (5 eq) and tetraethylammonium fluoride hydrate (1 eq) were dissolved in 1-methyl-2-pyrrolidinone (5.3 mL·mmol$^{-1}$) and the reaction vessel sealed and heated in a microwave oven for 45 minutes. The reaction mixture was allowed cool to room temperature before being partitioned between ethyl acetate (50 mL) and water (50 mL). The organic layer was washed with water (25 mL), dried over magnesium sulphate and concentrated in vacuo. The residue was purified by column chromatography on silica gel eluting with dichloromethane:ethyl acetate 50:50 to yield the desired product.

The monochloro compounds of preparations 73, 74, 75, 76, 77, 81, 86, 87, 88, 92, 97 and 102 were used.

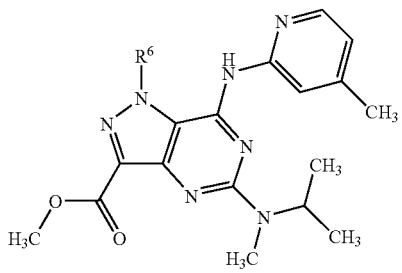

| No. | R$^6$ | Data |
|---|---|---|
| 104 | ▽–O–CH$_2$ | $^1$H NMR (CD$_3$OD, 400 MHz) δ: 0.03 (m, 2H), 0.24 (m, 2H), 0.96 (m, 1H), 1.25 (d, 6H), 2.40 (s, 3H), 3.09 (s, 3H), 3.38 (d, 2H), 3.94 (s, 3H), 3.98 (m, 2H), 4.81 (m, 2H), 5.15 (m, 1H), 6.93 (d, 1H), 8.15 (d, 1H), 8.31 (s, 1H). MS ES+ m/z 454 [MH]$^+$ |

-continued

| No. | | Data |
|---|---|---|
| 105 | 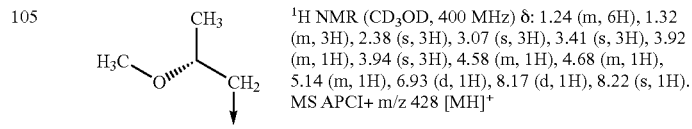 | ¹H NMR (CD₃OD, 400 MHz) δ: 1.24 (m, 6H), 1.32 (m, 3H), 2.38 (s, 3H), 3.07 (s, 3H), 3.41 (s, 3H), 3.92 (m, 1H), 3.94 (s, 3H), 4.58 (m, 1H), 4.68 (m, 1H), 5.14 (m, 1H), 6.93 (d, 1H), 8.17 (d, 1H), 8.22 (s, 1H). MS APCI+ m/z 428 [MH]⁺ |
| 106 | —(CH₂)₂OCH(CH₃)₂ | ¹H NMR (CD₃OD, 400 MHz) δ: 1.07 (d, 6H), 1.25 (d, 6H), 2.37 (s, 3H), 3.10 (s, 3H), 3.66 (m, 1H), 3.94 (s, 3H), 3.94 (m, 2H), 4.76 (t, 2H), 5.16 (m, 1H), 6.93 (d, 1H), 8.17 (d, 1H), 8.32 (s, 1H). MS ES+ m/z 442 [MH]⁺ |
| 107 | —(CH₂)₂CH(CH₃)OCH₃ | ¹H NMR (DMSO-D₆, 400 MHz) δ: 1.05 (m, 3H), 1.18-1.25 (m, 8H), 2.35 (s, 3H), 2.98 (s, 3H), 3.15 (s, 3H), 3.30 (m, 1H), 3.80 (s, 3H), 4.65 (m, 2H), 5.02 (m, 1H), 6.95 (m, 1H), 8.00 (m, 1H), 8.20 (m, 1H), 9.20 (m, 1H). MS ES+ m/z 442 [MH]⁺ |

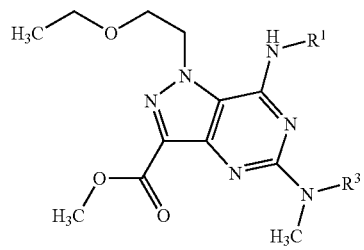

| No. | R¹ | R³ | Data |
|---|---|---|---|
| 108 | 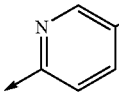 5-F-pyridin-2-yl | —CH(CH₃)₂ | ¹H NMR (CD₃OD, 400 MHz) δ: 1.20 (t, 3H), 1.23 (d, 6H), 3.07 (s, 3H), 3.66 (q, 2H), 3.96 (s, 3H), 4.00 (t, 2H), 4.80 (t, 2H), 5.10 (m, 1H), 7.64 (t, 1H), 8.21 (s, 1H), 8.32 (d, 1H). MS APCI– m/z 430 [M – H]⁻ |
| 109 | 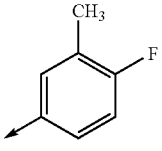 4-F-3-CH₃-phenyl | —CH(CH₃)₂ | ¹H NMR (CD₃OD, 400 MHz) δ: 1.14 (t, 3H), 1.22 (d, 6H), 2.30 (s, 3H), 3.04 (s, 3H), 3.63 (q, 2H), 3.96 (s, 3H), 3.98 (t, 2H), 4.79 (t, 2H), 5.08 (m, 1H), 7.02 (t, 1H), 7.42 (m, 1H), 7.68 (m, 1H). MS ES+ m/z 445 [MH]⁺ |
| 110 | 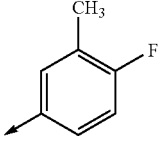 4-F-3-CH₃-phenyl | —CH₂CH₃ | ¹H NMR (CD₃OD, 400 MHz) δ: 1.15 (t, 3H), 1.20 (t, 3H), 2.30 (s, 3H), 3.19 (s, 3H), 3.60 (q, 2H), 3.70 (q, 2H), 3.96 (s, 3H), 3.98 (m, 2H), 4.80 (t, 2H), 7.01 (t, 1H), 7.42 (t, 1H), 7.67 (m, 1H). MS APCI+ m/z 431 [MH]⁺ |
| 111 | 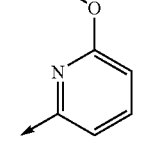 6-OCH₃-pyridin-2-yl | —CH(CH₃)₂ | ¹H NMR (CD₃OD, 400 MHz) δ: 1.15 (t, 3H), 1.23 (d, 6H), 3.05 (s, 3H), 3.65 (q, 2H), 3.95 (s, 3H), 3.98 (q, 2H), 4.02 (s, 3H), 4.78 (t, 2H), 5.01 (m, 1H), 6.49 (d, 1H), 7.66 (t, 1H), 7.82 (d, 1H). MS APCI+ m/z 444 [MH]⁺ |
| 112 | 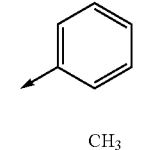 phenyl | —CH(CH₃)₂ | ¹H NMR (CD₃OD, 400 MHz) δ: 1.15 (t, 3H), 1.23 (d, 6H), 3.05 (s, 3H), 3.65 (q, 2H), 3.96 (s, 3H), 4.00 (t, 2H), 4.79 (t, 2H), 5.11 (m, 1H), 7.09 (t, 1H), 7.40 (t, 2H), 7.71 (d, 2H). MS APCI+ m/z 413 [MH]⁺ |
| 113 | 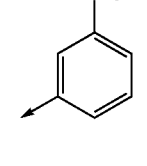 3-CH₃-phenyl | —CH(CH₃)₂ | ¹H NMR (CD₃OD, 400 MHz) δ: 1.16 (t, 3H), 1.22 (d, 6H), 2.37 (s, 3H), 3.06 (s, 3H), 3.45 (q, 2H), 3.98 (t, 3H), 4.00 (t, 2H), 4.79 (t, 2H), 5.10 (m, 1H), 6.93 (d, 1H), 7.23 (t, 1H), 7.43 (d, 1H), 7.65 (s, 1H). MS APCI+ m/z 427 [MH]⁺ |

| | | | |
|---|---|---|---|
| 114 | 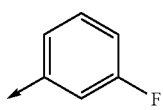 | —CH(CH₃)₂ | $^1$H NMR (CD₃OD, 400 MHz) δ: 1.15 (t, 3H), 1.25 (d, 6H), 3.07 (s, 3H), 3.64 (q, 2H), 3.96 (s, 3H), 4.00 (t, 3H), 4.80 (t, 2H), 5.10 (m, 1H), 6.80 (m, 1H), 7.33 (m, 1H), 7.44 (m, 1H), 7.78 (m, 1H). MS APCI+ m/z 431 [MH]⁺ |
| 115 | 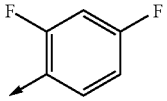 | —CH(CH₃)₂ | $^1$H NMR (CDCl₃, 400 MHz) δ: 1.10 (t, 3H), 1.18 (d, 6H), 3.05 (s, 3H), 3.60 (q, 2H), 3.97 (t, 2H), 4.02 (s, 3H), 4.78 (m, 2H), 5.00 (m, 1H), 6.90 (m, 2H), 8.18 (m, 1H), 8.90 (s, 1H). MS APCI+ m/z 449 [MH]⁺ |
| 116 | 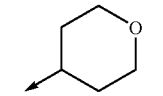 | —CH(CH₃)₂ | $^1$H NMR (CD₃OD, 400 MHz) δ: 1.15 (t, 3H), 1.20 (d, 6H), 1.69 (m, 2H), 2.15 (m, 2H), 3.02 (s, 3H), 3.56 (m, 4H), 3.88 (m, 2H), 3.95 (s, 3H), 4.02 (m, 2H), 4.25 (m, 1H), 4.66 (t, 2H), 5.12 (m, 1H). MS ES+ m/z 421 [MH]⁺ |
| 117 | 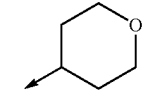 | —CH₃ | $^1$H NMR (CD₃OD, 400 MHz) δ: 1.15 (t, 3H), 1.70 (m, 2H), 2.13 (m, 2H), 3.19 (s, 6H), 3.54 (m, 4H), 3.88 (t, 2H), 3.94 (s, 3H), 4.00 (m, 2H), 4.30 (m, 1H), 4.65 (t, 2H). MS ES+ m/z 393 [MH]⁺ |

PREPARATION 118

Methyl 5-(N-isopropyl-N-methylamino)-1-[2-(2-methoxyethoxy)ethyl]-7-(4-methylpyridin-2-ylamino)-1H-pyrazolo[4,3-d]pyrimidine-3-carboxylate

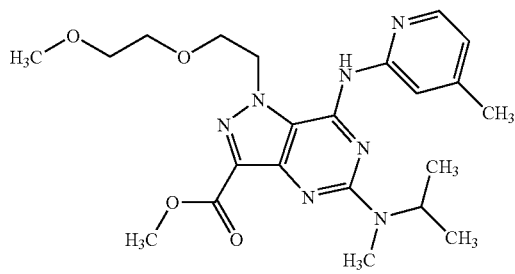

The monochloro compound of preparation 85 (150 mg, 0.36 mmol), N-ethyldiisopropylamine (186 μL, 1.07 mmol) and N-methyl-isopropylamine (50 μL, 0.43 mmol) were dissolved in dimethyl sulphoxide (1.5 mL) and the reaction mixture stirred at 120° C. for 18 hours. Additional N-methyl-isopropylamine (62 μL, 0.36 mmol) was added and the reaction stirred at 120° C. for a further 4 hours. The reaction mixture was concentrated in vacuo and the residue taken up in a mixture of dichloromethane (50 mL) and water (100 mL). The two layers were separated and the aqueous layer washed with dichloromethane (50 mL). The organics were combined and washed with water (2×50 mL) before being dried over magnesium sulphate and concentrated in vacuo. The crude product was purified by column chromatography on silica gel eluting with dichloromethane:methanol 95:5 to yield the title product as a yellow oil, 65 mg. $^1$H NMR (CD₃OD, 400 MHz) δ: 1.25 (d, 6H), 2.39 (s, 3H), 2.93 (m, 3H), 3.05 (s, 3H), 3.45 (t, 2H), 3.62 (m, 2H), 3.95 (s, 3H), 4.00 (t, 2H), 4.78 (m, 2H), 5.10 (m, 1H), 6.90 (m, 1H), 8.15 (d, 1H), 8.25 (m, 1H). MS APCI+ m/z 458 [MH]⁺

PREPARATION 119

Methyl 5-(dimethylamino)-1-(2-ethoxyethyl)-7-(6-ethylpyridin-2-ylamino)-1H-pyrazolo[4,3-d]pyrimidine-3-carboxylate

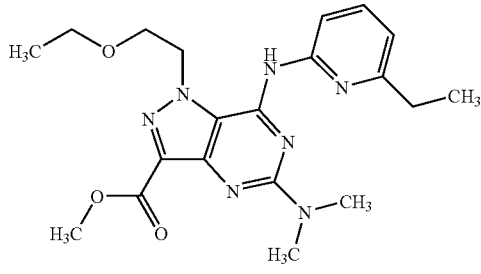

A solution of the monochloro compound of preparation 94 (200 mg, 0.50 mmol) and N-ethyldiisopropylamine (172 μL, 0.99 mmol) in dimethyl sulphoxide (2 mL) was treated with a 5.6M solution of dimethylamine in ethanol (180 μL, 1.0 mmol) and the reaction mixture stirred at 120° C. for 18 hours. The reaction mixture was concentrated in vacuo and the residue taken up in ether (100 mL) and washed with water (50 mL). The aqueous was extracted with ether (25 mL) and the combined organics washed with water (2×100 mL) and brine (50 mL), dried over magnesium sulphate and concentrated in vacuo. The residue was purified by column chromatography on silica gel eluting with dichloromethane:methanol 100:0 to 95:5. The crude product was recrystallised from ethanol to yield the title product. $^1$H NMR (CDCl₃, 400 MHz) δ: 1.30 (m, 6H), 2.76 (q, 2H), 3.30 (s, 6H), 3.70 (q, 2H), 4.01 (m, 2H), 4.02 (s, 3H), 4.80 (t, 2H), 6.83 (d, 1H), 7.60 (t, 1H), 8.10 (d, 1H), 9.80 (s, 1H). MS APCI- m/z 412 [M-H]⁻

The following compounds, of the general formula shown below, were prepared by a method similar to that described for preparation 119 using the appropriate HNR³R⁴ amine and monochloro compound of preparations 72, 78, 79, 80, 92, 94, 96, 97, 98, 99, 100 and 101.

| No. |
|---|

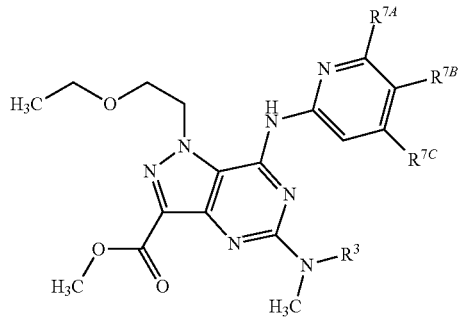

| 120 | $R^3 = -CH_2CH_3$; $R^{7A} = H$; $R^{7B} = H$; $R^{7C} = -CH_3$<br>¹H NMR (CD₃OD, 400 MHz) δ: 1.10 (t, 3H), 1.22 (t, 3H), 2.40 (s, 3H), 3.21 (s, 3H), 3.61 (q, 2H), 3.79 (q, 2H), 3.96 (m, 5H), 4.79 (t, 2H), 6.98 (d, 1H), 8.17 (d, 1H), 8.37 (s, 1H). MS APCI+ m/z 414 [MH]⁺ |
|---|---|
| 121 | $R^3 = -CH(CH_3)_2$; $R^{7A} = H$; $R^{7C} = -CH_3$<br>¹H NMR (CDCl₃, 400 MHz) δ: 1.16 (t, 3H), 1.24 (s, 6H), 2.36 (s, 3H), 3.11 (s, 3H), 3.60 (q, 2H), 3.94 (t, 2H), 4.02 (s, 3H), 4.77 (m, 2H), 5.15 (m, 1H), 6.82 (m, 1H), 8.18 (q, 1H), 8.24 (s, 1H). MS APCI+ m/z 426 [MH]⁺ |
| 122 | $R^3 = -CH_2CH_3$; $R^{7A} = -CH_2CH_3$; $R^{7B} = H$; $R^{7C} = -CH_3$<br>¹H NMR (CD₃OD, 400 MHz) δ: 1.20 (m, 6H), 1.30 (t, 3H), 2.78 (q, 2H), 3.21 (s, 3H), 3.65 (q, 2H), 3.78 (q, 2H), 3.97 (m, 5H), 4.81 (m, 2H), 6.98 (d, 1H) 7.70 (t, 1H), 8.20 (d, 1H). MS APCI– m/z 426 [M – H]⁻ |
| 123 | $R^3 = -CH(CH_3)_2$; $R^{7A} = H$; $R^{7B} = H$; $R^{7C} = H$<br>¹H NMR (CDCl₃, 400 MHz) δ: 1.20 (t, 3H), 1.25 (d, 6H), 3.12 (s, 3H), 3.64 (q, 2H), 3.98 (t, 2H), 4.03 (s, 3H), 4.79 (t, 2H), 5.15 (m, 1H), 6.98 (m, 1H), 7.68 (t, 1H), 8.33 (t, 2H), 9.81 (m, 1H). MS APCI+ m/z 414 [MH]⁺ |

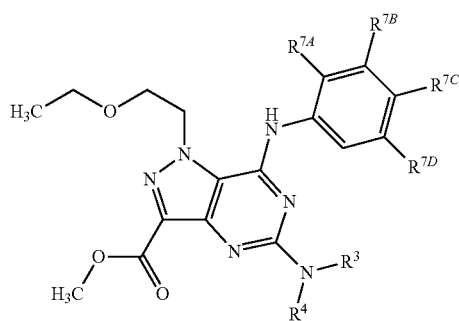

| 124 | $R^3 = -CH(CH_3)_2$; $R^4 = -CH_3$; $R^{7A} = H$; $R^{7B} = F$; $R^{7C} = F$; $R^{7D} = H$<br>¹H NMR (CDCl₃, 400 MHz) δ: 1.20 (t, 3H), 1.22 (d, 6H), 3.10 (s, 3H), 3.62 (m, 2H), 4.00 (m, 5H), 4.78 (m, 2H), 5.10 (m, 1H), 7.10 (m, 2H), 7.80 (m, 1H), 9.10 (s, 1H). MS APCI+ m/z 449 [MH]⁺ |
|---|---|
| 125 | $R^3 = -CH(CH_3)_2$; $R^4 = -CH_3$; $R^{7A} = H$; $R^{7B} = F$; $R^{7C} = H$; $R^{7D} = F$<br>¹H NMR (CDCl₃, 400 MHz) δ: 1.20 (t, 3H), 1.22 (d, 6H), 3.10 (s, 3H), 3.61 (q, 2H), 4.00 (m, 5H), 4.78 (m, 2H), 5.10 (m, 1H), 6.50 (t, 1H), 7.30 (m, 2H), 9.30 (s, 1H). MS APCI+ m/z 449 [MH]⁺ |
| 126 | $R^3 = -CH(CH_3)_2$; $R^4 = -CH_3$; $R^{7A} = F$; $R^{7B} = H$; $R^{7C} = H$; $R^{7D} = F$<br>¹H NMR (CDCl₃, 400 MHz) δ: 1.10 (t, 3H), 1.20 (d, 6H), 3.12 (s, 3H), 3.58 (q, 2H), 3.95 (t, 2H), 4.02 (s, 3H), 4.78 (m, 2H), 5.10 (m, 1H), 6.70 (m, 1H), 7.05 (m, 1H), 8.30 (m, 1H), 9.20 (m, 1H). MS APCI– m/z 447 [M – H]⁻ |
| 127 | $R^3 = -CH(CH_3)_2$; $R^4 = -CH_3$; $R^{7A} = F$; $R^{7B} = F$; $R^{7C} = H$; $R^{7D} = H$<br>¹H NMR (CDCl₃, 400 MHz) δ: 1.10 (t, 3H), 1.18 (d, 6H), 3.07 (s, 3H), 3.61 (q, 2H), 3.92 (t, 2H), 4.01 (s, 3H), 4.78 (m, 2H), 5.05 (m, 1H), 6.82 (m, 1H), 7.03 (m, 1H), 8.00 (m, 1H). MS APCI– m/z 447 [M – H]⁻ |
| 128 | $R^3 = -CH_2CH_3$; $R^4 = -CH_2CH_3$; $R^{7A} = H$; $R^{7B} = -CH_3$; $R^{7C} = F$; $R^{7D} = H$<br>¹H NMR (CDCl₃, 400 MHz) δ: 1.20 (m, 9H), 2.30 (s, 3H), 3.65 (q, 2H), 3.70 (m, 4H), 4.00 (m, 5H), 4.75 (t, 2H), 6.95 (t, 1H), 7.35 (m, 1H), 7.60 (m, 1H). MS APCI– m/z 443 [M – H]⁻ |

| No. | |
|---|---|
| 129 | $R^3$ = —$CH_3$; $R^4$ = —$CH_3$; $R^{7A}$ = F; $R^{7B}$ = H; $R^{7C}$ = H; $R^{7D}$ = —$CH_3$<br>$^1$H NMR (CDCl$_3$, 400 MHz) δ: 1.10 (t, 3H), 2.35 (s, 3H), 3.26 (s, 6H), 3.59 (q, 2H), 3.95 (t, 2H), 4.03 (s, 3H), 4.77 (t, 2H), 6.84 (m, 1H), 7.01 (m, 1H), 8.25 (d, 1H), 9.00 (s, 1H). MS APCI+ m/z 417 [MH]$^+$ |
| 130 | $R^3$ = —$CH_2CH_3$; $R^4$ = —$CH_3$; $R^{7A}$ = F; $R^{7B}$ = H; $R^{7C}$ = H; $R^{7D}$ = —$CH_3$<br>$^1$H NMR (CDCl$_3$, 400 MHz) δ: 1.10 (t, 3H), 1.22 (t, 3H), 2.35 (s, 3H), 3.25 (s, 3H), 3.59 (q, 2H), 3.63 (q, 2H), 3.95 (t, 2H), 4.03 (s, 3H), 4.76 (t, 2H), 6.82 (m, 1H), 7.02 (m, 1H), 8.23 (d, 1H), 8.98 (s, 1H).. MS APCI+ m/z 431 [MH]$^+$ |
| 131 | $R^3$ = —$CH_3$; $R^4$ = —$CH_3$; $R^{7A}$ = H; $R^{7B}$ = —$CH_3$; $R^{7C}$ = —$CH_3$; $R^{7D}$ = H<br>$^1$H NMR (CDCl$_3$, 400 MHz) δ: 1.19 (t, 3H), 2.27 (s, 3H), 2.29 (s, 3H), 3.26 (s, 6H), 3.62 (q, 2H), 4.00 (t, 2H), 4.03 (s, 3H), 4.74 (t, 2H), 7.10 (d, 1H), 7.40 (d, 1H), 7.52 (s, 1H), 8.90 (s, 1H). MS APCI+ m/z 413 [MH]$^+$ |
| 132 | $R^3$ = —$CH_2CH_3$; $R^4$ = —$CH_3$; $R^{7A}$ = H; $R^{7B}$ = —$CH_3$; $R^{7C}$ = —$CH_3$; $R^{7D}$ = H<br>$^1$H NMR (CDCl$_3$, 400 MHz) δ: 1.17 (t, 3H), 1.23 (t, 3H), 2.27 (s, 3H), 2.29 (s, 3H), 3.24 (s, 3H), 3.62 (q, 2H), 3.74 (q, 2H), 4.00 (t, 2H), 4.02 (s, 3H), 4.74 (t, 2H), 7.11 (d, 1H), 7.36 (d, 1H), 7.57 (s, 1H), 8.89 (s, 1H). MS APCI+ m/z 427 [MH]$^+$ |
| 133 | $R^3$ = —$CH(CH_3)_2$; $R^4$ = —$CH_3$; $R^{7A}$ = F; $R^{7B}$ = H; $R^{7C}$ = H; $R^{7D}$ = H<br>$^1$H NMR (CDCl$_3$, 400 MHz) δ: 1.10 (t, 3H), 1.21 (d, 6H), 3.08 (s, 3H), 3.61 (q, 2H), 3.96 (t, 2H), 4.03 (s, 3H), 4.78 (t, 2H), 5.01 (m, 1H), 7.05 (m, 1H), 7.14 (m, 2H), 8.29 (t, 1H), 9.01 (m, 1H). MS APCI+ m/z 431 [MH]$^+$ |

PREPARATION 134

Methyl 1-(2-(cyclopropyl methoxy)ethyl)-5-(N-ethyl-N-methyl-amino)-7-(4-methylpyridin-2-ylamino)-1H-pyrazolo[4,3-d]pyrimidine-3-carboxylate

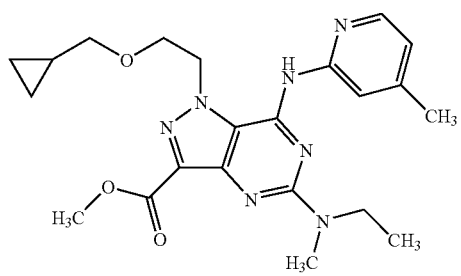

A solution of the chloro compound of preparation 102 (40 mg, 0.096 mmol) and N-ethyldiisopropylamine (83 μL, 0.48 mmol) in dimethyl sulphoxide (2 mL) was treated with N-methylethylamine (41 μL, 0.48 mmol) and the reaction mixture stirred at 120° C. for 18 hours. The reaction mixture was allowed to cool and partitioned between water (25 mL) and ethyl acetate (25 mL). The organic layer was washed with water (25 mL), dried over magnesium sulphate and concentrated in vacuo. The residue was purified by column chromatography on silica gel eluting with ethyl acetate to yield the title product. $^1$H NMR (CD$_3$OD, 400 MHz) δ: 0.02 (m, 2H), 0.23 (m, 2H), 0.95 (m, 1H), 1.24 (t, 3H), 2.37 (s, 3H), 3.21 (s, 3H), 3.35 (d, 2H), 3.76 (m, 2H), 3.95 (s, 3H), 3.98 (t, 2H), 4.79 (m, 2H), 6.94 (m, 1H), 8.13 (d, 1H), 8.32 (s, 1H). MS ES+ m/z 462 [MNa]$^+$

PREPARATION 135

5-Chloro-7-(4-methylpyridin-2-ylamino)-1-(2-propoxyethyl)-1H-pyrazolo[4,3-d]pyrimidine-3-carboxylic acid

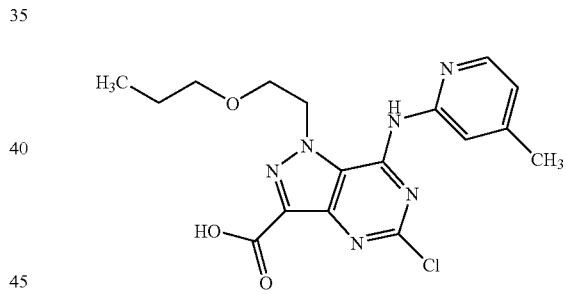

The ester of preparation 67 (500 mg, 1.24 mmol) was dissolved in dioxan (5 mL) and the solution treated with a 1M aqueous solution of sodium hydroxide (6.20 mL, 6.2 mmol). The reaction mixture was then stirred for 18 hours at room temperature. The reaction mixture was treated with 1M citric acid solution (10 mL) and a yellow precipitate formed. The mixture was stirred for 15 minutes before being filtered and the solid product dried in vacuo to yield the title product, 360 mg. $^1$H NMR (CDCl$_3$, 400 MHz) δ: 0.73 (t, 3H), 1.52 (m, 2H), 2.51 (s, 3H), 3.51 (t, 2H), 4.01 (t, 2H), 5.05 (m, 2H), 6.98 (m, 1H), 7.24 (m, 1H), 8.14 (m, 1H). MS APCI+ m/z 391 [MH]$^+$ The following compounds were prepared by a method similar to that described for preparation 135 using the appropriate ester of preparations 68, 69, 70, 71, 72, 80, 82, 83, 84, 87, 88, 89, 90, 91, 92, 93 and 103

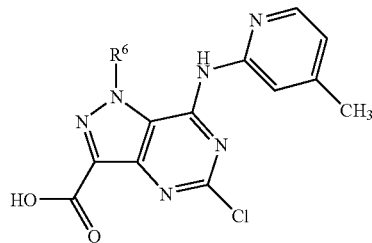

| No. | R⁶ | Data |
|---|---|---|
| 137 | —(CH₂)₂OCH₂CH₃ | ¹H NMR (DMSO-D₆, 400 MHz) δ: 1.00 (t, 3H), 2.34 (s, 3H), 3.45 (m, 2H), 3.81 (m, 2H), 4.84 (m, 2H), 6.93 (m, 1H), 7.89 (m, 1H), 8.16 (m, 1H). MS ES– m/z 375 [M – H]⁻ |
| 138 | tetrahydropyran-4-ylmethyl | ¹H NMR (DMSO-D₆, 400 MHz) δ: 1.32 (m, 4H), 2.12 (m, 1H), 2.38 (s, 3H), 3.20 (m, 2H), 3.78 (m, 2H), 4.76 (d, 2H), 6.90 (d, 1H), 7.60 (s, 1H), 8.30 (s, 1H). MS APCI+ m/z 403 [MH]⁺ |
| 139 | tetrahydropyran-2-ylmethyl | ¹H NMR (DMSO-D₆, 400 MHz) δ: 1.22 (m, 1H), 1.42 (m, 3H), 1.70 (m, 1H), 1.85 (m, 1H), 2.36 (s, 3H), 3.20-3.40 (m, 1H), 3.85 (m, 1H), 3.94 (m, 1H), 4.78 (m, 2H), 6.99 (d, 1H), 7,87 (m, 1H), 8.20 (m, 1H). MS APCI+ m/z 403 [MH]⁺ |
| 149 | —(CH₂)₂OCH₃ | ¹H NMR (DMSO-D₆, 400 MHz) δ: 2.21 (s, 3H), 3.25 (m, 3H), 3.82 (m, 2H), 4.96 (m, 2H), 6.97 (m, 1H), 7.77 (m, 1H), 8.17 (m, 1H). MS ES– m/z 361 [M – H]⁻ |
| 150 | —(CH₂)₂OCH(CH₃)₂ | ¹H NMR (DMSO-D₆, 400 MHz) δ: 0.93 (d, 6H), 2.38 (s, 3H), 3.54 (m, 1H), 3.84 (m, 2H), 4.89 (m, 2H), 7.04 (m, 1H), 7.90 (m, 1H), 8.23 (m, 1H). MS ES– m/z 389 [M – H]⁻ |
| 151 | (S)-2-methoxypropyl | ¹H NMR (DMSO-D₆, 400 MHz) δ: 1.13 (d, 3H), 2.43 (s, 3H), 3.20 (s, 3H), 3.86 (m, 1H), 4.80 (d, 2H), 7.10 (d, 1H), 7.80 (s, 1H), 8.27 (d, 1H). MS ES+ m/z 377 [MH]⁺ |

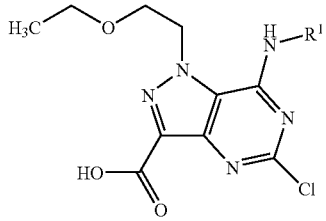

| No. | R¹ | Data |
|---|---|---|
| 136 | 6-methylpyridin-3-yl | ¹H NMR (DMSO-D₆, 400 MHz) δ: 1.03 (t, 3H), 2.24 (s, 3H), 3.50 (m, 2H), 3.86 (m, 2H), 4.88 (m, 2H), 7.77 (m, 1H), 8.03 (m, 1H), 8.17 (m, 1H). MS ES– m/z 375 [M – H]⁻ |
| 140 | 2-methyl-4-ethylpyridin-yl | ¹H NMR (DMSO-D₆, 400 MHz) δ: 1.02 (t, 3H), 1.22 (t, 3H), 2.66 (q, 2H), 3.43 (m, 2H), 3.85 (m, 2H), 4.92 (m, 2H), 7.01 (m, 1H), 7.95 (m, 1H), 8.20 (m, 1H). MS ES– m/z 389 [M – H]⁻ |

| | | |
|---|---|---|
| 141 |  | ¹H NMR (DMSO-D₆, 400 MHz) δ: 0.63 (m, 2H), 0.82 (m, 2H), 0.97 (t, 3H), 2.94 (m, 1H), 3.39 (m, 2H), 3.71 (m, 2H), 4.77 (m, 2H), 7.80 (m, 1H). MS ES- m/z 324 [M − H]⁻ |
| 142 |  | ¹H NMR (DMSO-D₆, 400 MHz) δ: 0.99 (t, 3H), 1.77 (m, 2H), 2.14 (m, 2H), 2.35 (m, 2H), 3.40 (m, 2H), 3.75 (m, 2H), 4.59 (m, 1H), 4.81 (m, 2H), 6.72 (m, 1H). MS ES- m/z 338 [M − H]⁻ |
| 143 |  | ¹H NMR (DMSO-D₆, 400 MHz) δ: 1.00 (t, 3H), 1.58 (m, 4H), 1.75 (m, 2H), 2.03 (m, 2H), 3.41 (m, 2H), 3.73 (m, 2H), 4.62 (m, 1H), 4.79 (m, 2H), 7.44 (m, 1H). MS ES- m/z 352 [M − H]⁻ |
| 144 |  | ¹H NMR (CDCl₃, 400 MHz) δ: 1.00 (t, 3H), 1.18 (m, 1H), 1.38 (m, 4H), 1.62 (m, 1H), 1.74 (m, 2H), 1.96 (m, 2H), 3.40 (t, 2H), 3.72 (m, 2H), 4.03 (m, 1H), 4.73 (m, 2H), 7.26 (d, 1H). MS ES- m/z 366 [M − H]⁻ |
| 145 |  | ¹H NMR (DMSO-D₆, 400 MHz) δ: 1.20 (t, 3H), 1.96 (m, 1H), 2.49 (m, 1H), 3.61 (q, 2H), 3.86 (m, 2H), 3.94 (t, 2H), 4.04 (m, 2H), 4.75 (t, 2H), 4.85 (m, 1H), 7.70 (m, 1H) |
| 146 | 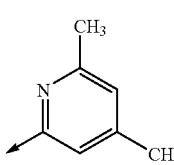 | ¹H NMR (CD₃OD, 400 MHz) δ: 1.11 (t, 3H), 2.40 (s, 3H), 2.49 (s, 3H), 3.58 (m, 2H), 3.97 (m, 2H), 5.01 (m, 2H), 6.92 (m, 1H), 7.94 (m, 1H). MS ES- m/z 389 [M − H]⁻ |
| 147 | 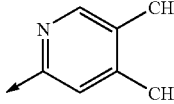 | ¹H NMR (CD₃OD, 400 MHz) δ: 1.08 (t, 3H), 2.26 (s, 3H), 2.38 (s, 3H), 3.65 (q, 2H), 3.98 (t, 2H), 4.99 (t, 2H), 7.95 (m, 1H), 8.00 (s, 1H). MS APCI+ m/z 391 [MH]⁺ |
| 148 | 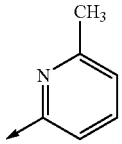 | ¹H NMR (CD₃OD, 400 MHz) δ: 1.08 (t, 3H), 2.45 (s, 3H), 3.52 (q, 2H), 3.85 (t, 2H), 4.92 (t, 2H), 7.01 (d, 1H), 7.82 (t, 1H), 7.94 (d, 1H). MS APCI+ m/z 377 [MH]⁺ |
| 152 | 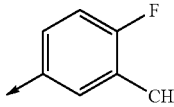 | ¹H NMR (CD₃OD, 400 MHz) δ: 0.95 (t, 3H), 2.27 (s, 3H), 3.45 (q, 2H), 3.82 (t, 2H), 4.04 (t, 2H), 7.22 (t, 1H), 7.51 (m, 2H), 9.35 (s, 1H). MS APCI- m/z 392 [MNa]⁺ |

PREPARATION 153

[5,7-Dichloro-1-(2-ethoxyethyl)-1H-pyrazolo[4,3-d]pyrimidin-3-yl]methanol

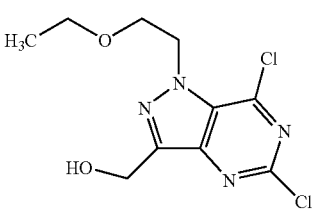

The dichloro compound of preparation 58 (2.4 g, 7.52 mmol) was dissolved in tetrahydrofuran (60 mL) and the solution cooled to −78° C. Diisobutylaluminium hydride (37.6 mL, 37.6 mmol) in tetrahydrofuran (20 mL) was added dropwise over 10 minutes and the reaction mixture stirred at −78° C. for 10 minutes and then at −10° C. for 1 hour. The reaction mixture was cooled to −78° C., quenched with ammonium chloride solution (25 mL) and allowed to return to room temperature. The reaction mixture was diluted with dichloromethane (200 mL) and water (100 mL) and the solution filtered through Arbocel®, washing through with dichloromethane (3×100 mL). The organic phase was separated, dried over magnesium sulphate and concentrated in vacuo. The crude product was purified by column chromatography on silica gel eluting with dichloromethane:methanol 99:1 to yield the title product, 1.67 g. ¹HNMR (CDCl₃, 400 MHz) δ: 1.08 (t, 3H), 3.42 (m, 2H), 3.80 (m, 2H), 4.90 (m, 2H), 5.10 (s, 2H). MS APCI+ m/z 291 [MH]⁺

PREPARATION 154

3-(tert-Butyldimethylsilyloxymethyl)-5,7-dichloro-1-(2-ethoxyethyl)-1H-pyrazolo[4,3-d]pyrimidine

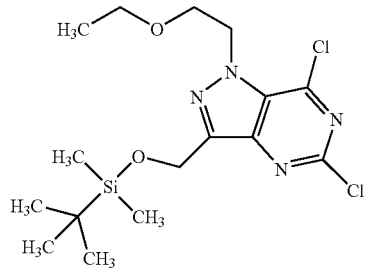

The alcohol of preparation 153 (1.32 g, 4.53 mmol) was dissolved in dichloromethane (25 mL) and the solution treated with imidazole (339 mg, 4.98 mmol) and then tert-butyldimethylsilyl chloride (750 mg, 4.98 mmol). The reaction mixture was then stirred at room temperature for 18 hours. The reaction mixture was diluted with dichloromethane (200 mL) and washed with 10% potassium carbonate solution (100 mL). The organic phase was dried over sodium sulphate and concentrated in vacuo. The crude product was purified by column chromatography on silica gel eluting with dichloromethane:methanol 99:1 to yield the title product, 1.56 g. $^1$HNMR (CDCl$_3$, 400 MHz) δ: 0.00 (s, 6H), 0.78 (s, 9H), 0.93 (t, 3H), 3.29 (m, 2H), 3.71 (t, 2H), 4.72 (m, 2H), 4.94 (s, 2H). MS APCI+ m/z 405 [MH]$^+$

PREPARATION 155

N-[3-(tert-Butyldimethylsilyloxymethyl)-5-chloro-1-(2-ethoxyethyl)-1H-pyrazolo[4,3-d]pyrimidin-7-yl]pyrimidin-4-ylamine

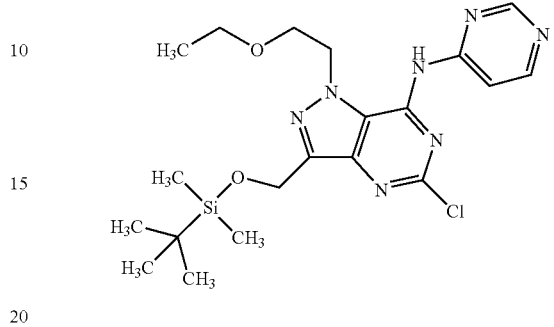

Pyrimidin-4-ylamine (1.10 g, 11.55 mmol) was dissolved in tetrahydrofuran (30 mL) and the solution treated with sodium hexamethyldisilazide (2.12 g, 11.55 mmol) and stirred at room temperature for 20 minutes. The solution was then treated with a solution of the dichloro compound of preparation 154 (1.56 g, 3.85 mmol) in tetrahydrofuran (10 mL) and the reaction mixture stirred for 90 minutes at room temperature. The reaction mixture was quenched with ammonium chloride solution (100 mL) and extracted with dichloromethane (200 mL). The organic phase was separated, dried over magnesium sulphate and concentrated in vacuo. The crude product was purified by column chromatography on silica gel eluting with dichloromethane:methanol 97:3 to yield the title product, 830 mg. $^1$HNMR (CDCl$_3$, 400 MHz) δ: 0.00 (s, 6H), 0.77 (s, 9H), 1.08 (t, 3H), 3.54 (m, 4H), 4.63 (m, 2H), 4.90 (s, 2H), 8.33 (d, 1H), 8.51 (d, 1H), 8.77 (s, 1H). MS APCI+ m/z 464 [MH]$^+$ The following compounds, of the general formula shown below, were prepared by a method similar to that described for preparation 155 using the appropriate HNR$^1$R$^2$-amine.

| No. | R$^1$ | Data |
|---|---|---|
| 156 | 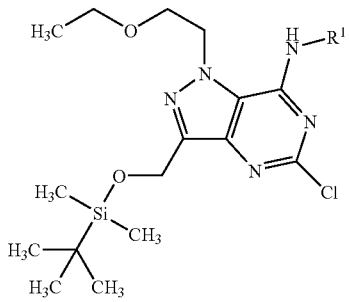 | $^1$H NMR (CDCl$_3$, 400 MHz) δ: 0.18 (s, 6H), 0.93 (s, 9H), 1.21 (t, 3H), 3.65 (q, 2H), 3.97 (m, 2H), 4.80 (m, 2H), 5.06 (m, 2H), 8.30 (m, 2H), 9.77 (m, 1H), 10.17 (m, 1H) |

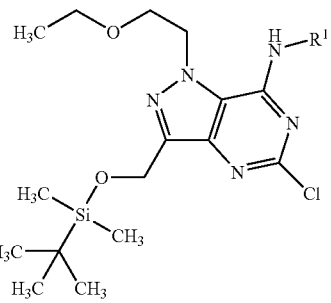

| No. | R¹ | Data |
|---|---|---|
| 157 | ![pyrimidine with OCH3] | $^1$H NMR (CDCl$_3$, 400 MHz) δ: 0.20 (s, 6H), 0.95 (s, 9H), 1.25 (q, 3H), 3.65 (m, 2H), 3.95 (t, 2H), 4.02 (s, 3H), 4.78 (t, 2H), 5.05 (s, 2H), 8.05 (d, 1H), 8.50 (d, 1H), 10.30 (s, 1H). MS APCI+ m/z 494 [MH]$^+$ |
| 158 | ![2-methylpyrimidine] | $^1$H NMR (CDCl$_3$, 400 MHz) δ: 0.00 (s, 6H), 0.77 (s, 9H), 1.13 (t, 3H), 2.48 (s, 3H), 3.53 (q, 2H), 3.80 (t, 2H), 4.62 (t, 2H), 4.89 (s, 2H), 8.03 (d, 1H), 8.41 (d, 1H), 10.12 (s, 1H). MS ES+ m/z 478 [MH]$^+$ |
| 159 | ![2,6-dimethylpyrimidine] | $^1$H NMR (CDCl$_3$, 400 MHz) δ: 0.10 (s, 6H), 0.95 (s, 9H), 1.38 (t, 3H), 2.42 (s, 6H), 3.65 (q, 2H), 3.95 (t, 2H), 4.79 (t, 2 h), 5.10 (s, 2H), 6.78 (s, 1H), 10.18 (s, 1H). MS APCI+ m/z 492 [MH]$^+$ |

Preparation 157 used the amine of preparation 6 as theHNR¹R² amine.

Preparation 158 used 2-methylpyrimidin-4-ylamine (J.Het. Chem, 1987, 24, 1377-1380) as theHNR¹R² amine.

PREPARATION 160

[5-Chloro-1-(2-ethoxyethyl)-7-(pyrimidin-4-ylamino)-1H-pyrazolo[4,3-d]pyrimidin-3-yl]-methanol

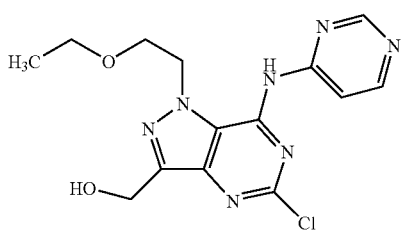

The protected alcohol of preparation 155 (815 mg, 1.76 mmol) was dissolved in tetrahydrofuran (40 mL) and the solution treated with a 1M solution of tetrabutylammonium fluoride in tetrahydrofuran (8.63 mL, 8.63 mmol). The reaction mixture was stirred for 90 minutes at room temperature and was then treated with additional tetrabutylammonium fluoride solution (4.32 mL) and stirred for another hour. The reaction mixture was diluted with water (50 mL) and the aqueous extracted with ethyl acetate (3×50 mL). The combined organics were dried over magnesium sulphate and concentrated in vacuo. The crude product was purified by column chromatography on silica gel eluting with dichloromethane:methanol 99:1 to 95:5 to yield the title product, 1.25 g. $^1$HNMR (CDCl$_3$, 400 MHz) δ: 1.26 (t, 3H), 3.70 (m, 2H), 3.97 (m, 2H), 4.76 (m, 2H), 5.10 (s, 2H), 8.51 (d, 1H), 8.72 (d, 1H), 8.99 (s, 1H). MS APCI+ m/z 350 [MH]$^+$ The following compounds, of the general formula shown below, were prepared by a method similar to that described for preparation 160 using the appropriate protected alcohol of preparations 156, 157, 158 and 159.

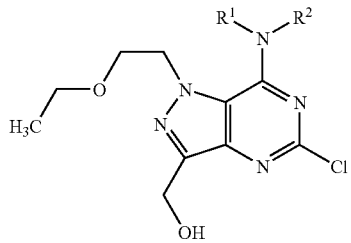

| No. | R¹ | Data |
|---|---|---|
| 161 | pyrazin-2-yl | $^1$H NMR (CDCl$_3$, 400 MHz) δ: 1.22 (t, 3H), 3.66 (m, 2H) 3.98 (m, 2H), 4.80 (m, 2H), 5.08 (s, 2H), 8.34 (m, 2H), 9.80 (m, 1H), 10.22 (m, 1H) |
| 162 | 2-methoxypyrimidin-4-yl | $^1$H NMR (DMSO-D$_6$, 400 MHz) δ: 1.10 (t, 3H), 3.58 (q, 2H), 3.83 (t, 2H), 3.90 (s, 3H), 4.65 (t, 2H), 4.78 (t, 2H), 5.48 (t, 1H), 7.80 (d, 1H), 8.58 (d, 1H), 10.42 (s, 1H). MS APCI– m/z 378 [M – H]$^-$ |
| 163 | 2-methylpyrimidin-4-yl | $^1$H NMR (DMSO-D$_6$, 400 MHz) δ: 1.11 (t, 3H), 2.55 (s, 3H), 3.56 (q, 2H), 3.85, 4.69 (d, 2H), 4.79 (t, 2H), 5.33 (t, 1H), 7.99 (d, 1H), 8.60 (d, 1H). MS ES+ m/z 364 [MH]$^+$ |
| 164 | 2,6-dimethylpyrimidin-4-yl | $^1$H NMR (DMSO-D$_6$, 400 MHz) δ: 1.10 (m, 3H), 2.38 (s, 6H), 3.43 (q, 2H), 3.75 (m, 2H), 4.55 (m, 2H), 4.70 (t, 2H), 5.35 (t, 1H), 6.98 (s, 1H), 10.44 (s, 1H). MS APCI+ m/z 378 [MH]$^+$ |

PREPARATION 165

5-Chloro-1-(2-ethoxyethyl)-7-(pyrazin-2-ylamino)-1H-pyrazolo[4,3-d]pyrimidine-3-carbaldehyde

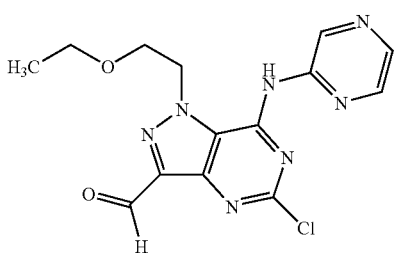

The alcohol of preparation 161 (251 mg, 0.72 mmol) was dissolved in dichloromethane (12 mL) and the solution cooled to 0° C. in an ice bath. 1,1,1-Triacetoxy-1,1-dihydro-1,2-benziodoxol-3(1H)-one (Dess-Martin periodinane, 456 mg, 1.08 mmol) was added and the reaction mixture stirred at room temperature for 2 hours. The reaction mixture was treated with a saturated solution of sodium thiosulphate in water (7.8 mL) and then with saturated sodium hydrogencarbonate solution (7.8 mL) and ether (7.8 mL). The mixture was stirred at room temperature for 15 minutes, the organic phase separated and the aqueous extracted with dichloromethane (×3). The organics were combined, dried over sodium sulphate and concentrated in vacuo. The crude product was purified by column chromatography on silica gel eluting with dichloromethane:methanol 99:1 to yield the title product, 200 mg. $^1$HNMR (CDCl$_3$, 400 MHz) δ: 1.22 (t, 3H), 3.69 (m, 2H), 4.06 (m, 2H), 4.92 (m, 2H), 7.22 (m, 1H), 8.32 (m, 1H), 8.40 (m, 1H), 9.77 (m, 1H), 10.35 (m, 1H)

The following compounds, of the general formula shown below, were prepared by a method similar to that described for preparation 165 using the appropriate alcohol of preparations 160, 162, 163, 164.

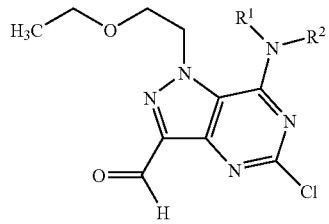

| No. | R¹ | Data |
|---|---|---|
| 166 | pyrimidin-4-yl | ¹H NMR (CDCl₃, 400 MHz) δ: 1.23 (t, 3H), 3.72 (q, 2H), 4.06 (t, 2H), 4.93 (m, 2H), 8.40 (d, 1H), 8.75 (d, 1H), 8.95 (s, 1H), 10.37 (s, 1H) |
| 167 | 2-methoxypyrimidin-4-yl | ¹H NMR (CDCl₃, 400 MHz) δ: 1.25 (t, 3H), 3.70 (q, 2H), 4.00 (m, 2H), 4.05 (s, 3H), 4.90 (t, 2H), 8.05 (d, 1H), 8.55 (d, 1H), 10.48 (m, 2H). MS APCI− m/z 376 [M − H]⁻ |
| 168 | 2-methylpyrimidin-4-yl | ¹H NMR (DMSO-D₆, 400 MHz) δ: 0.98 (t, 3H), 2.47 (s, 3H), 3.43 (q, 2H), 3.85 (t, 2H), 4.93 (t, 2H), 7.86 (d, 1H), 8.48 (d, 1H). MS ES− m/z 360 [M − H]⁻ |
| 169 | 2,6-dimethylpyrimidin-4-yl | ¹H NMR (CDCl₃, 400 MHz) δ: 1.30 (m, 3H), 2.60 (s, 6H), 3.70 (t, 2H), 4.00 (t, 2H), 4.90 (m, 2H), 6.80 (m, 1H), 10.30 (s, 1H), 10.35 (s, 1H). MS APCI− m/z 374 [M − H]⁻ |

PREPARATION 170

5-Chloro-1-(2-ethoxyethyl)-7-(pyrimidin-4-ylamino)-1H-pyrazolo[4,3-d]pyrimidine-3-carboxylic acid

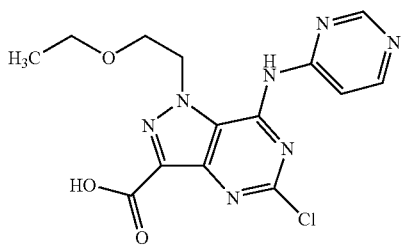

The aldehyde of preparation 166 (220 mg, 0.63 mmol) was dissolved in tert-butanol (40 mL) and the solution treated with a 2M solution of 2-methylbut-2-ene in tetrahydrofuran (44 mL). The solution was stirred at room temperature and then treated dropwise with a solution of sodium chlorite (683 mg, 7.59 mmol) and sodium dihydrogen orthophosphate (699 mg, 5.82 mmol) in water (8 mL) over 5 minutes. The reaction mixture was stirred at room temperature for 30 minutes. Water (40 mL) and dichloromethane (40 mL) were added to the reaction mixture and the phases separated. The aqueous layer was extracted with dichloromethane (2×40 mL) and the aqueous was then acidified to pH 3 and extracted once more with dichloromethane (2×40 mL). The organics were combined, dried over magnesium sulphate and concentrated in vacuo. The crude product was purified by column chromatography on silica gel eluting with first dichloromethane:methanol 97:3 and then dichloromethane:methanol:acetic acid 85:15:1 to yield the title product, 194 mg. ¹HNMR (CD₃OD, 400 MHz) δ: 1.20 (t, 3H), 3.68 (m, 2H), 4.01 (t, 2H), 4.92 (t, 2H), 8.42 (m, 1H), 8.68 (m, 1H), 8.87 (m, 1H). MS APCI+ m/z 364 [MH]⁺

The following compounds, of the general formula shown below, were prepared by a method similar to that described for preparation 170 using the appropriate aldehyde of preparations 165, 167, 168, 169.

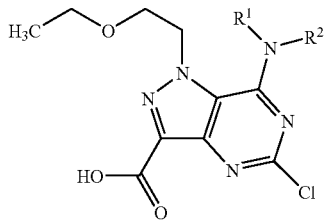

| No. | NR¹R² | Data |
|---|---|---|
| 171 | pyrazin-2-yl | ¹H NMR (CD₃OD, 400 MHz) δ: 1.20 (m, 3H), 3.65 (m, 2H), 3.99 (m, 2H), 4.96 (m, 2H), 8.36 (m, 1H), 8.42 (m, 1H), 9.60 (m, 1H). MS APCI+ m/z 364 [MH]⁺ |
| 172 | 2-methoxypyrimidin-4-yl | ¹H NMR (DMSO-D₆, 400 MHz) δ: 1.10 (m, 3H), 3.58 (q, 2H), 3.90 (m, 3H), 3.95 (s, 3H), 4.90 (t, 2H), 7.80 (d, 1H), 8.58 (d, 1H), 10.52 (m, 1H). MS APCI- m/z 392 [M − H]⁻ |
| 173 | 2-methylpyrimidin-4-yl | ¹H NMR (DMSO-D₆, 400 MHz) δ: 1.01 (t, 3H), 2.46 (s, 3H), 3.46 (q, 2H), 3.80 (t, 2H), 4.84 (t, 2H), 7.87 (d, 1H), 8.50 (d, 1H). MS ES- m/z 376 [M − H]⁻ |
| 174 | 2,6-dimethylpyrimidin-4-yl | ¹H NMR (DMSO-D₆, 400 MHz) δ: 1.01 (t, 3H), 2.40 (s, 3H), 3.35 (s, 3H), 3.46 (q, 2H), 3.80 (t, 2H), 4.75 (t, 2H), 7.00 (d, 1H),. MS ES- m/z 390 [M − H]⁻ |

PREPARATION 175

Ethyl 5-chloro-1-(2-ethoxyethyl)-7-(4-methylpyridin-2-ylamino)-1H-pyrazolo[4,3-d]pyrimidine-3-carboxylate

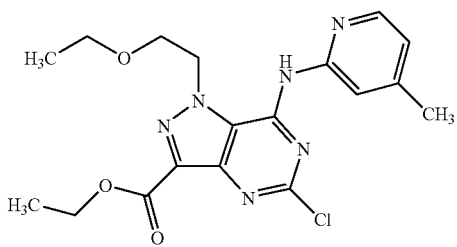

The carboxylic acid of preparation 137 (565 mg, 1.5 mmol) was suspended in 1-methyl-2-pyrrolidinone (5 mL) and the solution treated with N-ethyldiisopropylamine (313 μL, 1.8 mmol) and N,N'-carbonyldiimidazole (364 mg, 2.25 mmol) and stirred for 30 minutes at room temperature. The solution was treated with sodium ethoxide (408 mg, 6.0 mmol) and the reaction mixture stirred for a further 30 minutes at room temperature. The reaction mixture was quenched with citric acid solution (5 mL) and concentrated in vacuo. The residue was partitioned between dichloromethane (100 mL) and water (50 mL) and the organic phase separated, dried over magnesium sulphate and concentrated in vacuo. The residue was triturated with ethyl acetate (10 mL) and dried in vacuo to yield the title product. ¹H NMR (DMSO-D₆, 400 MHz) δ: 0.96 (t, 3H), 1.32 (t, 3H), 2.40 (s, 3H), 3.44 (q, 2H), 3.86 (t, 2H), 4.36 (q, 2H), 4.93 (t, 2H), 7.06 (m, 1H), 7.87 (s, 1H), 8.23 (d, 1H). MS APCI+ m/z 405 [MH]⁺

PREPARATION 176

2-(Dimethylamino)ethyl 5-chloro-1-(2-ethoxyethyl)-7-(4-methylpyridin-2-ylamino)-1H-pyrazolo[4,3-d]pyrimidine-3-carboxylate

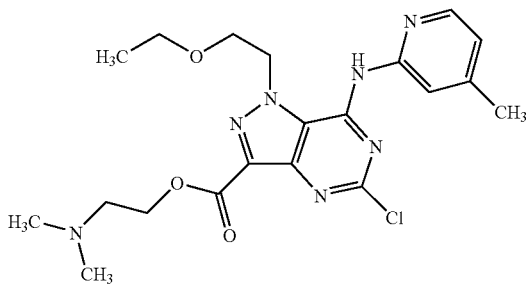

The carboxylic acid of preparation 137 (282 mg, 0.75 mmol) was suspended in 1-methyl-2-pyrrolidinone (2.5 mL) and the solution treated with N-ethyldiisopropylamine (157

μL, 0.9 mmol) and N,N'-carbonyldiimidazole (182 mg, 1.13 mmol) and stirred at room temperature for 30 minutes. The solution was treated with 2-(dimethylamino)ethanol (309 μL, 3.0 mmol) and 4-(N,N-dimethylamino)pyridine (12 mg, 0.1 mmol) and the reaction mixture heated to 50° C. for 18 hours. The reaction mixture was concentrated in vacuo and the residue purified by column chromatography on silica gel eluting with dichloromethane:methanol:0.88 ammonia 100:0:0 to 90:10:1 to yield the title product, 170 mg. $^1$H NMR (CD$_3$OD, 400 MHz) δ: 1.08 (t, 3H), 2.40 (s, 6H), 2.45 (s, 3H), 2.84 (t, 2H), 3.60 (m, 2H), 3.98 (t, 2H), 4.57 (t, 2H), 5.01 (m, 2H), 6.98 (d, 1H), 8.12 (m, 1H). MS APCI+ m/z 448 [MH]$^+$

PREPARATION 177

5-Chloro-1-(2-ethoxyethyl)-7-(4-methylpyridin-2-ylamino)-1H-pyrazolo[4,3-d]pyrimidine-3-carboxamide

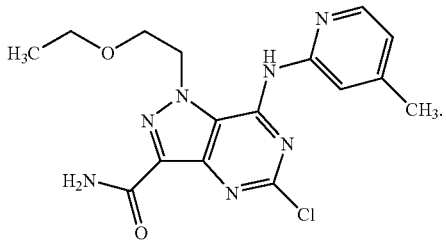

The carboxylic acid of preparation 137 (376 mg, 11.0 mmol) was added to a solution of N-[(dimethylamino)-1H-1,2,3-triazolo-[4,5-b]pyridin-1-yl-methylene]-N-methyl-methanaminium hexafluorophosphate N-oxide (HATU, 380 mg, 1.0 mmol) and N-ethyldiisopropylamine (1 mL, 5.6 mmol) in N,N-dimethylformamide (15 mL) The mixture was then treated with a saturated solution of ammonia in tetrahydrofuran (600 μL) and the reaction mixture stirred at room temperature for 48 hours. The reaction mixture was concentrated in vacuo and the residue partitioned between ethyl acetate (50 mL) and water (50 mL). The aqueous was extracted with ethyl acetate (2×50 mL) and dichloromethane (50 mL). The organics were combined, dried over magnesium sulphate and concentrated in vacuo. The residue was purified by column chromatography on silica gel eluting with dichloromethane: methanol 100:0 to 95:5 to yield the title product. $^1$H NMR (CDCl$_3$, 400 MHz) δ: 1.17 (t, 3H), 2.47 (s, 3H), 3.68 (m, 2H), 4.01 (t, 2H), 4.92 (m, 2H), 6.94 (m, 1H), 8.08 (m, 1H), 8.22 (m, 1H). MS APCI+ m/z 376 [MH]$^+$

PREPARATION 178

5-Chloro-1-(2-ethoxyethyl)-7-(4-fluoro-3-methylphenylamino)-1H-pyrazolo[4,3-d]pyrimidine-3-carboxamide

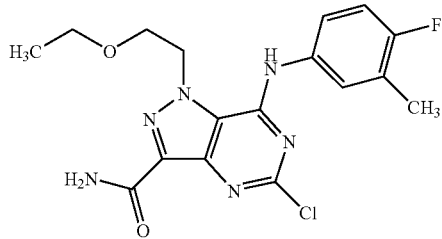

The title compound was prepared by a method similar to that described for preparation 177 using the carboxylic acid of preparation 152. $^1$H NMR (DMSO-D$_6$, 400 MHz) δ: 0.96 (t, 3H), 2.26 (s, 3H), 3.45 (q, 2H), 3.82 (m, 2H), 4.93 (m, 2H), 7.23 (t, 1H), 7.50 (m, 2H), 7.64 (s, 1H), 7.81 (s, 1H), 9.37 (s, 1H). MS APCI+ m/z 393 [MH]$^+$

PREPARATION 179

5-Chloro-1-(2-ethoxyethyl)-7-(4-methylpyridin-2-ylamino)-1H-pyrazolo[4,3-d]pyrimidine-3-carbonitrile

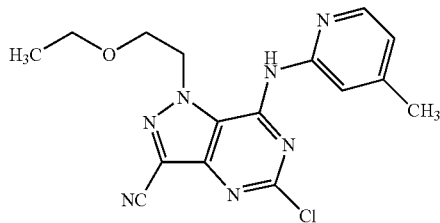

The amide of preparation 177 (140 mg, 0.37 mmol) was dissolved in a solution of trifluoroacetic anhydride (53 μL, 0.37 mmol) and pyridine (59 mg, 0.75 mmol) in tetrahydrofuran (5 mL) and the reaction mixture stirred at room temperature for 18 hours. The reaction mixture was concentrated in vacuo and the residue purified by column chromatography on silica gel eluting with dichloromethane to yield the title product. $^1$H NMR (CDCl$_3$, 400 MHz) δ: 1.09 (t, 3H), 2.40 (s, 3H), 3.66 (m, 2H), 3.91 (m, 2H), 5.00 (m, 2H), 6.85 (m, 1H), 8.05 (m, 1H), 8.08 (m, 1H). MS APCI+ m/z 358 [MH]$^+$

PREPARATION 180

5-Chloro-1-(2-ethoxyethyl)-7-(4-fluoro-3-methylphenylamino)-1H-pyrazolo[4,3-d]pyrimidine-3-carbonitrile

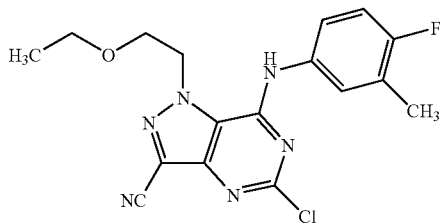

The title compound was prepared by a method similar to that described for preparation 179 using the amide of preparation 178. $^1$H NMR (CDCl$_3$, 400 MHz) δ: 1.19 (t, 3H), 2.32 (s, 3H), 3.68 (q, 2H), 4.04 (m, 2H), 4.80 (m, 2H), 7.05 (t, 1H), 7.56 (m, 2H), 9.37 (s, 1H). MS ES+ m/z 397 [MNa]$^+$

PREPARATION 181

5-Chloro-1-(2-ethoxyethyl)-N-hydroxy-7-(4-methylpyridin-2-ylamino)-1H-pyrazolo[4,3-d]pyrimidine-3-carboxamidine

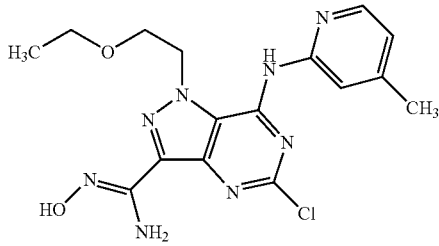

The nitrile of preparation 179 (100 mg, 0.28 mmol) was dissolved in a solution of hydroxylamine (23 mg, 0.34 mmol) in ethanol (2 mL) and the solution treated with a 5M aqueous solution of sodium hydroxide (68 µL, 0.34 mmol). The reaction mixture was stirred at 50° C. for 18 hours and then concentrated in vacuo to yield the title product. $^1$H NMR (DMSO-D$_6$, 400 MHz) δ: 1.02 (m, 3H), 2.37 (s, 3H), 3.50 (m, 2H), 3.85 (m, 2H), 4.84 (m, 2H), 6.96 (m, 1H), 8.16 (m, 1H), 8.20 (m, 1H). MS ES+ m/z 358 [MH]$^+$

PREPARATION 182

5-Chloro-1-(2-ethoxyethyl)-7-(4-fluoro-3-methylphenylamino)-N-hydroxy-1H-pyrazolo[4,3-d]pyrimidine-3-carboxamidine

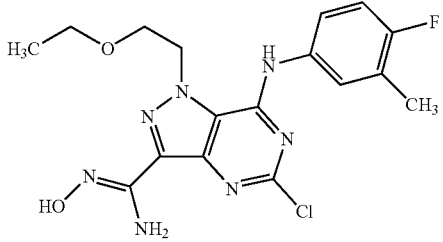

The title compound was prepared by a method similar to that described for preparation 181 using the nitrile of preparation 180. $^1$H NMR (DMSO-D$_6$, 400 MHz) δ: 0.95 (t, 3H), 2.26 (s, 3H), 3.44 (d, 2H), 3.79 (m, 2H), 4.88 (m, 2H), 7.21 (t, 1H), 7.50 (m, 2H), 9.30 (m, 1H), 9.95 (s, 1H). MS ES− m/z 406 [M-H]$^−$

PREPARATION 183

3-[5-Chloro-1-(2-ethoxyethyl)-7-(4-methylpyridin-2-ylamino)-1H-pyrazolo[4,3-d]pyrimidin-3-yl]-2H-1,2,4-oxadiazol-5-one

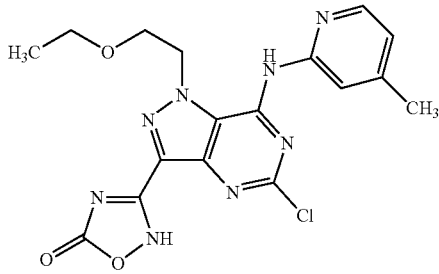

The product of preparation 181 (109 mg, 0.28 mmol) was dissolved in a solution of N,N'-carbonyldiimidazole (49 mg, 0.30 mmol) in N,N-dimethylformamide (2 mL) and the reaction mixture stirred at 80° C. for 2 hours. The reaction mixture was concentrated in vacuo and the residue triturated with acetone (3 mL), filtered and recrystalised from acetonitrile to yield the title product. $^1$H NMR (DMSO-D$_6$, 400 MHz) δ: 1.00 (t, 3H), 2.39 (s, 3H), 3.47 (m, 2H), 3.87 (t, 2H), 4.95 (t, 2H), 6.98 (d, 1H), 7.87 (s, 1H), 8.17 (m, 1H). MS APCI+ m/z 417 [MH]$^+$

PREPARATION 184

3-[5-Chloro-1-(2-ethoxyethyl)-7-(4-fluoro-3-methylphenylamino)-1H-pyrazolo[4,3-d]pyrimidin-3-yl]-2H-1,2,4-oxadiazol-5-one

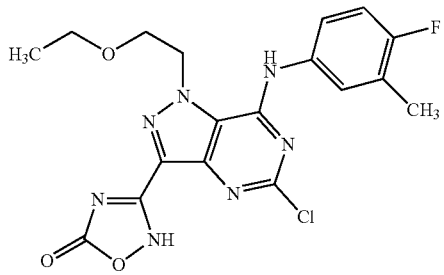

The title compound was prepared by a method similar to that described for preparation 183 using the product of preparation 182. $^1$H NMR (DMSO-D$_6$, 400 MHz) δ: 0.96 (t, 3H), 2.27 (s, 3H), 3.45 (m, 2H), 3.83 (m, 2H), 4.97 (m, 2H), 7.24 (t, 1H), 7.50 (m, 2H), 9.40 (s, 1H). MS APCI+ m/z 434 [MH]$^+$

PREPARATION 185

N-[5-Chloro-1-(2-ethoxyethyl)-3-(2H-tetrazol-5-yl)-1H-pyrazolo[4,3-d]pyrimidin-7-yl]-(4-methylpyridin-2-yl)amine

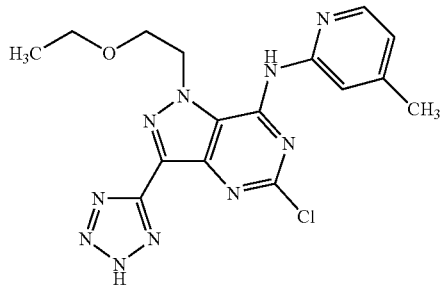

The nitrile of preparation 179 (100 mg, 0.28 mmol) was added to a solution of azidotributyltin (104 mg, 0.32 mmol) in dioxane (3 mL) and the reaction mixture heated to reflux for 18 hours. The reaction mixture was treated with further azidotributyltin (104 mg, 0.32 mmol) and the reaction mixture heated to reflux for a further 18 hours. The reaction mixture was diluted with a 2M solution of hydrochloric acid in ether (20 mL) and the mixture stirred at room temperature for 30 minutes. The reaction mixture was concentrated in vacuo and the residue adsorbed onto silica and purified by column chromatography on silica gel eluting with dichloromethane:methanol:acetic acid 100:0:0 to 90:10:1 to yield the title product. ¹H NMR (CD₃OD, 400 MHz) δ: 1.11 (t, 3H), 2.57 (s, 3H), 3.64 (q, 2H), 4.05 (t, 2H), 5.09 (t, 2H), 7.25 (d, 1H), 7.90 (s, 1H), 8.35 (d, 1H). MS APCI+ m/z 401 [MH]⁺

PREPARATION 186

N-[5-Chloro-1-(2-ethoxyethyl)-7-(4-methylpyridin-2-ylamino)-1H-pyrazolo[4,3-d]pyrimidine-3-carbonyl]methanesulfonamide

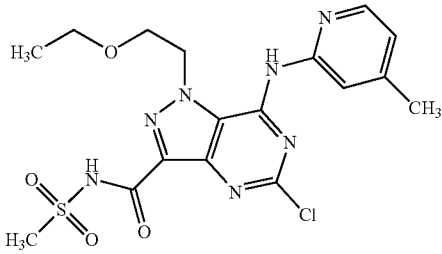

The carboxylic acid of preparation 137 (1.0 g, 2.70 mmol), methanesulphonamide (330 mg, 3.5 mmol), 1-(3-dimethylaminopropyl)-3-ethylcarbodiimide hydrochloride (660 mg, 3.5 mmol) and 4-dimethylaminopyridine (390 mg, 3.5 mmol) were dissolved in N,N-dimethylformamide (10 mL) and the reaction mixture stirred at room temperature for 60 hours. Additional methanesulphonamide (165 mg, 1.7 mmol), 1-(3-dimethylaminopropyl)-3-ethylcarbodiimide hydrochloride (330 1.7 mmol) and 4-dimethylaminopyridine (195 1.7 mmol) were added and the reaction mixture stirred for a further 20 hours. Further methanesulphonamide (165 1.7 mmol), 1-(3-dimethylaminopropyl)-3-ethylcarbodiimide hydrochloride (330 1.7 mmol) and 4-dimethylaminopyridine (195 1.7 mmol) were added and the reaction mixture stirred for a final 18 hours. The reaction mixture was concentrated in vacuo and the residue partitioned between dichloromethane (25 mL) and water (25 mL). The organic phase was separated, washed with water (2×25 mL), dried over magnesium sulphate and concentrated in vacuo. The residue was purified by column chromatography on silica gel eluting with dichloromethane:methanol:acetic acid 100:0:0 to 96:3.5:0.5. The crude product was triturated in warm ethyl acetate (10 mL) to yield the title product, 290 mg. ¹H NMR (DMSO-D₆, 400 MHz) δ: 0.95 (t, 3H), 2.40 (s, 3H), 3.40 (s, 3H), 3.45 (d, 2H), 3.85 (m, 2H), 4.95 (m, 2H), 7.15 (d, 1H), 7.85 (s, 1H), 8.25 (d, 1H). MS ES− m/z 452 [M-H]⁻

PREPARATION 187

3-(Methoxycarbonyl)-1-[(2S)-2-methoxypropyl]-4-nitro-1H-pyrazole-5-carboxylic acid

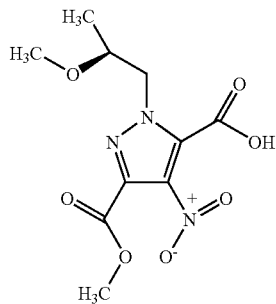

Diisopropyl azodicarboxylate (14.9 mL, 76 mmol) was added dropwise to a solution of dimethyl 4-nitropyrazole-3,5-dicarboxylate (15.73 g, 69 mmol), (S)-(+)-2-methoxypropanol (6.81 g, 76 mmol) and triphenylphosphine (19.9 g, 76 mmol) in tetrahydrofuran (220 mL) with stirring under nitrogen, keeping the reaction temperature between 0° C. and 110° C. by cooling in an ice bath. Once addition was complete the reaction was allowed to stir at room temperature for 18 hours. The reaction mixture was concentrated under reduced pressure and the residual oil re-dissolved in methanol (200 mL). Potassium hydroxide (3.88 g, 69 mmol) was added and the reaction was allowed to stir at room temperature for 18 hours. The mixture was concentrated under reduced pressure and the residue suspended in water (50 mL), and washed with dichloromethane (2×100 mL). The aqueous solution was acidified to pH 1 using concentrated hydrochloric acid, and then extracted with dichloromethane (3×100 mL). The combined organic extracts from extraction of the acidic solution were evaporated to dryness, then taken up in saturated aqueous sodium bicarbonate solution (100 ml). The aqueous solution was washed sequentially with dichloromethane (100 mL), and ethyl acetate (2×100 ml), then acidified to pH1 with concentrated hydrochloric acid and extracted with ethyl acetate (3×100 ml). The combined organic extracts from extraction of the acidic solution were dried over magnesium sulphate and concentrated under reduced pressure to afford the title compound as yellow oil. ¹H NMR (DMSO-D₆, 400 MHz) δ: 1.05 (d, 3H), 3.10 (s, 3H), 3.70 (m, 1H), 3.85 (d, 3H), 4.45-4.70 (m, 2H). MS APCI+ m/z 288 [MH]⁺

PREPARATION 188

2-(Cyclobutyloxy)ethanol

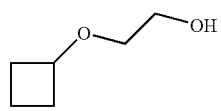

Butyl lithium (2.5M in hexanes, 61 mL, 0.152 mol) was added dropwise to an ice-cold solution of cyclobutanol (10 g, 0.139 mol) in tetrahydrofuran (250 mL) so as to maintain the reaction temperature below 110° C. The mixture was then stirred for a further 2 hours at 5-10° C., and a solution of 1,3,2-dioxathiolane 2,2-dioxide (18.90 g, 0.152 mol) in tetrahydrofuran (50 mL) was added dropwise so as to maintain the reaction temperature below 15° C. Once addition was complete the reaction was stirred for a further 3 hours at room temperature, water (3 mL) followed by concentrated sulphuric acid (7.5 mL) then added and the reaction stirred for an additional 18 hours. The reaction was carefully neutralised by the addition of solid sodium carbonate and sodium bicarbonate, and the mixture concentrated under reduced pressure at room temperature. The residue was diluted with water, saturated with sodium chloride added until saturation was achieved and the solution then extracted with ethyl acetate (4×100 mL). The combined organic extracts were dried over magnesium sulphate and evaporated under reduced pressure at room temperature. The residual orange oil was purified by Kugelrohr distillation to afford the title compound, 7.7 g. bp 70-80° C. at 10 mmHg. ¹H NMR (CDCl₃ 400 MHz) δ: 1.38-1.57 (m, 1H), 1.63 (m, 1H), 1.80-1.98 (m, 2H), 2.06-2.15 (m, 2H), 3.40 (t, 2H), 3.65 (t, 2H), 3.95 (m, 1H).

PREPARATION 189

1-[2-(Cyclobutyloxy)ethyl]-3-(methoxycarbonyl)-4-nitro-1H-pyrazole-5-carboxylic acid

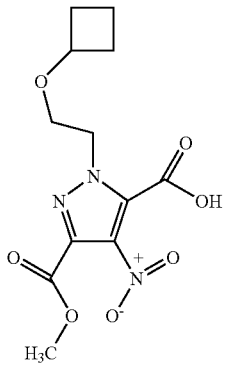

The title compound was obtained as a white solid from the alcohol from preparation 188 and dimethyl 4-nitropyrazole-3,5-dicarboxylate following a similar procedure to that described in preparation 187. 1H NMR (CDCl$_3$, 400 MHz) δ: 1.38-1.50 (m, 1H), 1.62 (m, 1H), 1.70-1.81 (m, 2H), 2.10 (m, 2H), 3.76 (m, 2H), 3.90 (m, 4H), 4.78 (t, 2H), 9.68 (br s, 1H). MS ES+ m/z 331 [MNH$_4$]$^+$

PREPARATION 190

2-(2,2-Difluoroethoxy)ethanol

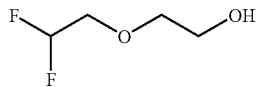

Tetra-butyl ammonium bromide (1.96 g, 6.08 mmol) was added portionwise to a solution of 2,2-difluoroethanol (25 g, 304.9 mmol) in triethylamine (45 mL, 322.9 mmol) and the mixture stirred for 5 minutes. Ethylene carbonate (29.53 g, 335.3 mmol) was added and the reaction mixture was heated at 100° C. for 18 hours. The cooled mixture was then distilled under reduced pressure, and the distillate containing the desired product was redistilled at atmospheric pressure to provide the title compound as a yellow liquid, 4.95 g (b.p. 127-128° C.). $^1$H NMR (CDCl$_3$,400 MHz) δ: 2.04 (br s, 1H), 3.65 (m, 2H), 3.72 (m, 4H), 5.70-6.02 (m, 1H).

PREPARATION 191

1-[2-(2,2-Difluoroethoxy)ethyl]-3-(methoxycarbonyl)-4-nitro-1H-pyrazole-5-carboxylic acid

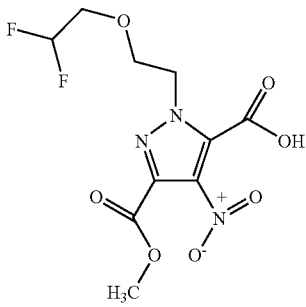

The title compound was obtained as a white solid, from the alcohol from preparation 190 and dimethyl 4-nitropyrazole-3,5-dicarboxylate, using a similar procedure to that described in preparation 187. $^1$H NMR (CDCl$_3$,400 MHz) δ: 3.61 (m, 2H), 3.92 (m, 5H), 4.80 (t, 2H), 5.60-5.88 (m, 1H). MS ES+ m/z 324 [MH]$^+$

PREPARATION 192

3-(Methoxycarbonyl)-4-nitro-1-[2-(2,2,2-trifluoroethoxy)ethyl]-1H-pyrazole-5-carboxylic acid

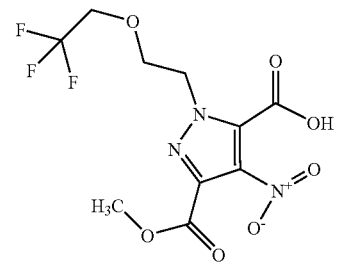

A solution of diisopropyl azodicarboxylate (71.9 mL, 366 mmol) in tetrahydrofuran (80 mL) was added dropwise to a solution of dimethyl 4-nitropyrazole-3,5-dicarboxylate (60 g, 260 mmol), 2,2,2-trifluoroethoxyethanol (Journal of Fluorine Chemistry (1992), 59(3), 387-96), (45.2 g, 314 mmol) and triphenylphosphine (96.15 g, 366 mmol) in tetrahydrofuran (650 mL) with stirring under nitrogen, maintaining the reaction temperature between 0° C. and 110° C. by cooling in an ice bath. After the addition was complete, the mixture was allowed to warm to room temperature and stirred for 2 days. The solvent was removed under reduced pressure and the residue was dissolved in methanol (800 mL) and cooled to 0° C. A solution of potassium hydroxide (16.16 g, 288 mmol) in methanol (200 mL) was added at 0° C. and the reaction was allowed to warm to room temperature and stirred for 16 hours. The solvent was removed under reduced pressure and the residue was partitioned between water (600 mL) and ethyl acetate (600 mL). The aqueous layer was washed with ethyl acetate (2×200 mL) and the aqueous phase then acidified with hydrochloric acid to pH1. The aqueous solution was extracted with ethyl acetate (3×400 mL), the combined extracts were dried over sodium sulphate and concentrated under reduced pressure to afford a colourless solid (52.86 g, 59%). The product was a mixture of 3-methoxycarbonyl-4-nitro-1-(2,2,2-trifluoroethoxy)ethylpyrazole-5-carboxylic acid (major) and 5-methoxycarbonyl-4-nitro-1-(2,2,2-trifluoroethoxy)ethylpyrazole-3-carboxylic acid (minor) and was used directly for the next step. $^1$H NMR (CDCl$_3$,400 MHz) δ: 3.77 (q, 2H), 3.93 (s, 3H), 4.00 (t, 2H), 4.84 (t, 2H).

PREPARATION 193

2-(3,3,3-Trifluoropropoxy)ethanol

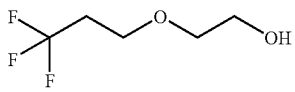

n-Butyl lithium (39 mL, 2.5M in hexanes, 97.5 mmol) was added dropwise to an ice-cooled solution of 3,3,3-trifluoropropan-1-ol (10 g, 87.7 mmol) in tetrahydrofuran (130 mL), so as to maintain the temperature below 5° C., and once addition was complete the reaction was stirred for a further hour at 0° C.

A solution of 1,3,2-dioxathiolane 2,2-dioxide (11.97 g, 96.5 mmol) in tetrahydrofuran (35 mL) was then added dropwise so as to maintain the internal temperature below 5° C., and once addition was complete the reaction was stirred at room temperature for 18 hours. Water (2 mL) followed by concentrated sulphuric acid (5 mL) were added and the reaction stirred for a further 6 hours at room temperature. The mixture was neutralised by the addition of sodium carbonate, then diluted with water (20 mL) and the resulting solid filtered off and washed with ethyl acetate. The filtrate was concentrated under reduced pressure and the residue suspended in brine and extracted with ethyl acetate (3×). The combined organic extracts were dried over magnesium sulphate and evaporated under reduced pressure. The residual gum was distilled under high vacuum to afford the title compound as a colourless liquid, 6.75 g (b.p. 57-80° C.).

$^1$H NMR (CDCl$_3$, 400 MHz) δ: 2.38 (m, 2H), 2.57 (m, 2H), 3.69 (m, 4H).

PREPARATION 194

3-(Methoxycarbonyl)-4-nitro-1-[2-(3,3,3-trifluoropropoxy)ethyl]-1H-pyrazole-5-carboxylic acid

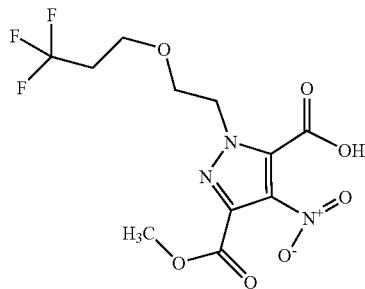

The title compound was obtained as a white solid, from the alcohol from preparation 193 and dimethyl 4-nitropyrazole-3,5-dicarboxylate, following the procedure described in preparation 187. $^1$H NMR (CDCl$_3$ 400 MHz) δ: 2.39 (m, 2H), 3.54 (t, 2H), 3.78 (m, 2H), 3.80 (s, 3H), 4.69 (t, 2H). MS ES+ m/z 356 [MH]$^+$

PREPARATION 195

2-(3-Fluoropropoxy)ethanol

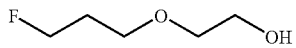

The title compound was obtained in 71% yield, from 3-fluoropropan-1-ol and 1,3,2-dioxathiolane 2,2-dioxide, following a similar procedure to that described in preparation 193.

$^1$H NMR (CDCl$_3$, 400 MHz) δ: 1.96 (m, 2H), 2.10 (bs, 1H), 3.58 (t, 2H), 3.62 (t, 2H), 3.75 (t, 2H), 4.50 (dd, 1H), 4.62 (dd, 1H).

PREPARATION 196

1-[2-(3-Fluoropropoxy)ethyl]-3-(methoxycarbonyl)-4-nitro-1H-pyrazole-5-carboxylic acid

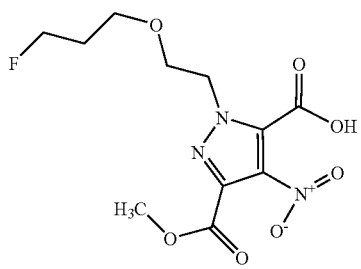

The title compound was obtained in 92% yield from dimethyl 4-nitropyrazole-3,5-dicarboxylate and the alcohol from preparation 195 following the procedure described in preparation 187. $^1$H NMR (CDCl$_3$, 400 MHz) δ: 1.81-1.95 (m, 2H), 3.56 (t, 2H), 3.83 (t, 2H), 3.97 (s, 3H), 4.38 (m, 1H), 4.48 (m, 1H), 4.82 (m, 2H). MS ES+ m/z 320 [MH]$^+$

PREPARATION 197

Methyl 5-(aminocarbonyl)-1-[(2S)-2-methoxypropyl]-4-nitro-1H-pyrazole-3-carboxylate

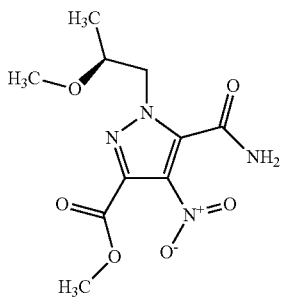

Oxalyl chloride (6.83 mL, 78.3 mmol) was added to a solution of the acid from preparation 187 (15 g, 52.2 mmol) in dichloromethane (250 mL) at 0° C. N,N-Dimethylformamide (0.15 mL) was added and the mixture was allowed to stir for 18 hours at room temperature. Tlc analysis (dichloromethane:methanol:0.88 ammonia, 95:5:1) showed starting material remaining, so additional oxalyl chloride (0.91 mL, 10 mmol) was added dropwise and the reaction stirred for a further 18 hours at room temperature. The solution was evaporated under reduced pressure and the residue was dissolved in tetrahydrofuran (250 mL). The solution was cooled to 0° C., 0.88 ammonia (20 mL) added dropwise, and once addition was complete, the reaction was stirred at room temperature for 1 hour. The reaction was concentrated under reduced pressure and the residue partitioned between dichloromethane (200 mL) and water (50 mL) and the layers separated. The aqueous solution was extracted with further dichloromethane (200 mL), the organic solutions combined, dried over magnesium sulphate and evaporated under reduced pressure to give the title compound as a white solid.
$^1$H NMR (DMSO-D$_6$, 400 MHz) δ: 1.25 (d, 3H), 3.30 (s, 3H), 3.85 (m, 1H), 4.00 (s, 3H), 4.40-4.50 (m, 2H), 6.20 (s, 1H), 7.50 (s, 1H). MS APCI+ m/z 287 [MH]$^+$

PREPARATION 198

Methyl 5-(aminocarbonyl)-1-[2-(cyclobutyloxy)ethyl]-4-nitro-1H-pyrazole-3-carboxylate

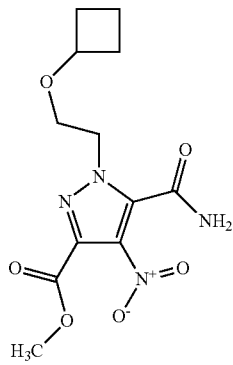

A solution of oxalyl chloride (6.71 mL, 76.7 mmol) in dichloromethane (30 mL) was added slowly to a solution of the acid from preparation 189 (20 g, 63.9 mmol) and N,N-dimethylformamide (0.28 mL) in dichloromethane (140 mL) with stirring and the mixture stirred at room temperature for 2 hours. The mixture was concentrated under reduced pressure and the residue azeotroped with dichloromethane (4×200 mL) to give an orange oil that was dried in vacuo. The residue was dissolved in tetrahydrofuran (170 mL), the solution cooled to −78° C. and concentrated aqueous ammonia (23.2 mL, 0.42 mol) was added dropwise. Once addition was complete, the reaction was stirred for a further 2 hours at −78° C. The reaction was quenched by the addition of excess 6N hydrochloric acid (17 mL) at −78° C. The mixture was allowed to warm to room temperature and the tetrahydrofuran was removed under reduced pressure. The resulting aqueous suspension was filtered, and the resulting solid washed with saturated sodium bicarbonate solution (2×50 mL). The solid was then washed with water until the filtrate was neutral, then dried in vacuo. The solid was stirred for 1 hour in a solution of ether:methanol (10:1 by volume, at 5 mL/g solid), then filtered and dried. The solid was then stirred in a solution of ether:methanol (5:1 by volume, 5 mL/g solid), filtered and dried in vacuo to afford the title compound, 10.34 g.

1H NMR (CDCl$_3$, 400 MHz) δ: 1.41-1.82 (m, 4H), 2.17 (m, 2H), 3.74 (t, 2H), 3.86 (m, 1H), 3.97 (s, 3H), 4.60 (t, 2H), 6.06 (br s, 1H), 7.54 (br s, 1H). MS ES+ m/z 330 [MNH$_4$]$^+$

PREPARATION 199

Methyl 5-(aminocarbonyl)-4-nitro-1-[2-(2,2,2-trifluoroethoxy)ethyl]-1H-pyrazole-3-carboxylate

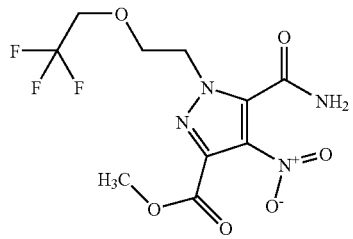

The carboxylic acid from preparation 192 (70.0 g, 204 mmol) was dissolved in a mixture of dichloromethane (1000 mL) and N,N-dimethylformamide (1 mL) under nitrogen at 20° C. Oxalyl chloride (25 mL, 366 mmol) was added dropwise with stirring. The mixture was stirred for 16 hours then concentrated under reduced pressure. Three portions of dichloromethane (200 mL) were added and evaporated sequentially to remove excess oxalyl chloride. The residue was dissolved in tetrahydrofuran (1000 mL) and cooled to −78° C. Concentrated aqueous 0.88 ammonia (70 mL) was added dropwise maintaining the mixture at −78° C. After the addition was complete the mixture was stirred for 1 hour, and then an excess of hydrochloric acid was added at −78° C. (to give pH1). The mixture was allowed to warm to room temperature and the solvent was removed under reduced pressure. The resulting cream-coloured solid was collected by filtration and washed with water (3×100 mL) to give a colourless solid (47.01 g). Trituration of the solid with a mixture of diethyl ether and methanol (20:1, 20 mL/g) gave the title compound as a colourless solid (40.0 g, 61%). $^1$H NMR (CDCl$_3$, 400 MHz) 3.78 (q, 2H), 3.95 (s, 3H), 3.98 (t, 2H), 4.76 (t, 2H), 5.91 (br s, 1H), 7.03 (br s, 1H).

PREPARATION 200

Methyl 5-(aminocarbonyl)-1-[2-(2,2-difluoroethoxy)ethyl]-4-nitro-1H-pyrazole-3-carboxylate

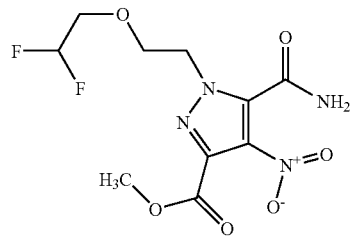

The title compound was obtained as a white solid from the compound from preparation 191, following the procedure described in preparation 199. $^1$H NMR (DMSO-d$_6$, 400 MHz) 3.63 (m, 2H), 3.85 (m, 5H), 4.39 (t, 2H), 5.84-6.19 (m, 1H), 8.38 (s, 1H), 8.45 (s, 1H). MS ES+ m/z 323 [MH]$^+$

PREPARATION 201

Methyl 5-(aminocarbonyl)-4-nitro-1-[2-(3,3,3-trifluoropropoxy)ethyl]-1H-pyrazole-3-carboxylate

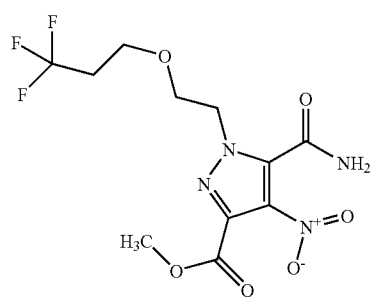

The title compound was obtained as a white solid from the acid from preparation 194, following a similar procedure to that described in preparation 199. $^1$H NMR (DMSO-d$_6$, 400

MHz) 2.43 (m, 2H), 2.55 (m, 2H), 3.76 (t, 2H), 3.94 (s, 3H), 4.28 (m, 2H), 8.38 (m, 2H). MS ES– m/z 353 [M-H]⁻

PREPARATION 202

Methyl 5-(aminocarbonyl)-1-[2-(3-fluoropropoxy)ethyl]-4-nitro-1H-pyrazole-3-carboxylate

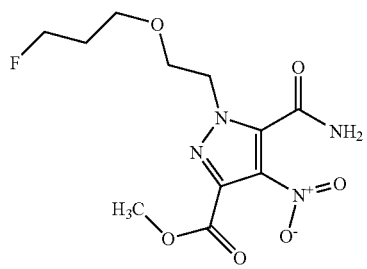

The title compound was obtained as a white solid from the acid from preparation 196, following a similar procedure to that described in preparation 199. ¹H NMR (CDCl₃, 400 MHz) δ: 1.83-1.99 (m, 2H), 3.58 (t, 2H), 3.84 (t, 2H), 3.98 (s, 3H), 4.40 (m, 1H), 4.54 (m, 1H), 4.70 (t, 2H). MS APCI+319 [MH]⁺

PREPARATION 203

Methyl 4-amino-5-(aminocarbonyl)-1-[(2S)-2-methoxypropyl]-1H-pyrazole-3-carboxylate

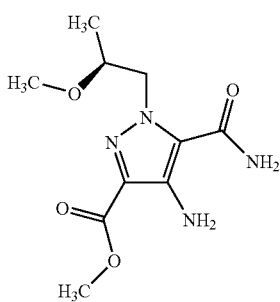

A solution of the compound from preparation 197 (7.1 g, 25 mmol) and palladium hydroxide (500 mg) in methanol (200 mL) was warmed to gentle reflux, and then ammonium formate (5.95 g, 94 mmol) added portionwise (care exotherm). Once the addition was complete the reaction was stirred under reflux for 18 hours under nitrogen. The cooled mixture was filtered through wet Arbocel®, and the filtrate evaporated under reduced pressure to give the title compound as yellow oil, 5.4 g. ¹H NMR (CDCl₃, 400 MHz) δ: 1.25 (d, 3H), 3.30 (s, 3H), 3.90 (m, 4H), 4.21-4.50 (m, 2H). MS APCI+ m/z 279 [MNa]⁺

PREPARATION 204

Methyl 4-amino-5-(aminocarbonyl)-1-[2-(cyclobutyloxy)ethyl]-1H-pyrazole-3-carboxylate

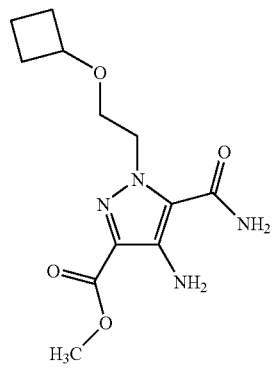

A solution of the compound from preparation 198 (10.34 g, 33 mmol) in methanol (400 mL) was hydrogenated over 10% palladium on charcoal (Degussa 101 type, 2.1 g) at 50 psi H₂ and 50° C. for 5 hours. The solution was filtered through Arbocel® filter aid. The filtrate was concentrated under reduced pressure, to afford the title compound as a colourless liquid, 9.32 g. ¹H NMR (CDCl₃, 400 MHz) δ: 1.39-1.52 (m, 1H), 1.60-1.80 (m, 3H), 2.12 (m, 2H), 3.80 (t, 2H), 3.90 (m, 4H), 4.32-4.70 (m, 2H). MS ES+ m/z 305 [MNa]⁺

PREPARATION 205

Methyl 4-amino-5-(aminocarbonyl)-1-[2-(2,2-difluoroethoxy)ethyl]-1H-pyrazole-3-carboxylate

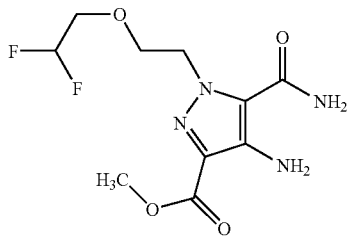

A mixture of the compound from preparation 200 (4.83 g, 15 mmol) and 10% palladium on charcoal (1.2 g) in methanol (250 mL) was hydrogenated at 3 Bar of hydrogen and room temperature for 24 hours. The mixture was warmed to 50° C., filtered through Arbocel®, washing through with warm methanol (500 mL). The filtrate was concentrated under reduced pressure, and the residue azeotroped with acetonitrile to afford the title compound as a white solid, 3.8 g. ¹H NMR (CDCl₃, 400 MHz) δ: 3.68 (m, 2H), 3.91 (s, 3H), 4.03 (t, 2H), 4.61 (t, 2H), 5.61-5.96 (m, 1H), 6.20-6.39 (br s, 2H). MS ES+ m/z 293 [MH]⁺

PREPARATION 206

Methyl 4-amino-5-(aminocarbonyl)-1-[2-(2,2,2-trifluoroethoxy)ethyl]-1H-pyrazole-3-carboxylate

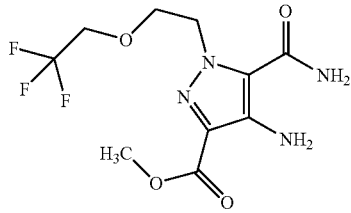

A solution of the compound from preparation 199 (40.0 g, 118 mmol) in methanol (640 mL) was hydrogenated over 10% palladium on charcoal (10.0 g) at 3 bar and 50° C. for 3 hours. The hot solution was filtered through Arbocel® filter aid and the filter cake was washed with dichloromethane. The filtrate was concentrated under reduced pressure. The residue was kept under vacuum overnight at room temperature to provide the title product as an off-white solid, (34.2 g, 94%). $^1$H NMR (CDCl$_3$, 400 MHz) δ: 3.80 (q, 2H), 3.91 (s, 3H), 4.07 (t, 2H), 4.63 (t, 2H), 6.29 (br s, 2H).

PREPARATION 207

Methyl 4-amino-5-(aminocarbonyl)-1-[2-(3,3,3-trifluoropropoxy)ethyl]-1H-pyrazole-3-carboxylate

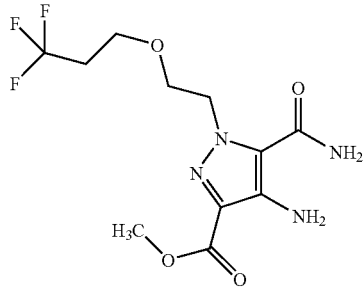

The title compound was obtained as an off-white solid, from the compound from preparation 201 following a similar procedure to that described in preparation 205. $^1$H NMR (DMSO-d$_6$, 400 MHz) δ: 2.41 (m, 2H), 3.52 (t, 2H), 3.68 (t, 2H), 3.74 (s, 3H), 4.49 (t, 2H), 5.09 (s, 2H), 7.40 (s, 2H). MS APCI+ m/z 325 [MH]$^+$

PREPARATION 208

Methyl 4-amino-5-(aminocarbonyl)-1-[2-(3-fluoropropoxy)ethyl]-1H-pyrazole-3-carboxylate

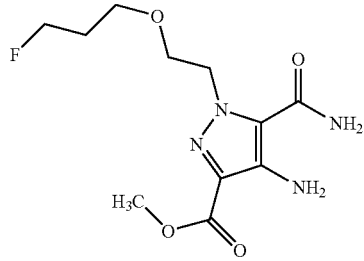

The title compound was prepared in quantitative yield from the compound from preparation 202, following the procedure described in preparation 206. $^1$H NMR (CDCl$_3$, 400 MHz) δ: 1.83-1.99 (m, 2H), 3.61 (t, 2H), 3.95 (m, 5H), 4.38 (m, 1H), 4.50 (m, 1H), 4.58 (m, 2H).

PREPARATION 209

Methyl 1-[(2S)-2-methoxypropyl]-5,7-dioxo-4,5,6,7-tetrahydro-1H-pyrazolo[4,3-d]pyrimidine-3-carboxylate

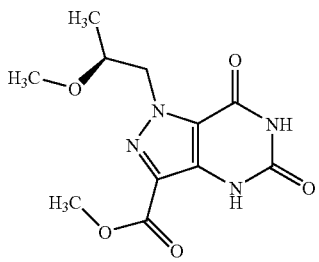

A mixture of the amine from preparation 203 (2.7 g, 9.7 mmol) and 1,1'-carbonyldiimidazole (1.89 g, 11.7 mmol) in N,N-dimethylformamide (80 mL) was stirred at room temperature for 1 hour. The mixture was concentrated under reduced pressure and the residue dissolved in acetone. The mixture was sonicated for 30 minutes, and the resulting precipitate filtered off and dried. The filtrate was sonicated again, the precipitate was filtered, dried and combined to afford the title compound, 740 mg. $^1$H NMR (DMSO-d$_6$, 400 MHz) δ: 1.05 (m, 3H), 3.15 (s, 3H), 3.75-3.85 (m, 1H), 3.88 (s, 3H), 4.40, 4.60 (2×m, 2H).

MS APCI+ 305 [MNa]$^+$

PREPARATION 210

Methyl 1-[2-(cyclobutyloxy)ethyl]-5,7-dioxo-4,5,6,7-tetrahydro-1H-pyrazolo[4,3-d]pyrimidine-3-carboxylate

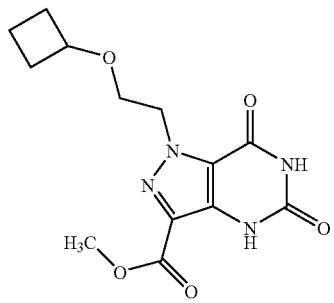

A solution of the amide from preparation 204 (9.32 g, 33 mmol) in acetonitrile (70 mL) was added dropwise to a refluxing solution of 1,1'-carbonyldiimidazole (13.38 g, 82.5 mmol) in acetonitrile (230 mL). The reaction was then stirred for a further 18 hours under reflux, and then cooled to 0° C. The resulting yellow precipitate was filtered off, washed with ice-cold acetonitrile and dried in vacuo to afford the title compound, 7.28 g. $^1$H NMR (CDCl$_3$, 400 MHz) δ: 1.26-1.40 (m, 1H), 1.54 (m, 1H), 1.63 (m, 2H), 2.01 (m, 1H), 3.63 (t, 2H), 3.81 (m, 4H), 4.59 (t, 2H), 11.78 (br s, 1H), 11.38 (br s, 1H). MS ES⁻ m/z 307 [M-H]⁻

PREPARATION 211

Methyl 1-[2-(2,2-difluoroethoxy)ethyl]-5,7-dioxo-4,5,6,7-tetrahydro-1H-pyrazolo[4,3-d]pyrimidine-3-carboxylate

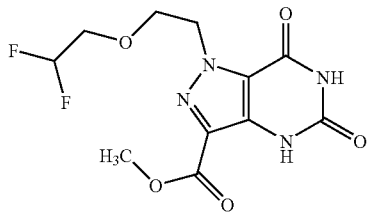

A solution of 1,1'-carbonyldiimidazole (3.16 g, 19.5 mmol) in acetonitrile (60 mL) was added portionwise over 3 hours to a solution of the compound from preparation 205 (3.8 g, 13.0 mmol) in acetonitrile (150 mL) stirring under reflux. The reaction was then stirred under reflux for a further 3 hours and allowed to cool. The reaction mixture was concentrated under reduced pressure and the residue triturated with water, the resulting solid filtered off, washed with water and dried in vacuo to afford the title compound as a pale grey solid, 3.17 g. ¹H NMR (DMSO-d₆, 400 MHz) δ: 3.61 (m, 2H), 3.79 (s, 3H), 3.90 (t, 2H), 3.64 (t, 2H), 5.99 (m, 1H), 10.78 (bs, 1H), 11.35 (bs, 1H). MS ES+ m/z 318 [MH]⁺

PREPARATION 212

Methyl 5,7-dioxo-1-[2-(2,2,2-trifluoroethoxy)ethyl]-4,5,6,7-tetrahydro-1H-pyrazolo[4,3-d]pyrimidine-3-carboxylate

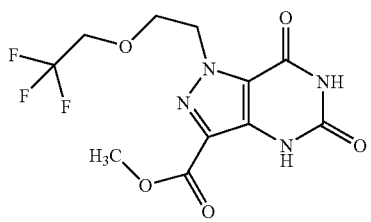

A solution of the amine from preparation 206 (21.7 g, 70.0 mmol) in acetonitrile (150 mL) was added dropwise over 2 hours to a stirred solution of 1,1'-carbonyldiimidazole (17.02 g, 105 mmol) in refluxing acetonitrile (850 mL) under nitrogen. The mixture was heated under reflux for 2 hours, cooled and the solvent was removed under reduced pressure. The residue was treated with water (150 mL). The resulting pale grey solid was filtered off, washed with water (3×100 mL), and dried in vacuo at 80° C. to provide the title compound, 21.26 g. ¹H NMR (CDCl₃, 400 MHz) δ: 3.79 (q, 2H), 3.98 (s, 3H), 4.07 (t, 2H), 4.77 (t, 2H), 7.87 (br s, 1H), 8.41 (br s, 1H). MS ES- m/z 335 [M-H]⁻

PREPARATION 213

Methyl 5,7-dioxo-1-[2-(3,3,3-trifluoropropoxy)ethyl]-4,5,6,7-tetrahydro-1H-pyrazolo[4,3-d]pyrimidine-3-carboxylate

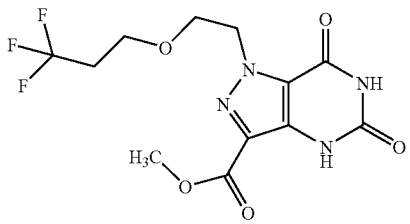

The title compound was obtained as a pale yellow solid from the compound from preparation 207 and 1,1'-carbonyldiimidazole, following a similar procedure to that described in preparation 212. ¹H NMR (CDCl₃, 400 MHz) δ: 2.26 (m, 2H), 3.61 (t, 2H), 3.88 (t, 2H), 3.98 (s, 3H), 4.75 (t, 2H), 8.05 (s, 1H), 8.49 (s, 1H). MS m/z 351 [MH]⁺

PREPARATION 214

Methyl 5,7-dioxo-1-[2-(3-fluoropropoxy)ethyl]-4,5,6,7-tetrahydro-1H-pyrazolo[4,3-d]pyrimidine-3-carboxylate

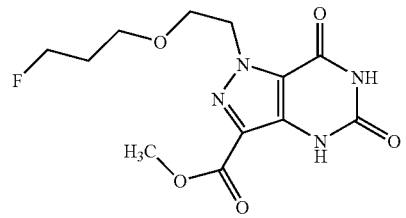

A solution of the amine from preparation 208 (2.3 g, 8.0 mmol) in acetonitrile (35 mL) was added dropwise to a stirred solution of 1,1'-carbonyldiimidazole (20.0 g, 12.3 mmol) in refluxing acetonitrile (35 mL) under nitrogen. The mixture was then heated under reflux for 2 hours, and cooled to room temperature. The resulting solid was filtered off, washed with acetonitrile and the filtrate evaporated under reduced pressure. The residue was triturated with water, the solid filtered off and the two isolated solids combined and dried in vacuo to afford the title compound, 2.3 g. ¹H NMR (DMSO-D₆, 400 MHz) δ: 1.70-1.92 (m, 2H), 3.42 (t, 2H), 3.79 (t, 2H), 3.83 (s, 3H), 4.27 (dd, 1H), 4.40 (dd, 1H), 4.65 (m, 2H). MS APCI+ m/z 315 [MH]⁺

PREPARATION 215

Methyl 5,7-dichloro-1-[(2S)-2-methoxypropyl]-1H-pyrazolo[4,3-d]pyrimidine-3-carboxylate

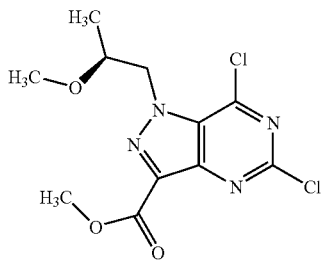

Phosphorous oxychloride (3.46 mL, 37.2 mmol) was added to a solution of the compound from preparation 209 (700 mg, 2.48 mmol) and tetraethylammonium chloride hydrate (616 mg, 3.72 mmol) in acetonitrile (8 mL) and the reaction mixture heated under reflux for 24 hours. The cooled mixture was concentrated under reduced pressure and the residue azeotroped with toluene (3×) to provide the title compound as a white solid. $^1$H NMR (CDCl$_3$, 400 MHz) δ: 1.30 (d, 3H), 3.15 (s, 3H), 3.90 (m, 1H), 4.10 (s, 3H), 4.68 (dd, 1H), 4.98 (dd, 1H).

PREPARATION 216

Methyl 5,7-dichloro-1-[2-(cyclobutyloxy)ethyl]-1H-pyrazolo[4,3-d]pyrimidine-3-carboxylate

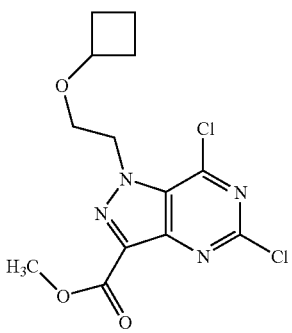

N,N-Diisopropylethylamine (3.4 mL, 19.5 mmol) was added dropwise to a solution of the compound from preparation 210 (2 g, 6.5 mmol), phosphorous oxychloride (9.04 mL, 97.3 mmol) and tetraethylammonium chloride (2.15 g, 13.0 mmol) in acetonitrile (25 mL) and the reaction heated under reflux for 18 hours. Tlc analysis showed starting material remaining, so additional phosphorous oxychloride (10 mL, 107 mmol) was added and the reaction heated under reflux for a further 24 hours. The cooled mixture was concentrated under reduced pressure and the residue azeotroped with toluene (2×100 mL). The product was dissolved in dichloromethane (500 mL), washed with water (3×200 mL), dried over magnesium sulphate and evaporated under reduced pressure. The crude product was purified by column chromatography using an Isolute® silica gel cartridge and an elution gradient of ethyl acetate:pentane (20:80 to 100:0) to provide the title compound as a white solid, 1.0 g. $^1$H NMR (CDCl$_3$, 400 MHz) δ: 1.40 (m, 1H), 1.55-1.75 (m, 3H), 2.10 (m, 2H), 3.80 (m, 3H), 4.10 (s, 3H), 5.00 (t, 2H).

PREPARATION 217

Methyl 5,7-dichloro-1-[2-(2,2-difluoroethoxy)ethyl]-1H-pyrazolo[4,3-d]pyrimidine-3-carboxylate

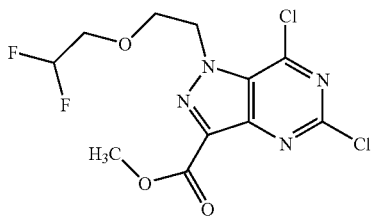

Phosphorous oxychloride (14 mL, 148 mmol) was added portionwise to a solution of the compound from preparation 211 (3.13 g, 9.84 mmol) and tetraethylammonium chloride (4.08 g, 2.46 mmol) in propionitrile (50 mL) and the reaction then stirred under reflux for 18 hours. The cooled mixture was concentrated under reduced pressure and the residue azeotroped with toluene (2×). The residual solid was triturated with pentane:ether (40 mL:10 mL), and the resulting solid filtered off. This was pre-adsorbed onto silica gel and purified by column chromatography on silica gel using ethyl acetate:pentane (34:66) to afford the title compound as a white solid, 2.69 g. $^1$H NMR (CDCl$_3$, 400 MHz) δ: 3.55 (m, 2H), 4.03 (t, 2H), 4.06 (s, 3H), 5.00 (t, 2H), 5.66 (m, 1H). Microanalysis found: C, 37.14; H, 2.85; N, 15.68. $C_{11}H_{10}Cl_2F_2N_4O_3$ requires C, 37.20; H, 2.84; N, 15.78%.

PREPARATION 218

Methyl 5,7-dichloro-1-[2-(2,2,2-trifluoroethoxy)ethyl]-1H-pyrazolo[4,3-d]pyrimidine-3-carboxylate

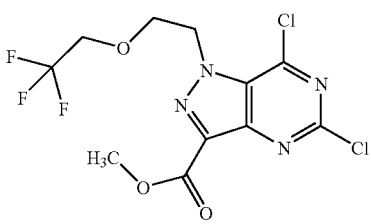

A mixture of the compound from preparation 212 (10 g, 29.8 mmol), phosphorous oxychloride (42 mL, 447 mmol) and tetraethylammonium chloride hydrate (14.8 g, 89.4 mmol) in propionitrile (125 mL) was stirred under reflux for 8 hours. The cooled mixture was concentrated under reduced pressure and the residue azeotroped with toluene. The product was partitioned between dichloromethane (600 mL) and water (500 mL) and the layers separated. The aqueous solution was further extracted with dichloromethane (2×500 mL) and the combined organic solutions washed with water (500 mL) and brine (200 mL), then dried over magnesium sulphate and concentrated under reduced pressure. The crude product was purified by column chromatography on silica gel using an elution gradient of ethyl acetate:pentane (33:67 to 50:50) to afford the title compound as a white solid, 5.4 g. $^1$H NMR (CDCl$_3$, 400 MHz) δ: 3.75 (q, 2H), 4.10 (s, 3H), 4.15 (t, 2H), 5.05 (t, 2H).
MS APCI+ m/z 373 [M]$^+$

PREPARATION 219

Methyl 5,7-dichloro-1-[2-(3,33-trifluoropropoxy)ethyl]-1H-pyrazolo[4,3-d]pyrimidine-3-carboxylate

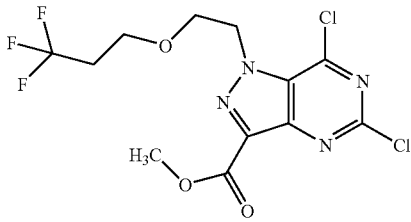

A mixture of the compound from preparation 213 (3.28 g, 9.37 mmol), phosphorous oxychloride (13.1 mL, 140 mmol) and tetraethylammonium chloride hydrate (3.88 g, 23.4 mmol) in propionitrile (50 mL) was stirred under reflux for 18 hours. The cooled mixture was concentrated under reduced pressure and the residue azeotroped with toluene. The product was partitioned between dichloromethane (50 mL) and water (50 mL) and the layers separated. The aqueous solution was further extracted with dichloromethane (2×50 mL) and the combined organic solutions dried over magnesium sulphate and concentrated under reduced pressure. The residue was triturated with pentane:ether, the resulting solid filtered off, washed with pentane and dried in vacuo to give the title compound as a solid, 3.2 g. $^1$H NMR (CDCl$_3$, 400 MHz) δ: 2.20 (m, 2H), 3.57 (t, 2H), 3.90 (t, 2H), 4.06 (s, 3H), 4.99 (t, 2H). MS+ m/z 387 [MH]$^+$

PREPARATION 220

Methyl 5,7-dichloro-1-[2-(3-fluoropropoxy)ethyl]-1H-pyrazolo[4,3-d]pyrimidine-3-carboxylate

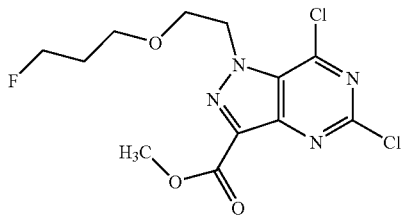

The title compound was obtained as a cream coloured solid in 86% yield, from the compound from preparation 214, following a similar procedure to that described in preparation 219. $^1$H NMR (CDCl$_3$, 400 MHz) δ: 1.76-86 (m, 2H), 3.48 (t, 2H), 3.95 (t, 2H), 4.09 (s, 3H), 4.29 (dd, 1H), 4.42 (dd, 1H), 5.01 (t, 2H). MS APCI+ m/z 351 [MH]$^+$

PREPARATION 221

Methyl 5-chloro-1-[(2S)-2-methoxypropyl]-7-[(4-methylpyridin-2-yl)amino]-1H-pyrazolo[4,3-d]pyrimidine-3-carboxylate

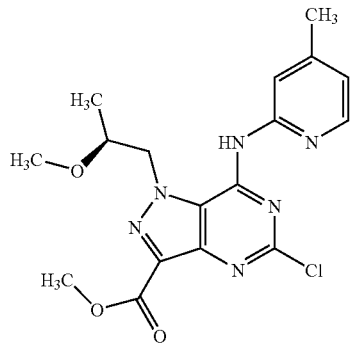

A solution of 2-amino-4-methylpyridine (850 mg, 7.83 mmol) in dimethylsulphoxide (7 mL) was warmed to 30° C., and the dichloro compound from preparation 215 (500 mg, 1.56 mmol) added. The reaction was stirred for a further 2 hours at 30° C. and then cooled to room temperature. The reaction mixture was poured into water (100 mL) and extracted with dichloromethane (2×200 mL). The combined organic solutions were washed with water (200 mL), 1M citric acid solution (100 mL) then dried over magnesium sulphate and concentrated under reduced pressure. The product was triturated with ether, the solid filtered and dried to afford the title compound as yellow crystals, 200 mg. $^1$H NMR (DMSO-D$_6$, 400 MHz) δ: 1.18 (d, 3H), 2.40 (s, 3H), 3.25 (m, 1H), 3.30 (s, 3H), 3.90 (s, 3H), 4.85 (d, 2H), 7.00 (br s, 1H), 8.20 (br s, 1H). MS APCI$^-$ m/z 389 [MH]$^-$

PREPARATION 222

Methyl 7-{[4-({[tert-butyl(dimethyl)silyl]oxy}methyl)pyridin-2-yl]amino}-5-chloro-1-(2-ethoxyethyl)-1H-pyrazolo[4,3-d]pyrimidine-3-carboxylate

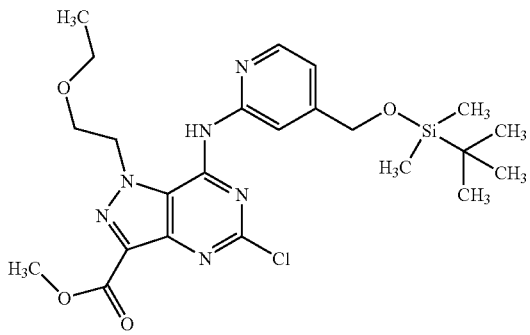

A mixture of the dichloro compound from preparation 58 (400 mg, 1.25 mmol) and 4-(tert-butyl-dimethyl-silanyloxymethyl)-pyridin-2-ylamine (WO 2001 017995, prep 8-5) (746 mg, 3.13 mmol) in dichloromethane (10 mL) was stirred at room temperature for 18 hours. The mixture was partitioned between water (30 mL) and dichloromethane (30 mL), the layers separated and the organic phase dried over magnesium sulphate and evaporated under reduced pressure. The resulting yellow oil was purified by column chromatography on an Isolute® silica gel cartridge using an elution gradient of ethyl acetate:pentane (0:100 to 70:30) to afford the title compound, 229 mg. $^1$H NMR (MeOD-D$_6$, 400 MHz) δ: 0.06 (s, 6H), 0.87 (s, 9H), 0.99 (t, 3H), 3.48 (q, 2H), 3.87 (m, 2H), 3.88 (s, 3H), 4.53 (s, 2H), 4.88 (m, 2H), 6.96 (m, 1H), 8.12 (m, 1H). MS ES+ m/z 521 [MH]$^+$

PREPARATION 223

Methyl 5-chloro-1-(2-propoxyethyl)-7-(pyridin-2-ylamino)-1H-pyrazolo[4,3-d]pyrimidine-3-carboxylate

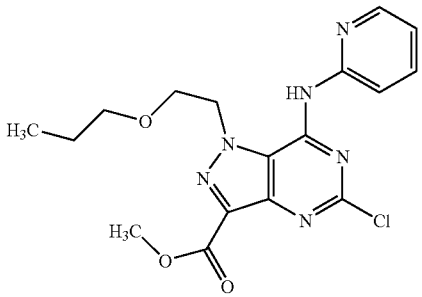

A mixture of the dichloro compound from preparation 57 (1.33 g, 4 mmol) and 2-aminopyridine (1.88 g, 20 mmol) in dichloromethane (16 mL) was stirred at 35° C. for 18 hours. The reaction was diluted with dichloromethane (200 mL), the mixture washed with 1M citric acid solution (2×50 mL), dried over magnesium sulphate and evaporated under reduced pressure to afford the title compound as a yellow solid, 1.48 g.

¹H NMR (DMSO-D₆+1 drop TFA-d, 400 MHz) δ: 0.80 (t, 3H), 1.38 (m, 2H), 3.37 (t, 2H), 3.85 (t, 2H), 3.88 (s, 3H), 4.94 (t, 2H), 7.20 (m, 1H), 8.01 (m, 1H), 8.10 (d, 1H), 8.38 (d, 1H). MS APCI+ m/z 391 [MH]⁺

PREPARATION 224

Methyl 5-chloro-1-[2-(cyclobutyloxy)ethyl]-7-[(4-methylpyridin-2-yl)amino]-1H-pyrazolo[4,3-d]pyrimidine-3-carboxylate

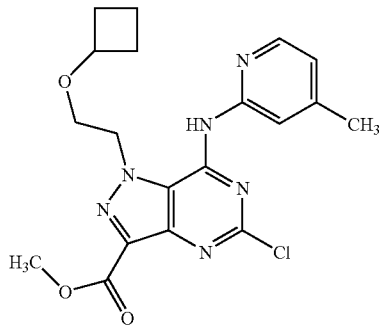

A mixture of the dichloro compound from preparation 216 (1.0 g, 2.90 mmol) and 2-amino-4-picoline (1.57 g, 14.53 mmol) in dichloromethane (12 mL) were stirred at room temperature for 18 hours. The mixture was partitioned between dichloromethane (250 mL) and 1M citric acid solution (100 mL) and the layers separated. The organic layer was washed again with 1M citric acid solution (100 mL), water (100 mL), and brine (20 mL) then dried over magnesium sulphate and evaporated under reduced pressure. The product was suspended in ether (50 mL), the mixture sonicated, then filtered and the solid dried in vacuo to afford the title compound as a yellow solid, 618 mg. ¹H NMR (DMSO-D₆+TFA-d, 400 MHz) δ: 1.35 (m, 1H), 1.50 (m, 1H), 1.70 (m, 2H), 2.00 (m, 2H), 2.42 (s, 3H), 3.75 (t, 2H), 3.90 (m, 4H), 4.95 (t, 2H), 7.10 (d, 1H), 7.82 (s, 1H), 8.30 (d, 1H). MS APCI+ m/z 417 [MH]⁺

PREPARATION 225

Methyl 5-chloro-1-[2-(2,2-difluoroethoxy)ethyl]-7-[(4-methylpyridin-2-yl)amino]-1H-pyrazolo[4,3-d]pyrimidine-3-carboxylate

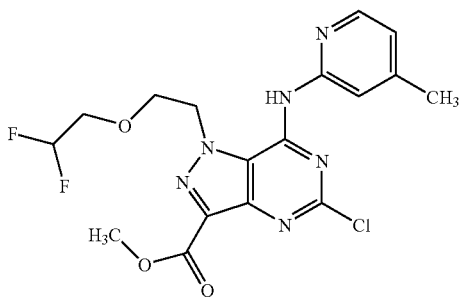

The title compound was prepared as a yellow solid n 56% yield from the chloro compound from preparation 217 and 2-amino-4-picoline (1.62 g, 15 mmol) following the procedure described in preparation 224. ¹H NMR (DMSO-D₆+1 drop TFA-d, 400 MHz) δ: 2.40 (s, 3H), 3.68 (m, 2H), 3.88 (s, 3H), 4.00 (t, 2H), 5.05 (t, 2H), 6.00 (m, 1H), 7.04 (d, 1H), 7.76 (s, 1H), 8.24 (d, 1H).

PREPARATION 226

Methyl 5-chloro-7-[(4-methylpyridin-2-yl)amino]1-[2-(2,2,2-trifluoroethoxy)ethyl]-1H-pyrazolo[4,3-d]pyrimidine-3-carboxylate

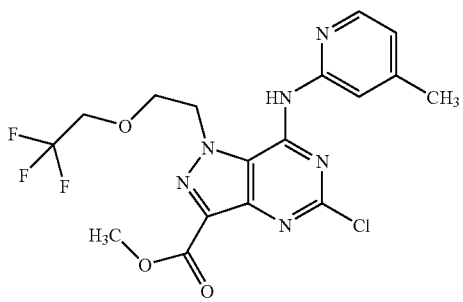

A mixture of the chloro compound from preparation 218 (5.6 g, 14.9 mmol) and 2-amino-4-picoline (4.85 g, 44.8 mmol) in acetonitrile (60 mL) was stirred under reflux for 5 hours. The reaction mixture was cooled and diluted with 10% aqueous citric acid solution (33.6 mL) and the mixture stirred for 10 minutes. The mixture was then cooled in ice for 30 minutes, the resulting precipitate filtered off, washed with ice-cold acetonitrile:water solution (50:50 by volume, 37 mL) and ice-cold water (19 mL). The solid was then dried in vacuo to afford the title compound, 5.05 g. ¹H NMR (DMSO-D₆, 400 MHz) δ: 2.38 (s, 3H), 3.81 (s, 3H), 4.00 (m, 4H), 5.02 (br s, 2H), 6.85 (br s, 1H), 7.64 (br s, 1H), 8.04 (br s, 1H). MS ES+ m/z 445 [MH]⁺

PREPARATION 227

Methyl 5-chloro-7-[(3-methylphenyl)amino]-1-[2-(2,2,2-trifluoroethoxy)ethyl]-1H-pyrazolo[4,3-d]pyrimidine-3-carboxylate

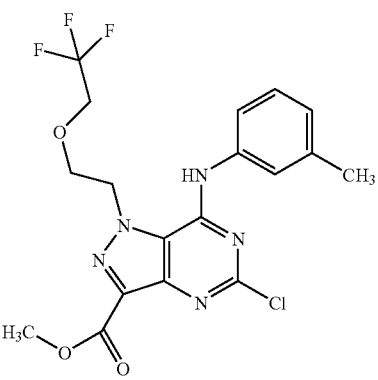

A mixture of the chloro compound from preparation 218 (746 mg, 2 mmol) and 3-methylaniline (650 μL, 6 mmol) in dimethylsulphoxide (8 mL) was stirred at room temperature for 3 hours. The mixture was partitioned between dichloromethane (200 mL) and water (50 mL), and the layers separated. The organic phase was washed with 1M hydrochloric acid (20 mL) and water (2×50 mL), then dried over magnesium sulphate and evaporated under reduced pressure to afford the title compound as a white solid, 880 mg. $^1$H NMR (CDCl$_3$, 400 MHz) δ: 2.38 (s, 3H), 3.98 (q, 2H), 4.05 (s, 3H), 4.30 (t, 2H), 4.90 (t, 2H), 7.00 (d, 1H), 7.31 (m, 1H), 7.35 (s, 1H), 7.55 (d, 1H), 8.45 (s, 1H). MS APCI+ m/z 444 [MH]$^+$

PREPARATION 228

Methyl 5-chloro-7-[(4-fluoro-3-methylphenyl)amino]-1-[2-(2,2,2-trifluoroethoxy)ethyl]-1H-pyrazolo[4,3-d]pyrimidine-3-carboxylate

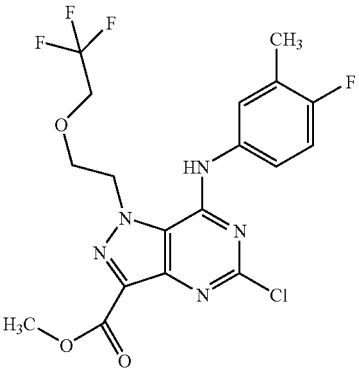

The title compound was obtained from the chloro compound from preparation 218 and 4-fluoro-3-methylamine, following the procedure described in preparation 227. $^1$H NMR (CDCl$_3$, 400 MHz) δ: 2.30 (s, 3H), 3.98 (q, 2H), 4.05 (s, 3H), 4.27 (t, 2H), 4.90 (s, 2H), 7.06 (m, 1H), 7.38 (m, 1H), 7.47 (m, 1H), 8.36 (s, 1H). MS APCI+ m/z 462 [MH]$^+$

PREPARATION 229

Methyl 5-chloro-7-[(4-methylpyridin-2-yl)amino]-1-[2-(3,3,3-trifluoropropoxy)ethyl]-1H-pyrazolo[4,3-d]pyrimidine-3-carboxylate

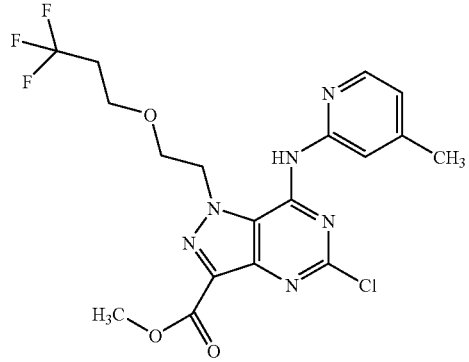

The title compound was obtained as a solid in 74% yield from the compound from preparation 219 and 2-amino-4-picoline, following the procedure described in preparation 223. $^1$H NMR (DMSO-D$_6$+1 drop TFA-d, 400 MHz) δ: 2.41 (s, 3H), 2.44 (t, 2H), 3.63 (t, 2H), 3.88 (s, 3H), 3.91 (t, 2H), 5.01 (t, 2H), 7.04 (d, 1H), 7.79 (s, 1H), 8.21 (d, 1H). MS APCI+ m/z 459 [M]$^-$

PREPARATION 230

Methyl 5-chloro-1-[2-(3-fluoropropoxy)ethyl]-7-[(4-methylpyridin-2-yl)amino]-1H-pyrazolo[4,3-d]pyrimidine-3-carboxylate

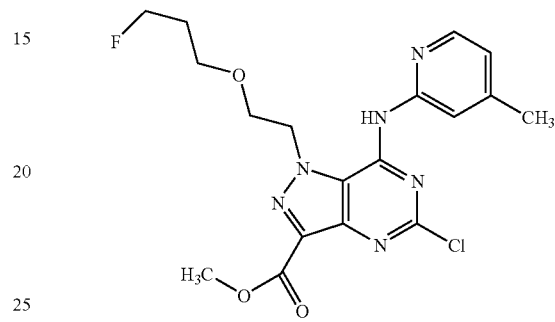

The title compound was obtained as a solid in 75% yield from the compound from preparation 220 and 2-amino-4-picoline, following the procedure described in preparation 223. $^1$H NMR (DMSO-D$_6$+1 drop TFA-d, 400 MHz) δ: 1.68-1.82 (m, 2H), 2.40 (s, 3H), 3.49 (t, 2H), 3.85-3.89 (m, 5H), 4.21-4.36 (m, 2H), 4.99 (t, 2H), 7.01 (d, 1H), 7.81 (s, 1H), 8.19 (d, 1H). MS APCI+ m/z 423 [M]$^+$

PREPARATION 231

5-Chloro-1-(2-ethoxyethyl)-7-{[4-(hydroxymethyl)pyridin-2-yl]amino}-1H-pyrazolo[4,3-d]pyrimidine-3-carboxylic acid

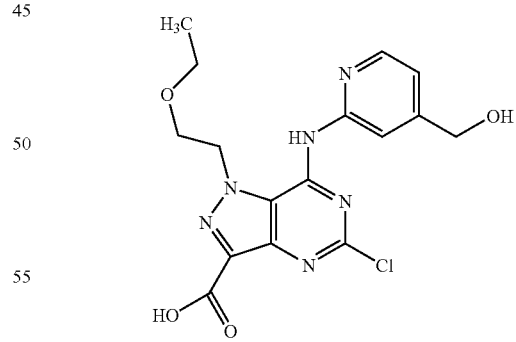

A solution of the compound from preparation 222 (229 mg, 0.44 mmol) in 1N sodium hydroxide solution (2.2 mL) and dioxan (10 mL) was stirred at room temperature for 72 hours. The mixture was acidified to pH 4 using 1N hydrochloric acid and extracted with a solution of 10% methanol in dichloromethane. The combined organic extracts were dried over magnesium sulphate and evaporated under reduced pressure to afford the title compound as a yellow solid, 140 mg. $^1$H NMR (DMSO-D$_6$, 400 MHz) δ: 1.07 (t, 3H), 3.55 (q, 2H), 3.93 (t, 2H), 4.65 (t, 2H), 4.99 (s, 2H), 5.60 (m, 1H), 7.10 (m, 1H), 8.29 (m, 1H).

PREPARATION 232

5-Chloro-1-[2-(cyclobutyloxy)ethyl]-7-[(4-methylpyridin-2-yl)amino]-1H-pyrazolo[4,3-d]pyrimidine-3-carboxylic acid

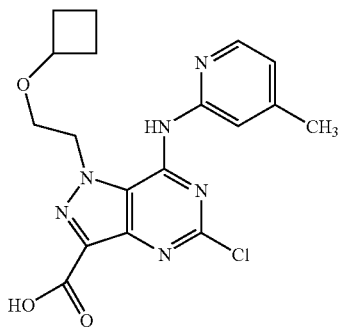

A solution of the ester from preparation 224 (600 mg, 1.44 mmol) in dioxane (5 mL) and 1N sodium hydroxide solution (5 mL) was stirred at room temperature for 18 hours. The solution was concentrated under reduced pressure and diluted with 1M citric acid solution (25 mL). The resulting precipitate was filtered off, washed with ether and dried in vacuo at 50° C. to afford the title compound as a yellow solid, 566 mg. $^1$H NMR (DMSO-D$_6$+TFA-d, 400 MHz) δ: 1.35 (m, 1H), 1.55 (m, 1H), 1.75 (t, 2H), 2.05 (m, 2H), 2.40 (s, 3H), 3.79 (t, 2H), 3.95 (m, 1H), 4.90 (t, 2H), 6.98 (d, 1H), 7.85 (s, 1H), 8.20 (d, 1H). MS APCI+ m/z 403 [MH]$^+$

PREPARATION 233

5-Chloro-7-[(4-methylpyridin-2-yl)amino]-1-[2-(2,2,2-trifluoroethoxy)ethyl]-1H-pyrazolo[4,3-d]pyrimidine-3-carboxylic acid

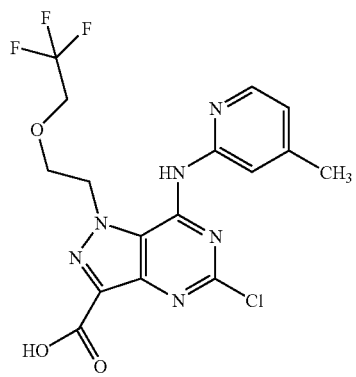

A mixture of the ester from preparation 226 (1.2 g, 2.70 mmol) and 1M sodium hydroxide solution (4.1 mL, 4.1 mmol) in dioxane (17.4 mL) was stirred at room temperature for 18 hours. The reaction mixture was concentrated under reduced pressure and the residue dissolved in water (50 mL). The solution was washed with dichloromethane (10 mL), and then acidified using 1M citric acid. The resulting solid was filtered off and dried in vacuo to afford the title compound, 925 mg. $^1$H NMR (DMSO-D$_6$, 400 MHz) δ: 2.50 (s, 3H), 3.32 (q, 2H), 4.07 (t, 2H), 5.06 (t, 2H), 6.93 (d, 1H), 7.73 (s, 1H), 8.13 (d, 1H).

PREPARATION 234

3-({[tert-Butyl(dimethyl)silyl]oxy}methyl)-5-chloro-1-(2-ethoxyethyl)-N-(6-methylpyrimidin-4-yl)-1H-pyrazolo[4,3-d]pyrimidin-7-amine

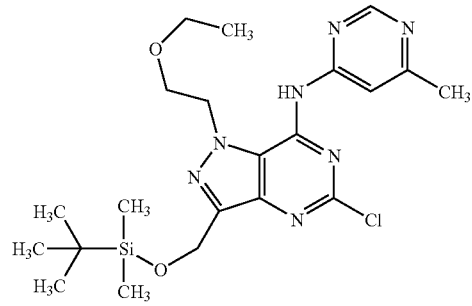

A solution of 4-amino-6-methylpyrimidine (1.13 g, 10.4 mmol) and sodium bis(trimethylsilyl)amide (3.80 g, 20.74 mmol) in tetrahydrofuran (40 mL) was stirred at room temperature for 15 minutes. A solution of the dichloro compound from preparation 154 (3.5 g, 8.64 mmol) in tetrahydrofuran (50 mL) was added and the reaction stirred at room temperature for 1.5 hours. The reaction mixture was concentrated under reduced pressure and the residue partitioned between dichloromethane and saturated ammonium chloride solution and the layers separated. The organic phase was dried over magnesium sulphate and evaporated under reduced pressure to give a red solid. The product was purified by column chromatography using an Isolute® silica gel cartridge and an elution gradient of methanol:dichloromethane (0:100 to 3:97) to provide the title compound as an orange solid, 3.7 g. $^1$H NMR (DMSO-D$_6$, 400 MHz) δ: 0.02 (s, 6H), 0.79 (s, 9H), 1.06 (t, 3H), 2.44 (s, 3H), 3.53 (q, 2H), 3.82 (t, 2H), 4.71 (t, 2H), 4.89 (s, 2H), 8.19 (s, 1H), 8.59 (s, 1H). MS ES+ m/z 478 [MH]$^+$

PREPARATION 235

{5-Chloro-1-(2-ethoxyethyl)-7-[(6-methylpyrimidin-4-yl)amino]-1H-pyrazolo[4,3-d]pyrimidin-3-yl}methanol

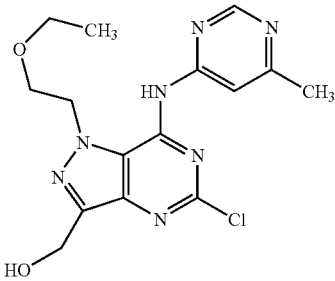

A mixture of the compound from preparation 234 (3.7 g, 7.75 mmol) and tetrabutylammonium fluoride (23.2 mL, 1M in tetrahydrofuran, 23.2 mmol) in tetrahydrofuran (61 mL) was stirred at room temperature for 18 hours. The mixture was concentrated under reduced pressure and the residue partitioned between ethyl acetate (100 mL) and water (100 mL) and the layers separated. The aqueous solution was extracted with further ethyl acetate (2×50 mL) and the combined organic solutions were concentrated under reduced pressure. The residue was purified by column chromatography using an Isolute® silica gel cartridge and an elution gradient of methanol:dichloromethane (0:100 to 2:98) to provide the title compound, 20.6 g. $^1$H NMR (CD$_3$OD, 400 MHz) δ: 1.19 (t, 3H), 2.57 (s, 3H), 3.66 (q, 2H), 3.96 (t, 2H), 4.84 (t, 2H), 4.90 (s, 2H), 8.33 (s, 1H), 8.72 (s, 1H). MS ES+ m/z 364 [MH]$^+$

PREPARATION 236

5-Chloro-1-(2-ethoxyethyl)-7-[(6-methylpyrimidin-4-yl)amino]-1H-pyrazolo[4,3-d]pyrimidine-3-carbaldehyde

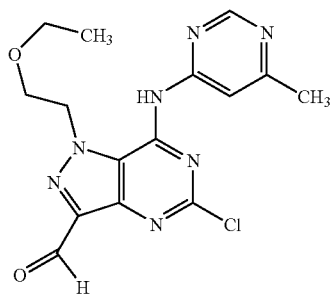

Dess-Martin periodinane (4.56 g, 10.73 mmol) was added portionwise to an ice-cooled solution of the alcohol from preparation 235 (2.6 g, 7.15 mmol) in dichloromethane (150 mL) and the reaction then stirred at room temperature for a further 2 hours. A solution of sodium thiosulphate (7.5 g, 30 mmol) in water (75 mL) was added dropwise, followed by saturated sodium bicarbonate solution (75 mL) and then ether (75 mL). The mixture was stirred for 15 minutes, and the layers separated. The aqueous solution was extracted with further dichloromethane (2×40 mL) and the combined organic solutions dried over magnesium sulphate and evaporated under reduced pressure. The residual brown solid was purified by column chromatography using an Isolute® silica gel cartridge and an elution gradient of ethyl acetate:pentane (0:100 to 100:0) to provide the title compound as a solid, 1.66 g. $^1$H NMR (CDCl$_3$, 400 MHz) δ: 1.25 (t, 3H), 2.63 (s, 3H), 3.72 (q, 2H), 4.06 (t, 2H), 4.91 (t, 2H), 8.29 (s, 1H), 8.81 (s, 1H), 10.34 (s, 1H), 10.42 (s, 1H). MS ES+ m/z 362 [MH]$^+$

PREPARATION 237

5-Chloro-1-(2-ethoxyethyl)-7-[(6-methylpyrimidin-4-yl)amino]-1H-pyrazolo[4,3-d]pyrimidine-3-carboxylic acid

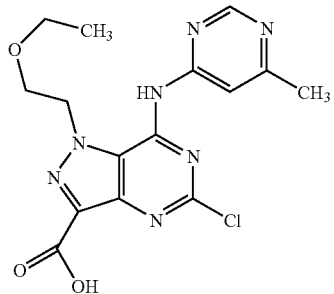

2-Methyl-2-butene (160 mL, 0.32 mol) was added to a solution of the aldehyde from preparation 236 (1.66 g, 4.59 mmol) in t-butanol (300 mL). A solution of sodium chlorite (4.96 g, 55.1 mmol) and sodium dihydrogen phosphate (5.07 g, 42.2 mmol) in water (60 mL) was added dropwise over 5 minutes, and the reaction then stirred at room temperature for 1 hour. The reaction mixture was diluted with dichloromethane (300 mL) and water (150 mL) and the layers separated. The aqueous layer was allowed to evaporate and the resulting precipitate was filtered off and dried in vacuo to give the title compound, 1.02 g. $^1$H NMR (400 MHz, DMSO-D$_6$) δ: 1.07 (t, 3H), 2.48 (s, 3H), 3.51 (m, 2H), 3.88 (t, 2H), 4.90 (t, 2H), 8.02 (br s, 1H), 8.78 (s, 1H). MS APCI+ m/z 378 [MH]$^+$

PREPARATION 238

5-Chloro-1-(2-ethoxyethyl)-7-[(3-methylphenyl)amino]-1H-indazole-3-carboxylic acid

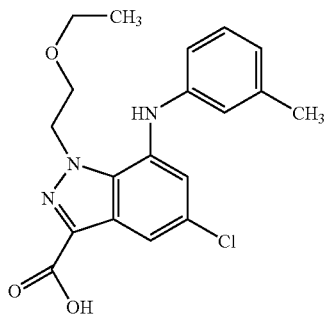

A mixture of the ester from preparation 81 (800 mg, 2.06 mmol) and 1N sodium hydroxide solution (5 mL, 5 mmol) in dioxan (3 mL) was stirred at room temperature for 18 hours. The reaction was concentrated under reduced pressure and the residue diluted with 1M citric acid solution and the mixture sonicated. The resulting precipitate was filtered off, washed with water and ether and dried in vacuo to give the title compound as a white solid, 600 mg. $^1$H NMR (DMSO-D$_6$, 400 MHz) δ: 1.00 (t, 3H), 2.35 (s, 3H), 3.50 (q, 2H), 3.82 (t, 2H), 4.95 (t, 2H), 7.01 (d, 1H), 7.35 (t, 1H), 7.41 (s, 1H), 7.50 (d, 1H), 9.39 (s, 1H). MS APCI+ m/z 376 [MH]$^+$

PREPARATION 239

5-Chloro-1-(2-ethoxyethyl)-7-[(1-methyl-6-oxo-1,6-dihydropyridin-3-yl)amino]-1H-indazole-3-carboxylic acid

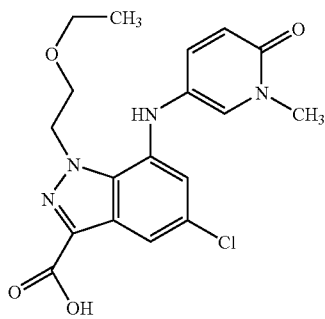

The compound from preparation 58 (10.85 g, 34 mmol) was added portionwise to a solution of 3-amino-1-methyl-1,6-dihydropyridin-6-one (EP 677519) (4.6 g, 37 mmol) and N-ethyldiisopropylamine (5.92 mL, 34 mmol) in dimethylsulphoxide (40 mL), and the reaction then stirred at room temperature for 4 hours. The mixture was diluted with water (600 mL), and the resulting solid filtered off, washed with water and dried in vacuo, 10.8 g. A portion of this solid (6.75 g, 16.59 mmol) was dissolved in dioxan (65 mL) and the solution treated with 1N sodium hydroxide (33 mL, 1M, 33 mmol), and the reaction stirred at room temperature for 18 hours. The reaction was concentrated under reduced pressure, the residue dissolved in water (120 mL), washed with dichloromethane (15 mL), and then acidified to pH 3 using solid citric acid. The resulting precipitate was filtered off, washed with water (3×20 mL) and dried in vacuo to afford the title compound as a yellow solid, 6.19 g. $^1$H NMR (DMSO-D$_6$, 400 MHz) δ: 0.95 (t, 3H), 3.40 (q, 2H), 3.47 (s, 3H), 3.79 (t, 2H), 4.92 (t, 2H), 6.49 (d, 1H), 7.58 (dd, 1H), 7.90 (s, 1H). MS APCI+ m/z 376 [MH]$^+$

PREPARATION 240

Benzyl cyclobutylcarbamate

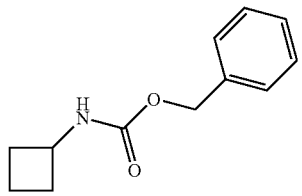

Benzyl chloroformate (5.2 mL, 36.4 mmol) was added dropwise to an ice-cold solution of cyclobutylamine (2 g, 28.1 mmol) in dichloromethane (20 mL), with stirring. Triethylamine (4.7 mL, 33.7 mmol) was added dropwise to the ice-cold solution, and once the addition was complete the reaction was allowed to warm to room temperature and stirred for 18 hours. The reaction was washed with saturated sodium bicarbonate solution (×2), dried over sodium sulphate and concentrated under reduced pressure. The residue was purified by column chromatography on silica gel using dichloromethane as eluant to afford the title compound, 3.72 g. $^1$H NMR (CDCl$_3$, 300 MHz) δ: 1.68 (m, 2H), 1.82 (m, 2H), 2.35 (m, 2H), 4.19 (m, 1H), 4.92 (m, 1H), 5.14 (s, 2H), 7.25-7.39 (m, 5H). MS TSP+ m/z 223.2 [MH]$^+$

PREPARATION 241

N-Cyclobutyl-N-methylamine hydrochloride

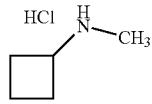

A solution of the compound from preparation 240 (500 mg, 2.43 mmol) was added dropwise to an ice-cold solution of lithium aluminium hydride (12.18 mL, 1M in tetrahydrofuran, 12.18 mmol) in tetrahydrofuran (12 mL), and the reaction mixture stirred at room temperature for 24 hours. The mixture was cooled to 0° C., water (0.46 mL), followed by 15% sodium hydroxide solution (0.46 mL) and finally further water (1.4 mL) were added dropwise. The resulting precipitate was filtered off and washed with ether. The filtrate was washed with water and acidified to pH 2 using 1M hydrochloric acid in ether. The solution was allowed to evaporate at room temperature, the residual oil dissolved in methanolic ether, dried over sodium sulphate and evaporated under reduced pressure to provide the title compound. $^1$H NMR (CDCl$_3$, 400 MHz) δ: 1.78-2.04 (m, 2H), 2.34 (m, 2H), 2.44 (m, 2H), 2.54 (s, 3H), 3.58 (m, 1H), 9.60 (br s, 2H).

Preparations 242 to 244

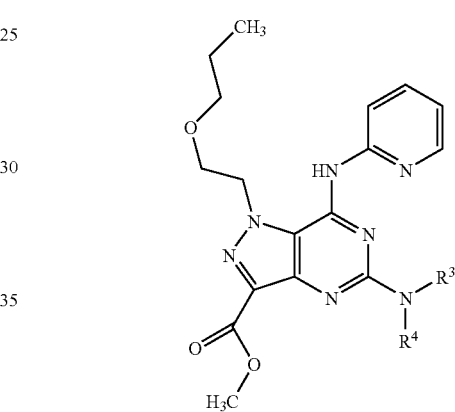

The appropriate amine (HNR$^3$R$^4$) (2 mmol) and cesium fluoride (100 mg, 0.67 mmol) were added to a solution of the chloride from preparation 233 (260 mg, 0.67 mmol) in dimethylsulphoxide (2 mL) in a Reactivial®. The reaction mixture was then sealed and heated at 120° C. for 18 hours. The cooled solution was partitioned between dichloromethane (50 mL) and water (50 mL) and the layers separated. The organic phase was washed with water (50 mL), dried over magnesium sulphate and evaporated under reduced pressure. The crude products were purified by column chromatography on silica gel using dichloromethane:methanol (98:2) as eluant to afford the title compounds.

| Prep No | —NR$^3$R$^4$ | Data |
|---|---|---|
| 242 | 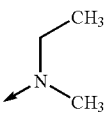 | $^1$H NMR (DMSO-d$_6$ + TFAd, 400 MHz) δ: 0.65 (t, 3H), 1.15 (t, 3H), 1.38 (m, 2H), 3.20 (s, 3H), 3.33 (t, 2H), 3.64 (q, 2H), 3.84 (t, 2H), 3.90 (s, 3H), 4.98 (t, 2H), 7.28 (m, 1H), 8.18 (m, 2H), 8.36 (d, 1H). MS APCI+ m/z 414 [MH]$^+$ |

-continued

| Prep No | —NR³R⁴ | Data |
|---|---|---|
| 243 |  | ¹H NMR (DMSO-d₆ + TFAd, 400 MHz) δ: 0.65 (t, 3H), 1.17 (t, 6H), 1.35 (m, 2H), 3.28 (t, 2H), 3.64 (m, 4H), 3.84 (t, 2H), 3.87 (s, 3H), 4.96 (t, 2H), 7.27 (m, 1H), 8.17 (m, 2H), 8.35 (m, 1H).<br>MS APCI+ m/z 428 [MH]⁺ |
| 244 |  | ¹H NMR (DMSO-d₆ + TFAd, 400 MHz) δ: 0.65 (t, 3H), 1.18 (d, 6H), 1.36 (m, 2H), 3.05 (s, 3H), 3.30 (t, 2H), 3.82 (t, 2H), 3.90 (s, 3H), 4.72 (m, 1H), 4.95 (t, 2H), 7.29 (m, 1H), 8.18 (m, 2H), 8.36 (d, 1H).<br>MS APCI+ m/z 428 [MH]⁺ |

Preparations 245 to 249

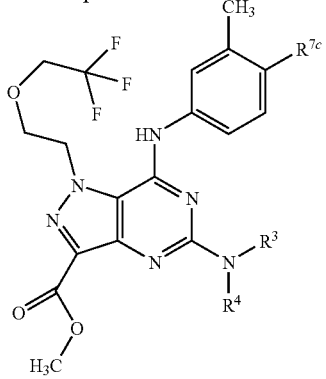

The appropriate amine (HNR³R⁴) (2 mmol) was added to a solution of the chloride from preparations 227 or 228 (296 mg, 0.67 mmol) and cesium fluoride (101 mg, 0.67 mmol) in dimethylsulphoxide (2.5 mL) in a Reactivial®. The reaction mixture was then sealed and heated to 120° C. for 12 hours. The cooled solution was partitioned between dichloromethane (200 mL) and water (50 mL) and the layers separated. The organic phase was washed with water (2×50 mL), dried over magnesium sulphate and evaporated under reduced pressure, to afford the title compound.

| Prep No | —NR³R⁴ | R⁷ᶜ | Yield/Data |
|---|---|---|---|
| 245 | 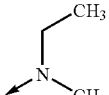 | H | 96% yellow gum.<br>¹H NMR (CD₃OD, 400 MHz) δ: 1.17 (t, 3H), 2.37 (s, 3H), 3.16 (s, 3H), 3.66 (q, 2H), 3.94 (s, 3H), 4.05 (q, 2H), 4.18 (t, 2H), 4.87 (t, 2H), 6.93 (d, 1H), 7.24 (dd, 1H), 7.43 (d, 1H), 7.55 (s, 1H).<br>MS APCI+ m/z 467 [MH]⁺ |
| 246 | 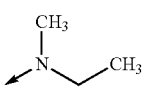 | F | Quantitative, Yellow gum<br>¹H NMR (CD₃OD, 400 MHz) δ: 1.12 (t, 3H), 2.27 (s, 3H), 3.14 (s, 3H), 3.66 (q, 2H), 3.96 (s, 3H), 4.04 (q, 2H), 4.18 (t, 2H), 4.87 (t, 2H), 7.04 (t, 1H), 7.42 (m, 1H), 7.58 (m, 1H).<br>MS APCI+ 485 [MH]⁺ |
| 247 | 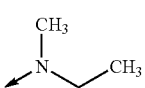 | H | 96% yellow gum<br>¹H NMR (CD₃OD, 400 MHz) δ: 1.20 (d, 6H), 2.34 (s, 3H), 3.05 (s, 3H), 3.95 (s, 3H), 4.09 (q, 2H), 4.18 (t, 2H), 4.87 (t, 2H), 5.10 (m, 1H), 6.95 (d, 1H), 7.24 (dd, 1H), 7.40 (d, 1H), 7.55 (s, 1H).<br>MS APCI+ m/z 481 [MH]⁺ |
| 248 | 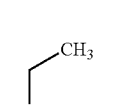 | F | 96% as a yellow gum<br>¹H NMR (CD₃OD, 400 MHz) δ: 1.08 (t, 6H), 2.28 (s, 3H), 3.66 (q, 4H), 3.96 (s, 3H), 4.04 (q, 2H), 4.15 (t, 2H), 4.86 (t, 2H), 7.01 (m, 1H), 7.38 (m, 1H), 7.58 (s, 1H).<br>MS APCI+ m/z 499 [MH]⁺ |

| Prep No | —NR³R⁴ | R⁷ᶜ | Yield/Data |
|---|---|---|---|
| 249 | CH₃—N(CH₃)—CH(CH₃) (isopropylmethylamino) | F | 93% as a yellow gum<br>¹H NMR (CD₃OD, 400 MHz) δ: 1.18 (d, 6H), 2.26 (s, 3H), 3.02 (s, 3H), 3.95 (s, 3H), 4.02 (q, 2H), 4.16 (t, 2H), 4.87 (t, 2H), 5.04 (m, 1H), 7.02 (t, 1H), 7.40 (m, 1H), 7.55 (m, 1H).<br>MS APCI+ m/z 499 [MH]⁺ |

Preparations 250 to 258

The compounds of the general formulae shown in the table below were prepared using the method described for preparations 245 to 249, from the compound from preparations 225, 229 and 230 and the appropriate HNR³R⁴ amines.

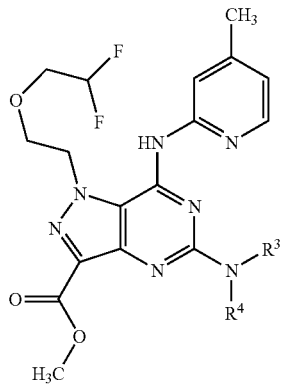

| Prep No | —NR³R⁴ | Data |
|---|---|---|
| 250 | N(CH₃)(CH₂CH₃) | ¹H NMR (CD₃OD, 400 MHz) δ: 1.27 (t, 3H), 2.38 (s, 3H), 3.20 (s, 3H), 3.74 (m, 4H), 3.95 (s, 3H), 4.10 (t, 2H), 4.80 (m, 2H), 6.00 (m, 1H), 6.98 (m, 1H), 8.18 (m, 1H), 8.25 (m, 1H).<br>MS APCI+ m/z 450 [MH]⁺ |
| 251 | N(CH₂CH₃)₂ | ¹H NMR (CD₃OD, 400 MHz) δ: 1.25 (t, 6H), 2.40 (s, 3H), 3.75 (m, 6H), 3.95 (s, 3H), 4.10 (t, 2H), 4.82 (m, 2H), 6.00 (m, 1H), 6.95 (m, 1H), 8.18 (m, 1H), 8.30 (m, 1H).<br>MS APCI+ m/z 464 [MH]⁺ |
| 252 | N(CH₃)CH(CH₃)₂ | ¹H NMR (CD₃OD, 400 MHz) δ: 1.24 (d, 6H), 2.40 (s, 3H), 3.06 (s, 3H), 3.60 (m, 2H), 3.95 (s, 3H), 4.08 (t, 2H), 4.80 (m, 2H), 5.10 (m, 1H), 6.00 (m, 1H), 6.95 (m, 1H), 8.18 (m, 1H), 8.20 (m, 1H).<br>MS APCI+ m/z 464 [MH]⁺ |

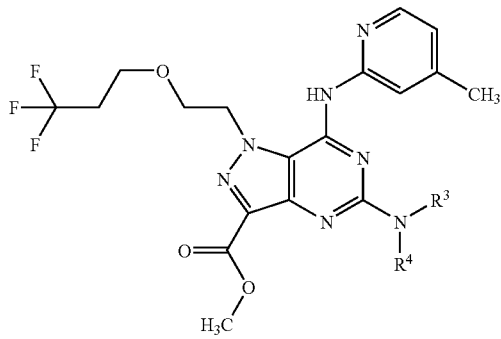

| | | |
|---|---|---|
| 253 | N(CH₃)(CH₂CH₃) | ¹H NMR (DMSO-d₆ + TFAd, 400 MHz) δ: 1.12 (t, 3H), 2.46 (s, 3H), 2.37-2.50 (m, 2H), 3.20 (s, 3H), 3.60 (t, 2H), 3.65 (m, 2H), 3.89-3.91 (m, 5H), 5.00 (t, 2H), 7.19 (d, 1H), 8.10 (s, 1H), 8.25 (d, 1H). MS APCI+ m/z 482 [MH]⁺ |
| 254 | N(CH₃)(CH(CH₃)₂) | ¹H NMR (DMSO-d₆ + TFAd, 400 MHz) δ: 1.20 (d, 6H), 2.45 (s, 3H), 2.37-2.50 (m, 2H), 3.04 (s, 3H), 3.60 (t, 2H), 3.89-3.91 (m, 5H), 4.70-4.78 (m, 1H), 4.99 (t, 2H), 7.18 (d, 1H), 8.08 (s, 1H), 8.25 (d, 1H). MS APCI+ m/z 496 [MH]⁺ |
| 255 | N(CH₂CH₃)₂ | ¹H NMR (DMSO-d₆ + TFAd, 400 MHz) δ: 1.21 (t, 6H), 2.35-2.50 (m, 5H), 3.60 (t, 2H), 3.65 (q, 4H), 3.90 (s, 3H), 4.99 (t, 2H), 7.19 (d, 1H), 8.10 (s, 1H), 8.25 (d, 1H). MS APCI+ m/z 496 [MH]⁺ |

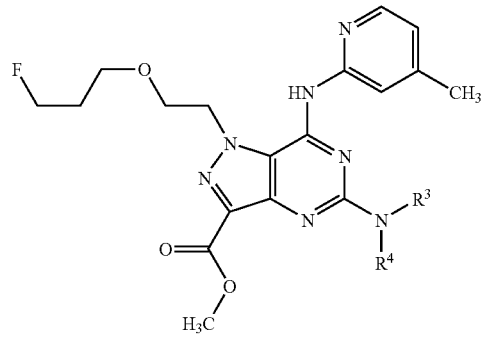

| | | |
|---|---|---|
| 256 | N(CH₃)(CH₂CH₃) | ¹H NMR (DMSO-d₆ + TFAd, 400 MHz) δ: 1.12 (t, 3H), 1.67-1.80 (m, 2H), 2.40 (s, 3H), 3.20 (s, 3H), 3.45 (t, 2H), 3.65 (q, 2H), 3.87 (t, 2H), 3.90 (s, 3H), 4.23-4.38 (m, 2H), 4.98 (t, 2H), 7.18 (d, 1H), 8.10 (s, 1H), 8.25 (d, 1H). MS APCI+ m/z 446 [MH]⁺ |
| 257 | N(CH₃)(CH(CH₃)₂) | ¹H NMR (DMSO-d₆ + TFAd, 400 MHz) δ: 1.20 (d, 6H), 1.69-1.78 (m, 2H), 2.45 (s, 3H), 3.00 (s, 3H), 3.45 (t, 2H), 3.86 (t, 2H), 3.90 (s, 3H), 4.23-4.38 (m, 2H), 4.98 (t, 2H), 4.69-4.76 (m, 1H), 7.18 (d, 1H), 8.08 (s, 1H), 8.24 (d, 1H). MS APCI+ m/z 460 [MH]⁺ |
| 258 | N(CH₂CH₃)₂ | ¹H NMR (DMSO-d₆ + TFAd, 400 MHz) δ: 1.20 (t, 6H), 1.68-1.80 (m, 2H), 2.45 (s, 3H), 3.45 (t, 2H), 3.65 (q, 4H), 3.87 (t, 2H), 3.90 (s, 3H), 4.24-4.39 (m, 2H), 4.97 (t, 2H), 7.18 (d, 1H), 8.04 (s, 1H), 8.25 (d, 1H). MS APCI+ m/z 460 [MH]⁺ |

PREPARATION 259

Methyl 1-(2-ethoxyethyl)-7-[(4-methylpyridin-2-yl)amino]-5-pyrrolidin-1-yl-1H-pyrazolo[4,3-d]pyrimidine-3-carboxylate

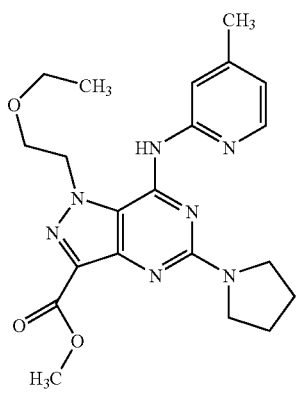

The title compound was obtained as a yellow oil, from the chloride from preparation 72 and pyrrolidine, following a similar procedure to that described in preparation 245-249, except 5 eq N-ethyldiisopropylamine was added to the reaction, and the product was purified by column chromatography using an Isolute® silica gel cartridge and dichloromethane: methanol:0.88 ammonia (100:0:0 to 95:5:0.5) as eluant. $^1$H NMR (CD$_3$OD, 400 MHz) δ: 1.05 (t, 3H), 2.02 (m, 4H), 2.40 (s, 3H), 3.60 (q, 2H), 3.65 (m, 4H), 3.90 (m, 5H), 4.80 (t, 2H), 6.95 (d, 1H), 8.18 (d, 1H), 8.50 (s, 1H). MS APCI+ m/z 426 [MH]$^+$

PREPARATION 260

Methyl 5-[isopropyl(methyl)amino]-1-[(2S)-2-methoxypropyl]-7-[(4-methylpyridin-2-yl)amino]-1H-pyrazolo[4,3-d]pyrimidine-3-carboxylate

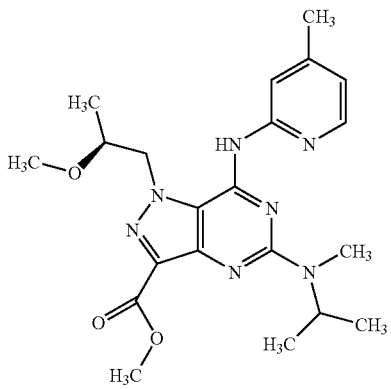

A mixture of the chloride from preparation 221 (110 mg, 0.28 mmol), N-ethyldiisopropylamine (0.25 mL, 1.40 mmol), N-ethylisopropylamine (0.15 mL, 1.40 mmol) and tetraethylammonium fluoride (37 mg, 0.28 mmol) in 1-methyl-2-pyrrolidinone (1 mL) was heated in a Reactivial® at 120° C. for 18 hours. The cooled mixture was concentrated under reduced pressure and the residue partitioned between dichloromethane (50 mL) and water (50 mL) and the layers separated. The aqueous phase was extracted with additional dichloromethane (50 mL), and the combined organic solutions washed with water (100 mL) dried over magnesium sulphate and evaporated under reduced pressure. The crude product was purified by column chromatography using an Isolute® silica gel cartridge using dichloromethane as eluant to provide the title compound as yellow oil, 43 mg. $^1$H NMR (CD$_3$OD, 400 MHz) δ: 1.21 (m, 6H), 1.28 (d, 3H), 2.39 (s, 3H), 3.03 (s, 3H), 3.40 (s, 3H), 3.98 (m, 4H), 4.50-4.70 (m, 2H), 5.17 (m, 1H), 6.92 (d, 1H), 8.18 (m, 2H). MS APCI+ m/z 428 [MH]$^+$

PREPARATION 261

5-Chloro-7-[(4-methylpyridin-2-yl)amino]-N-(methylsulfonyl)-1-[2-(2,2,2-trifluoroethoxy)ethyl]-1H-pyrazolo[4,3-d]pyrimidine-3-carboxamide

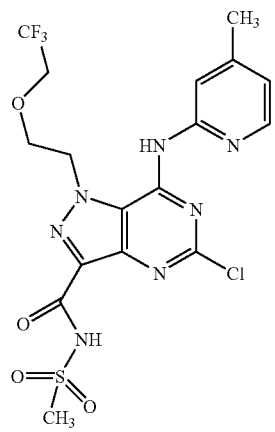

A mixture of the acid from preparation 233 (300 mg, 0.70 mmol), methanesulphonamide (87 mg, 0.91 mmol), 1-(3-dimethylaminopropyl)-3-ethylcarbodiimide hydrochloride (175 mg, 0.91 mmol) and 4-dimethylamino pyridine (102 mg, 0.91 mmol) in N,N-dimethylformamide (3 mL) was stirred at room temperature for 18 hours. Tlc analysis showed starting material remaining, so additional methanesulphonamide (43 mg, 0.45 mmol), 1-(3-dimethylaminopropyl)-3-ethylcarbodiimide hydrochloride (87 mg, 0.45 mmol) and 4-dimethylamino pyridine (51 mg, 0.45 mmol) were added and the mixture stirred for a further 4 hours. The mixture was partitioned between dichloromethane (50 mL) and water (50 mL) and the layers separated. The organic solution was washed with 1N hydrochloric acid (5 mL) and water (3×50 mL) then dried over sodium sulphate and evaporated under reduced pressure, to give the title compound, 100 mg. $^1$H NMR (CD$_3$OD, 400 MHz) δ: 2.42 (s, 3H), 3.39 (s, 3H), 4.02 (q, 2H), 4.17 (t, 2H), 5.07 (t, 2H), 6.99 (d, 1H), 7.81 (s, 1H), 8.18 (d, 1H). MS ES− m/z 506 [M-H]$^-$

EXAMPLE 1

Methyl 1-(2-ethoxyethyl)-5-(N-isopropyl-N-methylamino)-7-(4-methylpyridin-2-ylamino)-1H-pyrazolo[4,3-d]pyrimidine-3-carboxylate

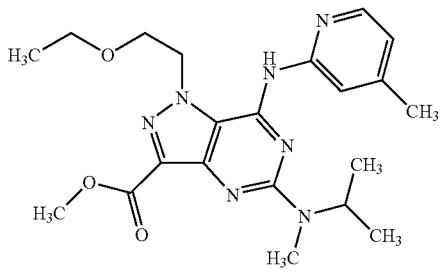

The chloro compound of preparation 72 (130 mg, 0.33 mmol) was dissolved in dimethyl sulphoxide (1 mL) and the solution treated with tetraethylammonium fluoride (50 mg, 0.33 mmol) and N-methylisopropylamine (104 µL, 1.0 mmol). The reaction mixture was stirred in a ReactiVial™ at 120° C. for 18 hours before being allowed to cool and concentrated in vacuo. The residue was partitioned between ethyl acetate (50 mL) and water (50 mL) and the organic phase dried over magnesium sulphate and concentrated in vacuo. The residue was purified by column chromatography on silica gel eluting with dichloromethane: methanol 100:0 to 97:3 to yield the title product. $^1$H NMR (CDCl$_3$, 400 MHz) δ: 1.18 (t, 3H), 1.24 (s, 6H), 2.40 (m, 3H), 3.11 (s, 3H), 3.60 (q, 2H), 3.96 (t, 2H), 4.02 (s, 3H), 4.80 (t, 2H), 5.10 (m, 1H), 6.91 (d, 1H), 8.18 (m, 1H), 8.37 (d, 1H). MS APCI+ m/z 428 [MH]$^+$

EXAMPLE 2

Methyl 1-(2-ethoxyethyl)-5-(N-ethyl-N-methylamino)-7-(4-methylpyridin-2-ylamino)-1H-pyrazolo[4,3-d]pyrimidine-3-carboxylate

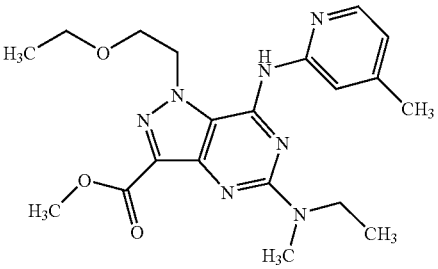

The chloro compound of preparation 72 (130 mg, 0.33 mmol) was dissolved in dimethyl sulphoxide (1 mL) and the solution treated with tetraethylammonium fluoride (50 mg, 0.33 mmol) and N-methylethylamine (86 µL, 1.0 mmol). The reaction mixture was heated to 110° C. in a ReactiVial™ for 18 hours and then allowed to cool to room temperature. The reaction mixture was partitioned between dichloromethane (50 mL) and water (50 mL) and the organic phase washed with water (2×30 mL), dried over magnesium sulphate and concentrated in vacuo. The residue was purified by column chromatography on silica gel eluting with dichloromethane: methanol 100:0 to 90:10 to yield the title product. $^1$H NMR (CD$_3$OD, 400 MHz) δ: 1.10 (t, 3H), 1.25 (m, 3H), 2.40 (s, 3H), 3.25 (s, 3H), 3.60 (q, 2H), 3.78 (q, 2H), 3.86 (m, 5H), 4.80 (t, 2H), 6.93 (d, 1H), 8.15 (d, 1H), 8.32 (s, 1H). MS APCI+ m/z 414 [MH]$^+$ The following compounds, of the general formula shown below, were prepared by a method similar to that described for example 2 using the appropriate HNR$^3$R$^4$ amine.

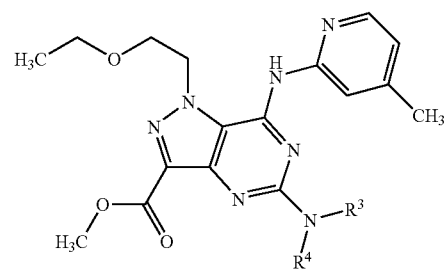

| No. | NR³R⁴ | Data |
|---|---|---|
| 3 | ![piperazine with CH3] | $^1$H NMR (CD$_3$OD, 400 MHz) δ: 1.13 (t, 3H), 1.18 (d, 3H), 2.40 (s, 3H), 2.64 (m, 1H), 2.84 (m, 2H), 3.03 (m, 2H), 3.42 (q, 2H), 3.94 (m, 5H), 4.64 (m, 2H), 4.80 (t, 2H), 6.94 (d, 1H), 8.18 (m, 2H). MS APCI+ m/z 455 [MH]$^+$ |
| 4 | ![diazabicyclic] | $^1$H NMR (CD$_3$OD, 400 MHz) δ: 1.08 (t, 3H), 1.84 (d, 1H), 1.96 (d, 1H), 2.40 (s, 3H), 3.08 (m, 2H), 3.60 (m, 3H), 3.73 (m, 1H), 3.85 (m, 1H), 3.92 (m, 5H), 4.82 (m, 2H), 4.97 (m, 1H), 6.95 (d, 1H), 8.16 (d, 1H), 8.30 (m, 1H). MS APCI+ m/z 453 [MH]$^+$ |
| 5 | —N(CH$_3$)$_2$ | $^1$H NMR (CD$_3$OD, 400 MHz) δ: 1.10 (t, 3H), 2.38 (s, 3H), 3.24 (s, 6H), 3.40 (q, 2H), 3.83 (m, 5H), 4.77 (m, 2H), 6.93 (d, 1H), 8.15 (d, 1H), 8.34 (s, 1H). MS APCI+ m/z 400 [MH]$^+$ |

Example 4 was prepared using tert-butyl (1S,4S)-2,5-diazabicyclo[2.2.1]heptane-2-carboxylate (Aldrich Chem.) as the HNR³R⁴ amine. Prior to being purified by column chromatography, the crude product was dissolved in dichloromethane (5 mL) and the solution treated with trifluoroacetic acid (5 mL) at room temperature for 4 Hours. The reaction mixture was concentrated in vacuo and the residue partitioned between dichloromethane (50 mL) and saturated sodium Hydrogencarbonate solution (50 mL). The organic phase was separated, dried over magnesium sulphate and concentrated in vacuo.

149
EXAMPLE 6

Methyl 1-(2-ethoxyethyl)-5-(N-isopropyl-N-methylamino)-7-(6-methylpyridin-2-ylamino)-1H-pyrazolo[4,3-d]pyrimidine-3-carboxylate

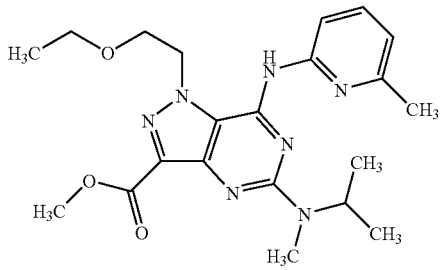

The chloro compound of preparation 93 (200 mg, 0.51 mmol) was added to a solution of N-ethyldiisopropylamine (440 μL, 2.55 mmol), isopropylmethylamine (260 μL, 2.55 mmol) and caesium fluoride (77 mg, 0.51 mmol) in dimethyl sulphoxide (1 mL) and the reaction mixture heated to 120° C. in a ReactiVial™ for 18 hours. The reaction mixture was concentrated in vacuo and the residue taken up in 1M citric acid solution (5 mL) and extracted with dichloromethane (3×25 mL). The organics were combined, dried over magnesium sulphate and concentrated in vacuo to yield the title product. $^1$H NMR (CDCl$_3$, 400 MHz) δ: 1.16 (t, 3H), 1.24 (d, 6H), 2.37 (s, 3H), 3.11 (s, 3H), 3.62 (q, 2H), 3.98 (t, 2H), 4.01 (s, 3H), 4.77 (m, 2H), 5.15 (m, 1H), 6.82 (d, 1H), 8.18 (d, 1H), 8.26 (s, 1H), 9.76 (s, 1H).

150
EXAMPLE 7

Ethyl 1-(2-ethoxyethyl)-5-(N-ethyl-N-methylamino)-7-(4-methylpyridin-2-ylamino-1H-pyrazolo[4,3-d]pyrimidine-3-carboxylate

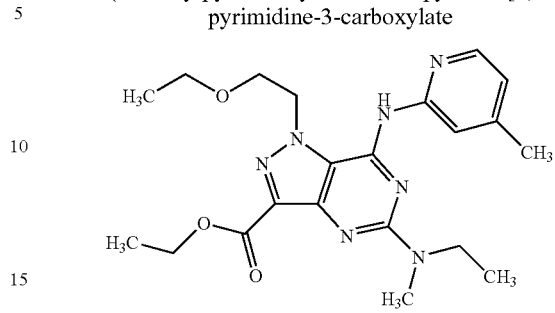

The ethyl ester of preparation 175 (100 mg, 0.25 mmol) was dissolved in dimethyl sulphoxide (1 mL) and the solution treated with N-methyl-ethylamine (78 μL, 0.75 mmol) and tetraethylammonium fluoride (37 mg, 0.25 mmol). The reaction mixture was then heated to 120° C. in a ReactiVial™ for 18 hours before being allowed to cool. The reaction mixture was concentrated in vacuo, the residue partitioned between ethyl acetate (50 mL) and water (50 mL) and the organic phase dried over magnesium sulphate and concentrated in vacuo. The residue was purified by column chromatography on silica gel eluting with dichloromethane:acetonitrile 100:0 to 90:10. The crude product was partitioned between dichloromethane (30 mL) and saturated sodium hydrogencarbonate solution (10 mL). The organic phase was separated, dried over magnesium sulphate and concentrated in vacuo. The residue was purified by column chromatography on silica gel eluting with dichloromethane:methanol:0.88 ammonia 95:5:0.5 to yield the title product. $^1$H NMR (CDCl$_3$, 400 MHz) δ: 1.14 (t, 3H), 1.24 (t, 3H), 1.46 (t, 3H), 2.39 (s, 3H), 3.25 (s, 3H), 3.62 (q, 2H), 3.80 (q, 2H), 3.95 (t, 2H), 4.52 (q, 2H), 4.78 (t, 2H), 6.82 (d, 1H), 8.20 (d, 1H), 8.30 (s, 1H), 9.75 (m, 1H). MS APCI+ m/z 428 [MH]$^+$ The following compounds, of the general formula shown below, were prepared by a method similar to that described for example 7 using the appropriate HNR$^3$R$^4$ amine.

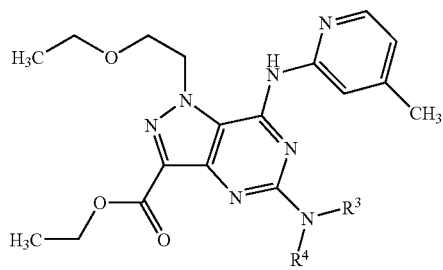

| No. | NR$^3$R$^4$ | Data |
|---|---|---|
| 8 | <img piperazine with CH3> | $^1$H NMR (CDCl$_3$, 400 MHz) δ: 1.12 (t, 3H), 1.14 (d, 3H), 1.42 (t, 3H), 2.40 (s, 3H), 2.66 (m, 1H), 2.84 (m, 2H), 3.04 (m, 2H), 3.62 (q, 2H), 3.94 (t, 2H), 4.43 (q, 2H), 4.64 (m, 2H), 4.80 (t, 2H), 6.96 (d, 1H), 8.14 (m, 2H). MS APCI+ m/z 469 [MH]$^+$ |

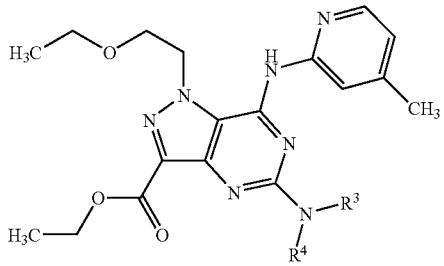

| No. | NR³R⁴ | Data |
|---|---|---|
| 9 | N(CH₃)(CH(CH₃)CH₃) — N-methyl, N-isopropyl (with additional CH₃) | ¹H NMR (CDCl₃, 400 MHz) δ: 1.05 (t, 3H), 1.30 (m, 6H), 1.48 (t, 3H), 2.44 (s, 3H), 3.08 (s, 3H), 3.55 (q, 2H), 3.94 (t, 2H), 4.50 (q, 2H), 4.95 (m, 3H), 6.96 (d, 1H), 8.12 (s, 1H), 8.33 (d, 1H). MS APCI+ m/z 442 [MH]⁺ |

Example 9-This compound was isolated without purification by column chromatography

EXAMPLE 10

2-(Dimethylamino)ethyl 5-dimethylamino-1-(2-ethoxyethyl)-7-(4-methylpyridin-2-ylamino)-1H-pyrazolo[4,3-d]pyrimidine-3-carboxylate

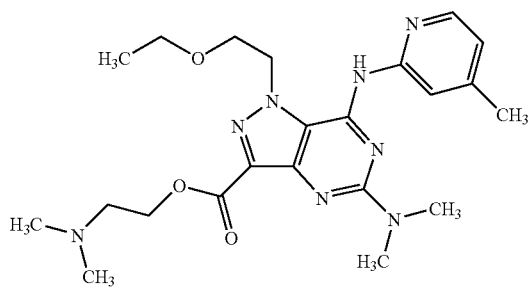

The title compound was prepared by a method similar to that described for example 7, using the ester of preparation 176 and a 2M solution of dimethylamine in methanol. ¹H NMR (CD₃OD, 400 MHz) δ: 1.10 (t, 3H), 2.38 (s, 6H), 2.40 (s, 3H), 2.84 (t, 2H), 3.26 (s, 6H), 3.60 (q, 2H), 3.94 (t, 2H), 4.52 (t, 2H), 4.80 (m, 2H), 6.94 (d, 1H), 8.15 (d, 1H), 8.34 (s, 1H). MS APCI+ m/z 457 [MH]⁺

EXAMPLES 11 TO 41

The appropriate monochloro precursor (1 eq) was dissolved in dimethyl sulphoxide (1-2 mLmmol⁻¹) and the solution treated with the appropriate HNR³R⁴ amine (3 eq) and N-ethyldiisopropylamine (3 eq). The reaction mixture was then stirred at 120° C. for 18 hours, allowed to cool to room temperature and concentrated in vacuo. The residue was dissolved in dichloromethane and the organic phase washed with citric acid solution (20 mL), dried over magnesium sulphate and concentrated in vacuo. The crude product was purified by column chromatography on silica gel eluting with dichloromethane:methanol 100:0 to 94:6 to yield the desired product.

Monochloro precursors from preparations 135, 136, 137, 140, 141, 142, 143, 144, 146, 147, 148, 149, 170 and 171 were used.

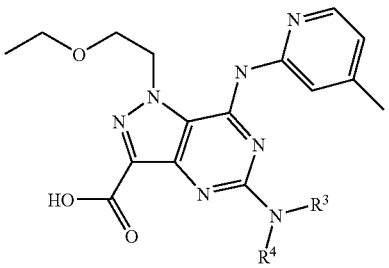

| Ex | —NR³R⁴ | Data |
|---|---|---|
| 11 | —N(CH₂CH₃)₂ | ¹H NMR (CD₃OD, 400 MHz) δ: 1.18 (t, 3H), 1.35 (t, 6H), 2.45 (s, 3H), 3.60 (m, 2H), 3.78 (m, 4H), 3.98 (m, 2H), 4.90 (m, 2H), 7.05 (m, 1H), 8.10 (m, 2H). MS APCI− m/z 412 [M − H]⁻ |

-continued

| | | |
|---|---|---|
| 12 | 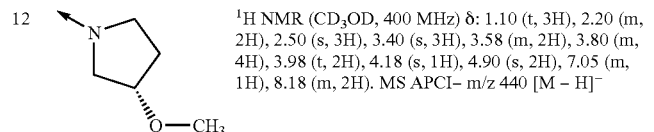 | ¹H NMR (CD₃OD, 400 MHz) δ: 1.10 (t, 3H), 2.20 (m, 2H), 2.50 (s, 3H), 3.40 (s, 3H), 3.58 (m, 2H), 3.80 (m, 4H), 3.98 (t, 2H), 4.18 (s, 1H), 4.90 (s, 2H), 7.05 (m, 1H), 8.18 (m, 2H). MS APCI- m/z 440 [M − H]⁻ |
| 13 | 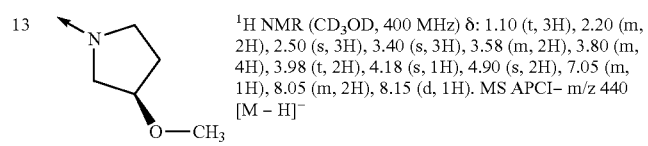 | ¹H NMR (CD₃OD, 400 MHz) δ: 1.10 (t, 3H), 2.20 (m, 2H), 2.50 (s, 3H), 3.40 (s, 3H), 3.58 (m, 2H), 3.80 (m, 4H), 3.98 (t, 2H), 4.18 (s, 1H), 4.90 (s, 2H), 7.05 (m, 1H), 8.05 (m, 2H), 8.15 (d, 1H). MS APCI- m/z 440 [M − H]⁻ |
| 14 | —N(CH₃)₂ | ¹H NMR (DMSO-D₆, 400 MHz) δ: 1.00 (t, 3H), 2.40 (s, 3H), 3.18 (s, 6H), 3.50 (m, 2H), 3.85 (t, 2H), 4.90 (m, 2H), 7.10 (m, 1H), 8.10 (m, 1H), 8.25 (m, 1H). MS APCI- m/z 384 [M − H]⁻ |
| 15 | 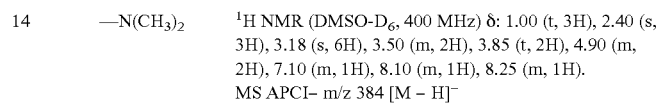 | ¹H NMR (DMSO-D₆, 400 MHz) δ: 0.81 (t, 3H), 1.05 (t, 3H), 1.60 (m, 2H), 2.31 (s, 3H), 3.13 (s, 3H), 3.45-3.60 (m, 4H), 3.83 (t, 2H), 4.74 (t, 2H), 6.93 (d, 1H), 8.05 (m, 1H), 8.19 (d, 1H), 9.73 (m, 1H). MS APCI+ m/z 414 [MH]⁺ |
| 16 | 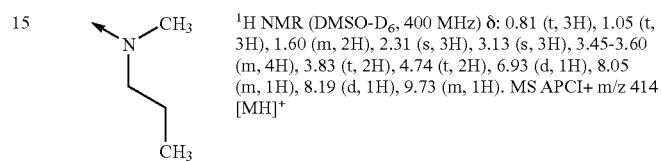 | ¹H NMR (DMSO-D₆, 400 MHz) δ: 0.82 (d, 6H), 1.04 (t, 3H), 2.06 (m, 1H), 2.38 (s, 3H), 3.14 (s, 3H), 3.45 (m, 2H), 3.57 (m, 2H), 3.85 (m, 2H), 4.73 (m, 2H), 6.92 (m, 1H), 8.06 (m, 1H), 8.20 (m, 1H), 9.70 (m, 1H). MS APCI+ m/z 428 [MH]⁺ |
| 17 | 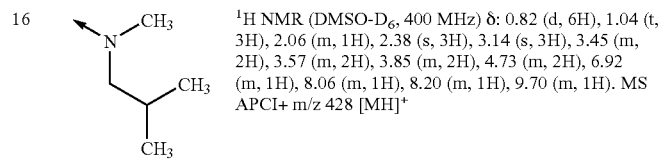 | ¹H NMR (CD₃OD, 400 MHz) δ: 1.12 (t, 3H), 2.45 (s, 3H), 3.36 (s, 3H), 3.41 (s, 3H), 3.58 (m, 2H), 3.74 (m, 2H), 3.88 (m, 2H), 3.97 (m, 2H), 4.88 (m, 2H), 7.05 (m, 1H), 8.09 (m, 1H), 8.16 (m, 1H). MS APCI- m/z 428 [M − H]⁻ |
| 18 | 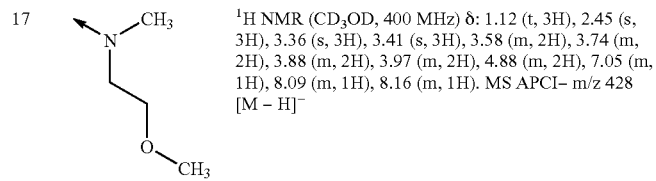 | ¹H NMR (DMSO-D₆, 400 MHz) δ: 1.04 (t, 3H), 1.15-1.85 (m, 8H), 2.32 (s, 3H), 3.00 (s, 3H), 3.52 (q, 2H), 3.84 (t, 2H), 4.75 (t, 2H), 5.13 (s, 1H), 6.92 (d, 1H), 8.11 (m, 1H), 8.18 (d, 1H), 9.72 (m, 1H). MS APCI+ m/z 440 [MH]⁺ |

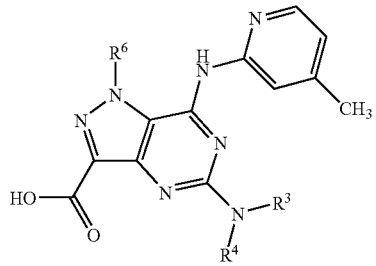

| Ex | —NR³R⁴ | R⁶ | Data |
|---|---|---|---|
| 19 | 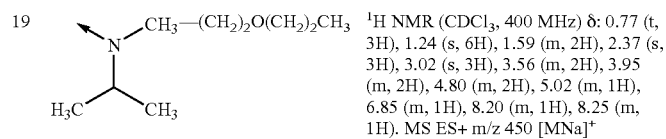 | —(CH₂)₂O(CH₂)₂CH₃ | ¹H NMR (CDCl₃, 400 MHz) δ: 0.77 (t, 3H), 1.24 (s, 6H), 1.59 (m, 2H), 2.37 (s, 3H), 3.02 (s, 3H), 3.56 (m, 2H), 3.95 (m, 2H), 4.80 (m, 2H), 5.02 (m, 1H), 6.85 (m, 1H), 8.20 (m, 1H), 8.25 (m, 1H). MS ES+ m/z 450 [MNa]⁺ |

-continued

| Ex | | | Data |
|---|---|---|---|
| 20 | 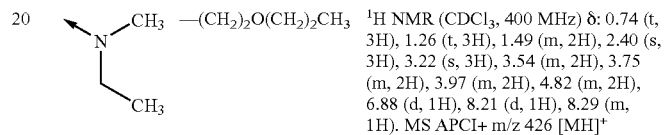 | —(CH₂)₂O(CH₂)₂CH₃ | ¹H NMR (CDCl₃, 400 MHz) δ: 0.74 (t, 3H), 1.26 (t, 3H), 1.49 (m, 2H), 2.40 (s, 3H), 3.22 (s, 3H), 3.54 (m, 2H), 3.75 (m, 2H), 3.97 (m, 2H), 4.82 (m, 2H), 6.88 (d, 1H), 8.21 (d, 1H), 8.29 (m, 1H). MS APCI+ m/z 426 [MH]⁺ |
| 21 | 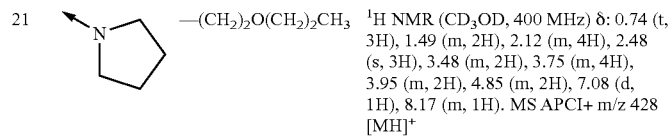 | —(CH₂)₂O(CH₂)₂CH₃ | ¹H NMR (CD₃OD, 400 MHz) δ: 0.74 (t, 3H), 1.49 (m, 2H), 2.12 (m, 4H), 2.48 (s, 3H), 3.48 (m, 2H), 3.75 (m, 4H), 3.95 (m, 2H), 4.85 (m, 2H), 7.08 (d, 1H), 8.17 (m, 1H). MS APCI+ m/z 428 [MH]⁺ |
| 22 | 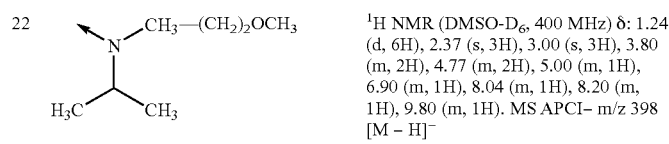 | —(CH₂)₂OCH₃ | ¹H NMR (DMSO-D₆, 400 MHz) δ: 1.24 (d, 6H), 2.37 (s, 3H), 3.00 (s, 3H), 3.80 (m, 2H), 4.77 (m, 2H), 5.00 (m, 1H), 6.90 (m, 1H), 8.04 (m, 1H), 8.20 (m, 1H), 9.80 (m, 1H). MS APCI– m/z 398 [M – H]⁻ |
| 23 | —N(CH₃)₂ | —(CH₂)₂OCH₃ | ¹H NMR (DMSO-D₆, 400 MHz) δ: 2.34 (s, 3H), 3.12 (s, 6H), 3.31 (s, 3H), 3.80 (m, 2H), 4.78 (m, 2H), 6.90 (d, 1H), 8.02 (m, 1H), 8.20 (d, 1H). MS APCI+ m/z 372 [M – H]⁺ |

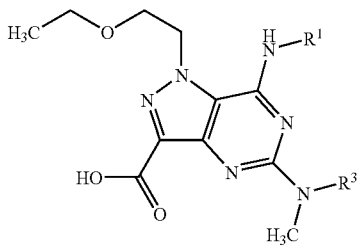

| Ex | R¹ | R³ | Data |
|---|---|---|---|
| 24 | 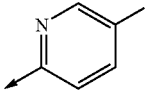 | —CH₃ | ¹H NMR (DMSO-D₆, 400 MHz) δ: 1.06 (t, 3H), 2.24 (s, 3H), 3.13 (s, 6H), 3.51 (m, 2H), 3.83 (m, 2H), 4.72 (m, 2H), 7.63 (m, 1H), 8.16 (m, 2H), 9.65 (m, 1H). MS ES– m/z 384 [M – H]⁻ |
| 25 | 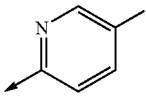 | —CH(CH₃)₂ | ¹H NMR (DMSO-D₆, 400 MHz) δ: 1.10 (t, 3H), 1.18 (d, 6H), 2.26 (s, 3H), 2.98 (s, 3H), 3.58 (q, 2H), 3.90 (m, 2H), 4.77 (m, 2H), 4.99 (m, 1H), 7.62 (m, 1H), 8.10 (m, 1H), 8.19 (m, 1H). MS APCI– m/z 412 [M – H]⁻ |
| 26 | 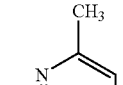 | —CH(CH₃)₂ | ¹H NMR (CD₃OD, 400 MHz) δ: 1.11 (t, 3H), 1.30 (d, 6H), 2.40 (s, 3H), 2.49 (s, 3H), 3.10 (s, 3H), 3.55 (m, 2H), 3.93 (m, 2H), 4.90 (m, 2H), 6.90 (m, 1H), 7.87 (m, 1H). MS ES– m/z 426 [M – H]⁻ |
| 27 | 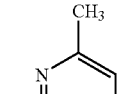 | —CH₃ | ¹H NMR (CD₃OD, 400 MHz) δ: 1.08 (t, 3H), 2.41 (s, 3H), 2.53 (s, 3H), 3.30 (s, 6H), 3.55 (m, 2H), 3.94 (m, 2H), 4.91 (m, 2H), 6.91 (m, 1H), 7.82 (m, 1H). MS ES+ m/z 400 [MH]⁺ |
| 28 | 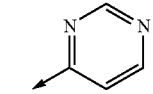 | —CH(CH₃)₂ | ¹H NMR (CD₃OD, 400 MHz) δ: 1.22 (t, 3H), 1.26 (d, 6H), 3.10 (s, 3H), 3.67 (q, 2H), 3.97 (t, 2H), 4.80 (t, 2H), 5.11 (m, 1H), 8.28 (m, 1H), 8.61 (d, 1H), 9.83 (s, 1H). MS APCI+ m/z 401 [MH]⁺ |

-continued

| # | Structure | R | NMR / MS |
|---|---|---|---|
| 29 | pyrazin-2-yl | —CH(CH₃)₂ | ¹H NMR (CD₃OD, 400 MHz) δ: 1.20 (t, 3H), 1.28 (d, 6H), 3.10 (s, 3H), 3.67 (q, 2H), 3.98 (t, 2H), 4.85 (m, 2H), 5.04 (m, 1H), 5.48 (s, 2H), 8.31 (m, 1H), 8.42 (m, 1H), 9.48 (m, 1H). MS APCI+ m/z 401 [MH]⁺ |
| 30 | cyclohexyl | —(CH₂)₂CH₃ | ¹H NMR (CD₃OD, 400 MHz) δ: 1.00 (t, 3H), 1.16 (t, 3H), 1.32 (m, 1H), 1.47 (m, 4H), 1.74 (m, 3H), 1.88 (m, 2H), 2.14 (m, 2H), 3.28 (s, 3H), 3.58 (q, 2H), 3.69 (t, 2H), 3.89 (t, 2H), 4.16 (m, 1H), 4.70 (t, 2H). MS ES+ m/z 405 [MH]⁺ |
| 31 | cyclopentyl | —CH(CH₃)₂ | ¹H NMR (CDCl₃, 400 MHz) δ: 0.86 (t, 3H), 1.18 (d, 6H), 1.57 (m, 2H), 1.73 (m, 2H), 1.88 (m, 2H), 2.16 (m, 2H), 2.98 (s, 3H), 3.51 (m, 2H), 3.86 (m, 2H), 4.40 (m, 1H), 4.61 (m, 2H), 7.07 (m, 1H). MS ES+ m/z 413 [MNa]⁺ |
| 32 | cyclobutyl | —CH(CH₃)₂ | ¹H NMR (CD₃OD, 400 MHz) δ: 1.19 (t, 3H), 1.31 (d, 6H), 1.96 (m, 2H), 2.22 (m, 2H), 2.52 (m, 2H), 3.12 (s, 3H), 3.57 (q, 2H), 3.90 (m, 2H), 4.65 (m, 1H), 4.76 (m, 2H), 5.03 (m, 1H). MS ES− m/z 375 [M − H]⁻ |
| 33 | cyclobutyl | —CH₃ | ¹H NMR (CD₃OD, 400 MHz) δ: 1.19 (t, 3H), 1.92 (m, 2H), 2.22 (m, 2H), 2.52 (m, 2H), 3.32 (s, 6H), 3.57 (q, 2H), 3.90 (m, 2H), 4.69 (m, 1H), 4.76 (m, 2H). MS ES− m/z 347 [M − H]⁻ |
| 34 | cyclopropyl | —CH(CH₃)₂ | ¹H NMR (CD₃OD, 400 MHz) δ: 0.80 (m, 2H), 0.98 (m, 2H), 1.17 (t, 3H), 1.31 (d, 6H), 3.07 (m, 1H), 3.15 (s, 3H), 3.52 (q, 2H), 3.86 (m, 2H), 4.70 (m, 2H), 5.10 (m, 1H). MS ES− m/z 361 [M − H]⁻ |
| 35 | cyclopropyl | —CH₃ | ¹H NMR (CD₃OD, 400 MHz) δ: 0.80 (m, 2H), 0.98 (q, 2H), 1.17 (t, 3H), 3.09 (m, 1H), 3.35 (s, 6H), 3.52 (q, 2H), 3.86 (m, 2H), 4.71 (m, 2H). MS ES− m/z 333 [M − H]⁻ |
| 36 | 4-methylpyridin-2-yl | —CH(CH₃)₂ | ¹H NMR (CD₃OD, 400 MHz) δ: 1.13 (t, 3H), 1.29 (m, 6H), 2.75 (q, 2H), 3.13 (s, 3H), 3.60 (q, 2H), 3.96 (t, 2H), 4.88 (m, 2H), 5.10 (m, 1H), 7.08 (d, 1H), 8.16 (s, 1H), 8.21 (d, 1H). MS ES− m/z 426 [M − H]⁻ |
| 37 | 4-methylpyridin-2-yl | —CH₃ | ¹H NMR (CD₃OD, 400 MHz) δδ: 1.11 (t, 3H), 1.31 (t, 3H), 2.75 (q, 2H), 3.30 (s, 6H), 3.58 (q, 2H), 3.95 (t, 2H), 4.88 (m, 2H), 7.08 (d, 1H), 8.19 (s, 1H), 8.20 (d, 1H). MS ES− m/z 398 [M − H]⁻ |
| 38 | 6-methylpyridin-2-yl | —CH₂CH₃ | ¹H NMR (CD₃OD, 400 MHz) δ: 1.17 (t, 3H), 1.28 (t, 3H), 2.54 (s, 3H), 3.27 (s, 3H), 3.62 (q, 2H), 3.76 (q, 2H), 3.97 (t, 2H), 4.88 (t, 2H), 7.03 (d, 1H), 7.80 (t, 1H), 8.02 (d, 1H). MS ES+ m/z 400 [MH]⁺ |
| 39 | 6-methylpyridin-2-yl | —CH₃ | ¹H NMR (CD₃OD, 400 MHz) δ: 1.16 (t, 3H), 2.54 (s, 3H), 3.29 (s, 6H), 3.60 (q, 2H), 3.95 (t, 2H), 4.89 (t, 2H), 7.02 (d, 1H), 7.80 (t, 1H), 8.02 (d, 1H). MS ES+ m/z 386 [MH]⁺ |

| | | |
|---|---|---|
| 40 | 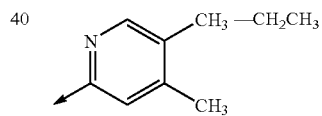 CH₃ —CH₂CH₃ | ¹H NMR (CD₃OD, 400 MHz) δ: 1.10 (t, 3H), 1.31 (t, 3H), 2.29 (s, 3H), 2.39 (s, 3H), 3.27 (s, 3H), 3.60 (q, 2H), 3.77 (q, 2H), 3.96 (t, 2H), 4.88 (t, 2H), 8.04 (s, 1H), 8.10 (s, 1H). MS ES+ m/z 414 [MH]⁺ |
| 41 | 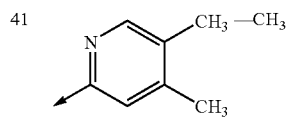 CH₃ —CH₃ | ¹H NMR (CD₃OD, 400 MHz) δ: 1.10 (t, 3H), 2.29 (s, 3H), 2.39 (s, 3H), 3.30 (s, 3H), 3.31 (s, 3H), 3.58 (q, 2H), 3.94 (q, 2H), 4.85 (t, 2H), 8.03 (s, 1H), 8.06 (s, 1H). MS ES+ m/z 400 [MH]⁺ |

Examples 14 and 24-31 were performed without N-ethyldiisopropylamine
Examples 38-41 were performed using caesium fluoride instead of N-ethyldiisopropylamine
Example 12 used the amine of preparation 4 as the HNR³R⁴ amine
Example 13 used the amine of preparation 3 as the HNR³R⁴

EXAMPLES 42 TO 48

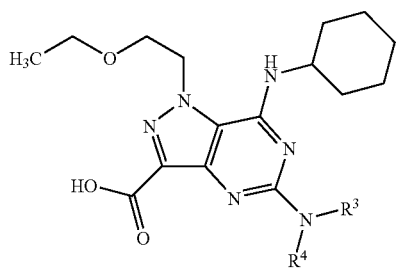

The monochloro compound of preparation 144 (99 mg, 0.27 mmol) was dissolved in dimethyl sulphoxide (3 mL) and the solution treated with the appropriate HNR³R⁴ amine (1.08 mmol). The reaction mixture was heated to 120° C. for 18 hours before being allowed to cool to room temperature. The reaction mixture was diluted with dichloromethane and washed with water, brine (×2) and citric acid. The dichloromethane phase was dried over magnesium sulphate and concentrated in vacuo. The residue was purified by column chromatography on silica gel eluting with dichloromethane:methanol 100:0 to 85:15. The crude product was triturated with ether to give the desired product.

| Ex | —NR³R⁴ | Data |
|---|---|---|
| 42 | —N(CH₃)₂ | ¹H NMR (CD₃OD, 400 MHz) δ: 1.16 (t, 3H), 1.30 (m, 1H), 1.48 (m, 4H), 1.72 (m, 1H), 1.86 (m, 2H), 2.15 (m, 2H), 3.30 (s, 6H), 3.58 (q, 2H), 3.89 (t, 2H), 4.20 (m, 1H), 4.70 (t, 2H). MS ES+ m/z 375 [MH]⁺ |
| 43 | N(CH₃)(CH₂CH₃) | ¹H NMR (CD₃OD, 400 MHz) δ: 1.16 (t, 3H), 1.29 (t, 4H), 1.48 (m, 4H), 1.73 (m, 1H), 1.86 (m, 2H), 2.14 (m, 2H), 3.27 (s, 3H), 3.58 (q, 2H), 3.77 (q, 2H), 3.90 (t, 2H), 4.19 (m, 1H), 4.71 (t, 2H). MS ES+ m/z 389 [MH]⁺ |
| 44 | pyrrolidinyl | ¹H NMR (CD₃OD, 400 MHz) δ: 1.16 (t, 3H), 1.31 (m, 1H), 1.48 (m, 4H), 1.73 (m, 1H), 1.86 (m, 2H), 2.13 (m, 6H), 3.58 (q, 2H), 3.71 (m, 4H), 3.90 (t, 2H), 4.21 (m, 1H), 4.71 (t, 2H). MS ES+ m/z 401 [MH]⁺ |
| 45 | —NHCH₂CH₃ | ¹H NMR (CD₃OD, 400 MHz) δ: 1.17 (t, 3H), 1.30 (t, 4H), 1.48 (m, 4H), 1.73 (m, 1H), 1.86 (m, 2H), 2.14 (m, 2H), 3.57 (m, 4H), 3.90 (t, 2H), 4.23 (m, 1H), 4.70 (t, 2H). MS ES+ m/z 375 [MH]⁺ |
| 46 | N(CH₃)CH(CH₃)₂ | ¹H NMR (CD₃OD, 400 MHz) δ: 1.16 (t, 3H), 1.30 (d, 7H), 1.48 (m, 4H), 1.72 (m, 1H), 1.87 (m, 2H), 2.14 (m, 2H), 3.12 (s, 3H), 3.58 (q, 2H), 3.90 (t, 2H), 4.16 (m, 1H), 4.70 (t, 2H), 4.95 (m, 1H). MS ES+ m/z 403 [MH]⁺ |
| 47 | —N(CH₃CH₃)₂ | ¹H NMR (CD₃OD, 400 MHz) δ: 1.16 (t, 3H), 1.32 (t, 7H), 1.48 (m, 4H), 1.72 (m, 1H), 1.86 (m, 2H), 2.13 (m, 2H), 3.58 (q, 2H), 3.72 (q, 4H), 3.90 (t, 2H), 4.17 (m, 1H), 4.71 (t, 2H). MS ES+ m/z 403 [MH]⁺ |
| 48 | —NHCH₃ | ¹H NMR (CD₃OD, 400 MHz) δ: 1.15 (t, 3H), 1.32 (m, 1H), 1.47 (m, 4H), 1.72 (m, 1H), 1.85 (m, 2H), 2.16 (m, 2H), 3.05 (s, 3H), 3.56 (q, 2H), 3.89 (m, 2H), 4.22 (m, 1H), 4.72 (m, 2H). MS ES+ m/z 367 [MH]⁺ |

EXAMPLES 49 TO 74

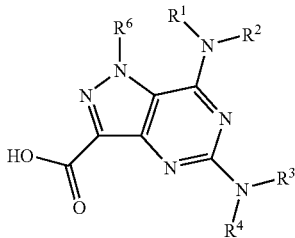

The appropriate monochloro precursor (0.266 mmol) and tetraethylammonium fluoride (39.6 mg, 0.266 mmol) were dissolved in dimethyl sulphoxide (11.0 mL) and the solution treated with N-ethyldiisopropylamine (230 µL, 1.33 mmol) and a solution of the appropriate $HNR^3R^4$ amine (1.33 mmol) in dimethyl sulphoxide (500 µL). The reaction mixture was placed in a sealed vessel and shaken at 350 rpm at 120° C. for 18 hours. The reaction mixture was diluted with dichloromethane and washed with 1M citric acid solution and water. The dichloromethane phase was then dried over magnesium sulphate and concentrated in vacuo. The residue was purified by column chromatography on silica gel eluting with dichloromethane:methanol 100:0 to 90:10 to yield the desired product.

Monochloro precursors from preparations 137, 138, 139, 145, 150, 151, 172, 173 and 174 were used.

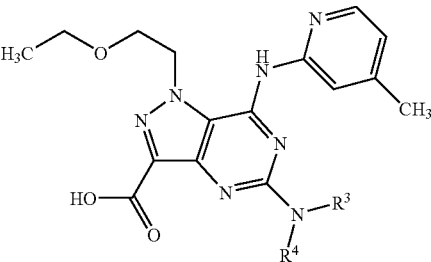

| Ex | —NR³R⁴ | Data |
|---|---|---|
| 49 | (N-CH2-cyclopropyl, N-propyl) | ¹H NMR (CD₃OD, 400 MHz) δ: 0.40 (q, 2H), 0.60 (q, 2H), 1.00 (t, 3H), 1.14 (t, 3H), 1.23 (m, 1H), 1.78 (q, 2H), 2.47 (q, 2H), 3.60 (m, 4H), 3.69 (m, 2H), 3.96 (t, 2H), 4.88 (m, 2H), 7.03 (d, 1H), 8.16 (m, 2H). MS ES+ m/z 454 [MH]⁺ |
| 50 | (N(CH3)-CH(CH3)-CH2CH3) | ¹H NMR (CD₃OD, 400 MHz) δ: 0.93 (t, 3H), 1.14 (t, 3H), 1.29 (d, 3H), 1.69 (m, 2H), 2.46 (s, 3H), 3.11 (s, 3H), 3.33 (m, 1H), 3.61 (m, 2H), 3.95 (t, 2H), 4.88 (m, 2H), 7.04 (d, 1H), 8.15 (s, 1H), 8.17 (d, 1H). MS ES+ m/z 428 [MH]⁺ |
| 51 | (N(CH3)-cyclobutyl) | ¹H NMR (CD₃OD, 400 MHz) δ: 1.12 (t, 3H), 1.81 (m, 2H), 2.35 (m, 4H), 2.48 (s, 3H), 3.24 (s, 3H), 3.33 (m, 1H), 3.59 (m, 2H), 3.95 (t, 2H), 4.88 (m, 2H), 7.04 (d, 1H), 8.16 (m, 2H). MS ES+ m/z 426 [MH]⁺ |
| 52 | (N(CH3)-CH2CH2-O-CH3, plus CH3 on N) | ¹H NMR (CD₃OD, 400 MHz) δ: 1.13 (t, 3H), 1.34 (t, 3H), 2.47 (s, 3H), 3.44 (s, 3H), 3.60 (m, 2H), 3.74-3.84 (m, 6H), 3.96 (t, 2H), 4.89 (m, 2H), 7.05 (d, 1H), 8.12 (s, 1H), 8.16 (d, 1H). MS ES+ m/z 444 [MH]⁺ |
| 53 | (2-methylpyrrolidin-1-yl) | ¹H NMR (CD₃OD, 400 MHz) δ: 1.12 (t, 3H), 1.39 (d, 3H), 1.87 (m, 1H), 2.23 (m, 3H), 2.48 (s, 3H), 3.60 (m, 3H), 3.80 (m, 1H), 3.96 (t, 2H), 4.46 (m, 1H), 4.89 (m, 2H), 7.07 (d, 1H), 8.18 (m, 2H). MS ES+ m/z 426 [MH]⁺ |
| 54 | (NH-CH(CH3)-C(CH3)3... isopropyl-like) | ¹H NMR (CD₃OD, 400 MHz) δ: 1.11 (t, 3H), 1.35 (d, 6H), 2.54 (s, 3H), 3.55 (m, 2H), 3.98 (t, 2H), 4.18 (m, 1H), 5.03 (t, 2H), 7.16 (d, 1H), 8.10 (s, 1H), 8.12 (d, 1H). MS ES+ m/z 400 [MH]⁺ |

| Ex | Structure | Data |
|---|---|---|
| 55 | ![structure: NH-CH(CH3)-CH2-CH3 with arrow] | ¹H NMR (CD₃OD, 400 MHz) δ: 1.00 (t, 3H), 1.10 (t, 3H), 1.30 (t, 3H), 1.67 (m, 2H), 2.53 (s, 3H), 3.54 (m, 2H), 3.98 (m, 3H), 5.02 (t, 2H), 7.17 (d, 1H), 8.10 (s, 1H), 8.13 (d, 1H). MS ES+ m/z 414 [MH]⁺ |
| 56 | ![structure: NH-CH(CH3)-CH2-CH3 with arrow] | ¹H NMR (CD₃OD, 400 MHz) δ: 1.00 (t, 3H), 1.10 (t, 3H), 1.30 (t, 3H), 1.67 (m, 2H), 2.53 (s, 3H), 3.54 (m, 2H), 3.98 (m, 3H), 5.02 (t, 2H), 7.17 (d, 1H), 8.10 (s, 1H), 8.13 (d, 1H). MS ES+ m/z 414 [MH]⁺ |

[Core structure: pyrazolo[3,4-d]pyrimidine with R⁶ on N1, carboxylic acid (HOOC-) at C3, 4-methylpyridin-2-ylamino at C7, and NR³R⁴ at C5]

| Ex | —NR³R⁴ | R⁶ | Data |
|---|---|---|---|
| 57 | —N(CH₃)₂ | tetrahydropyran-4-yl-CH₂— | ¹H NMR (CD₃OD, 400 MHz) δ: 1.47 (m, 4H), 2.30 (m, 1H), 2.50 (s, 3H), 3.28 (s, 6H), 3.36 (m, 2H), 3.90 (m, 2H), 4.70 (d, 2H), 7.08 (d, 1H), 7.80 (s, 1H), 8.10 (d, 1H). MS APCI+ m/z 412 [MH]⁺ |
| 58 | —N(CH₃)(CH₂CH₃) | tetrahydropyran-4-yl-CH₂— | ¹H NMR (CD₃OD, 400 MHz) δ: 1.28 (t, 3H), 1.44 (m, 4H), 2.30 (m, 1H), 2.48 (s, 3H), 3.24 (s, 3H), 3.34 (m, 2H), 3.73 (q, 2H), 3.90 (m, 2H), 4.70 (d, 2H), 7.07 (d, 1H), 7.84 (s, 1H), 8.08 (d, 1H). MS APCI+ m/z 426 [MH]⁺ |
| 59 | —N(CH₃)₂ | tetrahydropyran-2-yl-CH₂— | ¹H NMR (DMSO-D₆, 400 MHz) δ: 1.20 (m, 1H), 1.50 (m, 3H), 1.74 (m, 1H), 1.82 (m, 1H), 2.35 (s, 3H), 3.14 (s, 6H), 3.46 (m, 1H), 3.84 (m, 1H), 4.06 (m, 1H), 4.58 (m, 1H), 4.70 (m, 1H), 6.92 (d, 1H), 8.08 (m, 1H), 8.19 (m, 1H). MS APCI+ m/z 412 [MH]⁺ |
| 60 | —N(CH₃)(CH₂CH₃) | tetrahydropyran-2-yl-CH₂— | ¹H NMR (DMSO-D₆, 400 MHz) δ: 1.17 (t, 3H), 1.20 (m, 1H), 1.47 (m, 3H), 1.78 (m, 2H), 2.32 (s, 3H), 3.12 (s, 3H), 3.42 (m, 1H), 3.68 (m, 2H), 3.84 (m, 1H), 4.07 (m, 1H), 4.58 (m, 1H), 4.68 (m, 1H), 6.95 (d, 1H), 8.05 (m, 1H), 8.20 (m, 1H). MS APCI+ m/z 426 [MH]⁺ |
| 61 | —N(CH₃)₂ | —(CH₂)₂OCH(CH₃)₂ | ¹H NMR (CD₃OD, 400 MHz) δ: 1.06 (m, 6H), 2.42 (s, 3H), 3.27 (s, 6H), 3.67 (m, 1H), 3.94 (t, 2H), 4.82 (m, 2H), 7.07 (d, 1H), 8.17 (m, 2H). MS APCI+ m/z 400 [MH]⁺ |
| 62 | —N(CH₃)(CH₂CH₃) | —(CH₂)₂OCH(CH₃)₂ | ¹H NMR (CD₃OD, 400 MHz) δ: 1.08 (d, 6H), 1.27 (t, 3H), 2.43 (s, 3H), 3.28 (s, 3H), 3.65 (m, 1H), 3.80 (q, 2H), 3.95 (t, 2H), 4.85 (m, 2H), 7.06 (d, 1H), 8.20 (m, 2H). MS APCI+ m/z 414 [MH]⁺ |
| 63 | —NHCH₂CH₃ | —(CH₂)₂OCH(CH₃)₂ | ¹H NMR (DMSO-D₆, 400 MHz) δ: 0.97 (d, 6H), 1.16 (t, 3H), 2.44 (s, 3H), 3.37 (m, 2H), 3.50 (m, 1H), 3.81 (t, 2H), 4.90 (t, 2H), 7.05 (d, 1H), 8.08 (s, 1H), 8.22 (d, 1H). MS APCI+ m/z 400 [MH]⁺ |

| Ex | R¹ | —NR³R⁴ | Data |
|---|---|---|---|
| 64 | —N(CH₃)₂ | 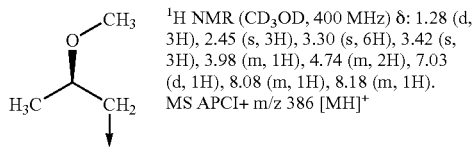 | ¹H NMR (CD₃OD, 400 MHz) δ: 1.28 (d, 3H), 2.45 (s, 3H), 3.30 (s, 6H), 3.42 (s, 3H), 3.98 (m, 1H), 4.74 (m, 2H), 7.03 (d, 1H), 8.08 (m, 1H), 8.18 (m, 1H). MS APCI+ m/z 386 [MH]⁺ |
| 65 | 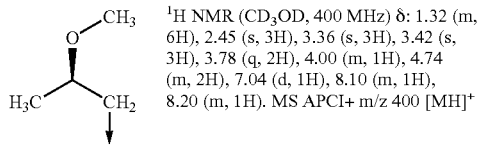 (left structure) | (right structure) | ¹H NMR (CD₃OD, 400 MHz) δ: 1.32 (m, 6H), 2.45 (s, 3H), 3.36 (s, 3H), 3.42 (s, 3H), 3.78 (q, 2H), 4.00 (m, 1H), 4.74 (m, 2H), 7.04 (d, 1H), 8.10 (m, 1H), 8.20 (m, 1H). MS APCI+ m/z 400 [MH]⁺ |
| 66 | —N(CH₂CH₃)₂ | 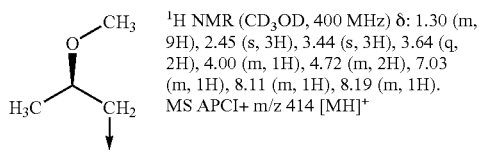 | ¹H NMR (CD₃OD, 400 MHz) δ: 1.30 (m, 9H), 2.45 (s, 3H), 3.44 (s, 3H), 3.64 (q, 2H), 4.00 (m, 1H), 4.72 (m, 2H), 7.03 (m, 1H), 8.11 (m, 1H), 8.19 (m, 1H). MS APCI+ m/z 414 [MH]⁺ |

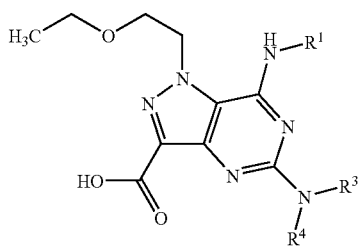

| Ex | R¹ | —NR³R⁴ | Data |
|---|---|---|---|
| 67 | 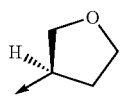 | 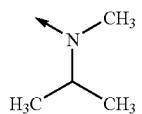 | ¹H NMR (DMSO-D₆, 400 MHz) δ: 1.03 (t, 3H), 1.23 (d, 6H), 2.09 (m, 1H), 2.33 (m, 1H), 3.07 (s, 3H), 3.44 (q, 2H), 3.77 (m, 2H), 3.95 (m, 2H), 4.75 (m, 2H), 4.84 (m, 2H). MS ES+ m/z 393 [MH]⁺ |
| 68 | 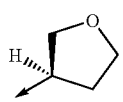 | —N(CH₂CH₃)₂ | ¹H NMR (DMSO-D₆, 400 MHz) δ: 1.04 (t, 3H), 1.22 (t, 6H), 2.09 (m, 1H), 2.32 (m, 1H), 3.44 (q, 2H), 3.77 (m, 8H), 3.94 (m, 2H), 4.75 (m, 1H), 4.84 (m, 2H). MS ES+ m/z 393 [MH]⁺ |
| 69 | 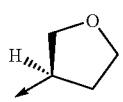 | 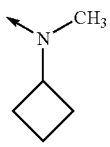 | ¹H NMR (CD₃OD, 400 MHz) δ: 1.16 (t, 3H), 1.84 (m, 2H), 2.09 (m, 1H), 2.35 (m, 4H), 2.48 (m, 1H), 3.26 (s, 3H), 3.58 (q, 2H), 3.89 (m, 4H), 4.05 (m, 2H), 4.73 (t, 2H), 4.85 (m, 2H). MS ES+ m/z 405 [MH]⁺ |
| 70 | 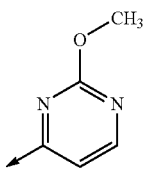 | 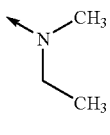 | ¹H NMR (CDCl₃, 400 MHz) δ: 1.25 (m, 6H), 3.22 (s, 3H), 3.70 (m, 4H), 3.99 (t, 2H), 4.01 (s, 3H), 4.80 (t, 2H), 7.90 (d, 1H), 8.42 (d, 1H), 10.18 (s, 1H). MS APCI− m/z 415 [M − H]⁻ |

| | | | |
|---|---|---|---|
| 71 | 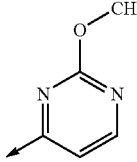 | —N(CH₃)₂ | ¹H NMR (CDCl₃, 400 MHz) δ: 1.25 (t, 3H), 3.30 (s, 6H), 3.70 (q, 2H), 3.99 (t, 2H), 4.02 (s, 3H), 4.80 (t, 2H), 8.42 (d, 1H), 8.45 (d, 1H), 10.18 (s, 1H). MS APCI– m/z 401 [M – H]⁻ |
| 72 | 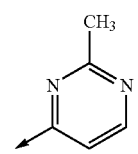 | 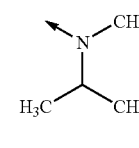 | ¹H NMR (CD₃OD, 400 MHz) δ: 1.24 (t, 3H), 1.28 (d, 6H), 2.60 (s, 3H), 3.10 (s, 3H), 3.69 (q, 2H), 3.99 (t, 2H), 4.82 (t, 2H), 5.09 (m, 1H), 8.09 (d, 1H), 8.51 (m, 1H). MS ES– m/z 413 [M – H]⁻ |
| 73 | 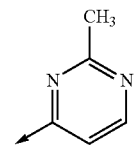 | 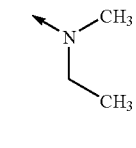 | ¹H NMR (CD₃OD, 400 MHz) δ: 1.23 (t, 6H), 2.60 (s, 3H), 3.23 (s, 3H), 3.71 (q, 2H), 3.78 (q, 2H), 3.98 (t, 2H), 4.81 (t, 2H), 8.11 (d, 1H), 8.51 (m, 1H). MS ES– m/z 399 [M – H]⁻ |
| 74 | 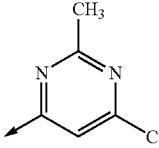 | 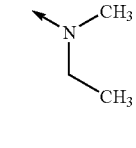 | ¹H NMR (CD₃OD, 400 MHz) δ: 1.25 (m, 6H), 2.45 (s, 6H), 3.25 (s, 3H), 3.61 (q, 2H), 3.78 (q, 2H), 3.98 (t, 2H), 4.90 (t, 2H), 6.99 (d, 1H). MS ES– m/z 413 [M – H]⁻ |

Example 51 was prepared using cyclobutyl-methyl-amine (J. Med. Chem., 1994, 37, 3482-3491) as the HNR³R⁴ amine.
Examples 67, 68 and 69 were purified by column chromatography on silica gel eluting with dichloromethane:methanol:acetic acid 90:10:1
Examples 70 and 71 were prepared without the use of N-ethyldiisopropylamine.

EXAMPLE 75

3-[1-(2-Ethoxyethyl)-5-(N-isopropyl-N-methylamino)-7-(4-methylpyridin-2-ylamino)-1H-pyrazolo[4,3-d]pyrimidin-3-yl]-2H-1,2,4-oxadiazol-5-one

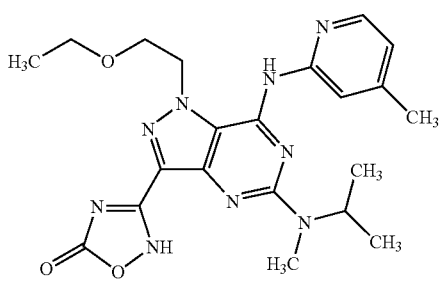

The oxadiazolone of preparation 183 (50 mg, 0.12 mmol) was added to a solution of methylisopropylamine (44 mg, 0.60 mmol) and N-ethyldiisopropylamine (83 µL, 0.60 mmol) in dimethyl sulphoxide (1 mL) and the reaction mixture stirred at 120° C. for 18 hours. The reaction mixture was diluted with ethyl acetate (20 mL) and washed with water (15 mL). The aqueous phase was then extracted with ethyl acetate (2×20 mL), acidified with acetic acid solution and extracted with further ethyl acetate (2×20 mL). The organics were combined, dried over magnesium sulphate and concentrated in vacuo. The residue was purified by column chromatography on silica gel eluting with dichloromethane:methanol:acetic acid 100:0:0 to 97.5:2.5:0.25 to yield the title product. ¹H NMR (CD₃OD, 400 MHz) δ: 1.11 (t, 3H), 1.25 (d, 6H), 2.41 (s, 3H), 3.09 (s, 3H), 3.60 (m, 2H), 3.95 (t, 2H), 4.83 (t, 2H), 5.16 (m, 1H), 6.95 (d, 1H), 8.16 (m, 1H), 8.25 (m, 1H). MS ES+ m/z 454 [MH]⁺

The following compounds, of the general formula shown below, were prepared by a method similar to that described for example 75 using the monochloro precursor from preparations 183, 184 and 185.

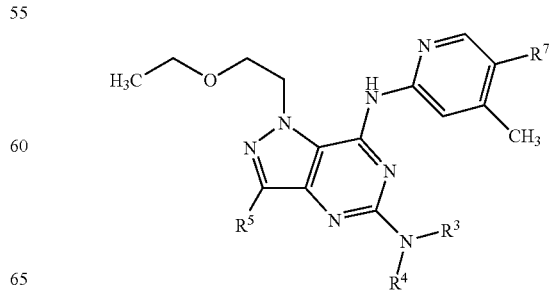

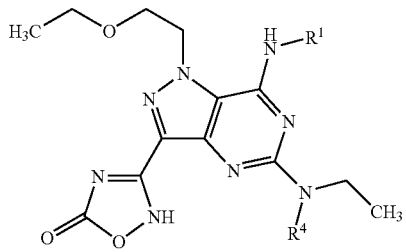

| Ex | R¹ | R⁴ | Data |
|---|---|---|---|
| 76 | 4-methyl-pyridin-2-yl | —CH₃ | $^1$H NMR (CD$_3$OD, 400 MHz) δ: 1.12 (t, 3H), 1.25 (t, 3H), 2.41 (s, 3H), 3.24 (s, 3H), 3.61 (m, 2H), 3.77 (m, 2H), 3.94 (t, 2H), 4.84 (t, 2H), 6.95 (d, 1H), 8.16 (s, 1H), 8.31 (m, 1H). MS ES+ m/z 440 [MH]⁺ |
| 77 | 4-fluoro-3-methylphenyl | —CH₃ | $^1$H NMR (DMSO-D$_6$, 400 MHz) δ: 0.99 (t, 3H), 1.10 (t, 3H), 2.26 (s, 3H), 3.07 (s, 3H), 3.50 (q, 2H), 3.58 (q, 2H), 3.84 (m, 2H), 4.84 (m, 2H), 7.14 (t, 1H), 7.47 (m, 1H), 7.68 (m, 1H), 8.87 (s, 1H),. MS ES+ m/z 457 [MH]⁺ |
| 78 | 4-fluoro-3-methylphenyl | —CH₂CH₃ | $^1$H NMR (DMSO-D$_6$, 400 MHz) δ: 1.00 (t, 3H), 1.10 (t, 6H), 2.25 (s, 3H), 3.50 (q, 2H), 3.58 (q, 4H), 3.84 (m, 2H), 4.84 (m, 2H), 7.15 (t, 1H), 7.40 (m, 1H), 7.69 (m, 1H), 8.85 (s, 1H). MS APCI– m/z 469 [M – H]⁻ |

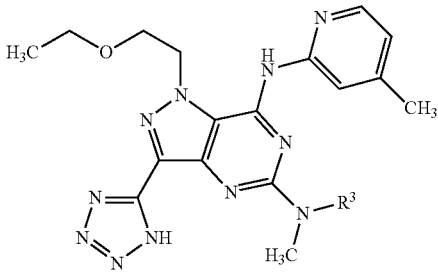

| Ex | R³ | Data |
|---|---|---|
| 79 | —CH(CH₃)₂ | $^1$H NMR (CD$_3$OD, 400 MHz) δ: 1.13 (t, 3H), 1.25 (d, 6H), 2.42 (s, 3H), 3.12 (s, 3H), 3.61 (m, 2H), 3.95 (m, 2H), 4.84 (m, 2H), 5.20 (m, 1H), 6.95 (d, 1H), 8.15 (m, 1H), 8.30 (m, 1H). MS ES– m/z 436 [M – H]⁻ |
| 80 | —CH₃ | $^1$H NMR (CD$_3$OD, 400 MHz) δ: 1.13 (t, 3H), 2.44 (s, 3H), 3.30 (s, 6H), 3.61 (m, 2H), 3.72 (t, 2H), 4.90 (t, 2H), 7.00 (d, 1H), 8.17 (m, 1H), 8.25 (m, 1H). MS APCI+ m/z 410 [MH]⁺ |

EXAMPLE 81

1-(2-Ethoxyethyl)-7-(5-fluoropyridin-2-ylamino)-5-(N-isopropyl-N-methylamino)-1H-pyrazolo[4,3-d]pyrimidine-3-carboxylic acid

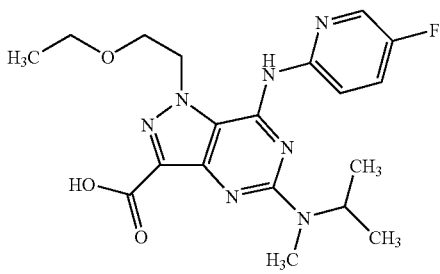

The ester of preparation 108 (30 mg, 0.07 mmol) and a 1M aqueous solution of sodium hydroxide (105 μL, 0.105 mmol) were dissolved in dioxane (1 mL) and the reaction mixture stirred at room temperature for 18 hours. The reaction mixture was concentrated in vacuo and the residue treated with 1M citric acid solution (5 mL) and extracted with dichloromethane (3×50 mL). The organics were combined, dried over sodium sulphate and concentrated in vacuo. The crude product was triturated with ether and then filtered to yield the title product as a white solid, 27 mg. $^1$H NMR (CD$_3$OD, 400 MHz) δ: 1.22 (t, 3H), 1.30 (d, 6H), 3.12 (s, 3H), 3.70 (q, 2H), 3.98 (t, 2H), 4.84 (t, 2H), 5.01 (m, 1H), 7.71 (m, 1H), 8.29 (m, 1H), 8.31 (d, 1H). MS ES– m/z 416 [M-H]$^-$ The following compounds, of the general formula shown below, were prepared by a method similar to that described for example 81 using the appropriate ester of preparations 103, 106, 108, 109, 110, 111, 112, 113, 114, 115, 116, 117, 118, 119, 121, 122, 123, 124, 125, 126, 128, 129, 130, 131, 132, 133, 134 and example 6.

| Ex | R$^1$ | —NR$^3$R$^4$ | Data |
|---|---|---|---|
| 82 | tetrahydropyran-4-yl | —N(CH$_3$)$_2$ | $^1$H NMR (CD$_3$OD, 400 MHz) δ: 1.16 (t, 3H), 1.78 (m, 2H), 2.14 (m, 2H), 3.32 (s, 6H), 3.59 (m, 4H), 3.90 (t, 2H), 4.04 (m, 2H), 4.40 (m, 1H), 4.74 (t, 2H). MS ES– /z 377 [M – H]$^-$ |
| 83 | tetrahydropyran-4-yl | N(CH$_3$)(iPr) | $^1$H NMR (CD$_3$OD, 400 MHz) δ: 1.19 (t, 3H), 1.32 (d, 6H), 1.85 (m, 2H), 2.10 (m, 2H), 3.16 (s, 3H), 3.60 (m, 4H), 3.93 (t, 2H), 4.05 (t, 2H), 4.45 (m, 1H), 4.89 (t, 2H), 5.01 (m, 1H). MS ES– m/z 405 [M – H]$^-$ |
| 84 | 6-methoxypyridin-2-yl | N(CH$_3$)(iPr) | $^1$H NMR (CD$_3$OD, 400 MHz) δ: 1.15 (t, 3H), 2.40 (d, 6H), 3.05 (s, 3H), 3.65 (q, 2H), 3.95 (s, 3H), 3.98 (q, 2H), 4.78 (t, 2H), 5.01 (m, 1H), 6.49 (d, 1H), 7.66 (t, 1H), 7.82 (d, 1H). MS ES– m/z 428 [M – H]$^-$ |
| 85 | 2-fluoro-3-methylphenyl | N(CH$_3$)(iPr) | $^1$H NMR (CD$_3$OD, 400 MHz) δ: 1.13 (t, 3H), 1.26 (d, 6H), 2.33 (s, 3H), 3.11 (s, 3H), 3.61 (q, 2H), 3.98 (t, 2H), 4.88 (t, 2H), 4.90 (m, 1H), 7.10 (t, 1H), 7.42 (m, 1H), 7.60 (m, 1H). MS ES+ m/z 431 [MH]$^+$ |

-continued

| | | | |
|---|---|---|---|
| 86 | 3-methyl-4-fluorophenyl | —N(CH₂CH₃)₂ | ¹H NMR (DMSO-D₆, 400 MHz) δ: 1.00 (t, 3H), 1.15 (t, 6H), 2.25 (s, 3H), 3.45 (m, 4H), 3.50 (m, 2H), 3.82 (t, 2H), 4.81 (t, 2H), 7.08 (t, 1H), 7.41 (m, 1H), 7.70 (m, 1H). MS APCI– m/z 429 [M – H]⁻ |
| 87 | 3-methyl-4-fluorophenyl | N(CH₃)(CH₂CH₃) | ¹H NMR (CD₃OD, 400 MHz) δ: 1.10 (t, 3H), 1.25 (t, 3H), 2.30 (s, 3H), 3.20 (s, 3H), 3.60 (q, 2H), 3.70 (q, 2H), 3.98 (t, 2H), 4.82 (m, 2H), 7.15 (t, 1H), 7.50 (t, 1H), 7.63 (m, 1H). MS APCI+ m/z 439 [MNa]⁺ |
| 88 | 3-fluorophenyl | N(CH₃)(CH(CH₃)₂) | ¹H NMR (CD₃OD, 400 MHz) δ: 1.15 (t, 3H), 1.31 (d, 6H), 3.17 (s, 3H), 3.64 (q, 2H), 3.99 (t, 2H), 4.89 (m, 1H), 4.96 (t, 2H), 7.08 (m, 1H), 7.43 (m, 1H), 7.51 (m, 1H), 7.62 (m, 1H). MS ES– m/z 415 [M – H]⁻ |
| 89 | 2,4-difluorophenyl | N(CH₃)(CH(CH₃)₂) | ¹H NMR (CDCl₃, 400 MHz) δ: 1.10 (m, 9H), 2.98 (s, 3H), 3.62 (q, 2H), 3.95 (m, 2H), 4.78 (m, 2H), 4.90 (m, 1H), 6.95 (m, 2H), 8.15 (m, 1H), 9.01 (s, 1H). MS APCI– m/z 453 [M – H]⁻ |
| 90 | 3,4-difluorophenyl | N(CH₃)(CH(CH₃)₂) | ¹H NMR (CDCl₃, 400 MHz) δ: 1.22 (m, 9H), 3.01 (s, 3H), 3.65 (q, 2H), 4.00 (m, 2H), 4.78 (m, 2H), 4.98 (m, 1H), 7.18 (m, 2H), 7.82 (m, 1H), 9.20 (m, 1H). MS APCI– m/z 433 [M – H]⁻ |
| 91 | 3,5-difluorophenyl | N(CH₃)(CH(CH₃)₂) | ¹H NMR (CDCl₃, 400 MHz) δ: 1.20 (m, 9H), 3.02 (s, 3H), 3.65 (q, 2H), 4.00 (t, 2H), 4.78 (t, 2H), 4.98 (m, 1H), 6.58 (m, 1H), 7.30 (m, 2H), 9.35 (m, 1H). MS APCI– m/z 433 [M – H]⁻ |
| 92 | 2,5-difluorophenyl | N(CH₃)(CH(CH₃)₂) | ¹H NMR (CDCl₃, 400 MHz) δ: 1.18 (t, 3H), 1.28 (m, 6H), 3.05 (s, 3H), 3.62 (q, 2H), 3.98 (t, 2H), 4.78 (t, 2H), 4.99 (m, 1H), 6.78 (m, 1H), 7.10 (m, 1H), 8.25 (m, 1H), 9.26 (m, 1H). MS APCI+ m/z 435 [MH]⁺ |
| 93 | 2,3-difluorophenyl | N(CH₃)(CH(CH₃)₂) | ¹H NMR (CDCl₃, 400 MHz) δ: 1.20 (m, 9H), 3.00 (s, 3H), 3.65 (q, 2H), 3.98 (t, 2H), 4.79 (t, 2H), 4.90 (m, 1H), 6.95 (m, 1H), 7.10 (m, 1H), 8.01 (m, 1H), 9.22 (m, 1H). MS APCI– m/z 433 [M – H]⁻ |
| 94 | 3-methylphenyl | N(CH₃)(CH(CH₃)₂) | ¹H NMR (CD₃OD, 400 MHz) δ: 1.15 (t, 3H), 1.30 (d, 6H), 2.42 (s, 3H), 3.15 (s, 3H), 3.64 (q, 2H), 4.00 (t, 2H), 4.88 (m, 1H), 4.94 (m, 2H), 7.16 (d, 1H), 7.34 (t, 1H), 7.42 (d, 1H), 7.57 (s, 1H),. MS ES– m/z 411 [M – H]⁻ |

| | | | |
|---|---|---|---|
| 95 | 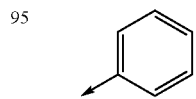 | 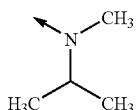 | $^1$H NMR (CD$_3$OD, 400 MHz) δ: 1.15 (t, 3H), 1.23 (d, 6H), 3.05 (s, 3H), 3.65 (q, 2H), 4.00 (t, 2H), 4.79 (t, 2H), 5.11 (m, 1H), 7.09 (t, 1H), 7.40 (t, 2H), 7.71 (d, 2H). MS ES− m/z 397 [M − H]$^+$ |
| 96 | 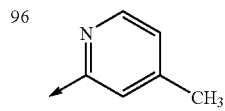 | 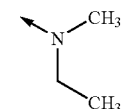 | $^1$H NMR (CD$_3$OD, 400 MHz) δ: 1.12 (t, 3H), 1.30 (t, 3H), 2.41 (s, 3H), 3.22 (s, 3H), 3.58 (q, 2H), 3.76 (q, 2H), 3.97 (t, 2H), 4.82 (t, 2H), 7.02 (d, 1H), 8.12 (s, 1H), 8.14 (d, 1H). MS APCI+ m/z 400 [MH]$^+$ |
| 97 | 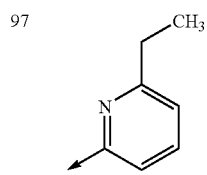 | 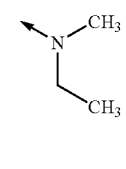 | $^1$H NMR (CDCl$_3$, 400 MHz) δ: 1.20-1.40 (m, 9H), 2.78 (q, 2H), 3.20 (s, 3H), 3.70 (m, 4H), 4.00 (t, 2H), 4.81 (t, 2H), 6.87 (d, 1H), 7.62 (t, 1H), 8.10 (d, 1H), 9.85 (s, 1H). MS APCI+ m/z 414 [MH]$^+$ |
| 98 | 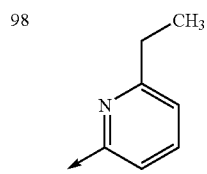 | 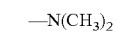 —N(CH$_3$)$_2$ | $^1$H NMR (CDCl$_3$, 400 MHz) δ: 1.30 (m, 6H), 2.78 (q, 2H), 3.25 (s, 6H), 3.70 (q, 2H), 4.00 (m, 2H), 4.82 (m, 2H), 6.90 (d, 1H), 7.65 (t, 1H), 8.10 (d, 1H), 9.90 (m, 1H). MS APCI+ m/z 400 [MH]$^+$ |
| 99 | 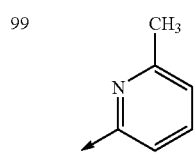 | 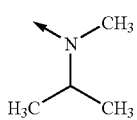 | $^1$H NMR (CD$_3$OD, 400 MHz) δ: 1.17 (t, 3H), 1.30 (d, 6H), 2.53 (s, 3H), 3.12 (s, 3H), 3.65 (q, 2H), 3.97 (t, 2H), 4.89 (t, 2H), 4.96 (m, 1H), 7.06 (d, 1H), 7.84 (t, 1H), 7.99 (d, 1H). MS ES− m/z 412 [M − H]$^-$ |
| 100 | 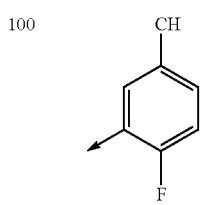 | —N(CH$_3$)$_2$ | $^1$H NMR(CD$_3$OD, 400 MHz) δ: 1.10 (t, 3H), 2.37 (s, 3H), 3.23 (s, 6H), 3.61 (q, 2H), 3.96 (t, 2H), 4.85 (t, 2H), 7.08 (m, 1H), 7.14 (m, 1H), 7.86 (d, 1H). MS ES+ m/z 403 [MH]$^+$ |
| 101 | 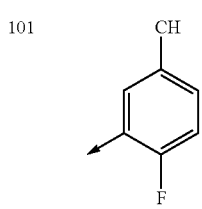 | 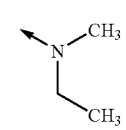 | $^1$H NMR (CD$_3$OD, 400 MHz) δ: 1.11 (t, 3H), 1.20 (t, 3H), 2.38 (s, 3H), 3.23 (s, 3H), 3.59 (q, 2H), 3.61 (q, 2H), 3.95 (t, 2H), 4.85 (t, 2H), 7.09 (m, 1H), 7.14 (m, 1H), 7.84 (d, 1H). MS ES+ m/z 417 [MH]$^+$ |
| 102 | 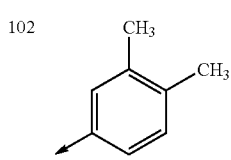 | —N(CH$_3$)$_2$ | $^1$H NMR (CD$_3$OD, 400 MHz) δ: 1.12 (t, 3H), 2.30 (s, 3H), 2.32 (s, 3H), 3.29 (s, 6H), 3.63 (q, 2H), 3.98 (t, 2H), 4.84 (t, 2H), 7.21 (d, 1H), 7.45 (d, 1H), 7.53 (s, 1H). MS ES+ m/z 399 [MH]$^+$ |

-continued

| | | | |
|---|---|---|---|
| 103 | (3,4-dimethylphenyl) | N(CH₃)(CH₂CH₃) | ¹H NMR (CD₃OD, 400 MHz) δ: 1.02 (t, 3H), 1.16 (t, 3H), 2.19 (s, 3H), 2.21 (s, 3H), 3.16 (s, 3H), 3.52 (q, 2H), 3.63 (q, 2H), 3.87 (t, 2H), 4.73 (t, 2H), 7.09 (d, 1H), 7.30 (d, 1H), 7.43 (m, 1H). MS ES+ m/z 413 [MH]⁺ |
| 104 | (2-fluorophenyl) | N(CH₃)CH(CH₃)₂ | ¹H NMR (CD₃OD, 400 MHz) δ: 1.11 (t, 3H), 1.21 (d, 6H), 3.06 (s, 3H), 3.61 (q, 2H), 3.96 (t, 2H), 4.83 (m, 1H), 4.85 (t, 2H), 7.28 (m, 3H), 7.90 (t, 1H). MS ES− m/z 415 [M − H]⁻ |
| 105 | (pyridin-2-yl) | N(CH₃)CH(CH₃)₂ | ¹H NMR (CD₃OD, 400 MHz) δ: 1.17 (t, 3H), 1.31 (d, 6H), 3.13 (s, 3H), 3.66 (q, 2H), 3.98 (t, 2H), 4.88 (t, 2H), 4.99 (m, 1H), 7.19 (t, 1H), 7.90 (t, 1H), 8.22 (d, 1H), 8.35 (d, 1H). MS ES− m/z 398 [M − H]⁻ |

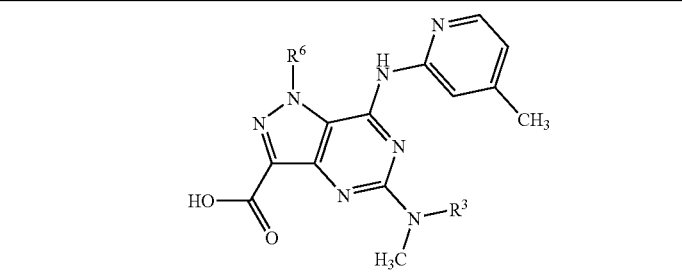

| | R³ | R⁶ | Data |
|---|---|---|---|
| 106 | —CH(CH₃)₂ | —(CH₂)₂O(CH₂)₂OCH₃ | ¹H NMR (CD₃OD, 400 MHz) δ: 1.30 (d, 6H), 2.42 (s, 3H), 3.02 (s, 3H), 3.10 (s, 3H), 3.30 (s, 1H), 3.45 (t, 2H), 3.62 (t, 2H), 4.00 (t, 2H), 4.98 (m, 2H), 7.05 (d, 1H), 8.10 (d, 1H), 8.20 (m, 1H). MS APCI+ m/z 458 [MH]⁺ |
| 107 | —CH(CH₃)₂ | —(CH₂)₂CH(CH₃)OCH₃ | ¹H NMR(CD₃OD, 400 MHz) δ: 1.18 (d, 3H), 1.35 (d, 6H), 2.10 (m, 2H), 2.50 (s, 3H), 3.10 (s, 3H), 3.32 (s, 3H), 3.38 (m, 1H), 4.80-4.90 (m, 3H), 7.10 (d, 1H), 7.90 (s, 1H), 8.10 (d, 1H). MS APCI+ m/z 428 [MH]⁺ |
| 108 | —CH(CH₃)₂ | —CH₂-O-cyclopropylmethyl | ¹H NMR (CD₃OD, 400 MHz) δ: 0.12 (m, 2H), 0.37 (m, 2H), 1.06 (m, 1H), 1.30 (d, 6H), 2.44 (s, 3H), 3.09 (s, 3H), 3.44 (d, 2H), 4.04 (t, 2H), 4.91 (m, 2H), 5.13 (m, 1H), 7.02 (d, 1H), 8.23 (m, 2H). MS ES− m/z 438 [M − H]⁻ |
| 109 | —CH₂CH₃ | —CH₂-O-cyclopropylmethyl | ¹H NMR (CD₃OD, 400 MHz) δ: 0.75 (m, 2H), 0.81 (m, 2H), 0.99 (m, 1H), 1.31 (t, 3H), 2.44 (s, 3H), 3.27 (s, 3H), 3.38 (d, 2H), 3.79 (q, 2H), 4.01 (m, 2H), 4.89 (m, 2H), 7.03 (d, 1H), 8.19 (m, 2H). MS ES+ m/z 426 [MH]⁺ |

EXAMPLE 110

1-(2-Ethoxyethyl)-5-(N-isopropyl-N-methylamino)-7-(4-methylpyridin-2-ylamino)-1H-pyrazolo[4,3-d]pyrimidine-3-carboxylic acid

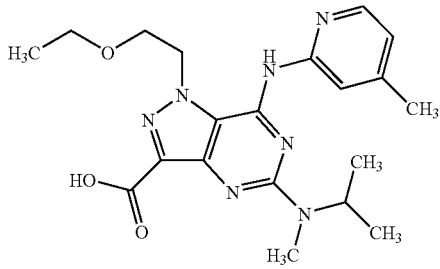

The ester of preparation 121 (219 mg, 0.51 mmol) was dissolved in a solution of 1M aqueous sodium hydroxide solution (3 mL) in dioxane (1.5 mL) and the reaction mixture stirred at room temperature for 18 hours. The reaction mixture was diluted with 1M citric acid solution (50 mL) and the mixture washed with dichloromethane (3×100 mL). The combined dichloromethane extracts were dried over magnesium sulphate and concentrated in vacuo. The residue was purified by column chromatography on silica gel eluting with dichloromethane:methanol 100:0 to 92:8 to yield the title product as a yellow oil, 80 mg (38%). $^1$H NMR (CD$_3$OD, 400 MHz) δ: 1.12 (t, 3H), 1.30 (d, 6H), 2.45 (s, 3H), 3.12 (s, 3H), 3.60 (m, 2H), 3.96 (t, 2H), 4.88 (m, 2H), 4.98 (m, 1H), 7.04 (d, 1H), 8.14 (s, 1H), 8.18 (d, 1H). MS APCI− m/z 412 [M-H]⁻

EXAMPLE 111

1-(2-Isopropoxyethyl)-5-(N-isopropyl-N-methylamino)-7-(4-methylpyridin-2-ylamino)-1H-pyrazolo[4,3-d]pyrimidine-3-carboxylic acid

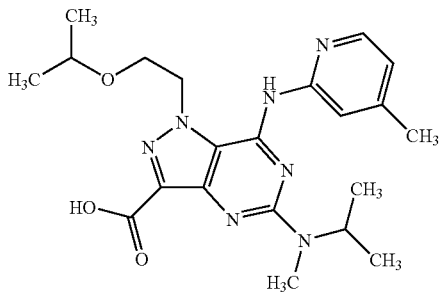

The ester of preparation 106 (140 mg, 0.32 mmol) was dissolved in methanol (2 mL) and the solution treated with 1M aqueous sodium hydroxide solution (640 μL). The reaction mixture was stirred at room temperature for 18 hours before being concentrated in vacuo. The residue was dissolved in water (20 mL), washed with ethyl acetate (10 mL), acidified with citric acid and extracted with dichloromethane (2×20 mL). The organics were combined, dried over magnesium sulphate and concentrated in vacuo. The residue was purified by column chromatography on silica gel eluting with dichloromethane:methanol 100:0 to 95:5. The product was triturated with ether to yield the title product as a white solid, 45 mg. $^1$H NMR (CD$_3$OD, 400 MHz) δ: 1.10 (d, 6H), 1.32 (d, 6H), 2.42 (s, 3H), 3.12 (s, 3H), 3.66 (m, 1H), 3.94 (t, 2H), 4.83 (t, 2H), 5.05 (m, 1H), 7.04 (d, 1H), 8.16 (s, 1H), 8.20 (d, 1H). MS ES+ m/z 428 [MH]⁺

EXAMPLE 112

(2'R)-5-(N-Isopropyl-N-methylamino)-1-(2'-methoxypropyl)-7-(4-methylpyridin-2-ylamino)-1H-pyrazolo[4,3-d]pyrimidine-3-carboxylic acid

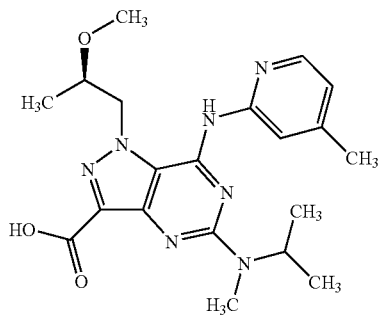

The title compound was prepared by a method similar to that described for example 111 using the ester of preparation 105. $^1$H NMR (CD$_3$OD, 400 MHz) δ: 1.32 (m, 9H), 2.44 (s, 3H), 3.10 (s, 3H), 3.42 (s, 3H), 3.97 (m, 1H), 4.73 (m, 2H), 4.99 (m, 1H), 7.08 (m, 1H), 8.08 (s, 1H), 8.20 (d, 1H). MS APCI+ m/z 414 [MH]⁺

EXAMPLE 113

N-[1-(2-Ethoxyethyl)-5-(N-isopropyl-N-methylamino)-7-(4-methylpyridin-2-ylamino)-1H-pyrazolo[4,3-d]pyrimidine-3-carbonyl]methanesulfonamide

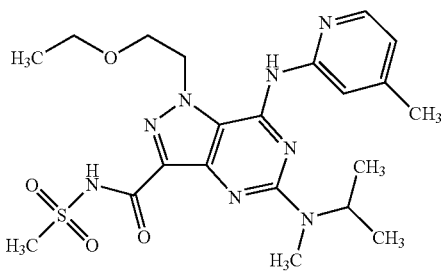

The chloro compound of preparation 186 (90 mg, 0.20 mmol), N-methyl-isopropylamine (73 mg, 10 mmol), N-ethyldiisopropylamine (170 μL, 1.0 mmol) and caesium fluoride (30 mg, 0.20 mmol) were dissolved in dimethyl sulphoxide (1 mL) and the reaction mixture stirred at 110° C. for 5 hours. The reaction mixture was allowed to cool and was then diluted with ethyl acetate (10 mL) and water (10 mL). The organic phase was separated and washed with water (2×10 mL), dried over magnesium sulphate and concentrated in vacuo. The residue was purified twice by column chromatography on silica gel eluting with dichloromethane:methanol 99:1 to 97:3. The crude product was dissolved in ethyl acetate (2 mL) and treated with pentane. The precipitate formed was filtered off and dried in vacuo to yield the title product, 42 mg. $^1$H NMR (DMSO-D$_6$+CF$_3$CO$_2$D, 400 MHz) δ: 0.98 (t, 3H), 1.18 (d, 6H), 2.44 (s, 3H), 3.02 (s, 3H), 3.40 (s, 3H), 3.44 (d, 2H), 3.86 (t, 2H), 4.75 (m, 1H), 4.94 (t, 2H), 7.18 (d, 1H), 8.06 (s, 1H), 8.25 (d, 1H). MS ES− m/z 489 [M-H]⁻

EXAMPLE 114

N-[5-(Dimethylamino)-1-(2-ethoxyethyl)-7-(4-methylpyridin-2-ylamino)-1H-pyrazolo[4,3-d]pyrimidine-3-carbonyl]methanesulfonamide

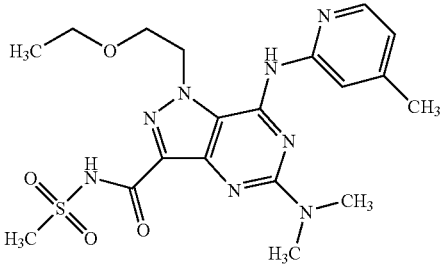

The title product was prepared by a method similar to that described for example 113 using a 33% solution of dimethylamine in ethanol as the source of the $HNR^3R^4$ amine. 55 mg of the desired product was produced. $^1$H NMR (DMSO-$D_6$+ $CF_3CO_2D$, 400 MHz) δ: 0.97 (t, 3H), 2.45 (s, 3H), 3.20 (s, 6H), 3.40 (s, 3H), 3.44 (d, 2H), 3.88 (t, 2H), 4.95 (t, 2H), 7.18 (d, 1H), 8.07 (s, 1H), 8.25 (d, 1H), 13.40 (s, 1H). MS ES+ m/z 485 [MNa]$^+$

EXAMPLE 115

N-[1-(2-Ethoxyethyl)-5-(N-ethyl-N-methylamino)-7-(4-methylpyridin-2-ylamino)-1H-pyrazolo[4,3-d]pyrimidine-3-carbonyl]methanesulfonamide

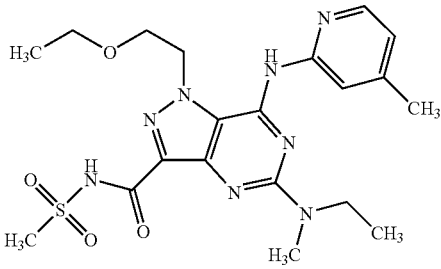

The chloro compound of preparation 186 (10 mg, 0.24 mmol), N-methyl-ethylamine (79 mg, 1.2 mmol), N-ethyldiisopropylamine (210 μL, 1.20 mmol) and caesium fluoride (37 mg, 0.24 mmol) were dissolved in dimethyl sulphoxide (1 mL) and the reaction mixture heated to 110° C. for 5 hours in a ReactiVial™. The reaction mixture was partitioned between ethyl acetate (10 mL) and water (10 mL) and the organic phase separated and washed with water (2×10 mL). The organic phase was then dried over magnesium sulphate and concentrated in vacuo. The residue was purified by column chromatography on silica gel eluting with dichloromethane:methanol 99:1 to 97:3 to yield the title product as a pale yellow solid, 66 mg.

Alternatively, example 115 may be prepared using the carboxylic acid of Example 96. The carboxylic acid of example 96 (1.0 g, 2.50 mmol), methanesulphonamide (356 mg, 3.75 mmol), 1-(3-dimethylaminopropyl)-3-ethylcarbodiimide hydrochloride (1.0 g, 5.2 mmol) and 4-dimethylaminopyridine (305 mg, 2.5 mmol) were dissolved in dichloromethane (5 mL) and the reaction mixture stirred at room temperature for 16 hours. The reaction mixture was diluted with 10% aqueous citric acid (3 mL) and the organic phase was separated, washed with water (3 mL), dried over magnesium sulphate and concentrated in vacuo. $^1$H NMR (DMSO-$D_6$+ $CF_3CO_2D$, 400 MHz) δ: 0.99 (t, 3H), 1.17 (t, 3H), 2.44 (s, 3H), 3.18 (s, 3H), 3.41 (s, 3H), 3.44 (d, 2H), 3.66 (d, 2H), 3.88 (t, 2H), 4.93 (t, 2H), 7.16 (d, 1H), 8.09 (s, 1H), 8.26 (d, 1H). MS ES– m/z 475 [M-H]$^-$

EXAMPLE 116

Methyl 1-(2-ethoxyethyl)-5-[ethyl(methyl)amino]-7-[(4-fluoro-3-methylphenyl)amino]-1H-pyrazolo[4,3-d]pyrimidine-3-carboxylate

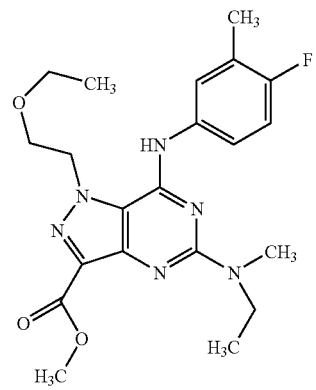

A mixture of the chloride from preparation 92 (200 mg, 0.49 mmol), N-ethylmethylamine (0.084 mL, 0.98 mmol) and N-ethyldiisopropylamine (0.17 mL, 0.98 mmol) in dimethylsulphoxide (2 mL) was heated in a Reactivial® at 120° C. for 18 hours. The cooled mixture was concentrated under reduced pressure and the residue partitioned between dichloromethane (100 mL) and water (100 mL) and the layers separated. The aqueous solution was extracted with further dichloromethane (50 mL) and the combined organic solutions were washed with water (100 mL), brine (50 mL), dried over magnesium sulphate and evaporated under reduced pressure. The crude product was purified by column chromatography on an Isolute® silica gel cartridge using dichloromethane:methanol (100:0 to 95:5) as an elution gradient to provide the title compound as a white crystalline solid, 70 mg. $^1$H NMR (CD$_3$OD, 400 MHz) δ: 1.15 (t, 3H), 1.20 (t, 3H), 2.30 (s, 3H), 3.19 (s, 3H), 3.60 (q, 2H), 3.70 (q, 2H), 3.96 (s, 3H), 3.98 (m, 2H), 4.80 (t, 2H), 7.01 (m, 1H), 7.42 (m, 1H), 7.67 (m, 1H). MS APCI+ m/z 431 [MH]$^+$

EXAMPLE 117

Methyl 5-(diethylamino)-1-(2-ethoxyethyl)-7-[(4-fluoro-3-methylphenyl)amino]-1H-pyrazolo[4,3-d]pyrimidine-3-carboxylate

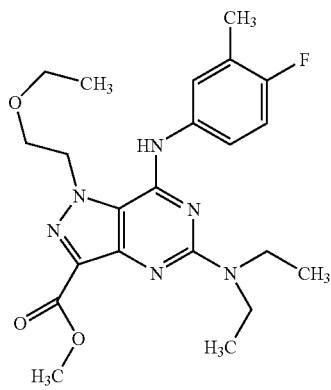

The title compound was obtained as a white crystalline solid from the compound from preparation 92, after re-crystallisation from methanol, following a similar procedure to that described in example 116. $^1$H NMR (CDCl$_3$, 400 MHz) δ: 1.20 (m, 9H), 2.30 (s, 3H), 3.65 (m, 6H), 4.00 (m, 5H), 4.75 (t, 2H), 6.95 (m, 1H), 7.35 (m, 1H), 7.60 (m, 1H). MS APCI+ m/z 445 [MH]$^+$

EXAMPLE 118

1-(2-Ethoxyethyl)-5-[ethyl(methyl)amino]-7-[(3-methylphenyl)amino]-1H-pyrazolo[4,3-d]pyrimidine-3-carboxylic acid

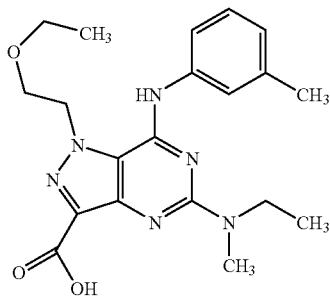

A mixture of the chloride from preparation 238 (200 mg, 0.53 mmol), cesium fluoride (81 mg, 0.53 mmol) and N-ethylmethylamine (0.25 mL, 2.65 mmol) in dimethylsulphoxide (1.5 mL) was heated in a Reactivial® at 110° C. for 18 hours. The cooled mixture was partitioned between dichloromethane (50 mL) and 1N citric acid solution (100 mL) and the layers separated. The aqueous solution was extracted with further dichloromethane (50 mL) and the combined organic solutions washed with water (2×100 mL) and then brine (50 mL). The solution was dried over magnesium sulphate and concentrated under reduced pressure to provide the title compound as a white solid, 150 mg. $^1$H NMR (400 MHz, CD$_3$OD) δ: 1.10 (t, 3H), 1.25 (t, 3H), 2.40 (s, 3H), 3.25 (s, 3H), 3.65 (q, 2H), 3.75 (q, 2H), 4.00 (t, 2H), 4.85 (t, 2H), 7.10 (d, 1H), 7.35 (m, 1H), 7.50 (d, 1H), 7.61 (s, 1H). MS APCI+ m/z 399 [MH]$^+$

EXAMPLES 119 TO 124

The following compounds of the general formula shown below:

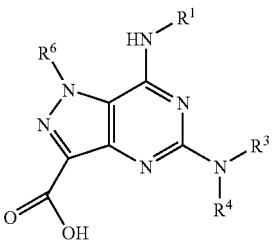

were prepared from the corresponding chloride compounds from preparations 149, 231, 232 and 237, following a similar procedure to that described in example 118.

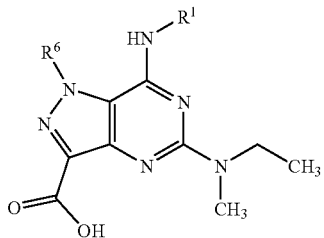

| Ex | R$^6$ | HNR$^1$ | Yield/Data |
|---|---|---|---|
| 119 | H$_3$C-O-CH$_2$CH$_2$- | 4-methyl-2-pyridylamino | Yellow crystals (93%) $^1$H NMR (DMSO-D$_6$ + drop TFA-d, 400 MHz) δ: 1.14 (t, 3H), 2.45 (s, 3H), 3.20 (s, 6H), 3.63 (q, 2H), 3.81 (t, 2H), 4.98 (t, 2H), 7.16 (d, 1H), 8.11 (s, 1H), 8.24 (d, 1H). MS m/z 386 [MH]$^+$ |
| 120 | H$_3$C-O-CH$_2$CH$_2$- | 5-methyl-4-pyrimidinylamino | Yellow solid (85%) $^1$H NMR (DMSO-D$_6$ + drop TFA-d, 400 MHz) δ: 1.02 (t, 3H), 1.19 (t, 3H), 2.57 (s, 3H), 3.19 (s, 3H), 3.48 (q, 2H), 3.68 (q, 2H), 3.83 (t, 2H), 4.82 (t, 2H), 8.08 (s, 1H), 9.02 (s, 1H). MS m/z 401 [MH]$^+$ |
| 121 | H$_3$C-O-CH$_2$CH$_2$- | 4-(hydroxymethyl)-2-pyridylamino | Yellow oil, (88%) $^1$H NMR (DMSO-D$_6$, 400 MHz) δ: 0.95 (t, 3H), 1.15 (t, 3H), 3.17 (s, 3H), 3.39 (q, 2H), 3.66 (q, 2H), 3.83 (t, 2H), 4.63 (s, 2H), 4.95 (t, 2H), 7.14 (d, 1H), 8.19 (d, 1H), 8.34 (s, 1H). MS m/z 416 [MH]$^+$ |

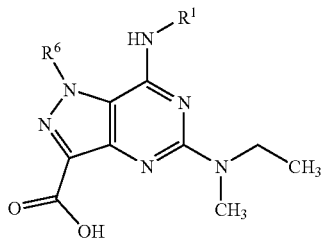

| Ex | R⁶ | HNR¹ | Yield/Data |
|---|---|---|---|
| 122[A] | cyclobutyl-O-CH₂CH₂- | 4-methylpyridin-2-ylamino | Yellow powder (50%) $^1$H NMR (CD$_3$OD, 400 MHz) δ: 1.30 (t, 3H), 1.50 (m, 1H), 1.60 (m, 1H), 1.90 (m, 2H), 2.12 (m, 2H), 2.45 (s, 3H), 3.30 (s, 3H), 3.80 (q, 2H), 3.90 (t, 2H), 4.00 (m, 1H), 4.90 (m, 2H), 7.05 (d, 1H), 8.20 (m, 2H). |
| 123 | H₃C-CH₂-O-CH₂CH₂- | 6-methylpyrimidin-4-ylamino | Yellow solid (69%) $^1$H NMR (DMSO-D$_6$ + drop TFA-d, 400 MHz) δ: 1.02 (t, 3H), 1.21 (d, 6H), 2.57 (s, 3H), 3.02 (s, 3H), 3.48 (q, 2H), 3.82 (t, 2H), 4.82 (t, 2H), 4.95 (m, 1H), 8.04 (s, 1H), 9.03 (s, 1H). MS m/z 415 [MH]⁺ |
| 124[A] | cyclobutyl-O-CH₂CH₂- | 4-methylpyridin-2-ylamino | Pale yellow powder (45%) $^1$H NMR (CD$_3$OD, 400 MHz) δ: 1.35 (d, 6H), 1.45 (m, 1H), 1.60 (m, 1H), 1.90 (m, 2H), 2.10 (m, 2H), 2.45 (s, 3H), 3.15 (s, 3H), 3.30 (m, 1H), 3.90 (t, 2H), 4.05 (m, 1H), 5.02 (m, 2H), 7.05 (d, 1H), 8.20 (m, 2H). MS APCI+ m/z 440 [MH]⁺ |

[A]The product was recrystallised from dichloromethane, then sonicated in ether and dried in vacuo.

EXAMPLE 125

5-(Diethylamino)-1-(2-ethoxyethyl)-7-[(1-methyl-6-oxo-1,6-dihydropyridin-3-yl)amino]-1H-pyrazolo[4,3-d]pyrimidine-3-carboxylic acid

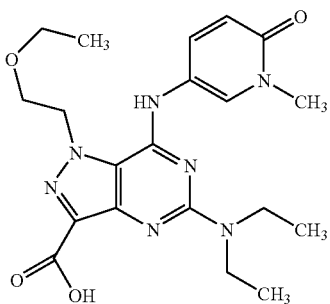

A mixture of the chloro compound from preparation 239 (170 mg, 0.43 mmol), diethylamine (0.18 mL, 1.73 mmol) and cesium fluoride (66 mg, 0.43 mmol) in dimethylsulphoxide (1 mL) was stirred at 110° C. for 2 hours. Additional diethylamine (0.18 mL, 1.73 mmol) in dimethylsulphoxide (0.5 mL) was added, the mixture transferred to a Reactivial® and stirred at 110° C. for a further 2 hours. The cooled mixture was diluted with dichloromethane (40 mL) and washed with 1M citric acid solution (3×20 mL). The combined aqueous solutions were washed with dichloromethane (20 mL), then basified to pH 6 using solid sodium bicarbonate. This solution was extracted with dichloromethane (3×30 mL) and the combined organic solutions washed with water (20 mL) and brine (20 mL) then dried (using a phase separation cartridge) and concentrated under reduced pressure. The resulting oil was suspended in water (30 mL) and the mixture sonicated for 30 minutes. The resulting solid was filtered off and dried in vacuo to provide the title compound as a solid. $^1$H NMR (CD$_3$OD, 400 MHz) δ: 1.12 (t, 3H), 1.25 (t, 6H), 3.59 (q, 2H), 3.62 (s, 3H), 3.65 (m, 4H), 3.92 (t, 2H), 4.90 (m, 2H), 6.65 (d, 1H), 7.75 (m, 1H), 8.10 (s, 1H). MS ES– m/z 428 [M-H]⁻

EXAMPLE 126

5-[Isopropyl(methyl)amino]-7-[(4-methylpyridin-2-yl)amino]-1-[2-(2,2,2-trifluoroethoxy)ethyl]-1H-pyrazolo[4,3-d]pyrimidine-3-carboxylic acid

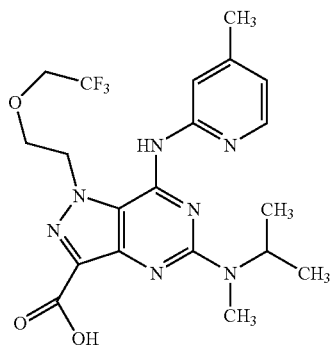

A mixture of the chloride from preparation 233 (75 mg, 0.17 mmol), N-ethyldiisopropylamine (0.15 mL, 0.85 mmol), cesium fluoride (26 mg, 0.17 mmol) and N-methylisopropylamine (0.09 mL, 0.85 mmol) in 1-methyl-2-pyrrolidinone (1 mL) was stirred at 110° C. in a Reactivial® for 4 hours. The cooled reaction mixture was purified directly using a Phenomenex Luna C18 reverse phase silica gel column and acetonitrile:95% water/5% methanol/0.1% trifluoroacetic acid (5:95 to 95:5) as elution gradient. The product was dissolved in dichloromethane and the solution washed with sodium bicarbonate solution, dried over magnesium sulphate and evaporated under reduced pressure to provide the title compound, 24 mg. $^1$H NMR (CD$_3$OD, 400 MHz) δ: 1.31 (d, 6H), 2.48 (s, 3H), 3.11 (s, 3H), 3.98 (q, 2H), 4.15 (t, 2H), 4.95 (m, 1H), 4.99 (t, 2H), 7.08 (d, 1H), 8.00 (s, 1H), 8.12 (d, 1H). MS ES− m/z 466 [M-H]$^-$

EXAMPLE 127

5-[Ethyl(methyl)amino]-7-[(4-methylpyridin-2-yl)amino]-1-[2-(2,2,2-trifluoroethoxy)ethyl]-1H-pyrazolo[4,3-d]pyrimidine-3-carboxylic acid

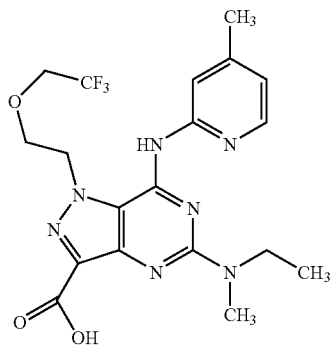

The title compound was prepared from the compound from preparation 233 and N-ethylmethylamine, following a similar procedure to that described in example 126, except only 2 equivalents of N-ethylmethylamine and N-ethyldiisopropylamine were used. $^1$H NMR (CD$_3$OD, 400 MHz) δ: 1.30 (t, 3H), 2.49 (s, 3H), 3.26 (s, 3H), 3.73 (q, 2H), 3.98 (q, 2H), 4.16 (t, 2H), 4.98 (t, 2H), 7.05 (d, 1H), 8.00 (s, 1H), 8.10 (d, 1H). MS ES− m/z 452 [M-H]$^-$

EXAMPLE 128

5-(Diethylamino)-7-[(4-methylpyridin-2-yl)amino]-1-[2-(2,2,2-trifluoroethoxy)ethyl]-1H-pyrazolo[4,3-d]pyrimidine-3-carboxylic acid

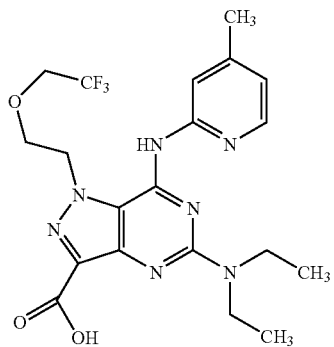

A mixture of the chloride from preparation 233 (100 mg, 0.23 mmol), cesium fluoride (35 mg, 0.23 mmol) and diethylamine (0.07 mL, 0.69 mmol) in dimethylsulphoxide (1 mL) was stirred at 120° C. in a Reactivial® for 18 hours. Tlc analysis showed starting material remaining, so additional diethylamine (0.07 mL, 0.69 mmol) was added and the reaction heated for a further 3 hours at 135° C. The cooled mixture was suspended in 1M citric acid solution (200 mL) and extracted with dichloromethane (3×50 mL). The combined organic extracts were washed with water (50 mL), brine (25 mL) and dried over sodium sulphate then concentrated under reduced pressure. The crude product was purified by column chromatography using a silica gel Isolute® cartridge and an elution gradient of 10% acetic acid in methanol:dichloromethane: (1:99 to 7:93). The product was triturated with ether and dried in vacuo to afford the title compound as a yellow powder, 44 mg. $^1$H NMR (CD$_3$OD, 400 MHz) δ: 1.35 (t, 6H), 2.50 (s, 3H), 3.70 (q, 4H), 4.00 (q, 2H), 4.18 (t, 2H), 5.00 (t, 2H), 7.10 (d, 1H), 8.05 (s, 1H), 8.13 (d, 1H). MS ES+ m/z 468 [MH]$^+$

EXAMPLE 129

7-[(4-Methylpyridin-2-yl)amino]-5-(2-methylpyrrolidin-1-yl)-1-[2-(2,2,2-trifluoroethoxy)ethyl]-1H-pyrazolo[4,3-d]pyrimidine-3-carboxylic acid

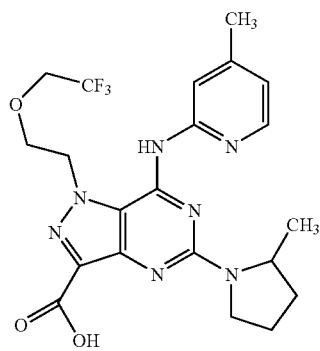

The title compound was obtained as a solid in 45% yield from 2-methylpyrrolidine and the chloride from preparation 233, following the procedure described in example 128. $^1$H NMR (CD$_3$OD, 400 MHz) δ: 1.38 (d, 3H), 1.85 (m, 1H), 2.10 (m, 1H), 2.25 (m, 2H), 2.50 (s, 3H), 3.60 (m, 1H), 3.79 (m, 1H), 3.98 (q, 2H), 4.15 (t, 2H), 4.45 (m, 1H), 5.00 (t, 2H), 7.10 (d, 1H), 7.98 (s, 1H), 8.15 (d, 1H). MS ES+ m/z 480 [MH]$^+$

EXAMPLE 130

5-[Cyclobutyl(methyl)amino]-7-[(4-methylpyridin-2-yl)amino]-1-[2-(2,2,2-trifluoroethoxy)ethyl]-1H-pyrazolo[4,3-d]pyrimidine-3-carboxylic acid

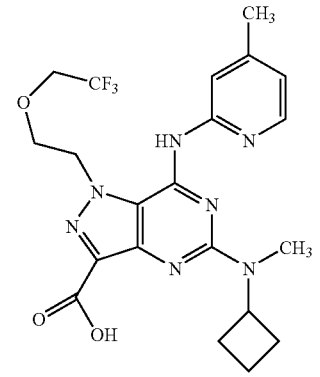

The title compound was obtained in 42% yield as a yellow solid, from the amine from preparation 241 and the chloro compound from preparation 233, following a similar procedure to that described in example 128, except 5 eq N-ethyldiisopropylamine was also added. $^1$H NMR (CD$_3$OD, 400 MHz) δ: 1.80 (m, 2H), 2.35 (m, 4H), 2.50 (s, 3H), 3.21 (s, 3H), 3.99 (q, 2H), 4.18 (t, 2H), 4.80 (m, 1H), 4.99 (t, 2H), 7.10 (d, 1H), 8.05 (s, 1H), 8.18 (d, 1H). MS APCI+ m/z 480 [MH]$^+$

EXAMPLES 131 TO 133

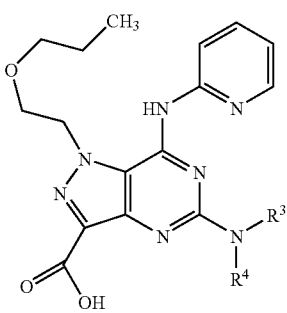

A solution of the appropriate esters from preparations 240-242 (0.5 mmol) in sodium hydroxide (1N, 4 mL, 4 mmol) and dioxan (2 mL) was stirred at room temperature for 18 hours. The solution was concentrated under reduced pressure and the residue partitioned between dichloromethane (20 mL) and 1M citric acid solution (10 mL). The layers were separated and the organic phase dried over magnesium sulphate and evaporated under reduced pressure to give the title compounds.

| Ex No | —NR$^3$R$^4$ | Data |
|---|---|---|
| 131 | N(CH$_3$)(CH$_2$CH$_2$CH$_3$) | $^1$H NMR (DMSO-D$_6$ + 1dp TFAD), 400 MHz) δ: 0.65 (t, 3H), 1.18 (t, 3H), 1.38 (m, 2H), 3.18 (s, 3H), 3.34 (t, 2H), 3.62 (q, 2H), 3.82 (t, 2H), 4.98 (t, 2H), 7.28 (m, 1H), 8.20 (m, 2H), 8.38 (d, 1H). MS APCI+ m/z 400 [MH]$^+$ |
| 132 | N(CH$_3$)(CH(CH$_3$)$_2$) | $^1$H NMR (DMSO-D$_6$ + 1dp TFAD, 400 MHz) δ: 0.65 (t, 3H), 1.18 (d, 6H), 1.38 (m, 2H), 3.04 (s, 3H), 3.22 (t, 2H), 3.84 (t, 2H), 4.70 (m, 1H), 4.98 (t, 2H), 7.30 (m, 1H), 8.20 (m, 2H), 8.40 (d, 1H). MS APCI+ m/z 414 [MH]$^+$ |
| 133 | N(CH$_2$CH$_3$)$_2$ | $^1$H NMR (DMSO-D$_6$ + 1dp TFAD, 400 MHz) δ: 0.66 (t, 3H), 1.20 (t, 6H), 1.39 (m, 2H), 3.30 (t, 2H), 3.62 (q, 4H), 3.84 (t, 2H), 4.98 (t, 2H), 7.28 (m, 1H), 8.20 (m, 2H), 8.38 (d, 1H). MS APCI+ m/z 414 [MH]$^+$ |

EXAMPLE 134

1-(2-Ethoxyethyl)-7-[(4-methylpyridin-2-yl)amino]-5-pyrrolidin-1-yl-1H-pyrazolo[4,3-d]pyrimidine-3-carboxylic acid

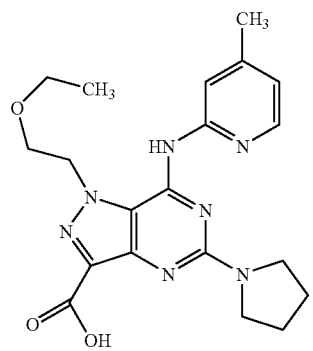

A solution of the ester from preparation 259 (50 mg, 0.12 mmol) in 1N sodium hydroxide solution (1 mL) and dioxan (0.5 mL) was stirred at room temperature for 18 hours. The mixture was diluted with 1M citric acid solution (50 mL) and extracted with dichloromethane (3×200 mL). The combined organic extracts were dried over magnesium sulphate and evaporated under reduced pressure. The crude product was purified by column chromatography using an Isolute® silica gel cartridge and an elution gradient of dichloromethane:methanol (100:0 to 90:10) to provide the title compound as a yellow solid, 23 mg. $^1$H NMR (CD$_3$OD, 400 MHz) δ: 1.10 (t, 3H), 2.10 (m, 4H), 2.45 (s, 3H), 3.59 (m, 2H), 3.70 (m, 4H), 3.90 (t, 2H), 4.90 (m, 2H), 7.05 (d, 1H), 8.20 (m, 2H). MS APCI+ m/z 412 [MH]$^+$

EXAMPLE 135

5-[Isopropyl(methyl)amino]-1-[(2S)-2-methoxypropyl]-7-[(4-methylpyridin-2-yl)amino]-1H-pyrazolo[4,3-d]pyrimidine-3-carboxylic acid

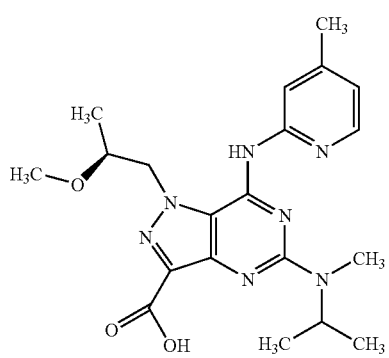

A solution of the ester from preparation 260 (43 mg, 0.1 mmol) in dioxan (2 mL) and sodium hydroxide (1N, 4 mL) was stirred at room temperature for 18 hours. The mixture was concentrated under reduced pressure and the residue diluted with citric acid solution (1M, 50 mL). This solution was extracted with dichloromethane (3×50 mL), the combined organic solutions washed with sodium bicarbonate solution (3×15 mL), dried over magnesium sulphate and evaporated under reduced pressure. The crude product was purified by column chromatography using an Isolute® silica gel cartridge and an elution gradient of dichloromethane:methanol (100:0 to 94:6) to give a yellow oil. This was triturated with ether and the resulting solid filtered off and dried to give the title compound as a white solid, 26 mg. $^1$H NMR (CD$_3$OD, 400 MHz) δ: 1.30 (m, 9H), 2.42 (s, 3H), 3.10 (s, 3H), 3.43 (s, 3H), 4.00 (m, 1H), 4.75 (m, 2H), 4.99 (m, 1H), 7.02 (d, 1H), 8.08 (s, 1H), 8.10 (d, 1H). MS APCI+ m/z 414 [MH]$^+$

EXAMPLES 136 TO 140

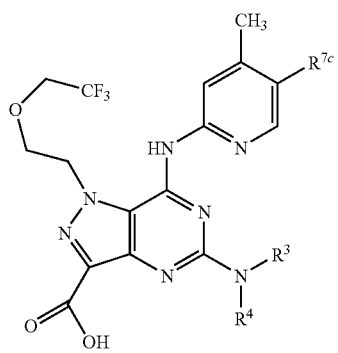

A solution of the appropriate esters from preparations 245-249 (1 eq) in sodium hydroxide (1N, 1.5-3 eq) and dioxan (6.5-7.5 mLmmol$^{-1}$) was stirred at room temperature for 18 hours. The solution was concentrated under reduced pressure and the residue partitioned between dichloromethane and 1M citric acid solution and the layers separated. The aqueous phase was extracted with additional dichloromethane, the combined organic solutions dried over magnesium sulphate and evaporated under reduced pressure. The products were triturated with ethyl acetate, and the solids filtered and dried to afford the title compounds as white crystalline solids.

| Ex No | —NR$^3$R$^4$ | R$^{7c}$ | Data |
|---|---|---|---|
| 136 | N(CH$_3$)(CH$_2$CH$_3$) | H | $^1$H NMR (CD$_3$OD, 400 MHz) δ: 1.20 (t, 3H), 2.38 (s, 3H), 3.24 (s, 3H), 3.57 (q, 2H), 4.02 (q, 2H), 4.15 (t, 2H), 4.94 (t, 2H), 7.10 (d, 1H), 7.32 (m, 1H), 7.40 (d, 1H), 7.50 (s, 1H). MS APCI+ m/z 453 [MH]$^+$ |
| 137 | N(CH$_3$)(CH$_2$CH$_3$) | F | $^1$H NMR (CD$_3$OD, 400 MHz) δ: 1.08 (t, 3H), 2.30 (s, 3H), 3.22 (s, 3H), 3.64 (q, 2H), 4.00 (q, 2H), 4.10 (t, 2H), 4.94 (t, 2H), 7.10 (d, 1H), 7.40 (m, 1H), 7.50 (s, 1H). MS APCI+ m/z 471 [MH]$^+$ |
| 138 | N(CH$_3$)(CH(CH$_3$)$_2$) | H | $^1$H NMR (CD$_3$OD, 400 MHz) δ: 1.22 (d, 6H), 2.40 (s, 3H), 3.08 (s, 3H), 4.04 (q, 2H), 4.13 (t, 2H), 4.85 (m, 1H), 4.94 (t, 2H), 7.12 (d, 1H), 7.32 (m, 1H), 7.39 (d, 1H), 7.50 (s, 1H). MS APCI+ m/z 467 [MH]$^+$ |
| 139 | N(CH$_3$)(CH(CH$_3$)$_2$) | F | $^1$H NMR (CD$_3$OD, 400 MHz) δ: 1.22 (d, 6H), 2.30 (s, 3H), 3.08 (s, 3H), 4.00 (q, 2H), 4.12 (t, 2H), 4.80 (m, 1H), 4.94 (t, 2H), 7.10 (m, 1H), 7.37 (m, 1H), 7.49 (m, 1H). MS APCI+ m/z 485 [MH]$^+$ |
| 140 | N(CH$_2$CH$_3$)$_2$ | F | $^1$H NMR (CD$_3$OD, 400 MHz) δ: 1.24 (t, 6H), 2.31 (s, 3H), 3.62 (q, 4H), 4.02 (q, 2H), 4.15 (t, 2H), 4.86 (t, 2H), 7.10 (m, 1H), 7.37 (m, 1H), 7.52 (m, 1H). MS APCI+ m/z 485 [MH]$^+$ |

EXAMPLES 141 TO 146

Sodium hydroxide solution (1M, 3 eq) was added to a solution of the esters from preparations 253-258 (1 eq) in dioxane (8.5-10.5 mLmmol$^{-1}$), and the reaction mixture stirred at room temperature for 18 hours. The solvent was removed under reduced pressure and the residue partitioned between citric acid (15 mL) and dichloromethane (15 mL). The phases were separated and the organic layer evaporated under reduced pressure to provide the title compounds.

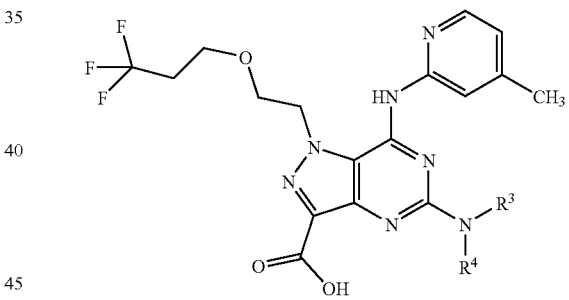

| Ex. No | —NR$^3$R$^4$ | Yield (%) | Data |
|---|---|---|---|
| 141 | N(CH$_3$)(CH$_2$CH$_3$) | 96 | MS APCI+ m/z 468 [MH]$^+$ |
| 142 | N(CH$_3$)(CH(CH$_3$)$_2$) | 89 | MS APCI+ m/z 482 [MH]$^+$ |
| 143 | N(CH$_2$CH$_3$)$_2$ | 99 | MS APCI+ m/z 482 [MH]$^+$ |

-continued

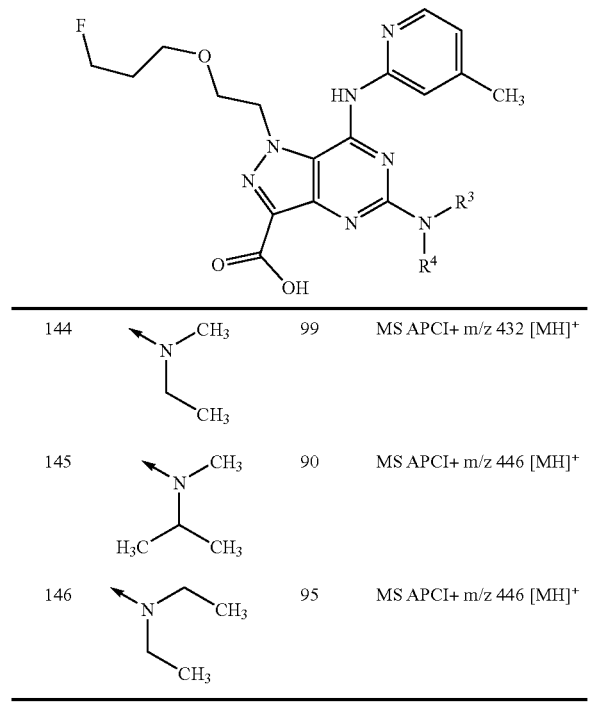

| | | | |
|---|---|---|---|
| 144 | ~N(CH₃)(CH₂CH₃) | 99 | MS APCI+ m/z 432 [MH]⁺ |
| 145 | ~N(CH₃)(CH(CH₃)₂) | 90 | MS APCI+ m/z 446 [MH]⁺ |
| 146 | ~N(CH₂CH₃)₂ | 95 | MS APCI+ m/z 446 [MH]⁺ |

EXAMPLE 147

2-(Dimethylamino)ethyl 1-(2-ethoxyethyl)-5-[isopropyl(methyl)amino]-7-[(4-methylpyridin-2-yl)amino]-1H-pyrazolo[4,3-d]pyrimidine-3-carboxylate

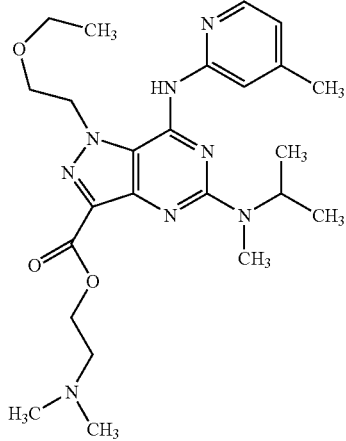

A mixture of the chloride from preparation 176 (160 mg, 0.36 mmol), cesium fluoride (54 mg, 0.36 mmol) and N-methylisopropylamine (186 μL, 1.79 mmol) in dimethylsulphoxide (3 mL) was heated at 110° C. in a Reactivial® for 18 hours. The cooled mixture was partitioned between dichloromethane (20 mL) and water (20 mL) and the layers separated. The aqueous solution was extracted further with dichloromethane (20 mL) and the combined organic solutions washed with water (3×20 mL), dried over magnesium sulphate and evaporated under reduced pressure. The residual orange oil was purified by column chromatography using an Isolute® silica gel cartridge and an elution gradient of methanol:dichloromethane (0:100 to 10:90), and then on reverse phase silica gel using acetonitrile:water:trifluoroacetic acid (95:5:0.1) as eluant to provide the title compound, 15 mg. ¹H NMR (CD₃OD, 400 MHz) δ: 1.09 (t, 3H), 1.33 (d, 6H), 2.54 (s, 3H), 3.05 (s, 6H), 3.16 (s, 3H), 3.51 (q, 2H), 3.65 (t, 2H), 3.98 (t, 2H), 4.78 (t, 2H), 4.89 (m, 1H), 5.04 (t, 2H), 7.18 (d, 1H), 8.08 (s, 1H), 8.14 (d, 1H). MS m/z 485 [MH]⁺

EXAMPLES 148 TO 164

4-Dimethylaminopyridine (1.3 eq) was added to a solution of the appropriate acid from examples 11, 14, 15, 17, 38, 96, 118-124, 136, 137 and 139 (1 eq), 1-(3-dimethylaminopropyl)-3-ethylcarbodiimide hydrochloride (1.3 eq) and the appropriate sulphonamide (1.2-1.3 eq) in dichloromethane (13-30 mLmmol⁻¹) and the reaction stirred at room temperature for 18 hours. The mixture was diluted with dichloromethane, washed with 1M citric acid solution, dried over magnesium sulphate and evaporated under reduced pressure to afford the title compounds

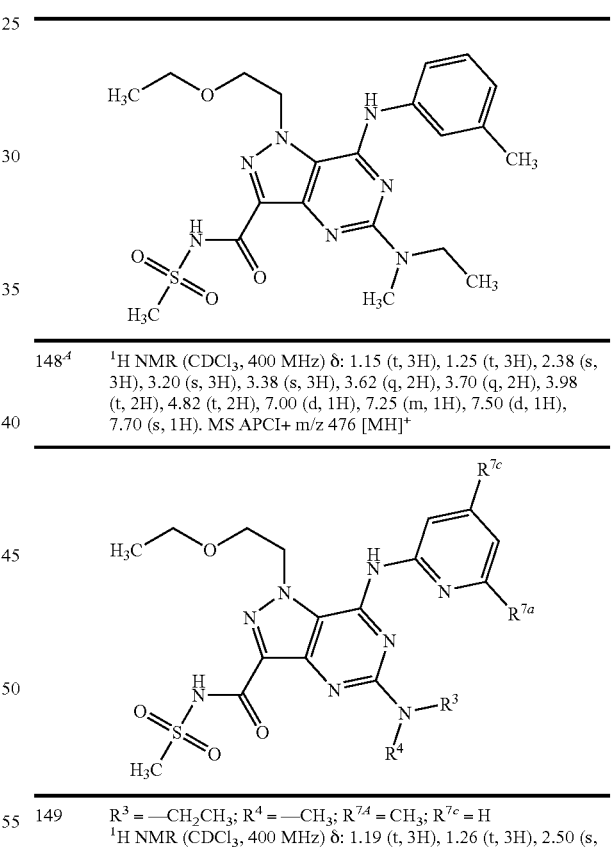

| | |
|---|---|
| 148ᴬ | ¹H NMR (CDCl₃, 400 MHz) δ: 1.15 (t, 3H), 1.25 (t, 3H), 2.38 (s, 3H), 3.20 (s, 3H), 3.38 (s, 3H), 3.62 (q, 2H), 3.70 (q, 2H), 3.98 (t, 2H), 4.82 (t, 2H), 7.00 (d, 1H), 7.25 (m, 1H), 7.50 (d, 1H), 7.70 (s, 1H). MS APCI+ m/z 476 [MH]⁺ |
| 149 | R³ = —CH₂CH₃; R⁴ = —CH₃; R⁷ᴬ = CH₃; R⁷ᶜ = H<br>¹H NMR (CDCl₃, 400 MHz) δ: 1.19 (t, 3H), 1.26 (t, 3H), 2.50 (s, 3H), 3.23 (s, 3H), 3.41 (s, 3H), 3.65 (q, 2H), 3.75 (q, 2H), 3.97 (t, 2H), 4.87 (m, 2H), 6.98 (d, 1H), 7.71 (m, 1H), 8.18 (br m, 1H). MS m/z 477 [MH]⁺ |
| 150ᴬ | R³ = —(CH₂)₄CH₃; R⁴ = —CH₃; R⁷ᴬ = H; R⁷ᶜ = CH₃<br>¹H NMR (DMSO-D₆ + drop TFAd, 400 MHz) δ: 0.88 (t, 3H), 1.01 (t, 3H), 1.63 (m, 2H), 2.41 (s, 3H), 3.18 (s, 3H), 3.42 (s, 3H), 3.47 (q, 2H), 3.55 (t, 2H), 3.87 (t, 2H), 4.89 (m, 2H), 7.09 (m, 1H), 8.05 (s, 1H), 8.24 (d, 1H).<br>MS ESI+ m/z 491 [MH]⁺ |
| 151ᴬ | R³ = —CH₂CH₃; R⁴ = —CH₂CH₃; R⁷ᴬ = H; R⁷ᶜ = CH₃<br>¹H NMR (DMSO-D₆ + drop TFAd, 400 MHz) δ: 1.02 (t, 3H), 1.20 (t, 6H), 2.39 (s, 3H), 3.41 (s, 3H), 3.48 (q, 2H), 3.61 (q, 4H), 3.87 (t, 2H), 4.87 (m, 2H), 7.08 (m, 1H), 8.10 (s, 1H), 8.24 |

| | |
|---|---|
| 152[A] | $R^3 = -(CH_2)_2OCH_3$; $R^4 = -CH_3$; $R^{7A} = H$; $R^{7C} = CH_3$<br>$^1$H NMR (DMSO-D$_6$ + drop TFAd, 400 MHz) δ: 0.99 (t, 3H), 2.44 (s, 3H), 3.21 (s, 3H), 3.30 (br s, 3H), 3.40 (s, 3H), 3.44 (q, 2H), 3.62 (m, 2H), 3.77 (m, 2H), 3.88 (t, 2H), 4.93 (t, 2H), 7.14 (d, 1H), 8.06 (s, 1H), 8.24 (d, 1H). MS ESI + m/z 507 [MH]$^+$ |
| 153 | $R^3 = -CH_2CH_3$; $R^4 = -CH_3$; R-hu 7A = H; $R^{7C} = CH_2OH$<br>$^1$H NMR (CD$_3$OD + drop TFAd, 400 MHz) δ: 1.10 (t, 3H), 1.30 (t, 3H), 3.28 (s, 3H), 3.40 (s, 3H), 3.56 (q, 2H), 3.79 (q, 2H), 3.99 (q, 2H), 4.78 (s, 2H), 5.06 (m, 2H), 7.24 (d, 1H), 8.19 (s, 1H), 8.40 (s, 1H). MS ESI− m/z 491 [M − H]$^−$ |

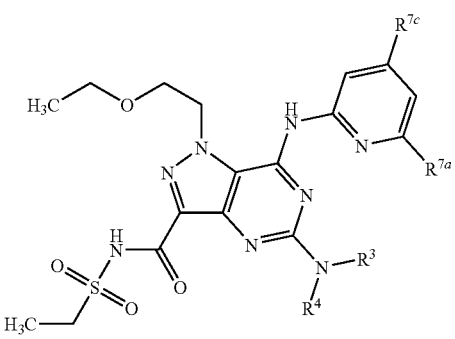

| | |
|---|---|
| 154[A,B] | $R^3 = -CH_3$; $R^4 = -CH_3$; $R^{7A} = H$; $R^{7C} = CH_3$<br>$^1$H NMR, (CD$_3$OD, 400 MHz) δ: 1.13 (t, 3H), 1.41 (t, 3H), 2.43 (s, 3H), 3.29 (s, 6H), 3.57 (q, 2H), 3.62 (q, 2H), 3.96 (t, 2H), 4.87 (m, 2H), 6.98 (d, 1H), 8.18 (d, 1H), 8.36 (s, 1H). MS m/z 477 [MH]$^+$ |
| 155[A,B] | $R^3 = -CH_2CH_3$; $R^4 = -CH_3$; $R^{7A} = H$; $R^{7C} = CH_3$<br>$^1$H NMR (CD$_3$OD, 400 MHz) δ: 1.14 (t, 3H), 1.29 (t, 3H), 1.41 (t, 3H), 2.43 (s, 3H), 3.25 (s, 3H), 3.57 (q, 2H), 3.63 (q, 2H), 3.78 (q, 2H), 3.97 (t, 2H), 4.87 (m, 2H), 6.99 (d, 1H), 8.18 (d, 1H), 8.35 (s, 1H). MS m/z 491 [MH]$^+$ |
| 156[A,C] | $R^3 = -CH_2CH_3$; $R^4 = -CH_2CH_3$; $R^{7A} = H$; $R^{7C} = CH_3$<br>$^1$H NMR (CD$_3$OD, 400 MHz) δ: 1.14 (t, 3H), 1.32 (t, 6H), 1.40 (t, 3H), 2.43 (s, 3H), 3.56 (q, 2H), 3.63 (q, 2H), 3.73 (q, 4H), 3.97 (t, 2H), 4.85 (m, 2H), 6.98 (d, 1H), 8.19 (d, 1H), 8.34 (s, 1H). MS m/z 505 [MH]$^+$ |

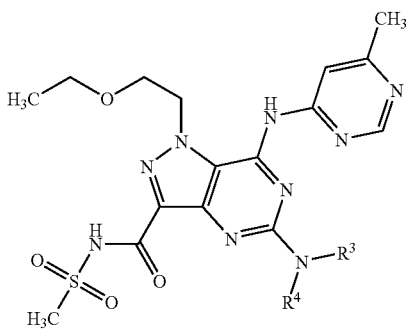

| | |
|---|---|
| 157 | $R^3 -CH_2CH_3$; $R^4 = -CH_3$<br>$^1$H NMR (CD$_3$OD, 400 MHz) δ: 1.21 (t, 3H), 1.30 (t, 3H), 2.54 (s, 3H), 3.27 (s, 3H), 3.43 (s, 3H), 3.67 (q, 2H), 3.79 (q, 2H), 3.98 (t, 2H), 4.84 (t, 2H), 8.30 (s, 1H), 8.71 (s, 1H).<br>MS m/z 478 [MH]$^+$ |
| 158 | $R^3 -CH_2CH_3$; $R^4 = -CH_2CH_3$<br>$^1$H NMR (CD$_3$OD, 400 MHz) δ: 1.21 (t, 3H), 1.33 (t, 6H), 2.54 (s, 3H), 3.43 (s, 3H), 3.67 (q, 2H), 3.75 (q, 4H), 3.98 (t, 2H), 4.86 (t, 2H), 8.31 (s, 1H), 8.72 (s, 1H).<br>MS m/z 492 [MH]$^+$ |

| | |
|---|---|
| 159[D] | $R^3 -CH_2CH_3$; $R^4 = -CH_3$; $R^{7B} = -CH_3$; $R^{7C} = F$<br>$^1$H NMR (CDCl$_3$, 400 MHz) δ: 1.18 (t, 3H), 2.30 (s, 3H), 3.17 (s, 3H), 3.43 (s, 3H), 3.66 (q, 2H), 3.93 (q, 2H), 4.26 (q, 2H), 4.80 (q, 2H), 7.00 (dd, 1H), 7.36 (br s, 1H), 8.05 (s, 1H).<br>MS APCI m/z 548 [MH]$^+$ |
| 160[D] | $R^3 -CH_2CH_3$; $R^4 = -CH_2CH_3$; $R^{7B} = -CH_3$; $R^{7C} = F$<br>$^1$H NMR (CDCl$_3$, 400 MHz) δ: 1.20 (m, 6H), 2.28 (s, 3H), 3.42 (s, 3H), 3.60 (q, 4H), 3.94 (q, 2H), 4.25 (t, 2H), 4.81 (t, 2H), 7.00 (dd, 1H), 7.30 (m, 1H), 7.50 (m, 1H), 8.06 (br s, 1H).<br>MS APCI+ m/z 562 [MH]$^+$ |
| 161[D] | $R^3 -CH_2CH_3$; $R^4 = -CH_3$; $R^{7B} = -CH_3$; $R^{7C} = H$<br>$^1$H NMR (CDCl$_3$, 400 MHz) δ: 1.20 (t, 3H), 2.38 (s, 3H), 3.17 (s, 3H), 3.44 (s, 3H), 3.67 (q, 2H), 3.95 (q, 2H), 4.26 (t, 2H), 4.82 (t, 2H), 6.95 (d, 1H), 7.26 (m, 1H), 7.40 (m, 1H), 7.50 (s, 1H), 8.18 (s, 1H). MS APCI+ m/z 530 [MH]$^+$ |

| | |
|---|---|
| 162 | $R^6 = -(CH_2)_2OCH_3$; $R^3 = -CH_2CH_3$; $R^4 = -CH_3$<br>$^1$H NMR (CD$_3$OD, 400 MHz) δ: 1.31 (t, 3H), 2.54 (s, 3H), 3.30 (s, 3H), 3.37 (s, 3H), 3.41 (s, 3H), 3.77 (q, 2H), 3.94 (q, 2H), 5.07 (t, 2H), 7.19 (d, 1H), 8.06 (s, 1H), 8.14 (d, 1H). MS m/z 463 [MH]$^+$ |
| 163[A,E] | $R^6 = $ cyclobutyl-O-CH$_2$CH$_2$-; $R^3 = -CH_2CH_3$; $R^4 = -CH_3$<br>$^1$H NMR (CD$_3$OD 400 MHz) δ: 1.30 (t, 3H), 1.45 (m, 1H), 1.60 (m, 1H), 1.90 (m, 2H), 2.10 (m, 2H), 2.41 (s, 3H), 3.25 (s, 3H), 3.42 (s, 3H), 3.75 (q, 2H), 3.90 (t, 2H), 4.00 (m, 1H), 4.85 (m, 2H), 7.00 (d, 1H), 8.20 (m, 1H), 8.35 (m, 1H).<br>MS APCI+ m/z 503 [MH]$^+$ |
| 164[A,E] | $R^6 = $ cyclobutyl-O-CH$_2$CH$_2$-; $R^3 = -CH(CH_3)_2$; $R^4 = -CH_3$<br>$^1$H NMR (CD$_3$OD, 400 MHz) δ: 1.30 (d, 6H), 1.50 (m, 1H), 1.62 (m, 1H), 1.90 (m, 2H), 2.10 (m, 2H), 2.40 (s, 3H), 3.10 (s, 3H), 3.40 (s, 3H), 3.85 (t, 2H), 4.00 (m, 2H), 5.05 (m, 1H), 6.99 (d, 1H), 8.20 (m, 1H), 8.30 (m, 1H).<br>MS APCI+ m/z 517 [MH]$^+$ |

[A]crude compounds were purified by column chromatography on an Isolute ® silica gel cartridge using dichloromethane:methanol as eluant.
[B]an additional 0.5 eq of sulphonamide and 4-dimethylaminopyridine were added after 18 hours, and the reaction stirred for a further 6 hours.
[C]1.5 eq of 1-(3-dimethylaminopropyl)-3-ethylcarbodiimide hydrochloride, 4-dimethylaminopyridine and ethylsulphonamide were used.
[D]the compound was isolated after trituration with methanol.
[E]4-dimethylaminopyridine (0.5 eq), 1-(3-dimethylaminopropyl)-3-ethylcarbodiimide hydrochloride (2 eq) and the appropriate sulphonamide (2 eq) were used.

EXAMPLES 165 TO 171

4-Dimethylaminopyridine (1.3 eq) was added to a solution of the appropriate acid from examples 20 and 131-133 (1 eq), 1-(3-dimethylaminopropyl)-3-ethylcarbodiimide hydrochloride (1.3 eq) and the appropriate sulphonamide (1.2-1.3 eq) in dichloromethane (13-30 mLmmol$^{-1}$) and the reaction stirred at room temperature for 18 hours. The mixture was washed with 1M citric acid solution (5 mL), the organic phase separated and purified directly by column chromatography on silica gel using an elution gradient of dichloromethane:methanol (100:0 to 95:5) to afford the title compounds as yellow solids.

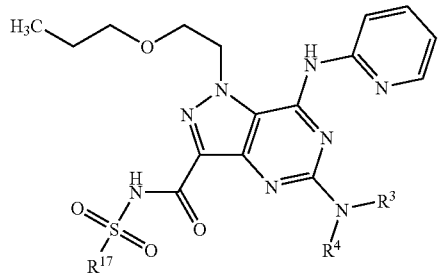

165 $R^3$ = —CH$_3$; $R^4$ = —CH$_2$CH$_3$; $R^{17}$ = —CH$_3$;
$^1$H NMR (CDCl$_3$, 400 MHz) δ: 0.75 (t, 3H), 1.24 (t, 3H), 1.60 (m, 2H), 3.24 (s, 3H), 3.42 (s, 3H), 3.56 (t, 2H), 3.75 (q, 2H), 3.98 (t, 2H), 4.84 (m, 2H), 7.04 (m, 1H), 7.75 (m, 1H), 8.35 (m, 2H). MS APCI+ m/z 477 [MH]$^+$

166 $R^3$ = —CH$_3$; $R^4$ = —CH$_2$CH$_3$; $R^{17}$ = —CH$_2$CH$_3$;
$^1$H NMR (CDCl$_3$, 400 MHz) δ: 0.75 (t, 3H), 1.24 (t, 3H), 1.42 (t, 3H), 1.60 (m, 2H), 3.22 (s, 3H), 3.56 (t, 2H), 3.60 (q, 2H), 3.75 (q, 2H), 3.97 (t, 2H), 4.82 (m, 2H), 7.04 (m, 1H), 7.78 (m, 1H), 8.40 (m, 2H). MS APCI+ m/z 491 [MH]$^+$

167 $R^3$ = —CH$_3$; $R^4$ = —CH$_3$CH$_2$; $R^{17}$ = —CH$_3$;
$^1$H NMR (CDCl$_3$, 400 MHz) δ: 0.75 (t, 3H), 1.24 (d, 6H), 1.58 (m, 2H), 3.06 (s, 3H), 3.44 (s, 3H), 3.50 (m, 2H), 3.98 (t, 2H), 4.84 (m, 2H), 4.95 (m, 1H), 7.04 (m, 1H), 7.80 (m, 1H), 8.35 (m, 2H). MS APCI+ m/z 491 [MH]$^+$

168 $R^3$ = —CH$_3$; $R^4$ = —CH(CH$_3$)$_2$; $R^{17}$ = —CH$_2$CH$_3$;
$^1$H NMR (CDCl$_3$, 400 MHz) δ: 0.73 (t, 3H), 1.24 (d, 6H), 1.42 (t, 3H), 1.56 (m, 2H), 3.04 (s, 3H), 3.55 (m, 2H), 3.60 (q, 2H), 3.98 (t, 2H), 4.82 (m, 2H), 4.95 (m, 1H), 7.04 (m, 1H), 7.80 (m, 1H), 8.35 (d, 1H), 8.40 (m, 1H). MS APCI+ m/z 505 [MH]$^+$

169 $R^3$ = —CH$_2$CH$_3$; $R^4$ = —CH$_2$CH$_3$; $R^{17}$ = —CH$_3$;
$^1$H NMR (CDCl$_3$, 400 MHz) δ: 0.75 (t, 3H), 1.26 (t, 6H), 1.60 (m, 2H), 3.42 (s, 3H), 3.55 (t, 2H), 3.66 (m, 4H), 3.97 (t, 2H), 4.87 (m, 2H), 7.06 (m, 1H), 7.78 (m, 1H), 8.36 (m, 1H), 8.44 (m, 1H). MS APCI+ m/z 491 [MH]$^+$

170 $R^3$ = —CH$_2$CH$_3$; $R^4$ = —CH$_2$CH$_3$; $R^{17}$ = —CH$_2$CH$_3$;
$^1$H NMR (CDCl$_3$, 400 MHz) δ: 0.75 (t, 3H), 1.24 (t, 6H), 1.42 (t, 3H), 1.60 (m, 2H), 3.52 (t, 2H), 3.60 (q, 2H), 3.65 (m, 4H), 3.98 (t, 2H), 4.84 (m, 2H), 7.06 (m, 1H), 7.75 (m, 1H), 8.34 (m, 1H), 8.42 (m, 1H). MS APCI+ m/z 505 [MH]$^+$

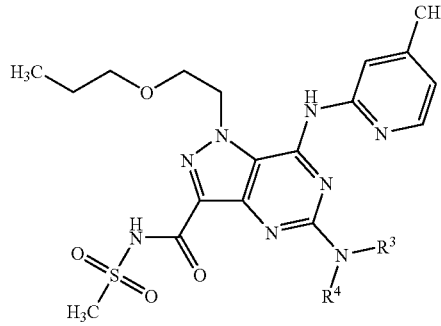

171 $R^3$ = —CH$_3$; $R^4$ = —CH$_2$CH$_3$;
$^1$H NMR (DMSO-d$_6$ TFAd, 400 MHz) δ: 0.64 (t, 3H), 1.16 (t, 3H), 1.35 (m, 2H), 2.45 (s, 3H), 3.15 (s, 3H), 3.32 (t, 2H), 3.40 (s, 3H), 3.64 (q, 2H), 3.86 (t, 2H), 4.94 (m, 2H), 7.18 (d, 1H), 8.04 (s, 1H), 8.25 (d, 1H). MS APCI+ m/z 491 [MH]$^+$

EXAMPLES 172 TO 177

4-Dimethylaminopyridine (1.3 eq) was added to a solution of the appropriate acid from examples 140-145 (1 eq), 1-(3-dimethylaminopropyl)-3-ethylcarbodiimide hydrochloride (1.3 eq) and methanesulphonamide (1.3 eq) in dichloromethane (13.5-16 mLmmol$^{-1}$) and the reaction stirred at room temperature for 18 hours. Tlc analysis showed starting material remaining, so additional 1-(3-dimethylaminopropyl)-3-ethylcarbodiimide hydrochloride (0.5 eq) and methanesulphonamide (0.5 eq) were added and the reaction stirred for a further 18 hours. The mixture was diluted with dichloromethane and 1M citric acid solution, stirring continued for a further 40 minutes, then the phases separated. The organic phase was purified directly by column chromatography on silica gel (using a Parallel Flashmaster system) using an elution gradient of methanol:dichloromethane (0:100 to 5:95) to provide the title compounds as yellow solids.

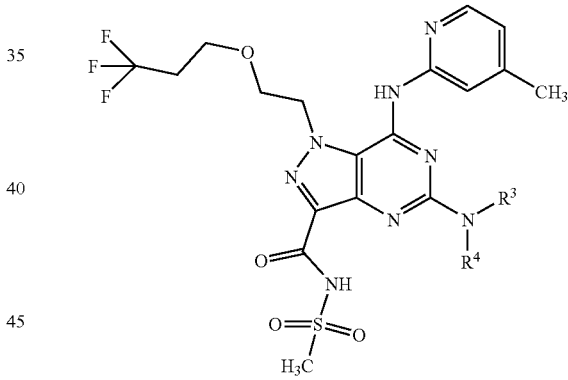

| Ex. No | —NR$^3$R$^4$ | Data |
|---|---|---|
| 172 | N(CH$_3$)(CH$_2$CH$_3$) | $^1$H NMR (DMSO-d$_6$ + TFAd, 400 MHz) δ: 1.17 (t, 3H), 2.35-2.46 (m, 5H), 3.18 (s, 3H), 3.39 (s, 3H), 3.60-3.67 (m, 4H), 3.94 (t, 2H), 4.98 (t, 2H), 7.18 (d, 1H), 8.08 (s, 1H), 8.26 (d, 1H). MS APCI+ m/z 545 [MH]$^+$ |
| 173 | N(CH$_3$)CH(CH$_3$)$_2$ | $^1$H NMR (DMSO-d$_6$ + TFAd, 400 MHz) δ: 1.19 (d, 6H), 2.40-2.50 (m, 5H), 3.02 (s, 3H), 3.40 (s, 3H), 3.63 (t, 2H), 3.94 (t, 2H), 4.97 (t, 2H), 7.15 (d, 1H), 8.05 (s, 1H), 8.24 (d, 1H). MS APCI+ m/z 559 [MH]$^+$ |
| 174 | N(CH$_2$CH$_3$)$_2$ | $^1$H NMR (DMSO-d$_6$ + TFAd, 400 MHz) δ: 1.19 (t, 6H), 2.42 (s, 3H), 2.44-2.53 (m, 2H), 3.40 (s, 3H), 3.64 (m, 6H), 3.93 (t, 2H), 4.94 (t, 2H), 7.15 (d, 1H), 8.05 (s, 1H), 8.26 (d, 1H). MS APCI+ m/z 559 [MH]$^+$ |

-continued

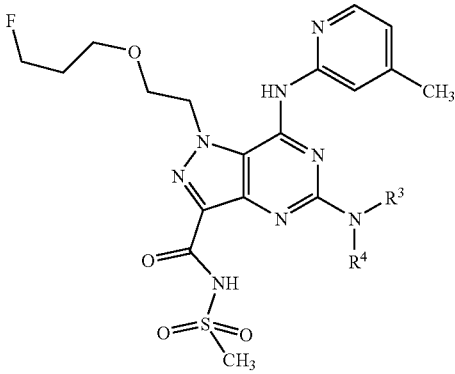

| 175 | <sub>N(CH3)(CH2CH3)</sub> | ¹H NMR (DMSO-d₆ + TFAd, 400 MHz) δ: 1.17 (t, 3H), 1.73-1.86 (m, 2H), 2.41 (s, 3H), 3.17 (s, 3H), 3.41 (s, 3H), 3.51 (t, 2H), 3.65 (q, 2H), 3.90 (t, 2H), 4.24-4.39 (m, 2H), 4.92 (m, 2H), 7.11 (d, 1H), 8.07 (s, 1H), 8.24 (d, 1H). MS APCI+ m/z 509 [MH]⁺ |
|---|---|---|
| 176 | <sub>N(CH3)(CH(CH3)2)</sub> | ¹H NMR (DMSO-d₆ + TFAd, 400 MHz) δ: 1.20 (d, 6H), 1.72-1.85 (m, 2H), 2.42 (s, 3H), 3.01 (s, 3H), 3.41 (s, 3H), 3.50 (t, 2H), 3.90 (t, 2H), 4.24-4.39 (m, 2H), 4.77 (m, 1H), 4.94 (t, 2H), 7.13 (d, 1H), 8.05 (s, 1H), 8.24 (d, 1H). MS APCI+ m/z 523 [MH]⁺ |
| 177 | <sub>N(CH2CH3)2</sub> | ¹H NMR (DMSO-d₆ + TFAd, 400 MHz) δ: 1.20 (t, 6H), 1.73-1.85 (m, 2H), 2.42 (s, 3H), 3.40 (s, 3H), 3.50 (t, 2H), 3.62 (q, 4H), 3.89 (t, 2H), 4.24-4.39 (m, 2H), 4.92 (t, 2H), 7.14 (d, 1H), 8.08 (s, 1H), 8.26 (d, 1H). MS APCI+ m/z 523 [MH]⁺ |

EXAMPLE 178

5-[Ethyl(methyl)amino]-7-[(4-methylpyridin-2-yl)amino]-N-(methylsulfonyl)-1-[2-(2,2,2-trifluoroethoxy)ethyl]-1H-pyrazolo[4,3-d]pyrimidine-3-carboxamide

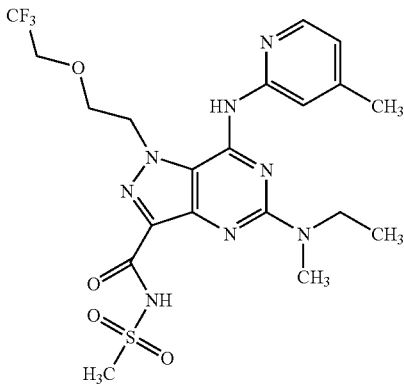

A mixture of the chloride from preparation 261 (50 mg, 0.1 mmol), N-ethyldiisopropylamine (0.05 mL, 0.3 mmol), N-ethylmethylamine (0.026 mL, 0.3 mmol) and cesium fluoride (15 mg, 0.1 mmol) in 1-methyl-2-pyrrolidinone (1 mL) was heated in a Reactivial® at 110° C. for 90 minutes. The cooled reaction mixture was purified directly using a Phenomenex Luna C18 column reverse phase column and acetonitrile:95% water/5% methanol/0.1% trifluoroacetic acid (5:95 to 95:5) as elution gradient. The product was dissolved in dichloromethane and the solution washed with sodium bicarbonate solution, dried over magnesium sulphate and evaporated under reduced pressure to provide the title compound, 24 mg. Alternatively, example 178 may be prepared by the method of examples 172-177. 4-Dimethylaminopyridine (22 mg, 0.20 mmol) was added to a solution of the acid from example 127 (70 mg, 0.15 mmol), 1-(3-dimethylaminopropyl)-3-ethylcarbodiimide hydrochloride (38 mg, 0.20 mmol) and methanesulphonamide (19 mg, 0.20 mmol) in dichloromethane (2 ml) and the reaction stirred at room temperature for 18 hours. The mixture was diluted with dichloromethane (20 mls) and 1M citric acid solution (10 ml), then the phases separated. The organic phase was purified directly by column chromatography on silica gel (using a Parallel Flashmaster system) using an elution gradient of methanol:dichloromethane (0:100 to 2:98) to provide the title compound as a yellow solid. ¹H NMR (DMSO-D₆+1 drop TFAd, 400 MHz) δ: 1.19 (t, 3H), 2.49 (s, 3H), 3.20 (s, 3H), 3.41 (s, 3H), 3.66 (q, 2H), 4.06 (q, 2H), 4.14 (t, 2H), 5.03 (t, 2H), 7.20 (d, 1H), 8.12 (s, 1H), 8.27 (d, 1H). MS ES− m/z 529 [M-H]⁻

EXAMPLE 179

5-[Isopropyl(methyl)amino]-7-[(4-methylpyridin-2-yl)amino]-N-(methylsulfonyl)-1-[2-(2,2,2-trifluoroethoxy)ethyl]-1H-pyrazolo[4,3-d]pyrimidine-3-carboxamide

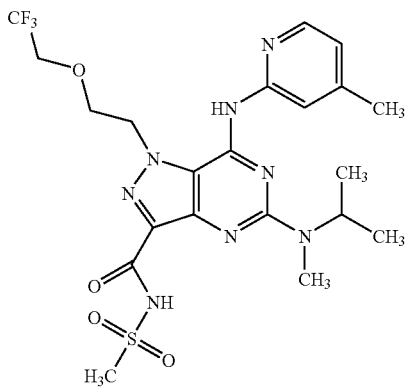

The title compound was obtained from the chloride from preparation 261 and N-methylisopropylamine, following the procedure described in example 178. ¹H NMR (DMSO-D₆+1 drop TFAd, 400 MHz) δ: 1.20 (d, 6H), 2.49 (s, 3H), 3.03 (s, 3H), 3.41 (s, 3H), 4.08 (q, 2H), 4.15 (t, 2H), 4.78 (m, 1H), 5.03 (t, 2H), 7.20 (d, 1H), 8.10 (s, 1H), 8.26 (d, 1H). MS ES− m/z 543 [M-H]⁻

EXAMPLES 180 TO 182

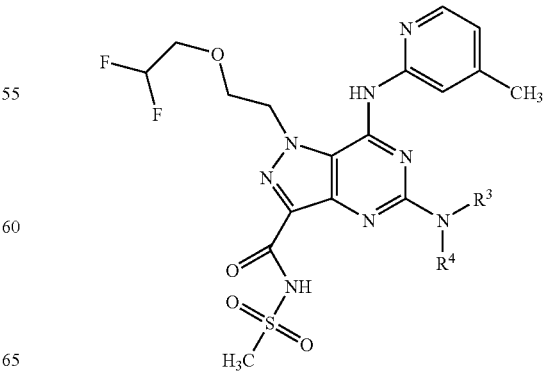

Sodium hydroxide solution (1M, 1 mL, 1 mmol) was added to a solution of the appropriate ester from preparation 250-252 (0.33 mmol) in dioxan (3 mL) and the solution stirred at room temperature for 18 hours. The reaction was evaporated under reduced pressure and the mixture partitioned between dichloromethane (50 mL) and 1M citric acid solution. The layers were separated and the organic solution dried over magnesium sulphate and evaporated under reduced pressure. The product was dissolved in dichloromethane (5 mL) and 1-(3-dimethylaminopropyl)-3-ethylcarbodiimide hydrochloride (82 mg, 0.43 mmol), methanesulphonamide (41 mg, 0.43 mmol) and 4-dimethylaminopyridine (48 mg, 0.43 mmol) added and the reaction stirred at room temperature for 72 hours. The mixture was diluted with dichloromethane (10 mL), 1M citric acid solution and the mixture stirred for 30 minutes. The phases were separated and the organic solution purified directly by column chromatography on silica gel using dichloromethane:methanol (98:2) as eluant to afford the title compounds.

| Ex No | —NR³R⁴ | Data |
|---|---|---|
| 180[A] | 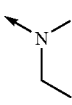 | ¹H NMR (DMSO-d₆ + TFA-d, 400 MHz) δ: 1.20 (t, 3H), 2.45 (s, 3H), 3.18 (s, 3H), 3.40 (s, 3H), 3.60-3.75 (m, 4H), 4.05 (t, 2H), 5.00 (t, 2H), 6.00 (m, 1H), 7.20 (d, 1H), 8.08 (s, 1H), 8.25 (d, 1H). MS APCI+ m/z 513 [MH]⁺ |
| 181 |  | ¹H NMR (DMSO-d₆ + TFA-d, 400 MHz) δ: 1.18 (d, 6H), 2.44 (s, 3H), 3.02 (s, 3H), 3.40 (s, 3H), 3.68 (m, 2H), 4.05 (t, 2H), 4.76 (m, 1H), 5.00 (t, 2H), 6.04 (m, 1H), 7.18 (m, 1H), 8.06 (s, 1H), 8.25 (d, 1H). MS APCI+ m/z 527 [MH]⁺ |
| 182 | 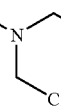 | ¹H NMR (DMSO-d₆ + TFA-d, 400 MHz) δ: 1.18 (t, 6H), 2.42 (s, 3H), 3.40 (s, 3H), 3.40-3.55 (m, 6H), 4.04 (t, 2H), 5.00 (t, 2H), 5.98 (m, 1H), 7.22 (d, 1H), 8.08 (s, 1H), 8.30 (d, 1H). MS APCI+ m/z 527 [MH]⁺ |

[A] = the product was crystallised from dichloromethane:isopropylalcohol

EXAMPLE 183

5-(Diethylamino)-7-[(4-methylpyridin-2-yl)amino]-N-(methylsulfonyl)-1-(2-propoxyethyl)-1H-pyrazolo[4,3-d]pyrimidine-3-carboxamide

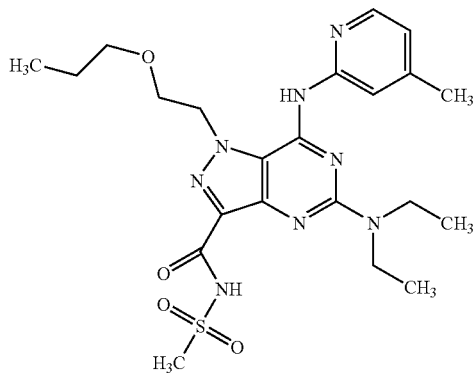

A mixture of the chloride from preparation 67 (135 mg, 0.33 mmol), cesium fluoride (50 mg, 0.33 mmol) and diethylamine (103 µL, 1 mmol) in dimethylsulphoxide (1 mL) was heated in a Reactivial® at 120° C. for 18 hours. The cooled mixture was partitioned between dichloromethane (20 mL) and water (20 mL) and the layers separated. The organic phase was washed with water (2×10 mL), dried over magnesium sulphate and evaporated under reduced pressure. Sodium hydroxide solution (1M, 0.5 mL, 0.5 mmol) and dioxan (1 mL) were added to the residue and the solution stirred at room temperature for 18 hours. The reaction was evaporated under reduced pressure and the mixture partitioned between dichloromethane (20 mL) and 1M citric acid solution (2 mL) and water (20 mL). The layers were separated and the organic solution dried over magnesium sulphate and evaporated under reduced pressure. The product was dissolved in dichloromethane (5 mL) and 1-(3-dimethylaminopropyl)-3-ethylcarbodiimide hydrochloride (82 mg, 0.43 mmol), methanesulphonamide (41 mg, 0.43 mmol) and 4-dimethylaminopyridine (48 mg, 0.43 mmol) added and the reaction stirred at room temperature for 18 hours. The mixture was diluted with dichloromethane (30 mL), washed with 1M citric acid solution (5 mL) then dried over magnesium sulphate and evaporated under reduced pressure. The crude product was purified by column chromatography on silica gel using dichloromethane:methanol (100:0 to 97:3) as eluant to afford the title compound, 75 mg. ¹H NMR (DMSO-d₆+TFAd, 400 MHz) δ: 0.62 (t, 3H), 1.20 (t, 6H), 1.40 (m, 2H), 2.41 (s, 3H), 3.38 (t, 2H), 3.41 (s, 3H), 3.60 (m, 4H), 3.85 (t, 2H), 4.90 (m, 2H), 7.14 (d, 1H), 8.05 (s, 1H), 8.24 (d, 1H). MS APCI+ m/z 505 [MH]⁺

EXAMPLE 184

5-[Isopropyl(methyl)amino]-7-[(4-methylpyridin-2-yl)amino]-N-(methylsulfonyl)-1-(2-propoxyethyl)-1H-pyrazolo[4,3-d]pyrimidine-3-carboxamide

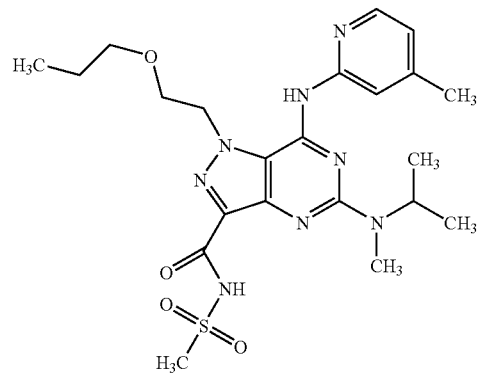

The title compound was obtained in 51% yield as a yellow solid, from the chloride of preparation 67, following a similar procedure to that described in example 183. ¹H NMR (DMSO-D₆+1 drop TFAd, 400 MHz) δ: 0.62 (t, 3H), 1.18 (d, 6H), 1.38 (m, 2H), 2.42 (s, 3H), 3.00 (s, 3H), 3.30 (t, 2H), 3.39 (s, 3H), 3.84 (t, 2H), 4.75 (m, 1H), 4.95 (t, 2H), 7.18 (d, 1H), 8.04 (s, 1H), 8.24 (d, 1H). MS APCI+− m/z 505 [MH]+

EXAMPLE 185

5-[Ethyl(methyl)amino]-1-(2-hydroxyethyl)-7-[(4-methylpyridin-2-yl)amino]-N-(methylsulfonyl)-1H-pyrazolo[4,3-d]pyrimidine-3-carboxamide

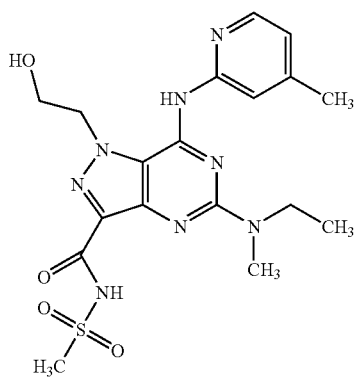

Boron tribromide (1M in dichloromethane, 1.95 mL, 1.95 mmol) was added dropwise to a solution of the compound from example 119 (100 mg, 0.22 mmol) in dichloromethane (5 mL) cooled to −25° C., so as to maintain the temperature below −20° C. The reaction was stirred at −25° C. for 3 hours, then quenched by the dropwise addition of saturated sodium bicarbonate solution until pH 7 was achieved. The mixture was allowed to warm to room temperature, then partitioned between water (10 mL) and dichloromethane (20 mL). The organic phase was washed with water, dried over magnesium sulphate and evaporated under reduced pressure to provide the title compound as a yellow solid, 31 mg. $^1$H NMR (CD$_3$OD+drop TFAd, 400 MHz) δ: 1.31 (t, 3H), 2.54 (s, 3H), 3.30 (s, 3H), 3.41 (s, 3H), 3.76 (q, 2H), 4.08 (t, 2H), 4.98 (t, 2H), 7.19 (d, 1H), 8.04 (s, 1H), 8.15 (d, 1H). MS m/z 449 [MH]$^+$

Assay

The compounds of the invention are inhibitors of cyclic guanylate monophosphate (cGMP)-specific phosphodiesterase type 5 (PDE-5 inhibitors). Preferred compounds suitable for use in accordance with the present invention are potent and selective PDE5 inhibitors. In vitro PDE inhibitory activities against cyclic guanosine 3',5'-monophosphate (cGMP) and cyclic adenosine 3',5'-monophosphate (cAMP) phosphodiesterases can be determined by measurement of their IC$_{50}$ values (the concentration of compound required for 50% inhibition of enzyme activity).

The required PDE enzymes can be isolated from a variety of sources, including human corpus cavernosum, human and rabbit platelets, human cardiac ventricle, human skeletal muscle and bovine retina, essentially by a modification of the method of Thompson, W J et al.; Biochemistry 18(23), 5228-5237, 1979, as described by Ballard S A et al.; J. Urology 159(6), 2164-2171, 1998. In particular, cGMP-specific PDE5 and cGMP-inhibited cAMP PDE3 can be obtained from human corpus cavernosum tissue, human platelets or rabbit platelets; cGMP-stimulated PDE2 was obtained from human corpus cavernosum; calcium/calmodulin (Ca/CAM)-dependent PDE1 from human cardiac ventricle; cAMP-specific PDE4 from human skeletal muscle; and photoreceptor PDE6 from bovine retina. Phosphodiesterases 7-11 can be generated from full length human recombinant clones transfected into SF9 cells.

Assays can be performed either using a modification of the "batch" method of Thompson W J and Appleman M M; Biochemistry 10(2), 311-316, 1971, essentially as described by Ballard S A et al.; J. Urology 159(6), 2164-2171, 1998, or using a scintillation proximity assay for the direct detection of [$^3$H]-labelled AMP/GMP using a modification of the protocol described by Amersham plc under product code TRKQ7090/7100. In summary, for the scintillation proximity assay the effect of PDE inhibitors was investigated by assaying a fixed amount of enzyme in the presence of varying inhibitor concentrations and low substrate, (cGMP or cAMP in a 3:1 ratio unlabelled to [$^3$H]-labeled at a concentration of ~⅓ K$_m$ or less) such that IC$_{50}$≅K$_i$. The final assay volume was made up to 100 µl with assay buffer [20 mM Tris-HCl pH 7.4, 5 mM MgCl$_2$, 1 mg/ml bovine serum albumin]. Reactions were initiated with enzyme, incubated for 30-60 min at 30° C. to give <30% substrate turnover and terminated with 50 µl yttrium silicate SPA beads (containing 3 mM of the respective unlabelled cyclic nucleotide for PDEs 9 and 11). Plates were re-sealed and shaken for 20 min, after which the beads were allowed to settle for 30 min in the dark and then counted on a TopCount plate reader (Packard, Meriden, Conn.) Radioactivity units were converted to % activity of an uninhibited control (100%), plotted against inhibitor concentration and inhibitor IC$_{50}$ values obtained using the 'Fit Curve' Microsoft Excel extension.

All compounds of the invention have an activity against PDE-5 of less than 10,000 nM. IC$_{50}$ values for representative compounds are listed in the table below.

| Example | IC$_{50}$ (nM) |
| --- | --- |
| 1 | 0.075 |
| 2 | 0.201 |
| 3 | 5.01 |
| 4 | 2.62 |
| 5 | 0.943 |
| 6 | 2.89 |
| 7 | 0.082 |
| 8 | 3.82 |
| 9 | 0.075 |
| 10 | 1.86 |
| 11 | 1.09 |
| 12 | 14.7 |
| 13 | 1.46 |
| 14 | 8.75 |
| 15 | 1.84 |
| 16 | 0.510 |
| 17 | 2.93 |
| 18 | 11.3 |
| 19 | 2.43 |
| 20 | 35.7 |
| 21 | 5.30 |
| 22 | 7.12 |
| 23 | 8.97 |
| 24 | 53.9 |
| 25 | 7.19 |
| 26 | 1.64 |
| 27 | 36.8 |
| 28 | 11.6 |
| 29 | 106 |
| 30 | 35.8 |
| 31 | 43.4 |
| 32 | 100 |
| 33 | 100 |
| 34 | 100 |
| 35 | 100 |
| 36 | 0.708 |
| 37 | 23.9 |

-continued

| Example | IC$_{50}$ (nM) |
|---|---|
| 38 | 16.7 |
| 39 | 57.2 |
| 40 | 0.167 |
| 41 | 3.20 |
| 42 | 86.6 |
| 43 | 17.4 |
| 44 | 94.7 |
| 45 | 47.1 |
| 46 | 17.9 |
| 47 | 8.00 |
| 48 | 100 |
| 49 | 4.92 |
| 50 | 1.66 |
| 51 | 2.57 |
| 52 | 3.40 |
| 53 | 0.797 |
| 54 | 2.03 |
| 55 | 2.60 |
| 56 | 9.11 |
| 57 | 100 |
| 58 | 100 |
| 59 | 43.6 |
| 60 | 8.02 |
| 61 | 13.1 |
| 62 | 1.85 |
| 63 | 4.58 |
| 64 | 100 |
| 65 | 25.0 |
| 66 | 13.5 |
| 67 | 100 |
| 68 | 100 |
| 69 | 100 |
| 70 | 0.451 |
| 71 | 2.46 |
| 72 | 59.2 |
| 73 | 52.3 |
| 74 | 100 |
| 75 | 0.371 |
| 76 | 0.465 |
| 77 | 0.162 |
| 78 | 0.240 |
| 79 | 0.332 |
| 80 | 2.88 |
| 81 | 16.7 |
| 82 | 55.1 |
| 83 | 27.8 |
| 84 | 2.37 |
| 85 | 0.0550 |
| 86 | 0.0630 |
| 87 | 0.0870 |
| 88 | 21.3 |
| 90 | 2.83 |
| 91 | 5.06 |
| 92 | 41.0 |
| 93 | 23.2 |
| 94 | 0.303 |
| 95 | 9.11 |
| 96 | 3.65 |
| 97 | 9.74 |
| 99 | 2.45 |
| 100 | 3.48 |
| 101 | 8.45 |
| 102 | 38.2 |
| 103 | 21.4 |
| 104 | 9.69 |
| 105 | 0.741 |
| 106 | 2.60 |
| 107 | 0.307 |
| 108 | 18.3 |
| 109 | 9.70 |
| 110 | 0.564 |
| 111 | 0.502 |
| 112 | 14.7 |
| 113 | 0.270 |
| 114 | 4.83 |
| 115 | 0.545 |
| 116 | 0.0320 |
| 117 | 0.0250 |

-continued

| Example | IC$_{50}$ (nM) |
|---|---|
| 118 | 1.72 |
| 119 | 11.5 |
| 120 | 1.12 |
| 122 | 2.54 |
| 123 | 0.628 |
| 124 | 0.776 |
| 125 | 1.53 |
| 126 | 3.05 |
| 127 | 6.34 |
| 128 | 3.94 |
| 129 | 7.78 |
| 130 | 19.5 |
| 134 | 5.02 |
| 135 | 7.70 |
| 136 | 0.414 |
| 137 | 0.0680 |
| 138 | 0.0650 |
| 139 | 0.0710 |
| 140 | 0.0990 |
| 147 | 0.141 |
| 148 | 0.198 |
| 149 | 14.4 |
| 150 | 1.55 |
| 151 | 0.513 |
| 152 | 4.68 |
| 153 | 0.398 |
| 154 | 1.16 |
| 155 | 0.341 |
| 156 | 0.162 |
| 157 | 0.771 |
| 158 | 0.608 |
| 159 | 0.0560 |
| 160 | 0.0250 |
| 161 | 0.101 |
| 162 | 3.10 |
| 163 | 0.591 |
| 164 | 0.324 |
| 171 | 1.21 |
| 175 | 0.57 |
| 176 | 0.17 |
| 177 | 0.17 |
| 178 | 2.21 |
| 179 | 0.914 |
| 180 | 2.88 |
| 181 | 1.29 |
| 182 | 1.4 |
| 183 | 0.383 |
| 184 | 0.5 |
| 185 | 11.5 |

The invention claimed is:

1. A compound of formula (I)

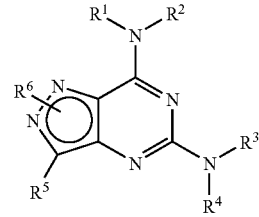

(I)

wherein
R$^1$ is a cyclic group selected from R$^A$, R$^B$, R$^C$ and R$^D$, each of which is optionally substituted with one or more R$^7$ groups;
R$^2$ is hydrogen or C$_1$-C$_2$ alkyl;
R$^3$ and R$^4$ are each independently C$_1$-C$_8$ alkyl, C$_2$-C$_8$ alkenyl, C$_2$-C$_8$ alkynyl or C$_3$-C$_{10}$ cycloalkyl, each of which is optionally substituted with one or more R$^8$ groups, or R$^E$, which is optionally substituted with one or more R$^9$ groups, or hydrogen;

or —NR$^3$R$^4$ forms R$^F$, which is optionally substituted with one or more R$^{10}$ groups;

R$^5$ is selected from —Y—CO$_2$R$^{15}$ and —Y—R$^{16}$;

R$^6$, which may be attached at N$^1$ or N$^2$, is C$_1$-C$_6$ alkyl, C$_1$-C$_8$ haloalkyl, C$_2$-C$_6$ alkenyl or C$_2$-C$_6$ alkynyl, each of which is optionally substituted by C$_1$-C$_8$ alkoxy, C$_1$-C$_6$ haloalkoxy or a cyclic group selected from R$^J$, R$^K$, R$^L$ and R$^M$, or R$^6$ is R$^N$, C$_3$-C$_7$ cycloalkyl or C$_3$-C$_7$ halocycloalkyl, each of which is optionally substituted by C$_1$-C$_6$ alkoxy or C$_1$-C$_6$ haloalkoxy, or R$^6$ is hydrogen;

R$^7$ is halo, C$_1$-C$_6$ alkyl, C$_1$-C$_6$ haloalkyl, C$_2$-C$_6$ alkenyl, C$_2$-C$_8$ alkynyl, cycloalkyl, C$_3$-C$_{10}$ halocycloalkyl, phenyl, OR$^{12}$, OC(O)R$^{12}$, NO$_2$, NR$^{12}$R$^{13}$, NR$^{12}$C(O)R$^{13}$, NR$^{12}$CO$_2$R$^{14}$, C(O)R$^{12}$, CO$_2$R$^{12}$, CONR$^{12}$R$^{13}$ or CN;

R$^8$ is halo, phenyl, C$_1$-C$_6$ alkoxyphenyl, OR$^{12}$, OC(O)R$^{12}$, NO$_2$, NR$^{12}$R$^{13}$, NR$^{12}$C(O)R$^{13}$, NR$^{12}$CO$_2$R$^{14}$, C(O)R$^{12}$, CO$_2$R$^{12}$, CONR$^{12}$R$^{13}$, CN, C$_3$-C$_8$ cycloalkyl, R$^G$ or R$^H$, the last two of which are optionally substituted with one or more R$^9$ groups;

R$^9$ is C$_1$-C$_8$ alkyl, C$_1$-C$_6$ haloalkyl or CO$_2$R$^{12}$;

R$^{10}$ is halo, C$_3$-C$_{10}$ cycloalkyl, C$_3$-C$_{10}$ halocycloalkyl, phenyl, OR$^{12}$, OC(O)R$^{12}$, NO$_2$, NR$^{12}$R$^{13}$, NR$^{12}$C(O)R$^{13}$, NR$^{12}$CO$_2$R$^{14}$, C(O)R$^{12}$, CO$_2$R$^{13}$, CONR$^{12}$R$^{13}$, CN, oxo, C$_1$-C$_6$ alkyl or C$_1$-C$_6$ haloalkyl, the last two of which are optionally substituted by R$^{11}$;

R$^{11}$ is phenyl, NR$^{12}$R$^{13}$ or NR$^{12}$CO$_2$R$^{14}$;

R$^{12}$ and R$^{13}$ are each independently hydrogen, C$_1$-C$_6$ alkyl or C$_1$-C$_6$ haloalkyl;

R$^{14}$ is C$_1$-C$_6$ alkyl or C$_1$-C$_6$ haloalkyl;

R$^{15}$ is hydrogen or C$_1$-C$_6$ alkyl optionally substituted with one or more groups selected from phenyl, halo, OH, C$_1$-C$_6$ alkyloxy, NH$_2$, NH(C$_1$-C$_6$alkyl) and N(C$_1$-C$_6$ alkyl)$_2$;

R$^{16}$ is a carboxylic acid isostere selected from tetrazol-5-yl, 5-trifluoromethyl-1,2,4-triazol-3-yl, 5-(methylsulfonyl)-1,2,4-triazol-3-yl, 2,5-dihydro-5-oxo-1,2,4-oxadiazol-3-yl, —SO$_2$NHR$^{17}$ and —CONHR$^{18}$;

R$^{17}$ is selected from C$_1$-C$_6$ alkyl, phenyl, —CO—(C$_1$-C$_6$ alkyl) and —CO-phenyl;

R$^{18}$ is selected from —SO$_2$—(C$_1$-C$_6$ alkyl) and —SO$_2$-phenyl;

R$^A$ and R$^J$ are each independently a C$_3$-C$_{10}$ cycloalkyl or C$_3$-C$_{10}$ cycloalkenyl group, each of which may be either monocyclic or, when there are an appropriate number of ring atoms, polycyclic and which may be fused to either
  (a) a monocyclic aromatic ring selected from a benzene ring and a 5- or 6-membered heteroaromatic ring containing up to three heteroatoms selected from nitrogen, oxygen and sulphur, or
  (b) a 5-, 6- or 7-membered heteroalicyclic ring containing up to three heteroatoms selected from nitrogen, oxygen and sulphur;

R$^B$ and R$^K$ are each independently a phenyl or naphthyl group, each of which may be fused to
  (a) a C$_5$-C$_7$ cycloalkyl or C$_5$-C$_7$ cycloalkenyl ring,
  (b) a 5-, 6- or 7-membered heteroalicyclic ring containing up to three heteroatoms selected from nitrogen, oxygen and sulphur, or
  (c) a 5- or 6-membered heteroaromatic ring containing up to three heteroatoms selected from nitrogen, oxygen and sulphur;

R$^C$, R$^L$ and R$^N$ are each independently a monocyclic or, when there are an appropriate number of ring atoms, polycyclic saturated or partly unsaturated ring system containing between 3 and 10 ring atoms, of which at least one is a heteroatom selected from nitrogen, oxygen and sulphur, which ring may be fused to a C$_5$-C$_7$ cycloalkyl or C$_5$-C$_7$ cycloalkenyl group or a monocyclic aromatic ring selected from a benzene ring and a 5- or 6-membered heteroaromatic ring containing up to three heteroatoms selected from nitrogen, oxygen and sulphur;

R$^D$ and R$^M$ are each independently a 5- or 6-membered heteroaromatic ring containing up to three heteroatoms independently selected from nitrogen, oxygen and sulphur, which ring may further be fused to
  (a) a second 5- or 6-membered heteroaromatic ring containing up to three heteroatoms selected from nitrogen, oxygen and sulphur;
  (b) C$_5$-C$_7$ cycloalkyl or C$_5$-C$_7$ cycloalkenyl ring;
  (c) a 5-, 6- or 7-membered heteroalicyclic ring containing up to three heteroatoms selected from nitrogen, oxygen and sulphur; or
  (d) a benzene ring;

R$^E$, R$^F$ and R$^G$ are each independently a monocyclic or, when there are an appropriate number of ring atoms, polycyclic saturated ring system containing between 3 and 10 ring atoms, of which at least one is a heteroatom selected from nitrogen, oxygen and sulphur;

R$^H$ is a 5- or 6-membered heteroaromatic ring containing up to three heteroatoms independently selected from nitrogen, oxygen and sulphur; and Y is a covalent bond, —CH$_2$—O—CH$_2$—, C$_1$-C$_6$ alkylenyl or C$_3$-C$_7$ cycloalkylenyl; or a tautomer thereof or a pharmaceutically acceptable salt of said compound or tautomer.

2. A compound according to claim 1 wherein R$^A$ is a monocyclic C$_3$-C$_8$ cycloalkyl group optionally substituted with one to three R$^7$ groups, or a tautomer thereof or a pharmaceutically acceptable salt of said compound or tautomer.

3. A compound according to claim 1 wherein R$^1$ is phenyl optionally substituted with one to three R$^7$ groups, or a tautomer thereof or a pharmaceutically acceptable salt of said compound or tautomer.

4. A compound according to claim 1 wherein R$^1$ is a monocyclic saturated or partly unsaturated ring system containing between 3 and 8 ring atoms, of which at least one is a heteroatom selected from nitrogen, oxygen and sulphur, said ring being optionally substituted with one to three R$^7$ groups, or a tautomer thereof or a pharmaceutically acceptable salt of said compound or tautomer.

5. A compound according to claim 1 wherein R$^1$ is a 5- or 6-membered heteroaromatic ring containing up to three heteroatoms independently selected from nitrogen, oxygen and sulphur, said ring being optionally substituted with one to three R$^7$ groups, or a tautomer thereof or a pharmaceutically acceptable salt of said compound or tautomer.

6. A compound according to claim 5 wherein R$^1$ is furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl or pyrazinyl, said furanyl, thienyl, pyrrolyl, pyrazolyl, imidazolyl, isoxazolyl, oxazolyl, isothiazolyl, thiazolyl, oxadiazolyl, pyridyl, pyridazinyl, pyrimidyl and pyrazinyl being optionally substituted with one to three $R^7$ groups, or a tautomer thereof or a pharmaceutically acceptable salt of said compound or tautomer.

7. A compound according to claim 6 wherein $R^1$ is pyrazolyl, imidazolyl, isoxazolyl, oxazolyl, oxadiazolyl, pyridyl, pyridazinyl, pyrimidyl or pyrazinyl, said pyrazolyl, imidazolyl, isoxazolyl, oxazolyl, oxadiazolyl, pyridyl, pyridazinyl, pyrimidyl and pyrazinyl being optionally substituted with one to three $R^7$ groups, or a tautomer thereof or a pharmaceutically acceptable salt of said compound or tautomer.

8. A compound according to claim 1 wherein $R^7$ is halo, $C_1$-$C_6$ alkyl, $C_1$-$C_6$ haloalkyl, $OR^{12}$ or $CONR^{12}R^{13}$, or a tautomer thereof or a pharmaceutically acceptable salt of said compound or tautomer.

9. A compound according to claim 8 wherein $R^7$ is halo, $C_1$-$C_3$ alkyl, $C_1$-$C_3$ alkoxy, hydroxy or $CONH(C_1$-$C_3$ alkyl), or a tautomer thereof or a pharmaceutically acceptable salt of said compound or tautomer.

10. A compound according to claim 9 wherein $R^7$ is fluoro, methyl, ethyl, hydroxy, methoxy, propoxy or CONHMe, or a tautomer thereof or a pharmaceutically acceptable salt of said compound or tautomer.

11. A compound according to claim 1 selected from:

methyl 5-((1S,4S)-2,5-diazabicyclo[2.2.1]hept-2-yl)-1-(2-ethoxyethyl)-7-(4-methylpyridin-2-ylamino)-1H-pyrazolo[4,3-d]pyrimidine-3-carboxylate, methyl 1-(2-ethoxyethyl)-5-(N-isopropyl-N-methylamino)-7-(6-methylpyridin-2-ylamino)-1H-pyrazolo[4,3-d]pyrimidine-3-carboxylate, ethyl 1-(2-ethoxyethyl)-5-(N-ethyl-N-methylamino)-7-(4-methylpyridin-2-ylamino)-1H-pyrazolo[4,3-d]pyrimidine-3-carboxylate, 2-(dimethylamino)ethyl 5-dimethylamino-1-(2-ethoxyethyl)-7-(4-methylpyridin-2-ylamino)-1H-pyrazolo[4,3-d]pyrimidine-3-carboxylate, 1-(2-ethoxyethyl)-5-(N-methyl-N-propylamino)-7-(4-methylpyridin-2-ylamino)-1H-pyrazolo[4,3-d]pyrimidine-3-carboxylic acid, 5-(N-isopropyl-N-methylamino)-7-(4-methylpyridin-2-ylamino)-1-(2-propoxy-ethyl)-1H-pyrazolo[4,3-d]pyrimidine-3-carboxylic acid, 7-(4,6-dimethylpyridin-2-ylamino)-1-(2-ethoxyethyl)-5-(N-isopropyl-N-methyl-amino)-1H-pyrazolo[4,3-d]pyrimidine-3-carboxylic acid, 5-(N-cyclobutyl-N-methylamino)-1-(2-ethoxyethyl)-7-(4-methylpyridin-2-yl-amino)-1H-pyrazolo[4,3-d]pyrimidine-3-carboxylic acid, 1-(2-ethoxyethyl)-5-isopropylamino-7-(4-methylpyridin-2-ylamino)-1H-pyrazolo[4,3-d]pyrimidine-3-carboxylic acid, 1-(2-ethoxyethyl)-5-(N-ethyl-N-methylamino)-7-(2-methoxypyrimidin-4-ylamino)-1H-pyrazolo[4,3-d]pyrimidine-3-carboxylic acid, 3-[1-(2-ethoxyethyl)-5-(N-isopropyl-N-methylamino)-7-(4-methylpyridin-2-yl-amino)-1H-pyrazolo[4,3-d]pyrimidin-3-yl]-2H-1,2,4-oxadiazol-5-one, 3-[1-(2-ethoxyethyl)-5-(N-ethyl-N-methylamino)-7-(4-methylpyridin-2-ylamino)-1H-pyrazolo[4,3-d]pyrimidin-3-yl]-2H-1,2,4-oxadiazol-5-one, 1-(2-ethoxyethyl)-7-(4-fluoro-3-methylphenylamino)-5-(N-isopropyl-N-methyl-amino)-1H-pyrazolo[4,3-d]-pyrimidine-3-carboxylic acid, 1-(2-ethoxyethyl)-5-(N-ethyl-N-methylamino)-7-(4-fluoro-3-methylphenylamino)-1H-pyrazolo[4,3-d]pyrimidine-3-carboxylic acid, 7-(3,4-dimethylphenylamino)-1-(2-ethoxyethyl)-5-(N-ethyl-N-methylamino)-1H-pyrazolo[4,3-d]pyrimidine-3-carboxylic acid, 1-(2-(cyclopropylmethoxy)ethyl)-5-(N-isopropyl-N-methylamino)-7-(4-methyl-pyridin-2-ylamino)-1H-pyrazolo[4,3-d]pyrimidine-3-carboxylic acid, 1-(2-(cyclopropylmethoxy)ethyl)-5-(N-ethyl-N-methylamino)-7-(4-methyl-pyridin-2-ylamino)-1H-pyrazolo[4,3-d]pyrimidine-3-carboxylic acid, 1-(2-ethoxyethyl)-5-(N-isopropyl-N-methylamino)-7-(4-methylpyridin-2-ylamino)-1H-pyrazolo[4,3-d]pyrimidine-3-carboxylic acid, 1-(2-isopropoxyethyl)-5-(N-isopropyl-N-methylamino)-7-(4-methylpyridin-2-yl-amino)-1H-pyrazolo[4,3-d]pyrimidine-3-carboxylic acid, N-[1-(2-ethoxyethyl)-5-(N-isopropyl-N-methylamino)-7-(4-methylpyridin-2-yl-amino)-1H-pyrazolo[4,3-d]pyrimidine-3-carbonyl]methanesulfonamide, N-[1-(2-ethoxyethyl)-5-(N-ethyl-N-methylamino)-7-(4-methylpyridin-2-ylamino)-1H-pyrazolo[4,3-d]pyrimidine-3-carbonyl]methanesulfonamide, N-[5-(Ethyl-methyl-amino)-1-[2-(3-fluoro-propoxy)-ethyl]-7-(4-methyl-pyridin-2-ylamino)-1H-pyrazolo[4,3-d]pyrimidine-3-carbonyl]-methanesulfonamide N-[1-[2-(3-Fluoro-propoxy)-ethyl]-5-(isopropyl-methyl-amino)-7-(4-methyl-pyridin-2-ylamino)-1H-pyrazolo[4,3-d]pyrimidine-3-carbonyl]-methanesulfonamide N-[5-Diethylamino-1-[2-(3-fluoro-propoxy)-ethyl]-7-(4-methyl-pyridin-2-ylamino)-1H-pyrazolo[4,3-d]pyrimidine-3-carbonyl]-methanesulfonamide N-[5-Diethylamino-1-[2-(2,2-difluoro-ethoxy)-ethyl]-7-(4-methyl-pyridin-2-ylamino)-1H-pyrazolo[4,3-d]pyrimidine-3-carbonyl]-methanesulfonamide N-[1-[2-(2,2-Difluoro-ethoxy)-ethyl]-5-(ethyl-methyl-amino)-7-(4-methyl-pyridin-2-ylamino)-1H-pyrazolo[4,3-d]pyrimidine-3-carbonyl]-methanesulfonamide, and N-[1-[2-(2,2-Difluoro-ethoxy)-ethyl]-5-(isopropyl-methyl-amino)-7-(4-methyl-pyridin-2-ylamino)-1H-pyrazolo[4,3-d]pyrimidine-3-carbonyl]-methanesulfonamide, or a tautomer thereof or a pharmaceutically acceptable salt of said compound or tautomer.

12. A compound of formula (I-AA)

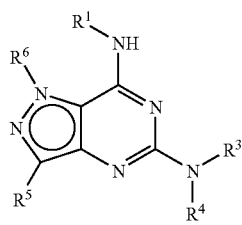

(I-AA)

wherein
R$^1$ is a pyridinyl optionally substituted with one or more C$_1$-C$_6$ alkyl groups;
R$^3$ and R$^4$ are each independently hydrogen or C$_1$-C$_6$ alkyl;
R$^5$ is —CONHR$^{18}$;
R$^6$ is C$_1$-C$_8$ alkyl optionally substituted by a substituent selected from the group consisting of —OH, C$_3$-C$_6$ cycloalkyloxy, C$_1$-C$_6$ alkoxy, and C$_1$-C$_6$ haloalkoxy;
R$^{18}$ is selected from the group consisting of —SO$_2$—(C$_1$-C$_6$ alkyl) and —SO$_2$-phenyl; or
a tautomer thereof or a pharmaceutically acceptable salt of said compound or tautomer.

13. A compound according to claim 12 wherein R$^1$ is 2-pyridinyl substituted with one or more methyl, or a tautomer thereof or a pharmaceutically acceptable salt of said compound or tautomer.

14. A compound according to claim 12 wherein R$^3$ and R$^4$ are independently selected from the group consisting of methyl, ethyl, propyl, and isopropyl, or a tautomer thereof or a pharmaceutically acceptable salt of said compound or tautomer.

15. A compound according to claim 12 wherein R$^{18}$ is selected from the group consisting of —SO$_2$CH$_3$ and —SO$_2$CH$_2$CH$_3$, or a tautomer thereof or a pharmaceutically acceptable salt of said compound or tautomer.

16. A compound according to claim 12 wherein R$^6$ is ethyl, optionally substituted by a substituent selected from the group consisting of hydroxyl, methoxy, ethoxy, propoxy, fluoromethoxy, fluoroethoxy, fluoropropoxy, difluoromethoxy, difluoroethoxy, difluoropropoxy, trifluoromethoxy, trifluoroethoxy, trifluoropropoxy, and cyclobutyloxy, or a tautomer thereof or a pharmaceutically acceptable salt of said compound or tautomer.

17. A compound according to claim 12 wherein
R$^1$ pyridinyl is substituted with one or more methyl;
R$^3$ and R$^4$ are independently selected from the group consisting of hydrogen, methyl, ethyl, propyl and isopropyl;
R$^6$ is ethyl, optionally substituted by a substituent selected from the group consisting of —OH, C$_3$-C$_6$ cycloalkyloxy, C$_1$-C$_6$alkoxy and C$_1$-C$_6$ haloalkoxy; and
R$^{18}$ is selected from the group consisting of —SO$_2$CH$_3$, and —SO$_2$CH$_2$CH$_3$, or a tautomer thereof or a pharmaceutically acceptable salt of said compound or tautomer.

18. A compound of formula (I-BB)

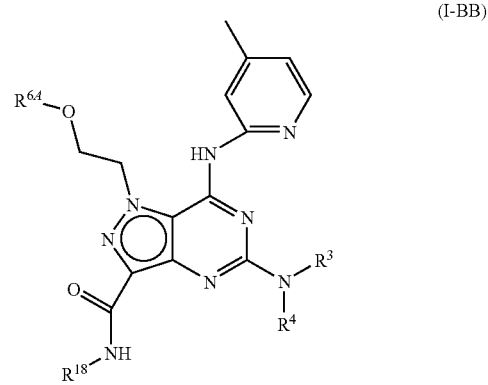

(I-BB)

wherein
R$^3$ and R$^4$ are each independently selected from the group consisting of methyl, ethyl, and isopropyl;
R$^{64}$ is selected from the group consisting of methyl, ethyl, propyl, fluoromethyl, fluoroethyl, fluoropropyl, difluoroethyl, difluoropropyl, trifluoroethyl, and trifluoropropyl; and
R$^{18}$ is selected from the group consisting of —SO$_2$CH$_3$ and —SO$_2$CH$_2$CH$_3$, or a tautomer thereof or a pharmaceutically acceptable salt of said compound or tautomer.

19. A pharmaceutical composition comprising a compound of claim 1, or a pharmaceutically acceptable salt thereof, and a pharmaceutically acceptable diluent or carrier.

20. A method of treating a disorder or condition in a mammal, said method comprising administering to said mammal a therapeutically effective amount of a compound of claim 1, or a tautomer thereof or a pharmaceutically acceptable salt of said compound or tautomer wherein said disorder or condition is hypertension.

21. A method according to claim 20 wherein the hypertension is essential hypertension, pulmonary hypertension, secondary hypertension, isolated systolic hypertension, hypertension associated with diabetes, hypertension associated with atherosclerosis or renovascular hypertension.

* * * * *